US008460666B2

(12) United States Patent
Throsby et al.

(10) Patent No.: US 8,460,666 B2
(45) **Date of Patent: *Jun. 11, 2013**

(54) HUMAN BINDING MOLECULES HAVING KILLING ACTIVITY AGAINST STAPHYLOCOCCI AND USES THEREOF

(75) Inventors: Mark Throsby, Utrecht (NL); Cecilia A. W. Geuijen, Moerkapelle (NL); Cornelis Adriaan De Kruif, De Bilt (NL)

(73) Assignee: Crucell Holland B.V., Leiden (NL)

( * ) Notice: Subject to any disclaimer, the term of this patent is extended or adjusted under 35 U.S.C. 154(b) by 0 days.

This patent is subject to a terminal disclaimer.

(21) Appl. No.: 13/397,606

(22) Filed: Feb. 15, 2012

(65) Prior Publication Data

US 2012/0141493 A1 Jun. 7, 2012

Related U.S. Application Data

(63) Continuation of application No. 12/227,029, filed as application No. PCT/EP2007/055527 on Jun. 5, 2007.

(60) Provisional application No. 60/811,477, filed on Jun. 6, 2006.

(30) Foreign Application Priority Data

Nov. 16, 2006 (EP) .................................... 06124231
Mar. 6, 2007 (EP) .................................... 07103584

(51) Int. Cl.
*A61K 39/40* (2006.01)

(52) U.S. Cl.
USPC .................. 424/142.1; 424/134.1; 424/165.1

(58) Field of Classification Search
None
See application file for complete search history.

(56) References Cited

U.S. PATENT DOCUMENTS

| | | | |
|---|---|---|---|
| 4,625,015 | A | 11/1986 | Green et al. |
| 4,901,307 | A | 2/1990 | Gilhousen et al. |
| 5,103,459 | A | 4/1992 | Gilhousen et al. |
| 5,494,671 | A | 2/1996 | Lai et al. |
| 5,514,375 | A | 5/1996 | Paoletti et al. |
| 5,565,332 | A | 10/1996 | Hoogenboom et al. |
| 5,631,350 | A | 5/1997 | Okuno et al. |
| 5,696,108 | A | 12/1997 | Heath, Jr. et al. |
| 5,744,140 | A | 4/1998 | Paoletti et al. |
| 5,744,141 | A | 4/1998 | Paoletti et al. |
| 5,914,950 | A | 6/1999 | Tiedemann et al. |
| 6,094,428 | A | 7/2000 | Bruckert et al. |
| 6,122,291 | A | 9/2000 | Robinson et al. |
| 6,184,024 | B1 | 2/2001 | Lai et al. |
| 6,258,788 | B1 | 7/2001 | Schmalijohn |
| 6,265,150 | B1 | 7/2001 | Terstappen et al. |
| 6,306,899 | B1 | 10/2001 | Cheng et al. |
| 6,331,415 | B1 | 12/2001 | Cabilly et al. |
| 6,335,922 | B1 | 1/2002 | Tiedemann et al. |
| 6,416,763 | B1 | 7/2002 | McDonnel et al. |
| 6,432,411 | B1 | 8/2002 | Ivy et al. |
| 6,455,509 | B1 | 9/2002 | Kochel et al. |
| 6,473,395 | B1 | 10/2002 | Lee |
| 6,685,948 | B1 | 2/2004 | Zeng et al. |
| 6,875,433 | B2 | 4/2005 | Hart et al. |
| 6,908,994 | B1 | 6/2005 | Rich et al. |
| 6,946,125 | B2 | 9/2005 | Rahal |
| 7,074,555 | B2 | 7/2006 | Esty et al. |
| 7,153,513 | B2 | 12/2006 | Chu |
| 7,244,430 | B2 | 7/2007 | Throsby et al. |
| 7,329,530 | B2 | 2/2008 | Houtzager et al. |
| 7,378,276 | B2 | 5/2008 | Ettinger et al. |
| 7,425,437 | B2 | 9/2008 | Uytdehaag et al. |
| 7,491,516 | B2 | 2/2009 | Collinson et al. |
| 7,537,764 | B2 | 5/2009 | Throsby et al. |
| 7,550,140 | B2 | 6/2009 | Bakker et al. |
| 7,579,446 | B2 | 8/2009 | Bakker et al. |
| 7,696,330 | B2 | 4/2010 | Meulen et al. |
| 7,740,852 | B2 | 6/2010 | Bakker et al. |
| 2002/0090606 | A1 | 7/2002 | Stewart et al. |
| 2003/0109042 | A1 | 6/2003 | Wu et al. |
| 2003/0148261 | A1 | 8/2003 | Fikrig et al. |
| 2003/0148463 | A1 | 8/2003 | Kufer et al. |
| 2004/0009178 | A1 | 1/2004 | Bowdish et al. |
| 2004/0013672 | A1 | 1/2004 | Hooper et al. |
| 2004/0077086 | A1 | 4/2004 | Reiter et al. |
| 2004/0197769 | A1 | 10/2004 | Wong et al. |
| 2004/0258699 | A1 | 12/2004 | Bowdish et al. |
| 2005/0069869 | A1 | 3/2005 | Ambrosino et al. |
| 2005/0180986 | A1 | 8/2005 | Rich et al. |
| 2005/0196755 | A1 | 9/2005 | Zauderer et al. |

(Continued)

FOREIGN PATENT DOCUMENTS

| | | | |
|---|---|---|---|
| AU | 7198291 | A1 | 9/1991 |
| CA | 2 591 665 | | 6/2006 |

(Continued)

OTHER PUBLICATIONS

Lefranc et al., IMGT, the international ImMunoGeneTics information system, Nucleic Acids Research, 2005, pp. D593-D597, vol. 33.
Agematsu et al. 2000, CD27: a memory B-cell marker, Immunology Today, 21(5): 204-206.
Amersdorfer et al, Genetic and immunological comparison of anti-botulinum type A antibodies from immune and non-immune human phage libraries, Vaccine, Feb. 22, 2002, pp. 1640-1648, vol. 20, No. 11-12.
Bae, et al., Production of Hantaan Virus from Human Immortalized Retina Cell and Its Immunogenicity, J. Microbiol. Biotechnol. Dec. 20, 2002, pp. 882-889, vol. 12, No. 6.
Bao, et al. Flavivirus Induces Mhc Antigen on Human Myoblasts: A Model of autimmuneMyositis?, Muscle and Nerve, Nov. 1992, pp. 1271-1277, vol. 15, No. 11.

(Continued)

*Primary Examiner* — Brian J Gangle
(74) *Attorney, Agent, or Firm* — TraskBritt, P.C.

(57) ABSTRACT

Described are human binding molecules specifically binding to staphylococci and having killing activity against staphylococci, nucleic acid molecules encoding the human binding molecules, compositions comprising the human binding molecules and methods of identifying or producing the human binding molecules. The human binding molecules can be used in the diagnosis, prophylaxis and/or treatment of a condition resulting from *Staphylococcus*.

15 Claims, 6 Drawing Sheets

U.S. PATENT DOCUMENTS

| | | | |
|---|---|---|---|
| 2005/0249739 | A1 | 11/2005 | Marasco et al. |
| 2006/0002939 | A1 | 1/2006 | Fischer et al. |
| 2006/0057149 | A1 | 3/2006 | Johnson et al. |
| 2006/0067940 | A1 | 3/2006 | Diamond et al. |
| 2006/0110803 | A1 | 5/2006 | Ter Meulen et al. |
| 2006/0115837 | A1 | 6/2006 | Fremont et al. |
| 2006/0115896 | A1 | 6/2006 | Wong et al. |
| 2006/0121580 | A1 | 6/2006 | Ter Meulen et al. |
| 2006/0154243 | A1 | 7/2006 | Ter Meulen et al. |
| 2006/0269571 | A1 | 11/2006 | Hall et al. |
| 2007/0025992 | A1 | 2/2007 | Takayama et al. |
| 2007/0042359 | A1 | 2/2007 | Throsby et al. |
| 2007/0122801 | A1 | 5/2007 | Throsby et al. |
| 2007/0128217 | A1 | 6/2007 | Ter Meulen et al. |
| 2008/0014204 | A1 | 1/2008 | Ter Meulen et al. |
| 2008/0070799 | A1 | 3/2008 | Bakker et al. |
| 2008/0095780 | A1 | 4/2008 | Geuijen et al. |
| 2009/0017068 | A1 | 1/2009 | UytdeHaag et al. |
| 2009/0017521 | A1 | 1/2009 | Houtzager et al. |
| 2009/0054254 | A1 | 2/2009 | Throsby et al. |
| 2009/0104204 | A1 | 4/2009 | Throsby et al. |
| 2009/0130652 | A1 | 5/2009 | Throsby et al. |
| 2009/0169562 | A1 | 7/2009 | Throsby et al. |
| 2009/0311265 | A1 | 12/2009 | Van den Brink et al. |
| 2010/0034829 | A1 | 2/2010 | Bakker et al. |
| 2010/0146647 | A1 | 6/2010 | Logtenberg et al. |
| 2010/0172917 | A1 | 7/2010 | Ter Meulen et al. |
| 2010/0272724 | A1 | 10/2010 | Bakker et al. |

FOREIGN PATENT DOCUMENTS

| | | | |
|---|---|---|---|
| EP | 0 102 228 | | 3/1984 |
| EP | 0 402 029 | | 12/1990 |
| EP | 0 691 404 | | 1/1996 |
| EP | 0 869 184 | | 10/1998 |
| EP | 0 872 553 | | 10/1998 |
| EP | 0 947 581 | | 10/1999 |
| EP | 1 134 994 | | 9/2001 |
| EP | 1 439 234 | | 7/2004 |
| JP | 00-078146 | | 3/2000 |
| JP | 01-036463 | | 2/2001 |
| WO | WO 84/03564 | | 9/1984 |
| WO | WO 93/09872 | | 5/1993 |
| WO | WO 97/33393 | | 9/1997 |
| WO | WO 98/15833 | | 4/1998 |
| WO | WO 98/30047 | | 7/1998 |
| WO | WO 98/37911 | | 9/1998 |
| WO | WO 98/52976 | | 11/1998 |
| WO | WO 98/57994 | | 12/1998 |
| WO | WO 99/18996 | | 4/1999 |
| WO | WO 99/26653 | | 6/1999 |
| WO | WO 99/45660 | | 9/1999 |
| WO | WO 99/63095 | | 12/1999 |
| WO | WO 00/10991 | | 3/2000 |
| WO | WO 00/12128 | | 3/2000 |
| WO | WO 00/14245 | | 3/2000 |
| WO | WO 00/25483 | | 5/2000 |
| WO | WO 00/63403 | | 10/2000 |
| WO | WO 01/03729 | | 1/2001 |
| WO | WO 01/38362 | | 5/2001 |
| WO | WO 01/39802 | | 6/2001 |
| WO | WO 01/54335 | | 7/2001 |
| WO | WO 01/60315 | | 8/2001 |
| WO | WO 01/60847 | | 8/2001 |
| WO | WO 01/71926 | | 9/2001 |
| WO | WO 02/15664 | | 2/2002 |
| WO | WO 02/072036 | | 9/2002 |
| WO | WO 02/103012 | A1 | 12/2002 |
| WO | WO 03/013599 | | 2/2003 |
| WO | WO 03/016501 | | 2/2003 |
| WO | WO 03/059259 | A | 7/2003 |
| WO | WO 03/059260 | A | 7/2003 |
| WO | WO 03/072607 | | 9/2003 |
| WO | WO 2004/009618 | | 1/2004 |
| WO | WO 2004/042042 | | 5/2004 |
| WO | WO 2004/043405 | | 5/2004 |
| WO | WO 2004/106375 | | 12/2004 |
| WO | WO 2004/111081 | | 12/2004 |
| WO | WO 2005/007800 | | 1/2005 |
| WO | WO 2005/012337 | | 2/2005 |
| WO | WO 2005/012338 | | 2/2005 |
| WO | WO 2005/012360 | | 2/2005 |
| WO | WO 2005/068622 | | 7/2005 |
| WO | WO 2005/103084 | A2 | 11/2005 |
| WO | WO 2005/106483 | | 11/2005 |
| WO | WO 2005/118644 | A2 | 12/2005 |
| WO | WO 2005/123774 | | 12/2005 |
| WO | WO 2006/067122 | A2 | 6/2006 |
| WO | WO 2007/031550 | | 3/2007 |
| WO | WO 2007/141274 | A2 | 12/2007 |
| WO | WO 2008/028946 | | 3/2008 |

OTHER PUBLICATIONS

Beasley, et al. Identification of Neutralizing Epitopes within Structural Domain III of the West Nile Envelope Protein, journal of Virology, Dec. 2002, pp. 13097-13100, vol. 76, No. 24.

Benmansour et al., Antigenicity of Rabies Virus Glycoprotein, Journal of Virology, 1991, pp. 4198-4203, vol. 65.

Ben-Nathan, et al., Using high titer West Nile intravenous immunoglobulin from selected Israeli donors for treatment of West Nile virus infection; BMC Infectious Diseases, 2009, vol. 9, No. 18, eight pages.

Bergman, et al. Formation of Intermolecular Disulfide Bonds on Nascent Immunoglobulin Polypeptides, The Journal of Biological Chemistry, 1979, pp. 5690-5694, vol. 254, No. 13.

Berry et al., Development and characterisation of neutralising monoclonal antibody to the SARS-coronavirus, Journal of Virological Methods, 2004, pp. 87-96, vol. 120.

Bisht et al., Severe acute respiratory syndrome coronavirus spike protein expressed by attenuated vaccinia virus protectively immunizes mice, PNAS, Apr. 27, 2004, pp. 6641-6646, vol. 101, No. 17.

Blitvich, et al., Epitope-Blocking Enzyme-Linked Immunosorbent Assays for the Detection of Serum Antibodies to West Nile Virus in Multiple Avian Species, Journal of Clinical Microbiology, Mar. 2003, pp. 1041-1047, vol. 41, No. 3.

Boel E., et al., Functional human monoclonal anibodies of all isotypes constructed from phage display library-derived single-chain Fv antibody fragments, J. Immunol. Methods, 2000, pp. 153-166, vol. 239.

Bost et al., Antibodies against peptides sequence within the HIV envelope protein crossreact with human interleukin-2, Immunological Investigations, 17(6&7): 577-586, 1998.

Boucher et al., Restricted Use of Cationic Germline VH Gene Segments in Human Ph(D) Red Cell Antibodies; (Blood 89: 3277-3286, 1997).

Brandt et al., Aberrant Expression of CD19 as a Marker of Monocytic Lineage in Acute Myelogenous Leukemia, Hematopathology, AJCP, Mar. 1997, vol. 107, No. 3, pp. 283-291.

Bregenholt et al., Pathogen-specific recombinant human polyclonal antibodies: biodefence applications; (Expert Opinion Biol. Ther. 4:387-396, 2004).

Buchholz et al., Contributions of the structural proteins of severe acute respiratory syndrome coronavirus to protective immunity, PNAS, Jun. 29, 2004, pp. 9804-9809, vol. 101, No. 26.

Bukreyev et al., Mucosal immunisation of African green monkeys (*Cercopithecus aethiops*) with an attenuated parainfluenza virus expressing the SARS coronavirus spike protein for the prevention of SARS, The Lancet, Jun. 26, 2004, pp. 2122-2127, vol. 363.

Burton D.R., et al., Human antibodies from combinatorial libraries, Adv. Immunol., 1994, pp. 191-280, vol. 57.

Cabezas, et al., Abstract A structure=based approach to a synthetic vaccine for HIV-1, Biochemistry, Nov. 28, 2000, pp. 14377-14391, vol. 39, No. 47.

Carsetti et al., 2004, Peripheral development of B cells in mouse and man, Immunological Reviews, 197: 179-191.

Champion et al., "The development of monoclonal human rabies virus-neutralizing antibodies as a substitute for pooled human immune globulin in the prophylactic treatment of rabies virus exposure," Journal of Immunological Methods, 2000, pp. 81-90, vol. 235.

Chan et al., Human recombinant antibodies specific for hepatitis C virus core and envelope E2 peptides from an immune phage display library; (Journal of General virology 77:2531-2539, 1996).

Chen, et al., Preparation of monoclonal antibodies against West Nile virus envelope protein domain, Chinese J. Exp. Clin Virol., Sep. 2006, pp. 213-215, vol. 20, No. 3.
Chung, et al., Antibodies against West Nile Virus Nonstructural Protein NS1 Prevent Lethal Infection through Fc gamma Receptor-Dependent and -Independent Mechanisms, Journal of Viorology, Feb. 2006, pp. 1340-1351, vol. 80, No. 3.
Clackson T., et al., Making antibody fragments using phage display libraries, Nature 1991, pp. 624-628, vol. 352.
Corapi et al., Localization of antigenic sites of the S glycoprotein of Feline Infectous Peritonitis Virus involved in neutralization and antibody-dependent enhancement, Journal of Virology, The American Society of Microbiology, May 1995, pp. 2858-2862, vol. 69, No. 5.
Database EMBL, Apr. 15, 2003, He et al., SARS coronavirus TOR2 complete genome, Database accession No. AY274119.
Database EMBL, Jun. 25, 2003, Vicenzi et al., SARS coronavirus HSR 1 complete genome, Database accession No. AY323977.
Database EMBL, online Apr. 23, 2003, SARS coronavirus Urbani, complete genome, Database accession No. AY278741.
Database ENTREZ Nucleotides, online, NCBI, Apr. 21, 2003, Monroe et al., SARS coronavirus Urbani Strain, Database accession No. AY278741.
Database Genbank NCBI; Jun. 26, 2003, Prosniak, M. et al., "*Homo sapiens* anti-rabies S057 immunoglobulin heavy chain mRNA" XP 002356864, retrieved from http://www.ncbi.nlr.nih.gov, Database accession No. AY172957.
Database Genbank NCBI; Jun. 26, 2003, Prosniak, M. et al., "*Homo sapiens* anti-rabies S057 immunoglobulin lambda light chain mRNA" XP 002356865, retrieved from http://www.ncbi.nlr.nih.gov, Database accession No. AY172960.
Database WPI, Section Ch, Week 200432, AN 2004-341229, Feb. 4, 2004.
Database WPI, Section Ch, Week 200442, AN 2004-441790, Apr. 14, 2004.
Database WPI, Section Ch, Week 200478, AN 2004-083758, Nov. 25, 2004.
De Haard et al., A Large Non-immunized Human Fab Fragment Phage Library That Permits Rapid Isolation and Kinetic Analysis of High Affinity Antibodies, 1999, Journal of Biological Chemistry, pp. 18218-18230, vol. 274, No. 26.
De Kruif J. et al. Selection and application of human single-chain Fv antibody fragments from a semi-synthetic phage antibody display library with designed CDR3 regions, J. Mol. Biol. 1995b, pp. 97-105, vol. 248.
De Kruif J., et al., Rapid selection of cell subpopulation-specific human monoclonal antibodies from a synthetic phage antibody library. Proc. Natl. Acad. Sci., 1995a, p. 3938, vol. 92.
Dietzschold et al., "Biological Characterization of Human Monoclonal Antibodies to Rabies Virus," Journal of Virology, Jun. 1990, pp. 3087-3090, vol. 64, No. 6.
Dionyssopoulou et al., Synthetic peptides as putative therapeutic agents in transplantation medicine: application of PEPSCAN to the identification of functional sequences in the extracellular domain of the interleukin-2 receptor beta chain (IL-2Rbeta), Journal of Immunological Methods, 2000, pp. 83-95, vol. 241.
Dorsam et al., Antibodies to steroids from a small human naïve IgM library, FEBS Letters, 1997, pp. 7-13, vol. 414.
Dubel, et al., Generation of a Human IgM Expression Library in *E. coli*, Methods in Molecular and Cellular Biology, 1992, pp. 47-52, vol. 3.
Engle, et al. Antibody Prophylaxis and Therapy against West Nile Virus Infection in Wild-Type and Immunodeficient Mice, Journal of Virology, Dec. 2003, pp. 12941-12949, vol. 77, No. 24.
Fields, et al., Virology (Third Ed.), excerpt. pp. 931-932, 1996.
Gallimore et al., Transformation of Human Embryo Retinoblasts with Simian Virus 40, Adenovirus and ras Ongogenes, Anticancer Research , May 3, 1986, pp. 499-508, vol. 6, No. 3.
Geuijen et al. A Proteomic Approach to Tumor Target Identification Using Phage Display, Affinity Purification and Mass Spectrometry, European Journal of Cancer 41 (2005) pp. 178-187.
Goncalvez, et al., Chimpanzee Fab Fragments and a Derived Humanized Immunoglobulin G1 Antibody That Efficiently Cross-Neutralize Dengue Type 1 and Type 2 Viruses, Journal of Virology, Dec. 2004, pp. 12910-12918, vol. 78. No. 23.
Gould et al., Protective and Therapeutic Capacity of Human Sigle-Chain Fv-Fc Fusion Proteins against West Nile Virus, Journal of Virology, Dec. 2005, pp. 14606-14613, vol. 79, No. 23.
Hanlon et al., "Experimental utility of rabies virus-neutralizing human monoclonal antibodies in post-exposure prophylaxis," Vaccine, 2001, pp. 3834-3842, vol. 19.
Hawkins et al. Cell selection strategies for making antibodies from variable gene libraries: trapping the memory pool, European Journal of Immunology, Mar. 1992, pp. 867-870, vol. 22, No. 3.
Hayes, West Nile Fever: in Arboviruses: Epidemiology and Ecology, ed. T.P. Monath, CRC press, Boca Raton, FL. 1988, p. 59-88.
He et al, Antigenic and immunogenic characterization of recombinant baculovirus-expressed severe acute respiratory syndrome coronavirs spike protein; implication for vaccine design, J. Virol., Jun. 2006, pp. 5757-5767, vol. 80, No. 12.
Heitner et al., Selection of cell binding and internalizing epidermal growth factor receptor antibodies from a phage display library, Journal of Immunological Methods, 2001, pp. 17-30, vol. 248.
Holt, et al., Domain antibodies: proteins for therapy, Trends in Biotechnology, Nov. 2003, pp. 484-490, vol. 21, No. 11.
Horimoto et al., Abstract Antigenic differences between H5N1 human influenza viruses isolated in 1997 and 2003, Journal of Veterinary Medical Science, Mar. 2004, pp. 303-305, vol. 66, No. 3.
Huang LR et al., Evaluation of antibody responses against SARS coronaviral nucleocapsid or spike proteins by immunoblotting or ELISA, J. Med. Virol. 73:338-346, 2004.
Huls G., et al., Antitumor immune effector mechanisms recruited by phage display-derived fully human IgG1 and IgA1 monoclonal antibodies, Cancers Res., 1999, pp. 5778-5784, vol. 59.
Ikematsu et al., Sequences of the Vh genes of human IgM, IgG and IgA to rabies virus reveal preferential utilization of VhIII segments and somatic hypermutation, 1993, The Journal of Immunology, pp. 1325-1337, vol. 150.
Jia, et al. Genetic analysis of West Nile Virus New York, 1999 encephalitis virus, The Lancet, Dec. 4, 1999, pp. 1971-1972, vol. 354, No. 9196.
Jones et al., "High-level Expression of Recombinant IgG in the Human Cell Line Per.C6," Biotechnol. Prog., 2003, pp. 163-168, vol. 19.
Kashmiri SV et al., SDR grafting—a new approach to antibody humanization, Methods, 36:25-34, 2005.
Keller et al. Passive immunity in prevention and treatment of infectious diseases, Clin Microbiol. Rev., Oct. 2000, pp. 602-614-, vol. 13, No. 4.
Klein et al., 1997, Evidence for a Large Compartment of IgM-Expressing Memory B cells in Humans, Blood, 89: 1288-1298.
Klein, et al., Human Immunoglobulin (Ig)M+IgD+ Peripheral Blood B Cells Expressing the CD27 Cell Surface Antigen Carry Somatically Mutated Variable Region Genes: CD27 as a General Marker for Somatically Mutated (Memory_) B Cells, J. Exp. Med., Nov. 2, 1998, pp. 1679-1689, vol. 188, No. 9, The Rockerfeller University Press.
Kramer, et al., The human antibody repertoire specific for rabies virus glycoprotein as selected from immune libraries, European Journal of Immunology, 2005, pp. 2131-2145, vol. 35.
Ksiazek, et al. A Novel Coronavirus Associated with Severe Acute Respiratory Syndrome, The New England Journal of Medicine, May 15, 2003, pp. 1953-1966, vol. 348, No. 20.
Lanciotti,e t al. Complete Genome Sequences and Phylogenetic Analysis of West Nile Virus Strains Isolated from the United States, Europe, and the Middle East; Virology, Jun. 20, 2002, pp. 96-105, vol. 298.
Lang et al., Abstract: Evaluation of the safety, immunogenicity, and pharmacokinetic profile of a new, highly purified, heat-treated quine rabies immunoglobulin, administered either alone or in association with a purified, Vero-cell rabies vaccine.; Biologicals, 1998, vol. 26, No. 7-15.
Lang, et al. Polyclonal Preparations of Anti-Tetanus Toxoid Antibodies Derived from a Combinatorial Library Confer Protection; (Bio/Technology 13:683-685, 1995).

Lazar, et al., Microcarriers as a culturing system of insect cells and insect viruses; Developments in Biological Standardization, 1985, pp. 315-323, vol. 66.
Leibl, et al. Adjuvant/carrier activity of inactivated tick=borne encephalitis virus, Vaccine, 1998, pp. 340-345, vol. 16, No. 4.
Leucht et al., The B cell superantigen-like interaction of intravenous immunoglobulin (IVIG) with Fab fragments of Vh 3-23 and 3-30/3-30.5 germline gene origin cloned from a patient with Kawasaki disease is enhanced after IVIG therapy, 2001, Clinical Immunology, pp. 18-29, vol. 99.
Li, et al. The Structural Characterization and Antigenicity of the S Protein of SARS-CoV, Geno., Prot. & Bioinform, May 2003, pp. 108-117, vol. 1, No. 2.
Lieby et al., 2003, Memory B cells producing somatically mutated antiphospholipid antibodies are present in healthy individuals, Hemostasis Thrombosis and Vascular Biology, 102(7): 2459-2465.
Lin, et al., Identification of an epitope of SARS-coronavirus nucleocapsid protein, Cell Research, 2003, pp. 141-145, vol. 13, No. 3.
Lloyd-Evans et al. Expression of Neutralizing Recombinant Human Antibodies Against Varicella Zoster Virus for Use as a Potential Prophylactic; (Hybridoma 19: 143-149, 2000).
Lu, et al. Abstract: Unified power control, error correction coding and scheduling for a CDMA downlink system; Wireless Networks 2 (1997) pp. 83-90.
Malkinson, et al. Abstract: Use of Live and Inactivated Vaccines in the Control of West Nile Virus in Domestic Geese, Annals of the New York Academy of Sciences, 2001, pp. 255-261.
Marissen et al., Novel Rabies Virus-Neutralizing Epitope Recognized by Human Monoclonal Antibody: Fine Mapping and Escape Mutant Analysis, Journal of Virology, Apr. 2005, pp. 4672-4678, vol. 79, No. 8.
Marks et al., Molecular evolution of proteins on filamentous phage, Mimicking the strategy of the immune system, Journal of Biological Chemistry, Aug. 15, 1992, pp. 16007-16010, vol. 267, No. 23.
Marks, et al., By-passing Immunization: Building High Affinity Human Antibodies by Chain Shuffling, Bio/Technology, Jul. 1992, pp. 779-783, vol. 10.
Marra, et al., The genome sequence of the SARS-associated coronavirus, Science, May 30, 2003, pp. 1399-1404, vol. 300, No. 5624.
Mehlhop, et al., Complement Activation is Required for Induction of a Protective Antibody Response against West Nile Virus Infection, Journal of Virology, Jun. 2005, pp. 7466-7477, vol. 79, No. 12.
Mitsuki, et al. Abstract: A single amino acid substitution in the S1 and S2 Spike protein domains detennins the neutralization escape phenotype of SARS-CoV, Microbes infect., Jul. 2008, pp. 908-915, vol. 10, No. 8, Epub Jun. 19, 2008.
Myers et al. Large Scale Manufacturing of TXU(Anti-CD7)-Pokeweed Antiviral Protein (PAP) Immunoconjugate for Clinical Trials, Overseas Publisher Association Amersterdam B.V. (1997) Published in the Netherlands by Harwood Academic Publishers pp. 257-285.
Nicacio et al., Neutralizing human fab fragments against measles virus recovered by phage display, Journal of Virology, 2002, pp. 251-258, vol. 76.
Niedrig, et al., Monoclonal Antibodies Directed Against Tick-Borne Encephalitis Virus with Neutralizing Activity in Vivo, Acta Virologica, 1994, pp. 141-149, vol. 38.
Nybakken, e t al.; Structural basis of West Nile virus neutralization by a therapeutic antibody, Nature, Sep. 29, 2005, pp. 764-768, vol. 437.
Okuno, et al. A common Neutralizing Epitope Conserved Between the Hemagglutinins of Influenca A Virus H1 and H2 Strains, Journal of Virology, May 1993, pp. 2552-2558, vol. 67, No. 5.
Oliphant, et al. Development of a humanized monoclonal antibody with therapeutic potential against West Nile Virus, Nature Medicine, May 2005, pp. 522-530, vol. 11, No. 5.
Pau, et al., The human cell line PER.C6 provides a new manufacturing system for the production of influenza vaccines, Vaccine 2001, pp. 2716-2721, vol. 19.
Paul, Fundamental Immunology, (textbook), 1993, pp. 292-295, Lippincott-Raven Publishers, Philadelphia, PA (in copending U.S. Appl. No. 11/978,742).
PCT International Preliminary Examination Report—PCT/US02/033929; IPEA/US Jul. 26, 2004.
PCT International Preliminary Examination Report, PCT/EP2003/50806, dated Feb. 17, 2005.
PCT International Preliminary Report on Patentability for PCT/EP2005/055163 on Jul. 12, 2006.
PCT International Preliminary Report on Patentability, PCT/EP2005/055876, dated Feb. 16, 2007.
PCT International Preliminary Report on Patentability, PCT/EP2005/052410, dated Aug. 28, 2006.
PCT International Preliminary Report on Patentability, PCT/EP2006/063463, dated Sep. 10, 2007.
PCT International Preliminary Report on Patentability, PCT/EP2006/062250, dated Oct. 1, 2007.
PCT International Search Report—PCT/US02/033929, International Searching Authority—European Patent Office Jan. 30, 2003.
PCT International Search Report PCT/EP2003/50806, dated Apr. 26, 2004.
PCT International Search Report PCT/EP2006/066355, dated Apr. 11, 2007.
PCT International Search Report PCT/EP2007/059356, dated Aug. 21, 2008.
PCT International Search Report, PCT/EP2004/051568, dated Aug. 22, 2005.
PCT International Search Report, PCT/EP2005/052410, dated Jan. 9, 2006.
PCT International Search Report, PCT/EP2005/055876, dated Mar. 3, 2006.
PCT International Search Report, PCT/EP2006/062250, dated May 3, 2007.
PCT International Search Report, PCT/EP2006/063463, dated Oct. 6, 2006.
PCT International Search Report, PCT/EP2007/055527, dated Jan. 29, 2008.
Persson et al, Generation of Diverse high-affinity human monoclonal antibodies by repertoire cloning, Proceedings of the National Academy of Sciences of USA, Mar. 15, 1991, pp. 2432-2436, vol. 88, Nol. 6.
Posthumas, et al. Analysis and Simulation of a Neutralizing Epitope of Transmissible Gastroenteritis Virus, Journal of Virology, Jul. 1, 1990, pp. 3304-3309, vol. 64, No. 7.
Prosniak et al., "Development of a Cocktail of Recombinant-Expressed Human Rabies Virus-Neutralizing Monoclonal Antibodies for Postexposure Prophylaxis of Rabies," Journal of Infectious Diseases, Jul. 1, 2003, pp. 53-56, vol. 188.
Ray et al., Selection of single chain variable fragments (scFv) against the glycoprotein antigen of the rabies virus from a human synthetic scFv phage display library and their fusion with the Fc region of human IgG1, Clinical and Experimental Immunology, 2001, pp. 94-101, vol. 125.
Razumov et al., Neutralizing Monoclonal Antibodies Against Russian Strain of the West Nile Virus, Viral Immunology, 2005, pp. 558-568, vol. 18, No. 3.
Roehrig, et al., Antibody Prophylaxis and Therapy for Flavivirus Encephalitis Invections, Ann. N.Y Acad. Sci., Dec. 2001, pp. 286-297, vol. 951.
Rogers et al.; Abstract, Thiol-reactive compounds prevent nonspecific antibody binding in immunohistochemistry, Laboratory Investigation: A Journal of Technical Methods and Pathology, 2006, pp. 526-533, vol. 86, No. 5.
Rota, et al. Characterization of a Novel Coronavirus Associated with Severe Acute Respiratory Syndrome, Science, May 30, 2003 pp. 1394-1399, vol. 300.
Rudikoff, et al. Single Amino Acid Substitution Altering Antigen-binding specificity; PNAS, vol. 79, pp. 1979-1983, Mar. 1982.
Sanchez, et al. Characterization of neutralizing antibodies to West Nile Virus, Virology, 2005, pp. 70-82, vol. 336.
Schumacher et al. "Use of mouse anti-rabies monoclonal antibodies in post-exposure treatment of rabies." J. Chin. Invest. 84:971-975 (1989).
Sharon et al. Recombinant Polyclonal Antibody Libraries; (Combinatorial Chemistry & High Throughput Screening 3:185-196, 2000).

Sheets, et al. Efficient construction of a large nonimmune phage antibody library: The production of high-affinity human single-chain antibodies to protein antigens, Proc. Natl. Acad. Sci., vol. 95, pp. 6157-6162, May 1998.
Shen, et al. Early Induction of Interferon-Independent Virus-Specific ICAM-1(CD54) Expression by Flavivurs in Quiescent but Not Proliferating Fibroblasts—Implications for Virus-Host Interaction, Virology, 1995, pp. 437-449, vol. 208, No. 2.
Shi, et al. Funtional analysis of human memory B-cell subpopulations: IgD+CD27+ B cells are crucial in secondary immune response by producing high affinity IgM, Clinical Immunology, 2003, pp. 128-137, vol. 108.
Shi, et al., Infectious cDNA Clone of the Epidemic West nile Virus from new York City, J. of Virology Jun. 2002, pp. 5847-5856, vol. 76, No. 12.
Smirnov et al., Abstract: An epitope shared by the hemagglutinis of H1, H2, H5 and H6 subtypes of influenza A virus, Acta Virologica, pp. 237-244, Aug. 1999, vol. 43, No. 4.
Streuli et al. Expression of the Receptor-Linked Protein Tyrosine Phsphatase LAR: Proteolytic Cleavage and Shedding of the CAM-Like Extracellular Region, The EMBO Journal (1992) vol. 11 No. 3, pp. 897-907.
Sui et al., Potent neutralization of severe acute respiratory syndrome (SARS) coronavirus by a human mAb to S1 protein that blocks receptor association, PNAS, Feb. 24, 2004, pp. 2536-2541, vol. 101, No. 8.
Ter Meulen et al. Human monoclonal antibody as prophylaxis for SARS coronavirus infection in ferrets, The Lancet, Jun. 26, 2004, pp. 2139-2141, vol. 363.
Thiel, et al. Mechanisms and enzymes involved in SARS coronavirus genome expression, Journal of General Virology, 2003, pp. 2305-2315, vol. 84.
Throsby et al., Isolation and Characterization of Human Monoclonal Antibodies from Individuals Infected with West Nile Virus, Journal of Virology, Jul. 2006, pp. 6982-6992, vol. 80 No. 14.
Tirado et al., Antibody-Dependent Enhancement of Virus Infection and Disease, Viral Immunology, 2003, pp. 69-86, vol. 16, No. 1.
Van Den Brink et al., Molecular and Biological Characterization of Human Monoclonal Antibodies Binding to the Spike and Nucleocapsid Proteins of Severe Acute Respiratory Syndrome Coronavirus, Journal of Virology, Feb. 2005, pp. 1635-1644, vol. 79, No. 3.
Vicenzi et al., Coronaviridae and SARS-associated Coronavirus Strain HSR1, Emerging Infectious Diseases, Mar. 2004, pp. 413-418, vol. 10, No. 3.
Vogt, et al., Human Monoclonal Antibodies against West Nile Virus Induced by Natural Infection Neutralize at a Postattachment Step; Journal of Virology, Jul. 2009, 8303): 6494-6507.
Weiss et al., Coronavirus pathogenesis and the emerging pathogen sever acute respiratory syndrome coronavirus, Microbiol. Mol. Biol. Rev. 2005, pp. 635-664, vol. 69, No. 4.
Weller et al., Human blood IgM "memory" B cells are circulating splenic marginal zone B cells harboring a prediversified immunoglobulin repertoire, Blood, Dec. 1, 2004, pp. 3647-3654, vol. 104.
Winter, et al. Mad-made antibodies, nature, Jan. 24, 1991, pp. 293-299, vol. 349, Nature Publishing Group, London, UK.
Wong et al., A 193-Amino Acid Fragment of the SARS Coronavirus S Protein Efficiently Binds Angiotensin-converting Enzyme 2, The Journal of Biological Chemistry, 2004, pp. 3197-3201, vol. 279, No. 5.
Yamshchikov, et al., Abstract: An Infectious Clone of the West Nile Flavivirus, Virology, Mar. 15, 2001, pp. 294-304, vol. 281, No. 2.
Yoo et al. Abstract: A single amino acid change within antigenic domain II of the spike protein of bovine coronavirus confers resistance to virus neutralization, Clin Diagn. Lab Immunol. 2001, pp. 297-302, vol. 8, No. 2.
Bowie et al., Science, 1990, 247:1306-10.
Brown et al., J. Immunol., 156:3285-91, 1996.
Campbell, Monoclonal Antibody Technology, Elsevier Science Publishing Co., 1984, Chapter 1, pp. 1-32.
Chen et al., The EMBO Journal, 1995, pp. 2784-2794, vol. 14, No. 12.
Cruse et al., Illustrated Dict. of Immunology, $2^{nd}$ ed., CRC Press, 2003, p. 46.
Dorland's Medical Dictionary for Healthcare Consumers; definition of infection, one page (http://www.mercksource.com/pp/us/cns/cns_hl_dorlands_split.jsp?pg=/ppdocs/us/common/dorlands/dorland/four/000053439.htm), 2007
http://www.uniprot.org/uniprot/P01834, accessed Sep. 7, 2011.
http://www.uniprot.org/uniprot/P0CG04, accessed Sep. 7, 2011.
Kussie et al., J. Immunol., 152:146-52, 1994.
PCT International Search Report, PCT/EP2007/055535, dated Jun. 5, 2007.
Stedman's Online Medical Dictionary, definition of infection, one page, 2005
The Biology Project (University of Arizona, http://www.biology.arizona.edu/immunology/tutorials/antibody/sructure.html, accessed Feb. 10, 2011).
Van Der Woude, Clinical Microbiology Reviews, Jul. 2004, pp. 481-611, vol. 17, No. 3.

HUMAN BINDING MOLECULES HAVING KILLING ACTIVITY AGAINST STAPHYLOCOCCI AND USES THEREOF

CROSS-REFERENCE TO RELATED APPLICATION

This application is a continuation of co-pending U.S. patent application Ser. No. 12/227,029, filed Nov. 5, 2008, which is the national phase entry of PCT International Patent Application No. PCT/EP2007/055527, filed on Jun. 5, 2007, designating the United States of America, and published, in English, as PCT International Publication No. WO 2007/141274 A2 on Dec. 13, 2007, which itself claims the benefit of U.S. Provisional Patent Application Ser. No. 60/811,477, filed Jun. 6, 2006, EP 06124231.9, filed Nov. 16, 2006, and EP 07103584.4 filed on Mar. 6, 2007, the contents of the entirety of each of which are incorporated herein by this reference.

STATEMENT ACCORDING TO 37 C.F.R. §1.821(c) or (e)-SEQUENCE LISTING SUBMITTED AS ASCII TEXT FILE

Pursuant to 37 C.F.R. §1.821(c) or (e), a file containing an ASCII text version of the Sequence Listing has been submitted concomitant with this application, the contents of which are hereby incorporated by reference.

TECHNICAL FIELD

The disclosure relates to biotechnology and medicine. In particular, the disclosure relates to the diagnosis, prophylaxis and/or treatment of infection from staphylococci.

BACKGROUND

*Staphylococcus* is a genus of gram-positive bacteria and a member of the micrococcaceae family. Staphylococci are spherical bacteria that are found primarily on the skin and in the mucous membranes of humans and other warm-blooded animals, and aggregate into small, grape-like clumps. Staphylococci can be divided into two groups, i.e., coagulase-positive and coagulase-negative staphylococci. Overall, there are about thirty species of staphylococci.

Staphylococci can cause a wide variety of diseases in humans either through toxin production or invasion. *Staphylococcus aureus* (*S. aureus*) has been recognized as one of the most important and lethal human bacterial pathogens since the beginning of the previous century. Until the antibiotic era, more than 80% of the patients growing *S. aureus* from their blood died. Through infections caused by coagulase-positive *S. aureus* were generally known to be potentially lethal, coagulase-negative staphylococci has been dismissed as avirulent skin commensals incapable of causing human disease. However, over the past 30 years, coagulase-negative staphylococcal infections have emerged as one of the major complications of medical progress. They are currently the pathogens most commonly isolated from infections of indwelling foreign devices and are the leading cause of nosocomial (hospital-acquired) bacteremias in US hospitals. Staphylococcal infections are commonly treated with antimicrobial agents. However, the ascendancy of staphylococci as pre-eminent nosocomial pathogens also has been associated with a major increase in the proportion of these isolates that are resistant to (multiple) antimicrobial agents. Of the estimated 2 million hospital infections in the US in 2004, 70% was resistant to at least one antibiotic, thereby causing major medical and consequently economic problems. Ninety percent of the staphylococci strains are penicillin resistant, leaving only methicillin and vancomycin to treat the majority of infections. However, with increasing numbers of reports of methicillin-resistant *Staphylococcus aureus* (MRSA) chemists are faced with the daunting task of generating new antibiotics with novel modes of action. Despite the urgent need for the development of new antibiotics, the major pharmaceutical companies appear to have lost interest in the antibiotic market. In 2002, only five out of the more than 500 drugs in phase II or phase III clinical development were new antibiotics. In the last six years, only ten antibiotics have been registered and only 2 of those did not exhibit cross-reactivity with existing drugs (and thus not subject to the same patterns of drug resistance). This trend has been attributed to several factors: the cost of new drug development and the relatively small return on investment that infectious disease treatments yield compared to drugs against hypertension, arthritis and lifestyle drugs, e.g., for impotence. Another contributing factor is the increasing difficulty in finding new targets, further driving up development costs. Therefore, investigation into novel therapies or preventative measures for (multi-drug-resistant) bacterial infections is urgently needed to meet this impending healthcare crisis.

Active immunization with vaccines and passive immunization with immunoglobulins are promising alternatives to classical small molecule therapy. A few bacterial diseases that once caused widespread illness, disability, and death can now be prevented through the use of vaccines. The vaccines are based on weakened (attenuated) or dead bacteria, components of the bacterial surface or on inactivated toxins. The immune response raised by a vaccine is mainly directed to immunogenic structures, a limited number of proteins or sugar structures on the bacteria that are actively processed by the immune system. Since these immunogenic structures are very specific to the organism, the vaccine needs to comprise the immunogenic components of all variants of the bacteria against which the vaccine should be protective. As a consequence thereof, vaccines are very complex, take long and are expensive to develop. Further complicating the design of vaccines is the phenomenon of "antigen replacement." This occurs when new strains become prevalent that are serologically and thus antigenically distinct from those strains covered by the vaccines. The immune status of the populations at risk for nosocomial infections further complicates vaccine design. These patients are inherently unwell and may even be immunocompromised (due to the effect of immunosuppressive drugs) resulting in delayed or insufficient immunity against the infecting pathogens. Furthermore, except in the case of certain elective procedures, it may not be possible to identify and vaccinate the at risk patients in time to give them sufficient immune protection from infection.

Direct administration of therapeutic immunoglobulins, also referred to as passive immunization, does not require an immune response from the patient and therefore gives immediate protection. In addition, passive immunization can be directed to bacterial structures that are not immunogenic and that are less specific to the organism. Passive immunization against pathogenic organisms has been based on immunoglobulins derived from sera of human or non-human donors. However, blood-derived products have potential health risks inherently associated with these products. In addition, the immunoglobulins can display batch-to-batch variation and may be of limited availability in case of sudden mass exposures. Recombinantly produced antibodies do not have these disadvantages and thus offer an opportunity to replace immunoglobulins derived from sera.

Murine monoclonal antibodies directed against staphylococci are known in the art (see WO 03/059259 and WO 03/059260). However, murine antibodies are limited for their use in vivo due to problems associated with administration of murine antibodies to humans, such as short serum half life, an inability to trigger certain human effector functions and elicitation of an unwanted dramatic immune response against the murine antibody in a human (HAMA).

In WO 03/059259 and WO 03/059260 the attempts have been made to overcome the problems associated with the use of fully murine antibodies in humans by preparing chimeric antibodies. A disadvantage of these chimeric antibodies is however that they still retain some murine sequences and therefore still elicit an unwanted immune reaction, especially when administered for prolonged periods.

WO 2004/043405 relates to polysaccharide vaccines for staphylococcal infections, prepared from poly N-acetylglucosamine (PNAG) surface polysaccharide from Staphylococci, and the deacetylated form thereof (dPNAG). WO 2004/043405 also discloses rabbit antiserum to PNAG and dPNAG, coupled to Diphtheria Toxoid (DTm).

Although WO 03/059259, WO 03/059260 and WO 2004/043405 refer to human antibodies as desired molecules, the antibodies actually disclosed and used therein are partly of murine or completely of rabbit origin, and none of these documents actually discloses any human antibodies, nor sequences thereof.

SUMMARY OF THE DISCLOSURE

Described are human binding molecules capable of specifically binding to staphylococci and exhibiting killing and/or growth inhibiting activity against staphylococci. Also described are nucleic acid molecules encoding at least the binding region of the human binding molecules. Further described is the use of the human binding molecules hereof in the prophylaxis and/or treatment of a subject having, or at risk of developing, a *Staphylococcus* infection. Besides that, described is the use of the human binding molecules hereof in the diagnosis/detection of *Staphylococcus*.

DETAILED DESCRIPTION

Definitions

Figure 1:
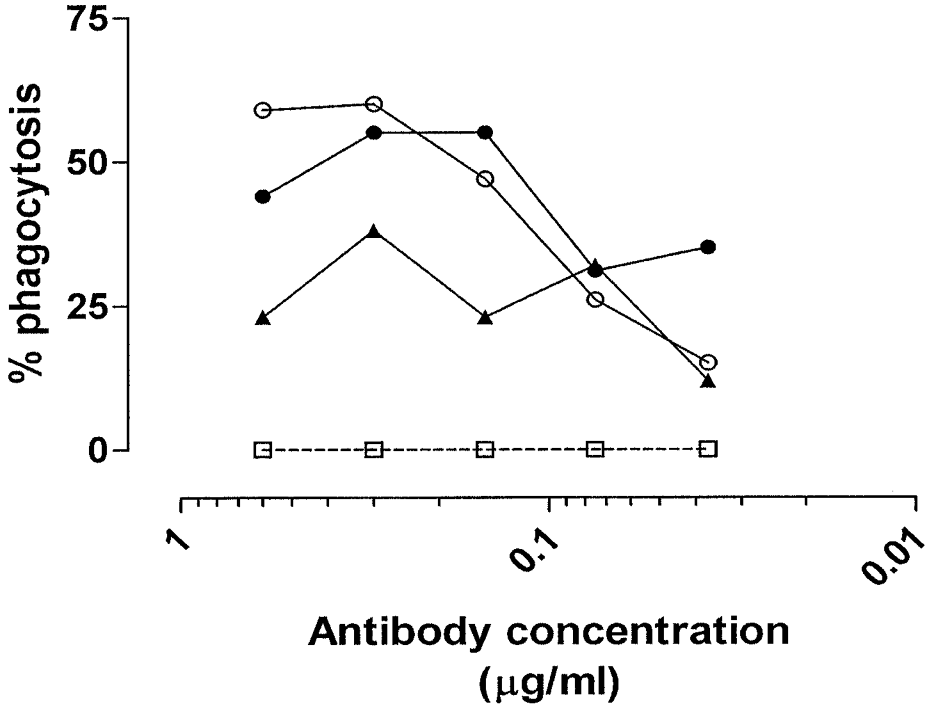
FIG. 1 shows antibody-mediated phagocytosis of *S. aureus* strain Cowan harvested during the log phase of growth in the absence of complement with the antibodies CR2430 (white dot), CR5132 (black triangle), CR5133 (black dot), and a negative control monoclonal antibody (white square).

The term "amino acid sequence" (or "amino acid molecule") as used herein, refers to naturally occurring or synthetic molecules and to a peptide, oligopeptide, polypeptide or protein sequence.

As used herein, the term "binding molecule" refers to an intact immunoglobulin including monoclonal antibodies, such as chimeric, humanized or human monoclonal antibodies, or to an antigen-binding and/or variable domain comprising fragment of an immunoglobulin that competes with the intact immunoglobulin for specific binding to the binding partner of the immunoglobulin, e.g., staphylococci. Regardless of structure, the antigen-binding fragment binds with the same antigen that is recognized by the intact immunoglobulin. An antigen-binding fragment can comprise a peptide or polypeptide comprising an amino acid sequence of at least 2 contiguous amino acid residues, at least 5 contiguous amino acid residues, at least 10 contiguous amino acid residues, at least 15 contiguous amino acid residues, at least 20 contiguous amino acid residues, at least 25 contiguous amino acid residues, at least 30 contiguous amino acid residues, at least 35 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least 100 contiguous amino acid residues, at least 125 contiguous amino acid residues, at least 150 contiguous amino acid residues, at least 175 contiguous amino acid residues, at least 200 contiguous amino acid residues, or at least 250 contiguous amino acid residues of the amino acid sequence of the binding molecule.

The term "binding molecule," as used herein, includes all immunoglobulin classes and subclasses known in the art. Depending on the amino acid sequence of the constant domain of their heavy chains, binding molecules can be divided into the five major classes of intact antibodies: IgA, IgD, IgE, IgG, and IgM, and several of these may be further divided into subclasses (isotypes), e.g., IgA1, IgA2, IgG1, IgG2, IgG3 and IgG4.

Antigen-binding fragments include, inter alia, Fab, F(ab'), F(ab')2, Fv, dAb, Fd, complementarity-determining region (CDR) fragments, single-chain antibodies (scFv), bivalent single-chain antibodies, single-chain phage antibodies, diabodies, triabodies, tetrabodies, (poly)peptides that contain at least a fragment of an immunoglobulin that is sufficient to confer specific antigen binding to the (poly)peptide, etc. The above fragments may be produced synthetically or by enzymatic or chemical cleavage of intact immunoglobulins or they may be genetically engineered by recombinant DNA techniques. The methods of production are well known in the art and are described, for example, in *Antibodies: A Laboratory Manual*, edited by E. Harlow and D. Lane (1988), Cold Spring Harbor Laboratory, Cold Spring Harbor, N.Y., which is incorporated herein by reference. A binding molecule or antigen-binding fragment thereof may have one or more binding sites. If there is more than one binding site, the binding sites may be identical to one another or they may be different.

The binding molecule can be a naked or unconjugated binding molecule but can also be part of an immunoconjugate. A naked or unconjugated binding molecule is intended to refer to a binding molecule that is not conjugated, operatively linked or otherwise physically or functionally associated with an effector moiety or tag, such as inter alia a toxic substance, a radioactive substance, a liposome, an enzyme. It will be understood that naked or unconjugated binding molecules do not exclude binding molecules that have been stabilized, multimerized, humanized or in any other way manipulated, other than by the attachment of an effector moiety or tag. Accordingly, all post-translationally modified naked and unconjugated binding molecules are included herewith, including where the modifications are made in the natural binding molecule-producing cell environment, by a recombinant binding molecule-producing cell, and are introduced by the hand of man after initial binding molecule preparation. Of course, the term naked or unconjugated binding molecule does not exclude the ability of the binding molecule to form functional associations with effector cells and/or molecules after administration to the body, as some of such interactions are necessary in order to exert a biological effect. The lack of associated effector group or tag is therefore applied in definition to the naked or unconjugated binding molecule in vitro, not in vivo.

As used herein, the term "biological sample" encompasses a variety of sample types, including blood and other liquid samples of biological origin, solid tissue samples such as a biopsy specimen or tissue cultures, or cells derived therefrom and the progeny thereof. The term also includes samples that have been manipulated in any way after their procurement, such as by treatment with reagents, solubilization, or enrichment for certain components, such as proteins or polynucleotides. The term encompasses various kinds of clinical samples obtained from any species, and also includes cells in culture, cell supernatants and cell lysates.

The term "complementarity-determining regions" (CDR), as used herein, means sequences within the variable regions of binding molecules, such as immunoglobulins, that usually contribute to a large extent to the antigen binding site which is complementary in shape and charge distribution to the epitope recognized on the antigen. The CDR regions can be specific for linear epitopes, discontinuous epitopes, or conformational epitopes of proteins or protein fragments, either as present on the protein in its native conformation or, in some cases, as present on the proteins as denatured, e.g., by solubilization in SDS. Epitopes may also consist of posttranslational modifications of proteins.

The term "deletion," as used herein, denotes a change in either amino acid or nucleotide sequence in which one or more amino acid or nucleotide residues, respectively, are absent as compared to the parent, often the naturally occurring, molecule.

The term "expression-regulating nucleic acid sequence", as used herein, refers to polynucleotide sequences necessary for and/or affecting the expression of an operably linked coding sequence in a particular host organism. The expression-regulating nucleic acid sequences, such as inter alia appropriate transcription initiation, termination, promoter, enhancer sequences; repressor or activator sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion, can be any nucleic acid sequence showing activity in the host organism of choice and can be derived from genes encoding proteins, which are either homologous or heterologous to the host organism. The identification and employment of expression-regulating sequences is routine to the person skilled in the art.

The term "functional variant," as used herein, refers to a binding molecule that comprises a nucleotide and/or amino acid sequence that is altered by one or more nucleotides and/or amino acids compared to the nucleotide and/or amino acid sequences of the parent binding molecule and that is still capable of competing for binding to the binding partner, e.g., staphylococci, with the parent binding molecule. In other words, the modifications in the amino acid and/or nucleotide sequence of the parent binding molecule do not significantly affect or alter the binding characteristics of the binding molecule encoded by the nucleotide sequence or containing the amino acid sequence, i.e., the binding molecule is still able to recognize and bind its target. The functional variant may have conservative sequence modifications including nucleotide and amino acid substitutions, additions and deletions. These modifications can be introduced by standard techniques known in the art, such as site-directed mutagenesis and random PCR-mediated mutagenesis, and may comprise natural as well as non-natural nucleotides and amino acids.

Conservative amino acid substitutions include the ones in which the amino acid residue is replaced with an amino acid residue having similar structural or chemical properties. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., asparagine, glutamine, serine, threonine, tyrosine, cysteine, tryptophan), nonpolar side chains (e.g., glycine, alanine, valine, leucine, isoleucine, proline, phenylalanine, methionine), beta-branched side chains (e.g., threonine, valine, isoleucine) and aromatic side chains (e.g., tyrosine, phenylalanine, tryptophan). It will be clear to the skilled artisan that other classifications of amino acid residue families than the one used above can also be employed. Furthermore, a variant may have non-conservative amino acid substitutions, e.g., replacement of an amino acid with an amino acid residue having different structural or chemical properties. Similar minor variations may also include amino acid deletions or insertions, or both. Guidance in determining which amino acid residues may be substituted, inserted, or deleted without abolishing immunological activity may be found using computer programs well known in the art.

A mutation in a nucleotide sequence can be a single alteration made at a locus (a point mutation), such as transition or transversion mutations, or alternatively, multiple nucleotides may be inserted, deleted or changed at a single locus. In addition, one or more alterations may be made at any number of loci within a nucleotide sequence. The mutations may be performed by any suitable method known in the art.

The term "host," as used herein, is intended to refer to an organism or a cell into which a vector such as a cloning vector or an expression vector has been introduced. The organism or cell can be prokaryotic or eukaryotic. It should be understood that this term is intended to refer not only to the particular subject organism or cell, but to the progeny of such an organism or cell as well. Because certain modifications may occur in succeeding generations due to either mutation or environmental influences, such progeny may not, in fact, be identical to the parent organism or cell, but are still included within the scope of the term "host" as used herein.

The term "human," when applied to binding molecules as defined herein, refers to molecules that are either directly derived from a human or based upon a human sequence. When a binding molecule is derived from or based on a human sequence and subsequently modified, it is still to be considered human as used throughout the specification. In other words, the term human, when applied to binding molecules is intended to include binding molecules having variable and constant regions derived from human germline immunoglobulin sequences or based on variable or constant regions occurring in a human or human lymphocyte and modified in some form. Thus, the human binding molecules may include amino acid residues not encoded by human germline immunoglobulin sequences, comprise substitutions and/or deletions (e.g., mutations introduced by, for instance, random or site-specific mutagenesis in vitro or by somatic mutation in vivo). "Based on" as used herein, refers to the situation that a nucleic acid sequence may be exactly copied from a template, or with minor mutations, such as by error-prone PCR methods, or synthetically made matching the template exactly or with minor modifications. Semi-synthetic molecules based on human sequences are also considered to be human as used herein.

The term "insertion," also known as the term "addition," denotes a change in an amino acid or nucleotide sequence resulting in the addition of one or more amino acid or nucleotide residues, respectively, as compared to the parent sequence.

The term "intrinsic activity," when applied to binding molecules as defined herein, refers to binding molecules that are capable of binding to certain protein or carbohydrate antigens on the surface of pathogens such as bacteria and that can inhibit the ability of the pathogen to grow and divide normally. Such binding molecules can, for example, block the entry of specific nutrients required for growth or the transport of toxic waste elements from the bacteria. Through the latter action they may also increase the sensitivity of bacteria to the action of antibiotic drugs.

The term "isolated," when applied to binding molecules as defined herein, refers to binding molecules that are substantially free of other proteins or polypeptides, particularly free of other binding molecules having different antigenic specificities, and are also substantially free of other cellular material and/or chemicals. For example, when the binding molecules are recombinantly produced, they are preferably substantially free of culture medium, and when the binding molecules are produced by chemical synthesis, they are preferably substantially free of chemical precursors or other chemicals, i.e., they are separated from chemical precursors or other chemicals which are involved in the synthesis of the protein. The term "isolated" when applied to nucleic acid molecules encoding binding molecules as defined herein, is intended to refer to nucleic acid molecules in which the nucleotide sequences encoding the binding molecules are free of other nucleotide sequences, particularly nucleotide sequences encoding binding molecules that bind binding partners other than staphylococci. Furthermore, the term "isolated" refers to nucleic acid molecules that are substantially separated from other cellular components that naturally accompany the native nucleic acid molecule in its natural host, e.g., ribosomes, polymerases, or genomic sequences with which it is naturally associated. Moreover, "isolated" nucleic acid molecules, such as cDNA molecules, can be substantially free of other cellular material, or culture medium when produced by recombinant techniques, or substantially free of chemical precursors or other chemicals when chemically synthesized.

The term "monoclonal antibody" as used herein, refers to a preparation of antibody molecules of single molecular composition. A monoclonal antibody displays a single binding specificity and affinity for a particular epitope. Accordingly, the term "human monoclonal antibody" refers to an antibody displaying a single binding specificity which has variable and constant regions derived from or based on human germline immunoglobulin sequences or derived from completely synthetic sequences. The method of preparing the monoclonal antibody is not relevant.

The term "naturally occurring" as used herein, as applied to an object refers to the fact that an object can be found in nature. For example, a polypeptide or polynucleotide sequence that is present in an organism that can be isolated from a source in nature and which has not been intentionally modified by man in the laboratory is naturally occurring.

The term "nucleic acid molecule," as used herein, refers to a polymeric form of nucleotides and includes both sense and anti-sense strands of RNA, cDNA, genomic DNA, and synthetic forms and mixed polymers of the above. A nucleotide refers to a ribonucleotide, deoxynucleotide or a modified form of either type of nucleotide. The term also includes single- and double-stranded forms of DNA. In addition, a polynucleotide may include either or both naturally occurring and modified nucleotides linked together by naturally occurring and/or non-naturally occurring nucleotide linkages. The nucleic acid molecules may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). The above term is also intended to include any topological conformation, including single-stranded, double-stranded, partially duplexed, triplex, hair-pinned, circular and padlocked conformations. Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule. A reference to a nucleic acid sequence encompasses its complement unless otherwise specified. Thus, a reference to a nucleic acid molecule having a particular sequence should be understood to encompass its complementary strand, with its complementary sequence. The complementary strand is also useful, e.g., for anti-sense therapy, hybridization probes and PCR primers.

The term "operably linked" refers to two or more nucleic acid sequence elements that are usually physically linked and are in a functional relationship with each other. For instance, a promoter is operably linked to a coding sequence, if the promoter is able to initiate or regulate the transcription or expression of a coding sequence, in which case the coding sequence should be understood as being "under the control of" the promoter.

"Opsonic activity" refers to the ability of an opsonin (generally either a binding molecule, e.g., an antibody, or serum complement factors) to bind to the surface of a pathogen either by specific antigenic recognition (in the case of antibodies) or through the catalytic effect of surface bound molecules (e.g., the increased deposition of C3b as a result of surface bound antibodies). Phagocytosis of opsonized pathogens is enhanced due to the specific recognition of receptors on the phagocyte for the opsonin (the Fc receptor in case the antibodies themselves are the opsonins and the complement receptor in case complement is the opsonin). Certain bacteria, especially encapsulated bacteria that resist phagocytosis due to the presence of the capsule, become extremely attractive to phagocytes such as neutrophils and macrophages when coated with an opsonic antibody and their rate of clearance from the bloodstream and infected organs is strikingly enhanced. Opsonic activity may be measured in any conventional manner (e.g., the opsonic phagocytic killing assay).

By "pharmaceutically acceptable excipient" is meant any inert substance that is combined with an active molecule such as a drug, agent, or binding molecule for preparing an agreeable or convenient dosage form. The "pharmaceutically acceptable excipient" is an excipient that is non-toxic to recipients at the dosages and concentrations employed, and is compatible with other ingredients of the formulation comprising the drug, agent or binding molecule.

The term "specifically binding," as used herein, in reference to the interaction of a binding molecule, e.g., an antibody, and its binding partner, e.g., an antigen, means that the interaction is dependent upon the presence of a particular structure, e.g., an antigenic determinant or epitope, on the binding partner. In other words, the antibody preferentially binds or recognizes the binding partner even when the binding partner is present in a mixture of other molecules or organisms. The binding may be mediated by covalent or non-covalent interactions or a combination of both. In yet other words, the term "specifically binding" means immunospecifically binding to an antigen or a fragment thereof and not immunospecifically binding to other antigens. A binding molecule that immunospecifically binds to an antigen may bind to other peptides or polypeptides with lower affinity as determined by, e.g., radioimmunoassays (RIA), enzyme-linked immunosorbent assays (ELISA), BIACORE, or other assays known in the art. Binding molecules or fragments thereof that immunospecifically bind to an antigen may be cross-reactive with related antigens. Binding molecules or fragments thereof that immunospecifically bind to an antigen preferably do not cross-react with other antigens.

A "substitution," as used herein, denotes the replacement of one or more amino acids or nucleotides by different amino acids or nucleotides, respectively.

The term "therapeutically effective amount" refers to an amount of the binding molecule as defined herein that is effective for preventing, ameliorating and/or treating a condition resulting from infection with *Staphylococcus.*

The term "treatment" refers to therapeutic treatment as well as prophylactic or preventative measures to cure or halt or at least retard disease progress. Those in need of treatment include those already inflicted with a condition resulting from infection with *Staphylococcus* as well as those in which infection with *Staphylococcus* is to be prevented. Subjects partially or totally recovered from infection with *Staphylococcus* might also be in need of treatment. Prevention encompasses inhibiting or reducing the spread of *Staphylococcus* or inhibiting or reducing the onset, development or progression of one or more of the symptoms associated with infection with *Staphylococcus.*

The term "vector" denotes a nucleic acid molecule into which a second nucleic acid molecule can be inserted for introduction into a host where it will be replicated, and in some cases expressed. In other words, a vector is capable of transporting a nucleic acid molecule to which it has been linked. Cloning as well as expression vectors are contemplated by the term "vector," as used herein. Vectors include, but are not limited to, plasmids, cosmids, bacterial artificial chromosomes (BAC) and yeast artificial chromosomes (YAC) and vectors derived from bacteriophages or plant or animal (including human) viruses. Vectors comprise an origin of replication recognized by the proposed host and in case of expression vectors, promoter and other regulatory regions recognized by the host. A vector containing a second nucleic acid molecule is introduced into a cell by transformation, transfection, or by making use of viral entry mechanisms. Certain vectors are capable of autonomous replication in a host into which they are introduced (e.g., vectors having a bacterial origin of replication can replicate in bacteria). Other vectors can be integrated into the genome of a host upon introduction into the host, and thereby are replicated along with the host genome.

In a first aspect, provided are binding molecules capable of specifically binding to staphylococci. Preferably, the binding molecules are human binding molecules. Preferably, the binding molecules hereof exhibit killing activity against staphylococci. In a further aspect the binding molecules hereof are capable of specifically binding to and/or have killing activity against at least two different *Staphylococcus* species. Preferably, the binding molecules hereof are capable of specifically binding to and/or have killing activity against at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30 different *Staphylococcus* species. *Staphylococcus* species that the binding molecules hereof are capable of specifically binding to and/or have killing activity against are selected from the group consisting of *S. aureus, S. auricularis, S. capitis, S. caprae, S. caseolyticus, S. chromogenes, S. cohnii, S. epidermidis, S. haemolyticus, S. hominis, S. hyicus, S. intermedium, S. lentus, S. lugdunensis, S. saprophyticus, S. schleiferi, S. sciuri, S. simulans, S. warneri*, and *S. xylosus*. In an embodiment the binding molecules hereof are capable of specifically binding to and have killing activity against different strains within one *Staphylococcus* species. In a further embodiment the binding molecules hereof are capable of specifically binding to and have killing activity against a *Staphylococcus* strain in the lag phase, log phase, stationary phase and/or death phase. Preferably, they specifically bind to and have killing activity against a *Staphylococcus* strain in the log phase and stationary phase. In another embodiment, the binding molecules hereof may even be capable of specifically binding to and/or have killing activity against at least one other gram-positive bacterium and/or gram-negative bacterium including, but not limited to, Group A streptococci; *streptococcus pyrogenes*, Group B streptococci; *streptococcus agalactiae, streptococcus milleri, streptococcus pneumoniae, Viridans streptococci; streptococcus mutans, Enterococcus; Enterococcus faecalis* and *Enterococcus faecium, Corynebacterium diphtheriae, Corynebacterium ulcerans, Corynebacterium pseudotuberculosis, Corynebacterium jeikeium, Corynebacterium xerosis, Corynebacterium pseudodiphtheriticum, Bacillus anthracis, Bacillus cereus, Listeria monocytogenes, Clostridium perfringens, Clostridium tetani, Clostridium botulinum, Clostridium difficile, Mycobacterium tuberculosis, Mycobacterium leprae, Actinomyces israelii, Norcardia asteroides, Norcardia brasiliensis, Escherichia coli, Proteus mirabilis, Proteus vulgaris, Klebsiella pneumoniae, Salmonella typhi, Salmonella paratyphi* A, B & C, *Salmonella enteritidis, Salmonella cholerae-suis, Salmonella virchow, Salmonella typhimurium, Shigella dysenteriae, Shigella boydii, Shigella flexneri, Shigella*

*sonnei, Pseudomonas aeruginosa, Pseudomonas mallei, Vibrio cholerae, Vibrio parahaemolyticus, Vibrio vulnificus, Vibrio alginolyticus, Campylobacter pylori, Helicobacter pylori, Campylobacter jejuni, Bacteroides fragilis, Neisseria gonorrhoeae, Neisseria meningitidis, Branhamella catarrhalis, Haemophilus influenzae, Haemophilus ducreyi, Bordetella pertussis, Brucella abortus, Brucella abortus, Brucella melitensis, Legionella pneumophila, Treponema pallidum, Treponema carateum, Leptospira interrogans, Leptospira biflexa, Borrelia recurrentis, Borrelia burgdorferi, Mycoplasma pneumoniae, Coxiella burnetii, Clamydia trachomatis, Clamydia psittaci, Clamydia pneumoniae*. The binding molecules hereof may be capable of specifically binding to staphylococci and optionally other gram-positive and/or gram-negative bacteria that are viable, living and/or infective or that are in inactivated/attenuated form. Methods for inactivating/attenuating bacteria are well known in the art and include, but are not limited to, antibiotic treatment, UV treatment, formaldehyde treatment, etc.

The binding molecules hereof may also be capable of specifically binding to one or more fragments of staphylococci (and other gram-positive and/or gram-negative bacteria) such as inter alia a preparation of one or more proteins and/or (poly)peptides derived from staphylococci or one or more recombinantly produced staphylococci proteins and/or polypeptides. For methods of treatment and/or prevention of staphylococcal infections the binding molecules are preferably capable of specifically binding to surface accessible proteins of staphylococci. For diagnostical purposes the binding molecules may also be capable of specifically binding to proteins not present on the surface of staphylococci. The nucleotide and/or amino acid sequence of proteins of various *Staphylococcus* species and strains can be found in the GenBank-database, EMBL-database and/or other databases. It is well within the reach of the skilled person to find such sequences in the respective databases.

Alternatively, binding molecules hereof may also be capable of specifically binding to other staphylococcal molecules including, but not limited to, surface factors that inhibit phagocytic engulfment; factors that enhance their survival in phagocytes; invasins that lyse eukaryotic cell membranes; exotoxins that damage host tissues or otherwise provoke symptoms of disease; polysaccharides; other cell wall components such as teichoic acid, lipoteichoic acid, ribitol, peptidoglycan, pentaglycine oligopeptide, N-acetylglucosamine, N-acetylmuramic acid, N-acetylgalactosaminuronic acid, N-acetylfucosamine, N-acetylglucosaminuronic acid, N-acetylmannosaminuronic acid, O-acetyl, glucosamine, muramic acid, galactosaminuronic acid, fucosamine, glucosaminuronic acid, mannosaminuronic acid and linkage units between any of these components.

In another embodiment, the binding molecules hereof are capable of specifically binding to a fragment of the above-mentioned proteins and/or other molecules, wherein the fragment at least comprises an antigenic determinant recognized by the binding molecules hereof. An "antigenic determinant" as used herein, is a moiety that is capable of binding to a binding molecule hereof with sufficiently high affinity to form a detectable antigen-binding molecule complex.

The binding molecules hereof can be intact immunoglobulin molecules such as polyclonal or monoclonal antibodies or the binding molecules can be antigen-binding fragments including, but not limited to, Fab, F(ab'), $F(ab')_2$, Fv, dAb, Fd, complementarity-determining region (CDR) fragments, single-chain antibodies (scFv), bivalent single-chain antibodies, single-chain phage antibodies, diabodies, triabodies, tetrabodies, and (poly)peptides that contain at least a fragment of an immunoglobulin that is sufficient to confer specific antigen binding to staphylococci or a fragment thereof. In certain embodiments the binding molecules hereof are human monoclonal antibodies.

The binding molecules hereof can be used in non-isolated or isolated form. Furthermore, the binding molecules hereof can be used alone or in a mixture comprising at least one binding molecule (or variant or fragment thereof) hereof. In other words, the binding molecules can be used in combination, e.g., as a pharmaceutical composition comprising two or more binding molecules hereof, variants or fragments thereof. For example, binding molecules having different, but complementary activities can be combined in a single therapy to achieve a desired prophylactic, therapeutic or diagnostic effect, but alternatively, binding molecules having identical activities can also be combined in a single therapy to achieve a desired prophylactic, therapeutic or diagnostic effect. Optionally, the mixture further comprises at least one other therapeutic agent. Preferably, the therapeutic agent such as, e.g., an antibiotic is useful in the prophylaxis and/or treatment of a staphylococcal infection.

Typically, binding molecules hereof can bind to their binding partners, i.e., staphylococci or fragments thereof, with an affinity constant ($K_d$-value) that is lower than $0.2\times10^{-4}$ M, $1.0\times10^{-5}$ M, $1.0\times10^{-6}$ M, $1.0\times10^{-7}$ M, preferably lower than $1.0\times10^{-8}$ M, more preferably lower than $1.0\times10^{-9}$ M, more preferably lower than $1.0\times10^{-10}$ M, even more preferably lower than $1.0\times10^{-11}$ M, and in particular lower than $1.0\times10^{-12}$ M. The affinity constants can vary for antibody isotypes. For example, affinity binding for an IgM isotype refers to a binding affinity of at least about $1.0\times10^{-7}$ M. Affinity constants can, for instance, be measured using surface plasmon resonance, for example, using the BIACORE system (Pharmacia Biosensor AB, Uppsala, Sweden).

The binding molecules hereof may bind to staphylococci or a fragment thereof in soluble form such as, for instance, in a sample or in suspension or may bind to staphylococci or a fragment thereof bound or attached to a carrier or substrate, e.g., microtiter plates, membranes and beads, etc. Carriers or substrates may be made of glass, plastic (e.g., polystyrene), polysaccharides, nylon, nitrocellulose, or Teflon, etc. The surface of such supports may be solid or porous and of any convenient shape. Furthermore, the binding molecules may bind to staphylococci in purified/isolated or non-purified/non-isolated form.

The binding molecules hereof exhibit killing activity. "Killing activity" as used herein includes, but is not limited to, opsonic activity or any other activity increasing/augmenting/enhancing phagocytosis and/or phagocytic killing of bacteria, e.g., staphylococci; intrinsic (killing) activity, e.g., reduce or inhibit bacterial growth or directly kill bacteria; increase the sensitivity of bacteria to antibiotic treatment; or any combination thereof. Opsonic activity can, for instance, be measured as described herein. Alternative assays measuring opsonic activity are described in, for instance, *Manual of Molecular and Clinical Laboratory Immunology,* 7th Edition. Assays to measure the other mentioned activities are also known.

In certain embodiments, the binding molecules hereof comprise at least a CDR3 region, preferably a heavy chain CDR3 region, comprising the amino acid sequence selected from the group consisting of SEQ ID NO:9 and SEQ ID NO:15. The CDR regions of the binding molecules hereof are shown in Table 12. CDR regions are according to Kabat et al. (1991) as described in *Sequences of Proteins of Immunological Interest*, U.S. Dept. Health and Human Services, NIH, USA (fifth edition). In one embodiment, binding molecules may comprise two, three, four, five or even all six CDR regions of the binding molecules hereof.

In yet another embodiment, the binding molecules hereof comprise a heavy chain comprising the variable heavy chain of the amino acid sequence selected from the group consisting of SEQ ID NO:28 and SEQ ID NO:30. In a further embodiment, the binding molecules hereof comprise a light chain comprising the variable light chain of the amino acid sequence selected from the group consisting of SEQ ID NO:34 and SEQ ID NO:36. Table 13 specifies the heavy and light chain variable regions of the binding molecule hereof.

In another aspect, the binding molecules hereof are capable of specifically binding to one specific *Staphylococcus* species, preferably one specific *Staphylococcus* strain. In other words, they are species- and even strain-specific. Preferably, the binding molecules hereof exhibit killing activity against the specific *Staphylococcus* species/strain. In certain embodiments the *Staphylococcus* species is *S. aureus* and the strain is *S. aureus* strain Cowan. The binding molecules hereof may be capable of specifically binding to and exhibit killing activity against the specific *Staphylococcus* species/strain in any phase, e.g., log and/or stationary phase. In certain embodiments the binding molecules comprise at least a CDR3 region, preferably a heavy chain CDR3 region, comprising the amino acid sequence of SEQ ID NO:3. The CDR regions of the binding molecules are shown in Table 12. CDR regions are according to Kabat et al. (1991) as described in *Sequences of Proteins of Immunological Interest*, U.S. Dept. Health and Human Services, NIH, USA (fifth edition). In an embodiment binding molecules may comprise two, three, four, five or even all six CDR regions of the binding molecules hereof. In yet another embodiment, the binding molecules comprise a heavy chain comprising the variable heavy chain of the amino acid sequence of SEQ ID NO:26. In a further embodiment, the binding molecules comprise a light chain comprising the variable light chain of the amino acid sequence of SEQ ID NO:32. Table 13 specifies the heavy and light chain variable regions of the binding molecule hereof.

Another aspect includes functional variants of the binding molecules as defined herein. Molecules are considered to be functional variants of a binding molecule hereof, if the variants are capable of competing for specifically binding to staphylococci (or other gram-positive and/or gram-negative bacteria) or a fragment thereof with the parent human binding molecules. In other words, when the functional variants are still capable of binding to staphylococci or a fragment thereof. Preferably, the functional variants are capable of competing for specifically binding to the at least two (or more) different *Staphylococcus* species or fragments thereof that are specifically bound by the parent human binding molecules. Furthermore, molecules are considered to be functional variants of a binding molecule hereof, if they have killing activity against staphylococci, preferably against the at least two (or more) *Staphylococcus* species against which the parental binding molecule exhibits killing activity. In another embodiment the functional variants of a binding molecule hereof also have killing activity against other gram-positive and/or gram-negative bacteria. Functional variants include, but are not limited to, derivatives that are substantially similar in primary structural sequence, but which contain, e.g., in vitro or in vivo modifications, chemical and/or biochemical, that are not found in the parental binding molecule. Such modifications include inter alia acetylation, acylation, covalent attachment of a nucleotide or nucleotide derivative, covalent attachment of a lipid or lipid derivative, cross-linking, disulfide bond formation, glycosylation, hydroxylation, methylation, oxidation, pegylation, proteolytic processing, phosphorylation, and the like.

Alternatively, functional variants can be binding molecules as defined herein comprising an amino acid sequence containing substitutions, insertions, deletions or combinations thereof of one or more amino acids compared to the amino acid sequences of the parent binding molecules. Furthermore, functional variants can comprise truncations of the amino acid sequence at either or both the amino or carboxyl termini. Functional variants hereof may have the same or different, either higher or lower, binding affinities compared to the parental binding molecule but are still capable of binding to staphylococci or a fragment thereof. For instance, functional variants hereof may have increased or decreased binding affinities for staphylococci or a fragment thereof compared to the parent binding molecules. Preferably, the amino acid sequences of the variable regions, including, but not limited to, framework regions, hypervariable regions, in particular the CDR3 regions, are modified. Generally, the light chain and the heavy chain variable regions comprise three hypervariable regions, comprising three CDRs, and more conserved regions, the so-called framework regions (FRs). The hypervariable regions comprise amino acid residues from CDRs and amino acid residues from hypervariable loops. Functional variants intended to fall within the scope hereof have at least about 50% to about 99%, preferably at least about 60% to about 99%, more preferably at least about 70% to about 99%, even more preferably at least about 80% to about 99%, most preferably at least about 90% to about 99%, in particular at least about 95% to about 99%, and in particular at least about 97% to about 99% amino acid sequence homology with the parent human binding molecules as defined herein. Computer algorithms such as inter alia Gap or Bestfit known to a person skilled in the art can be used to optimally align amino acid sequences to be compared and to define similar or identical amino acid residues. Functional variants can be obtained by altering the parent binding molecules or parts thereof by general molecular biology methods known in the art including, but not limited to, error-prone PCR, oligonucleotide-directed mutagenesis, site-directed mutagenesis and heavy and/or light chain shuffling. In an embodiment the functional variants hereof have killing activity against staphylococci. The killing activity may either be identical, or be higher or lower compared to the parent binding molecules. Furthermore, the functional variants having killing activity may have a further activity suitable in staphylococcal control. Other activities are mentioned above. Henceforth, when the term (human) binding molecule is used, this also encompasses functional variants of the (human) binding molecule.

Provided is a panel of useful human monoclonal antibodies that have opsonic phagocytic killing activity against Staphylococci, the antibodies comprising the heavy and light chain variable regions of any one of the antibodies named CR2430, CR5132, CR5133CR6166, CR6171, CR6176, CR6187, CR6193, CR6249, CR6273, CR6389, CR6403, CR6406, CR6410, CR6446, CR6450, CR6452, CR6453, CR6464, CR6471, CR6516, CR6517, CR6526, CR6528, CR6531, CR6533, CR6536, CR6537, CR6538, CR6540, CR6544, CR6566, or CR6625, or comprising variable regions with sequences that are at least 80%, preferably at least 90%, more preferably at least 95%, identical thereto. Preferably, the sequences of the complete antibodies are at least 80%, more preferably at least 90%, still more preferably at least 95% identical to the sequences of these antibodies as disclosed herein. The antibodies fell into five distinct groups, based on a target competition assay. Group A consisted of CR5132, CR5133, CR6187 and CR6453; Group B consisted of CR5140 and CR6171; Group C consisted of CR6176; Group D consisted of CR6526; and Group E consisted of the rest of the panel CR6166, CR6193, CR6249, CR6273, CR6403, CR6406, CR6410, CR6446, CR6450, CR6452, CR6464, CR6471, CR6516, CR6517, CR6528, CR6531, CR6533, CR6536, CR6537, CR6538, CR6540, CR6544, CR6566, CR6625. Based on the potency, one antibody from each group was identified as preferred antibody, and the preferred antibodies are: CR5133, CR6166, CR6171, CR6176 and CR6526. These antibodies were all shown to bind and have opsonic phagocytic killing activity against at least two different *Staphylococcus* species (*S. aureus* and *S. epidermidis*), and against at least three different strains of *S. aureus* (502, Mn8, Newman) Also described are compositions comprising at least two, at least three, at least four, at least five, or more, of the human monoclonal antibodies hereof. In preferred embodiments, at least two of the antibodies in the composition are from different target groups. This has the advantage that different targets on the staphylococci are recognized and thus the chances of killing the bacteria are increased. Of course, higher affinity mutants or mutants with other advantageous properties can be prepared according to routine methods, based on the sequences of the antibodies as disclosed herein. Such improved antibodies are included within the scope hereof, when the variable regions of heavy and light chain are at least 80%, preferably at least 90%, still more preferably at least 95% identical to the sequences of the variable regions of the antibodies disclosed herein.

Also disclosed are immunoconjugates, i.e., molecules comprising at least one binding molecule as defined herein and further comprising at least one tag, such as inter alia a detectable moiety/agent. Also contemplated are mixtures of immunoconjugates hereof or mixtures of at least one immunoconjugates hereof and another molecule, such as a therapeutic agent or another binding molecule or immunoconjugate. In a further embodiment, the immunoconjugates hereof may comprise more than one tag. These tags can be the same or distinct from each other and can be joined/conjugated non-covalently to the binding molecules. The tag(s) can also be joined/conjugated directly to the human binding molecules through covalent bonding. Alternatively, the tag(s) can be joined/conjugated to the binding molecules by means of one or more linking compounds. Techniques for conjugating tags to binding molecules are well known to the skilled artisan.

The tags of the immunoconjugates hereof may be therapeutic agents, but they can also be detectable moieties/agents. Tags suitable in therapy and/or prevention may be toxins or functional parts thereof, antibiotics, enzymes, other binding molecules that enhance phagocytosis or immune stimulation. Immunoconjugates comprising a detectable agent can be used diagnostically to, for example, assess if a subject has been infected with a *Staphylococcus* species or monitor the development or progression of a staphylococcal infection as part of a clinical testing procedure to, e.g., determine the efficacy of a given treatment regimen. However, they may also be used for other detection and/or analytical and/or diagnostic purposes. Detectable moieties/agents include, but are not limited to, enzymes, prosthetic groups, fluorescent materials, luminescent materials, bioluminescent materials, radioactive materials, positron emitting metals, and non-radioactive paramagnetic metal ions. The tags used to label the binding molecules for detection and/or analytical and/or diagnostic purposes depend on the specific detection/analysis/diagnosis techniques and/or methods used such as inter alia immunohistochemical staining of (tissue) samples, flow cytometric detection, scanning laser cytometric detection, fluorescent immunoassays, enzyme-linked immunosorbent assays (ELISAs), radioimmunoassays (RIAs), bioassays (e.g., phagocytosis assays), Western blotting applications, etc. Suitable labels for the detection/analysis/diagnosis techniques and/or methods known in the art are well within the reach of the skilled artisan.

Furthermore, the human binding molecules or immunoconjugates hereof can also be attached to solid supports, which are particularly useful for in vitro immunoassays or purification of staphylococci or a fragment thereof. Such solid supports might be porous or nonporous, planar or nonplanar. The binding molecules hereof can be fused to marker sequences, such as a peptide to facilitate purification. Examples include, but are not limited to, the hexa-histidine tag, the hemagglutinin (HA) tag, the myc tag or the flag tag. Alternatively, an antibody can be conjugated to a second antibody to form an antibody heteroconjugate. In another aspect the binding molecules hereof may be conjugated/attached to one or more antigens. Preferably, these antigens are antigens which are recognized by the immune system of a subject to which the binding molecule-antigen conjugate is administered. The antigens may be identical, but may also differ from each other. Conjugation methods for attaching the antigens and binding molecules are well known in the art and include, but are not limited to, the use of cross-linking agents. The binding molecules hereof will bind to staphylococci and the antigens attached to the binding molecules will initiate a powerful T-cell attack on the conjugate, which will eventually lead to the destruction of the staphylococci.

Next to producing immunoconjugates chemically by conjugating, directly or indirectly, via, for instance, a linker, the immunoconjugates can be produced as fusion proteins comprising the binding molecules hereof and a suitable tag. Fusion proteins can be produced by methods known in the art such as, e.g., recombinantly by constructing nucleic acid molecules comprising nucleotide sequences encoding the binding molecules in frame with nucleotide sequences encoding the suitable tag(s) and then expressing the nucleic acid molecules.

Also described are nucleic acid molecules encoding at least a binding molecule, functional variant or immunoconjugate hereof. Such nucleic acid molecules can be used as intermediates for cloning purposes, e.g., in the process of affinity maturation as described above. In certain embodiments, the nucleic acid molecules are isolated or purified.

The skilled person will appreciate that functional variants of these nucleic acid molecules are also intended to be a part hereof. Functional variants are nucleic acid sequences that can be directly translated, using the standard genetic code, to provide an amino acid sequence identical to that translated from the parent nucleic acid molecules.

Preferably, the nucleic acid molecules encode binding molecules comprising a CDR3 region, preferably a heavy chain CDR3 region, comprising an amino acid sequence selected from the group consisting of SEQ ID NO:3, SEQ ID NO:9 and SEQ ID NO:15. In a further embodiment the nucleic acid molecules encode binding molecules comprising two, three, four, five or even all six CDR regions of the binding molecules hereof.

In another embodiment, the nucleic acid molecules encode binding molecules comprising a heavy chain comprising the variable heavy chain of the amino acid sequence selected from the group consisting of SEQ ID NO:26, SEQ ID NO:28 and SEQ ID NO:30. In another embodiment the nucleic acid molecules encode binding molecules comprising a light chain comprising the variable light chain of the amino acid sequence selected from the group consisting of SEQ ID NO:32, SEQ ID NO:34 and SEQ ID NO:36.

It is another aspect to provide vectors, i.e., nucleic acid constructs, comprising one or more nucleic acid molecules hereof. Vectors can be derived from plasmids such as inter alia F, R1, RP1, Col, pBR322, TOL, Ti, etc; cosmids; phages such as lambda, lambdoid, M13, Mu, P1, P22, Qβ, T-even, T-odd, T2, T4, T7, etc; plant viruses. Vectors can be used for cloning and/or for expression of the binding molecules hereof and might even be used for gene therapy purposes. Vectors comprising one or more nucleic acid molecules hereof operably linked to one or more expression-regulating nucleic acid molecules are also covered hereby. The choice of the vector is dependent on the recombinant procedures followed and the host used. Introduction of vectors in host cells can be effected by inter alia calcium phosphate transfection, virus infection, DEAE-dextran mediated transfection, lipofectamin transfection or electroporation. Vectors may be autonomously replicating or may replicate together with the chromosome into which they have been integrated. Preferably, the vectors contain one or more selection markers. The choice of the markers may depend on the host cells of choice, although this is not critical. They include, but are not limited to, kanamycin, neomycin, puromycin, hygromycin, ZEOCIN® antibiotic, thymidine kinase gene from Herpes simplex virus (HSV-TK), dihydrofolate reductase gene from mouse (dhfr). Vectors comprising one or more nucleic acid molecules encoding the human binding molecules as described above operably linked to one or more nucleic acid molecules encoding proteins or peptides that can be used to isolate the human binding molecules are also covered hereby. These proteins or peptides include, but are not limited to, glutathione-S-transferase, maltose binding protein, metal-binding polyhistidine, green fluorescent protein, luciferase and beta-galactosidase.

Hosts containing one or more copies of the vectors mentioned above are an additional subject hereof. Preferably, the hosts are host cells. Host cells include, but are not limited to, cells of mammalian, plant, insect, fungal or bacterial origin. Bacterial cells include, but are not limited to, cells from gram-positive bacteria or gram-negative bacteria such as several species of the genera *Escherichia*, such as *E. coli*, and *Pseudomonas*. In the group of fungal cells preferably yeast cells are used. Expression in yeast can be achieved by using yeast strains such as inter alia *Pichia pastoris, Saccharomyces cerevisiae* and *Hansenula polymorpha*. Furthermore, insect cells such as cells from *Drosophila* and Sf9 can be used as host cells. Besides that, the host cells can be plant cells such as inter alia cells from crop plants such as forestry plants, or cells from plants providing food and raw materials such as cereal plants, or medicinal plants, or cells from ornamentals, or cells from flower bulb crops. Transformed (transgenic) plants or plant cells are produced by known methods, for example, *Agrobacterium*-mediated gene transfer, transformation of leaf discs, protoplast transformation by polyethylene glycol-induced DNA transfer, electroporation, sonication, microinjection or bolistic gene transfer. Additionally, a suitable expression system can be a baculovirus system. Expression systems using mammalian cells such as Chinese Hamster Ovary (CHO) cells, COS cells, BHK cells or Bowes melanoma cells are preferred. Mammalian cells provide expressed proteins with posttranslational modifications that are most similar to natural molecules of mammalian origin. Since this disclosure deals with molecules that may have to be administered to humans, a completely human expression system would be particularly preferred. Therefore, even more preferably, the host cells are human cells. Examples of human cells are inter alia HeLa, 911, AT1080, A549, 293 and HEK293T cells. In preferred embodiments, the human producer cells comprise at least a functional part of a nucleic acid sequence encoding an adenovirus E1 region in expressible format. In even more preferred embodiments, the host cells are derived from a human retina and immortalized with nucleic acids comprising adenoviral E1 sequences, such as 911 cells or the cell line deposited at the European Collection of Cell Cultures (ECACC), CAMR, Salisbury, Wiltshire SP4 OJG, Great Britain on 29 Feb. 1996 under number 96022940 and marketed under the trademark PER.C6® (PER.C6® is a registered trademark of Crucell Holland B.V.). For the purposes of this application "PER.C6®" refers to cells deposited under number 96022940 or ancestors, passages up-stream or downstream as well as descendants from ancestors of deposited cells, as well as derivatives of any of the foregoing. Production of recombinant proteins in host cells can be performed according to methods well known in the art. The use of the cells marketed under the trademark PER.C6® as a production platform for proteins of interest has been described in WO 00/63403 the disclosure of which is incorporated herein by reference in its entirety.

A method of producing a binding molecule hereof is an additional part of the disclosure. Such a method comprises the steps of a) culturing a host hereof under conditions conducive to the expression of the binding molecule, and b) optionally, recovering the expressed binding molecule. The expressed binding molecules or immunoconjugates can be recovered from the cell free extract, but preferably they are recovered from the culture medium. The above method of producing can also be used to make functional variants of the binding molecules and/or immunoconjugates hereof. Methods to recover proteins, such as binding molecules, from cell free extracts or culture medium are well known to the person skilled in the art. Binding molecules, functional variants and/or immunoconjugates as obtainable by the above-described method are also a part hereof.

Alternatively, next to the expression in hosts, such as host cells, the binding molecules and immunoconjugates hereof can be produced synthetically by conventional peptide synthesizers or in cell-free translation systems using RNA nucleic acid derived from DNA molecules hereof. Binding molecules and immunoconjugates as obtainable by the above described synthetic production methods or cell-free translation systems are also a part hereof.

In yet another embodiment, the binding molecules can also be produced in transgenic, non-human, mammals such as inter alia rabbits, goats or cows, and secreted into, for instance, the milk thereof.

In yet another alternative embodiment, binding molecules hereof, preferably human binding molecules specifically binding to staphylococci or a fragment thereof, may be generated by transgenic non-human mammals, such as, for instance, transgenic mice or rabbits, that express human immunoglobulin genes. Preferably, the transgenic non-human mammals have a genome comprising a human heavy chain transgene and a human light chain transgene encoding all or a portion of the human binding molecules as described above. The transgenic non-human mammals can be immunized with a purified or enriched preparation of staphylococci or a fragment thereof. Protocols for immunizing non-human mammals are well established in the art. See *Using Antibodies: A Laboratory Manual*, edited by E. Harlow, D. Lane (1998), Cold Spring Harbor Laboratory, Cold Spring Harbor, N.Y. and *Current Protocols in Immunology*, edited by J. E. Coligan, A. M. Kruisbeek, D. H. Margulies, E. M. Shevach, W. Strober (2001), John Wiley & Sons Inc., New York, the disclosures of which are incorporated herein by reference.

Immunization protocols often include multiple immunizations, either with or without adjuvants such as Freund's complete adjuvant and Freund's incomplete adjuvant, but may also include naked DNA immunizations. In another embodiment, the human binding molecules are produced by B cells or plasma cells derived from the transgenic animals. In yet another embodiment, the human binding molecules are produced by hybridomas, which are prepared by fusion of B cells obtained from the above-described transgenic non-human mammals to immortalized cells. B cells, plasma cells and hybridomas as obtainable from the above-described transgenic non-human mammals and human binding molecules as obtainable from the above-described transgenic non-human mammals, B cells, plasma cells and hybridomas are also a part hereof.

In a further aspect, provided is a method of identifying a binding molecule, such as a human binding molecule, e.g., a human monoclonal antibody or fragment thereof, specifically binding to at least two different bacterial organisms or nucleic acid molecules encoding such binding molecules and comprises the steps of: (a) contacting a collection of binding molecules on the surface of replicable genetic packages with a first bacterial organism under conditions conducive to binding, (b) selecting at least once for a replicable genetic package binding to the first bacterial organism, (c) optionally, separating the replicable genetic package binding to the first bacterial organism from replicable genetic packages that do not bind to the first bacterial organism, contacting the separated replicable genetic packages with a second bacterial organism under conditions conducive to binding and selecting at least once for a replicable genetic package binding to the second bacterial organism, and (d) separating and recovering the replicable genetic package binding to the first and/or second bacterial organism from replicable genetic packages that do not bind to the first and/or second bacterial organism. Of course, the above methods extended with selections on third and further bacterial organisms are also part hereof.

A replicable genetic package as used herein, can be prokaryotic or eukaryotic and includes cells, spores, yeasts, bacteria, viruses, (bacterio)phage, ribosomes and polysomes. A preferred replicable genetic package is a phage. The binding molecules, such as, for instance, single chain Fvs, are displayed on the replicable genetic package, i.e., they are attached to a group or molecule located at an exterior surface of the replicable genetic package. The replicable genetic package is a screenable unit comprising a binding molecule to be screened linked to a nucleic acid molecule encoding the binding molecule. The nucleic acid molecule should be replicable either in vivo (e.g., as a vector) or in vitro (e.g., by PCR, transcription and translation). In vivo replication can be autonomous (as for a cell), with the assistance of host factors (as for a virus) or with the assistance of both host and helper virus (as for a phagemid). Replicable genetic packages displaying a collection of binding molecules is formed by introducing nucleic acid molecules encoding exogenous binding molecules to be displayed into the genomes of the replicable genetic packages to form fusion proteins with endogenous proteins that are normally expressed from the outer surface of the replicable genetic packages. Expression of the fusion proteins, transport to the outer surface and assembly results in display of exogenous binding molecules from the outer surface of the replicable genetic packages.

The selection step(s) in the method hereof can be performed with bacterial organisms that are live and still infective or inactivated. Inactivation of bacterial organism may be performed by bacterial inactivation methods well known to the skilled artisan such as inter alia treatment with low pH, i.e., pH 4 for six hours to 21 days; treatment with organic solvent/detergent, i.e., addition of organic solvents and detergents (Triton X-100 or TWEEN-80™) to the bacterium; UV/light irradiation; gamma-irradiation; and treatment with relevant antibiotics. Methods to test, if a bacterial organism is still alive, infective and/or viable or partly or completely inactivated are well known to the person skilled in the art. The bacterial organisms used in the above method may be non-isolated, e.g., present in serum and/or blood of an infected individual. The bacterial organisms used may also be isolated as discrete colonies after overnight culture at 37° C. on a suitable medium such as sheep blood agar.

In an embodiment, the first and/or second bacterial organisms are in suspension when contacted with the replicable genetic packages. Alternatively, they may also be coupled to a carrier when contact takes place. In another embodiment, the first and second bacterial organisms are from a different bacterial family, e.g., the first is from a gram-negative bacterium and the second is from a gram-positive bacterium. This way, binding molecules capable of specifically binding to gram-positive and gram-negative bacteria can be found. Preferably, the first and second bacterial organisms are both gram-positive bacteria. The first and second bacterial organism can both be staphylococci. In one embodiment the first and second bacterial organism are different strains from the same bacterial species, e.g., a *Staphylococcus* species such as *S. aureus* or *S. epidermidis*. This way, species-specific binding molecules can be found that are capable of specifically binding to different strains within one species. In another embodiment the first and second bacterial organism are each a member of a different *Staphylococcus* species, e.g., the first and second *Staphylococcus* species are selected from the group consisting of *S. aureus* and *S. epidermidis*. This way, binding molecules capable of specifically binding to different species within one bacterial genus can be found. Alternatively, first and second bacterial organisms can both be enterococci. In one embodiment the first and second bacterial organism are different strains from the same bacterial species, e.g., an *Enterococcus* species such as *E. faecalis* or *E. faecium*. This way, species-specific binding molecules can be found that are capable of specifically binding to different strains within one species. In another embodiment the first and second bacterial organism are each a member of a different *Enterococcus* species, e.g., the first and second *Enterococcus* species are selected from the group consisting of *E. faecalis* and *E. faecium*.

Alternatively, the selection step may be performed in the presence of a fragment of the bacterial organisms such as, e.g., cell membrane preparations, cell membrane preparations that have been enzymically treated to remove proteins (e.g., with protease K), cell membrane preparations that have been enzymically treated to remove carbohydrate moieties (e.g., with periodate), recombinant proteins or polysaccharides. In yet another embodiment, the selection step may be performed in the presence of one or more proteins or (poly)peptides derived from the bacterial organisms, fusion proteins comprising these proteins or (poly)peptides, and the like. Extracellularly exposed parts of these proteins can also be used as selection material. The live or inactivated bacterial organisms or fragments thereof may be immobilized to a suitable material before use. Alternatively, live or inactivated bacteria in suspension are used. In an embodiment the selection can be performed on different materials derived from bacterial organisms. For instance, the first selection round can be performed on live or inactivated bacterial organisms in suspension, while the second and third selection round can be performed on recombinant bacterial proteins and polysaccharides, respectively. Of course, other combinations are also contemplated herein. Different bacterial materials can also be used during one selection/panning step. In a further aspect, provided are methods wherein the bacterial organisms used in the selection step(s) are derived from the same or different growth phases of the bacteria, e.g., the lag phase, log phase, stationary phase or death phase. This way, phase-specific anti-bacterial binding molecules may be found. For instance, the first bacterial organism may be a *S. aureus* in stationary phase, while the second bacterial organism is a *S. aureus* in log phase or the first bacterial organism may be a *S. aureus* in lag phase, while the second bacterial organism is a *S. epidermidis* in lag phase. Further combinations are well within the reach of the skilled artisan.

In a specific embodiment, provided is a method as described above wherein, if the first and/or second *Staphylococcus* species is a *S. aureus* strain, Protein A present on the surface of the *S. aureus* strain is blocked before the *S. aureus* strain is contacted with replicable genetic packages. Suitable blocking agent may be rabbit serum, purified rabbit immunoglobulin, fetal calf serum, pooled human serum In yet a further aspect, provided is a method of obtaining a binding molecule specifically binding to at least two different bacterial organisms or a nucleic acid molecule encoding such a binding molecule, wherein the method comprises the steps of a) performing the above described method of identifying binding molecules, and b) isolating from the recovered replicable genetic package the binding molecule and/or the nucleic acid molecule encoding the binding molecule. The collection of binding molecules on the surface of replicable genetic packages can be a collection of scFvs or Fabs. Once a new scFv or Fab has been established or identified with the above-mentioned method of identifying binding molecules or nucleic acid molecules encoding the binding molecules, the DNA encoding the scFv or Fab can be isolated from the bacteria or phages and combined with standard molecular biological techniques to make constructs encoding bivalent scFvs or complete human immunoglobulins of a desired specificity (e.g., IgG, IgA or IgM). These constructs can be transfected into suitable cell lines and complete human monoclonal antibodies can be produced (see Huls et al., 1999; Boel et al., 2000).

As mentioned before, the preferred replicable genetic package is a phage. Phage display methods for identifying and obtaining (human) binding molecules, e.g., (human) monoclonal antibodies, are by now well-established methods known by the person skilled in the art. They are, e.g., described in U.S. Pat. No. 5,696,108; Burton and Barbas, 1994; de Kruif et al., 1995b; and *Phage Display: A Laboratory Manual*, edited by C. F. Barbas, D. R. Burton, J. K. Scott and G. J. Silverman (2001), Cold Spring Harbor Laboratory Press, Cold Spring Harbor, N.Y. All these references are herewith incorporated herein in their entirety. For the construction of phage display libraries, collections of human monoclonal antibody heavy and light chain variable region genes are expressed on the surface of bacteriophage, preferably filamentous bacteriophage, particles, in, for example, single-chain Fv (scFv) or in Fab format (see de Kruif et al., 1995b). Large libraries of antibody fragment-expressing phages typically contain more than $1.0\times10^9$ antibody specificities and may be assembled from the immunoglobulin V regions expressed in the B-lymphocytes of immunized- or non-immunized individuals. In a specific embodiment hereof, the phage library of binding molecules, preferably scFv phage library, is prepared from RNA isolated from cells obtained from a subject that has been vaccinated against a bacterium, recently vaccinated against an unrelated pathogen, recently suffered from a chronic or acute bacterial infection, e.g., staphylococcal infection, or from a healthy individual. RNA can be isolated from inter alia bone marrow or peripheral blood, preferably peripheral blood lymphocytes or on isolated B cells or even on subpopulations of B cells. The subject can be an animal vaccinated against a bacterium or an animal that has or has had a bacterial infection. Preferably, the animal is a human subject that has been vaccinated against a bacterium or has or has had a chronic bacterial infection or an acute bacterial infection. Preferably, the human subject has recently recovered from the bacterial infection.

Alternatively, phage display libraries may be constructed from immunoglobulin variable regions that have been partially assembled in vitro to introduce additional antibody diversity in the library (semi-synthetic libraries). For example, in vitro assembled variable regions contain stretches of synthetically produced, randomized or partially randomized DNA in those regions of the molecules that are important for antibody specificity, e.g., CDR regions. Phage antibodies specific for bacteria such as staphylococci can be selected from the library by exposing the bacteria or material thereof to a phage library to allow binding of phages expressing antibody fragments specific for the bacteria or material thereof. Non-bound phages are removed by washing and bound phages eluted for infection of *E. coli* bacteria and subsequent propagation. Multiple rounds of selection and propagation are usually required to sufficiently enrich for phages binding specifically to the bacteria or material thereof. If desired, before exposing the phage library to the bacteria or material thereof the phage library can first be subtracted by exposing the phage library to non-target material such as bacteria of a different family, species and/or strain or bacteria in a different growth phase or material of these bacteria. These subtractor bacteria or material thereof can be bound to a solid phase or can be in suspension. Phages may also be selected for binding to complex antigens such as complex mixtures of bacterial proteins or (poly)peptides optionally supplemented with bacterial polysaccharides or other bacterial material. Host cells expressing one or more proteins or (poly)peptides of bacteria such as staphylococci may also be used for selection purposes. A phage display method using these host cells can be extended and improved by subtracting non-relevant binders during screening by addition of an excess of host cells comprising no target molecules or non-target molecules that are similar, but not identical, to the target, and thereby strongly enhance the chance of finding relevant binding molecules. Of course, the subtraction may be performed before, during or after the screening with bacterial organisms or material thereof. The process is referred to as the MABSTRACT® process (MABSTRACT® is a registered trademark of Crucell Holland B.V., see also U.S. Pat. No. 6,265,150 which is incorporated herein by reference).

In yet another aspect, provided is a method of obtaining a binding molecule potentially having killing activity against at least two different bacterial organisms, wherein the method comprises the steps of (a) performing the method of obtaining a binding molecule specifically binding to at least two different bacterial organisms or a nucleic acid molecule encoding such a binding molecule as described above, and (b) verifying if the binding molecule isolated has killing activity against at least two different bacterial organisms. Assays for verifying if a binding molecule has killing activity such as opsonic activity are well known in the art (see, for instance, *Manual of Molecular and Clinical Laboratory Immunology,* 7th Edition). In a further embodiment the binding molecule is also tested for any other activity. Other useful activities are mentioned above.

In a further aspect, described is a binding molecule having killing activity against at least two, preferably at least three or more, different bacterial organisms, such as, e.g., staphylococci, and being obtainable by the methods as described above. A pharmaceutical composition comprising the binding molecule, the pharmaceutical composition further comprising at least one pharmaceutically acceptable excipient is also an aspect hereof. Pharmaceutically acceptable excipients are well known to the skilled person. The pharmaceutical composition hereof may further comprise at least one other therapeutic agent. Suitable agents are also well known to the skilled artisan.

In yet a further aspect, described are compositions comprising at least one binding molecule preferably a human monoclonal antibody hereof, at least one functional variant thereof, at least one immunoconjugate hereof or a combination thereof. In addition to that, the compositions may comprise inter alia stabilizing molecules, such as albumin or polyethylene glycol, or salts. Preferably, the salts used are salts that retain the desired biological activity of the binding molecules and do not impart any undesired toxicological effects. If necessary, the human binding molecules hereof may be coated in or on a material to protect them from the action of acids or other natural or non-natural conditions that may inactivate the binding molecules.

In yet a further aspect, provided are compositions comprising at least one nucleic acid molecule as defined herein. The compositions may comprise aqueous solutions such as aqueous solutions containing salts (e.g., NaCl or salts as described above), detergents (e.g., SDS) and/or other suitable components.

Furthermore, described are pharmaceutical compositions comprising at least one binding molecule such as a human monoclonal antibody hereof (or functional fragment or variant thereof), at least one immunoconjugate hereof, at least one composition hereof, or combinations thereof. The pharmaceutical composition hereof further comprises at least one pharmaceutically acceptable excipient.

In one embodiment, the pharmaceutical compositions may comprise two or more binding molecules that have killing activity against a bacterial organism, e.g., a *Staphylococcus* species. In an embodiment, the binding molecules exhibit synergistic killing activity, when used in combination. In other words, the compositions comprise at least two binding molecules having killing activity, characterized in that the binding molecules act synergistically in killing a bacterial organism such as, e.g., a *Staphylococcus* species. As used herein, the term "synergistic" means that the combined effect of the binding molecules when used in combination is greater than their additive effects when used individually. The synergistically acting binding molecules may bind to different structures on the same of distinct fragments of the bacterial organism. In an embodiment the binding molecules acting synergistically in killing a bacterial organism may also be capable of killing other bacterial organisms synergistically. A way of calculating synergy is by means of the combination index. The concept of the combination index (CI) has been described by Chou and Talalay, 1984. The two or more binding molecules having synergistic activity have distinct modes of action. For instance, a first binding molecule may have opsonizing activity, while the second binding molecule has another activity increasing/augmenting/enhancing phagocytosis or a first binding molecule may have intrinsic (killing) activity, e.g., reduce or inhibit bacterial growth or directly kill bacteria, while the second binding molecule increases the sensitivity of bacteria to antibiotic treatment. It is to be understood that other combinations are also contemplated herein.

A pharmaceutical composition hereof can further comprise at least one other therapeutic, prophylactic and/or diagnostic agent. Preferably, the pharmaceutical composition comprises at least one other prophylactic and/or therapeutic agent. Preferably, the further therapeutic and/or prophylactic agents are agents capable of preventing and/or treating a bacterial, e.g., staphylococcal, infection and/or a condition resulting from such an infection. Therapeutic and/or prophylactic agents include, but are not limited to, anti-bacterial agents. Such agents can be binding molecules, small molecules, organic or inorganic compounds, enzymes, polynucleotide sequences, anti-microbial peptides, etc. Other agents that are currently used to treat patients infected with bacterial infections such as staphylococcal infections are antibiotics such as methicillin, $2^{nd}$ and $3^{rd}$ generation cephalosporins, aminoglycosides, Carbapenems, Macrolides, Ketolides, Quinolones and miscellaneous antibiotics such as daptomycin, linezolid, nitrofurantoin, quinupristin/dalfopristin, trimethoprim/sulfa, vancomycin. These can be used in combination with the binding molecules hereof. Agents capable of preventing and/or treating an infection with bacteria and/or a condition resulting from such an infection that are in the experimental phase might also be used as other therapeutic and/or prophylactic agents useful herein.

The binding molecules or pharmaceutical compositions hereof can be tested in suitable animal model systems prior to use in humans. Such animal model systems include, but are not limited to, murine sepsis and peritonitis models, rat sepsis and endocarditis models, and rabbit endocarditis models.

Typically, pharmaceutical compositions must be sterile and stable under the conditions of manufacture and storage. The binding molecules, immunoconjugates, nucleic acid molecules or compositions hereof can be in powder form for reconstitution in the appropriate pharmaceutically acceptable excipient before or at the time of delivery. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Alternatively, the binding molecules, immunoconjugates, nucleic acid molecules or compositions hereof can be in solution and the appropriate pharmaceutically acceptable excipient can be added and/or mixed before or at the time of delivery to provide a unit dosage injectable form. Preferably, the pharmaceutically acceptable excipient used herein is suitable to high drug concentration, can maintain proper fluidity and, if necessary, can delay absorption.

The choice of the optimal route of administration of the pharmaceutical compositions will be influenced by several factors including the physico-chemical properties of the active molecules within the compositions, the urgency of the clinical situation and the relationship of the plasma concentrations of the active molecules to the desired therapeutic effect. For instance, if necessary, the binding molecules hereof can be prepared with carriers that will protect them against rapid release, such as a controlled release formulation, including implants, transdermal patches, and microencapsulated delivery systems. Biodegradable, biocompatible polymers can inter alia be used, such as ethylene vinyl acetate, polyanhydrides, polyglycolic acid, collagen, polyorthoesters, and polylactic acid. Furthermore, it may be necessary to coat the binding molecules with, or co-administer the binding molecules with, a material or compound that prevents the inactivation of the human binding molecules. For example, the binding molecules may be administered to a subject in an appropriate carrier, for example, liposomes or a diluent.

The routes of administration can be divided into two main categories, oral and parenteral administration. The preferred administration route is intravenous.

Oral dosage forms can be formulated inter alia as tablets, troches, lozenges, aqueous or oily suspensions, dispersible powders or granules, emulsions, hard capsules, soft gelatin capsules, syrups or elixirs, pills, dragees, liquids, gels, or slurries. These formulations can contain pharmaceutically excipients including, but not limited to, inert diluents, granulating and disintegrating agents, binding agents, lubricating agents, preservatives, coloring, flavoring or sweetening agents, vegetable or mineral oils, wetting agents, and thickening agents.

The pharmaceutical compositions hereof can also be formulated for parenteral administration. Formulations for parenteral administration can be inter alia in the form of aqueous or non-aqueous isotonic sterile non-toxic injection or infusion solutions or suspensions. The solutions or suspensions may comprise agents that are non-toxic to recipients at the dosages and concentrations employed such as 1,3-butanediol, Ringer's solution, Hank's solution, isotonic sodium chloride solution, oils, fatty acids, local anesthetic agents, preservatives, buffers, viscosity or solubility increasing agents, water-soluble antioxidants, oil-soluble antioxidants, and metal chelating agents.

In a further aspect, the binding molecules such as human monoclonal antibodies (functional fragments and variants thereof), immunoconjugates, compositions, or pharmaceutical compositions hereof can be used as a medicament. So, a method of treatment and/or prevention of a bacterial (gram-positive and/or gram-negative), e.g., a staphylococcal, infection using the binding molecules, immunoconjugates, compositions, or pharmaceutical compositions hereof is another part hereof. The above-mentioned molecules can inter alia be used in the diagnosis, prophylaxis, treatment, or combination thereof, of a bacterial infection. They are suitable for treatment of yet untreated patients suffering from a bacterial infection and patients who have been or are treated for a bacterial infection. They may be used for patients such as hospitalized infants, premature infants, burn victims, elderly patients, immunocompromised patients, immunosuppressed patients, patient undergoing an invasive procedure, and health care workers. Each administration may protect against further infection by the bacterial organism for up to three or four weeks and/or will retard the onset or progress of the symptoms associated with the infection. The binding molecules hereof may also increase the effectiveness of existing antibiotic treatment by increasing the sensitivity of the bacterium to the antibiotic, may stimulate the immune system to attack the bacterium in ways other than through opsonization. This activation may result in long lasting protection to the infection bacterium. Furthermore, the binding molecules hereof may directly inhibit the growth of the bacterium or inhibit virulence factors required for its survival during the infection.

The above-mentioned molecules or compositions may be employed in conjunction with other molecules useful in diagnosis, prophylaxis and/or treatment. They can be used in vitro, ex vivo or in vivo. For instance, the binding molecules such as human monoclonal antibodies (or functional variants thereof), immunoconjugates, compositions or pharmaceutical compositions hereof can be co-administered with a vaccine against the bacterial organism (if available). Alternatively, the vaccine may also be administered before or after administration of the molecules hereof. Instead of a vaccine, anti-bacterial agents can also be employed in conjunction with the binding molecules hereof. Suitable anti-bacterial agents are mentioned above.

The molecules are typically formulated in the compositions and pharmaceutical compositions hereof in a therapeutically or diagnostically effective amount. Alternatively, they may be formulated and administered separately. For instance, the other molecules such as the anti-bacterial agents may be applied systemically, while the binding molecules hereof may be applied intrathecally or intraventricularly.

Dosage regimens can be adjusted to provide the optimum desired response (e.g., a therapeutic response). A suitable dosage range may, for instance, be 0.1-100 mg/kg body weight, preferably 0.5-15 mg/kg body weight. Furthermore, for example, a single bolus may be administered, several divided doses may be administered over time or the dose may be proportionally reduced or increased as indicated by the exigencies of the therapeutic situation. The molecules and compositions hereof are preferably sterile. Methods to render these molecules and compositions sterile are well known in the art. The other molecules useful in diagnosis, prophylaxis and/or treatment can be administered in a similar dosage regimen as proposed for the binding molecules hereof. If the other molecules are administered separately, they may be administered to a patient prior to (e.g., 2 minutes, 5 minutes, 10 minutes, 15 minutes, 30 minutes, 45 minutes, 60 minutes, 2 hours, 4 hours, 6 hours, 8 hours, 10 hours, 12 hours, 14 hours, 16 hours, 18 hours, 20 hours, 22 hours, 24 hours, 2 days, 3 days, 4 days, 5 days, 7 days, 2 weeks, 4 weeks or 6 weeks before), concomitantly with, or subsequent to (e.g., 2 minutes, 5 minutes, 10 minutes, 15 minutes, 30 minutes, 45 minutes, 60 minutes, 2 hours, 4 hours, 6 hours, 8 hours, 10 hours, 12 hours, 14 hours, 16 hours, 18 hours, 20 hours, 22 hours, 24 hours, 2 days, 3 days, 4 days, 5 days, 7 days, 2 weeks, 4 weeks or 6 weeks after) the administration of one or more of the human binding molecules or pharmaceutical compositions hereof. The exact dosing regimen is usually sorted out during clinical trials in human patients.

Human binding molecules and pharmaceutical compositions comprising the human binding molecules are particularly useful, and often preferred, when to be administered to human beings as in vivo therapeutic agents, since recipient immune response to the administered antibody will often be substantially less than that occasioned by administration of a monoclonal murine, chimeric or humanized binding molecule.

In another aspect, described is the use of the binding molecules such as killing human monoclonal antibodies (functional fragments and variants thereof), immunoconjugates, nucleic acid molecules, compositions or pharmaceutical compositions hereof in the preparation of a medicament for the diagnosis, prophylaxis, treatment, or combination thereof, of a bacterial (gram-positive and/or gram-negative), e.g., staphylococcal infection.

Next to that, kits comprising at least one binding molecule such as a killing human monoclonal antibody (functional fragments and variants thereof), at least one immunoconjugate, at least one nucleic acid molecule, at least one composition, at least one pharmaceutical composition, at least one vector, at least one host hereof or a combination thereof are also a part hereof. Optionally, the above-described components of the kits hereof are packed in suitable containers and labeled for diagnosis, prophylaxis and/or treatment of the indicated conditions. The above-mentioned components may be stored in unit or multi-dose containers as an aqueous, preferably sterile, solution or as a lyophilized, preferably sterile, formulation for reconstitution. The containers may be formed from a variety of materials such as glass or plastic and may have a sterile access port (for example, the container may be an intravenous solution bag or a vial having a stopper pierceable by a hypodermic injection needle). The kit may further comprise more containers comprising a pharmaceutically acceptable buffer. It may further include other materials desirable from a commercial and user standpoint, including other buffers, diluents, filters, needles, syringes, culture medium for one or more of the suitable hosts and, possibly, even at least one other therapeutic, prophylactic or diagnostic agent. Associated with the kits can be instructions customarily included in commercial packages of therapeutic, prophylactic or diagnostic products, that contain information about, for example, the indications, usage, dosage, manufacture, administration, contra-indications and/or warnings concerning the use of such therapeutic, prophylactic or diagnostic products.

The binding molecules hereof may also be used to coat medical devices or polymeric biomaterials.

Further described is a method of detecting a bacterial organism (gram-positive and/or gram-negative) in a sample, wherein the method comprises the steps of (a) contacting a sample with a diagnostically effective amount of a binding molecule (functional fragments and variants thereof) or an immunoconjugate hereof, and (b) determining whether the binding molecule or immunoconjugate specifically binds to a molecule of the sample. Preferably, the method is used to detect a *Staphylococcus* in a sample. The sample may be a biological sample including, but not limited to blood, serum, urine, tissue or other biological material from (potentially) infected subjects, or a non-biological sample such as water, drink, etc. The (potentially) infected subjects may be human subjects, but also animals that are suspected as carriers of such a bacterial organism might be tested for the presence of the organism using the human binding molecules or immunoconjugates hereof. The sample may first be manipulated to make it more suitable for the method of detection. Manipulation means inter alia treating the sample suspected to contain and/or containing the bacterial organism in such a way that the organism will disintegrate into antigenic components such as proteins, (poly)peptides or other antigenic fragments. Preferably, the human binding molecules or immunoconjugates hereof are contacted with the sample under conditions which allow the formation of an immunological complex between the human binding molecules and the bacterial organism or antigenic components thereof that may be present in the sample. The formation of an immunological complex, if any, indicating the presence of the bacterial organism in the sample, is then detected and measured by suitable means. Such methods include, inter alia, homogeneous and heterogeneous binding immunoassays, such as radio-immunoassays (RIA), ELISA, immunofluorescence, immunohistochemistry, FACS, BIACORE and Western blot analyses.

Preferred assay techniques, especially for large-scale clinical screening of patient sera and blood and blood-derived products are ELISA and Western blot techniques. ELISA tests are particularly preferred. For use as reagents in these assays, the binding molecules or immunoconjugates hereof are conveniently bonded to the inside surface of microtiter wells. The binding molecules or immunoconjugates hereof may be directly bonded to the microtiter well. However, maximum binding of the binding molecules or immunoconjugates hereof to the wells might be accomplished by pretreating the wells with polylysine prior to the addition of the binding molecules or immunoconjugates hereof. Furthermore, the binding molecules or immunoconjugates hereof may be covalently attached by known means to the wells. Generally, the binding molecules or immunoconjugates are used between 0.01 to 100 μg/ml for coating, although higher as well as lower amounts may also be used. Samples are then added to the wells coated with the binding molecules or immunoconjugates hereof.

Furthermore, binding molecules hereof can be used to identify specific binding structures of a bacterial organism, e.g., a *Staphylococcus*. The binding structures can be epitopes on proteins and/or polypeptides. They can be linear, but also structural and/or conformational. In one embodiment, the binding structures can be analyzed by means of PEPSCAN analysis (see inter alia WO 84/03564, WO 93/09872, Slootstra et al., 1996). Alternatively, a random peptide library comprising peptides from a protein of a bacterial organism can be screened for peptides capable of binding to the binding molecules hereof. The binding structures/peptides/epitopes found can be used as vaccines and for the diagnosis of bacterial infections. In case fragments other than proteins and/or polypeptides are bound by the binding molecules binding structures can be identified by mass spectrometry, high performance liquid chromatography and nuclear magnetic resonance.

In a further aspect, provided is a method of screening a binding molecule (or a functional fragment or variant thereof) for specific binding to the same epitope of a bacterial organism (gram-positive and/or gram-negative), e.g., *Staphylococcus*, as the epitope bound by a human binding molecule hereof, wherein the method comprises the steps of (a) contacting a binding molecule to be screened, a binding molecule hereof and a bacterial organism or fragment thereof, (b) measure if the binding molecule to be screened is capable of competing for specifically binding to the bacterial organism or fragment thereof with the binding molecule hereof. In a further step it may be determined, if the screened binding molecules that are capable of competing for specifically binding to the bacterial organism or fragment thereof have killing activity, e.g., opsonic activity. A binding molecule that is capable of competing for specifically binding to the bacterial organism or a fragment thereof with the binding molecule hereof is another part hereof. In the above-described screening method, "specifically binding to the same epitope" also contemplates specific binding to substantially or essentially the same epitope as the epitope bound by the a binding molecule hereof. The capacity to block, or compete with, the binding of the binding molecules hereof to the bacterial organism typically indicates that a binding molecule to be screened binds to an epitope or binding site on the bacterial organism that structurally overlaps with the binding site on the bacterial organism that is immunospecifically recognized by the binding molecules hereof. Alternatively, this can indicate that a binding molecule to be screened binds to an epitope or binding site which is sufficiently proximal to the binding site immunospecifically recognized by the binding molecules hereof to sterically or otherwise inhibit binding of the binding molecules hereof to the bacterial organism.

In general, competitive inhibition is measured by means of an assay, wherein an antigen composition, i.e., a composition comprising a bacterial organism or fragments thereof, is admixed with reference binding molecules, i.e., the binding molecules hereof, and binding molecules to be screened. Usually, the binding molecules to be screened are present in excess. Protocols based upon ELISAs and Western blotting are suitable for use in such simple competition studies. By using species or isotype secondary antibodies one will be able to detect only the bound reference binding molecules, the binding of which will be reduced by the presence of a binding molecule to be screened that recognizes substantially the same epitope. In conducting a binding molecule competition study between a reference binding molecule and any binding molecule to be screened (irrespective of species or isotype), one may first label the reference binding molecule with a detectable label, such as, e.g., biotin, an enzymatic, a radioactive or other label to enable subsequent identification. Binding molecules identified by these competition assays ("competitive binding molecules" or "cross-reactive binding molecules") include, but are not limited to, antibodies, antibody fragments and other binding agents that bind to an epitope or binding site bound by the reference binding molecule, i.e., a binding molecule hereof, as well as antibodies, antibody fragments and other binding agents that bind to an epitope or binding site sufficiently proximal to an epitope bound by the reference binding molecule for competitive binding between the binding molecules to be screened and the reference binding molecule to occur. Preferably, competitive binding molecules hereof will, when present in excess, inhibit specific binding of a reference binding molecule to a selected target species by at least 10%, preferably by at least 25%, more preferably by at least 50%, and most preferably by at least 75%-90% or even greater. The identification of one or more competitive binding molecules that bind to about, substantially, essentially or at the same epitope as the binding molecules hereof is a straightforward technical matter. As the identification of competitive binding molecules is determined in comparison to a reference binding molecule, i.e., a binding molecule hereof, it will be understood that actually determining the epitope to which the reference binding molecule and the competitive binding molecule bind is not in any way required in order to identify a competitive binding molecule that binds to the same or substantially the same epitope as the reference binding molecule.

EXAMPLES

The following illustrative Examples are provided.

Example 1

Construction of scFv Phage Display Libraries Using RNA Extracted from Donors Screened for Opsonic Activity Samples of blood were taken from donors reporting a recent gram-positive bacterial infection as well as healthy adults between 25-50 years of age. Peripheral blood leukocytes were isolated by centrifugation and the blood serum was saved and frozen at −80° C. Donor serum was screened for opsonic activity using a FACS-based phagocytosis assay (Cantinieaux et al., 1989) and compared to a pool of normal healthy donor serum. Sera from donors having a higher phagocytic activity compared to normal serum were chosen to use for the generation of phage display libraries. Total RNA was prepared from the peripheral blood leukocytes of these donors using organic phase separation and subsequent ethanol precipitation. The obtained RNA was dissolved in RNAse-free water and the concentration was determined by OD 260 nm measurement. Thereafter, the RNA was diluted to a concentration of 100 ng/μl. Next, 1 μg of RNA was converted into cDNA as follows: To 10 μl total RNA, 13 μl DEPC-treated ultrapure water and 1 μl random hexamers (500 ng/μl) were added and the obtained mixture was heated at 65° C. for 5 minutes and quickly cooled on wet-ice. Then, 8 μl 5 X First-Strand buffer, 2 μl dNTP (10 mM each), 2 μl DTT (0.1 M), 2 μl RNAse-inhibitor (40 U/μl) and 2 μl SUPERSCRIPT™ III MMLV reverse transcriptase (200 U/μl) were added to the mixture, incubated at room temperature for 5 minutes and incubated for 1 hour at 50° C. The reaction was terminated by heat inactivation, i.e., by incubating the mixture for 15 minutes at 75° C. The obtained cDNA products were diluted to a final volume of 200 μl with DEPC-treated ultrapure water. The OD 260 nm of a 50 times diluted solution (in 10 mM Tris buffer) of the dilution of the obtained cDNA products was used to determine the cDNA concentration. For each donor 5 to 10 μl of the diluted cDNA products were used as template for PCR amplification of the immunoglobulin gamma heavy chain family and kappa or lambda light chain sequences using specific oligonucleotide primers (see Tables 1-7). In addition, for one donor PCR amplification of the immunoglobulin mu heavy chain family and kappa or lambda light chain sequences was carried out. PCR reaction mixtures contained, besides the diluted cDNA products, pmol sense primer and 25 pmol anti-sense primer in a final volume of 50 μl of 20 mM Tris-HCl (pH 8.4), 50 mM KCl, 1.5 mM $MgCl_2$, 250 μM dNTPs and 1.25 units Taq polymerase. In a heated-lid thermal cycler having a temperature of 96° C., the mixtures obtained were quickly melted for 2 minutes, followed by 30 cycles of: 30 seconds at 96° C., 30 seconds at 55° C. or 60° C. and 60 seconds at 72° C. Finally, the samples were incubated 10 minutes at 72° C. and refrigerated at 4° C. until further use.

In a first round amplification, each of eighteen light chain variable region sense primers (twelve for the lambda light chain (see Table 1; the HuVL1A-Back, HuVL1B-Back and HuVL1C-Back sense primers were mixed to equimolarity before use, as well as the HuVL9-Back and HuVL10-Back sense primers) and six for the kappa light chain (see Table 2)) were combined with an anti-sense primer recognizing the C-kappa constant region called HuCK-FOR 5'-ACACTCTCCCCTGTTGAAGCTCTT-3' (SEQ ID NO:37) or C-lambda constant region HuCL2-FOR 5'-TGAACATTCTGTAGGGGCCACTG-3' (SEQ ID NO:38) and HuCL7-FOR 5'-AGAGCATTCTGCAGGGGCCACTG-3' (SEQ ID NO:39) (the HuCL2-FOR and HuCL7-FOR anti-sense primers were mixed to equimolarity before use), yielding 15 products of about 650 base pairs. These products were purified on agarose gel and isolated from the gel using QIAGEN™ gel-extraction columns. 1/10 of each of the isolated products was used in an identical PCR reaction as described above using eighteen sense primers, whereby each lambda light chain sense primer was combined with one of the three Jlambda-region specific anti-sense primers and each kappa light chain sense primer was combined with one of the five Jkappa-region specific anti-sense primers (see Table 3; the HuVL1A-Back-SAL, HuVL1B-Back-SAL and HuVL1C-Back-SAL sense primers were mixed to equimolarity before use, as well as the HuVL9-Back-SAL and HuVL10-Back-SAL sense primers). The sense primers used in the second amplification were the same primers as used in the first amplification, but extended with restriction sites (see Table 3) to enable directed cloning in the phage display vector PDV-C06 (SEQ ID NO:40). This resulted in 57 products of approximately 400 base pairs that were pooled as shown in Table 4 to maintain the natural distribution of the different J segments and light chain families within the library and not to over or under represent certain families. The pooled products were purified using QIAGEN™ PCR purification columns. In the next step, 3 μg of pooled products and 100 μg PDV-006 vector were digested with SalI and NotI and purified from gel. Thereafter, a ligation was performed overnight at 16° C. as follows. To 500 ng PDV-006 vector either 35, 70 or 140 ng pooled products were added in a total volume of 50 μl ligation mix containing 50 mM Tris-HCl (pH 7.5), 10 mM $MgCl_2$, 10 mM DTT, 1 mM ATP, 25 μg/ml BSA and 2.5 μl T4 DNA Ligase (400 U/μl). The ligation mixes were purified by phenol/chloroform extraction, followed by a chloroform extraction and ethanol precipitation, methods well known to the skilled artisan. The DNA obtained was dissolved in 50 μl 10 mM Tris-HCl pH 8.5 and per ligation mix 1 or 2 μl was electroporated into 40 μl of TG1 competent *E. coli* bacteria according to the manufacturer's protocol (Stratagene). Transformants were grown overnight at 37° C. on 2TY agar supplemented with 50 μg/ml ampicillin and 4.5% glucose. Colonies were counted to determine the optimal vector to insert ratio. From the ligation mix with the optimal ratio, multiple 1 or 2 μl aliquots were electroporated as above and transformants were grown overnight at 37° C., typically yielding ~$10^7$ colonies. A (sub) library of variable light chain regions was obtained by scraping the transformants from the agar plates. This (sub)library was directly used for plasmid DNA preparation using a QIAGEN™ QIAFilter MAXI prep kit.

Heavy chain immunoglobulin sequences were amplified from the same cDNA preparations in a similar two round PCR procedure and identical reaction parameters as described above for the light chain regions with the proviso that the primers depicted in Tables 5 and 6 were used. The first amplification was performed using a set of eight sense directed primers (see Table 5; the HuVH1B/7A-Back and HuVH1C-Back sense primers were mixed to equimolarity before use) each combined with an IgG specific constant region anti-sense primer called HuCIgG 5'-GTC CAC CTT GGT GTT GCT GGG CTT-3' (SEQ ID NO:41) yielding seven products of about 650 base pairs. For one donor an IgM specific constant region anti-sense primer called HuCIgM 5'-TGG AAG AGG CAC GTT CTT TTC TTT-3' (SEQ ID NO:42) was used instead of primer HuCIgG. The products were purified on agarose gel and isolated from the gel using QIAGEN™ gel-extraction columns. 1/10 of each of the isolated products was used in an identical PCR reaction as described above using eight sense primers, whereby each heavy chain sense primer was combined with one of the four JH-region specific anti-sense primers (see Table 6; the HuVH1B/7A-Back-Sfi and HuVH1C-Back-Sfi sense primers were mixed to equimolarity before use). The sense primers used in the second round were the same primers as used in the first amplification, but extended with restriction sites (see Table 6) to enable directed cloning in the light chain (sub)library vector. This resulted in 28 products of approximately 400 base pairs that were pooled as shown in Table 7 to maintain the natural distribution of the different J segments and heavy chain families within the library and not to over or under represent certain families. The pooled products were purified using QIAGEN™ PCR purification columns. Next, 3 μg of purified products was digested with SfiI and XhoI and ligated in the light chain (sub)library vector, which was cut with the same restriction enzymes, using the same ligation procedure and volumes as described above for the light chain (sub)library. Ligation mix purification and subsequent transformation of the resulting definitive library was also performed as described above for the light chain (sub)library. All bacteria, typically ~$10^7$, were harvested in 2TY culture medium containing 50 μg/ml ampicillin and 4.5% glucose, mixed with glycerol to 15% (v/v) and frozen in 1.5 ml aliquots at −80° C. Rescue and selection of each library were performed as described below. The various libraries were named GPB-05-M01, GPB-05-G01, GPB-05-G02, GPB-05-G03, GPB-05-G04 and GPB-05-G05. Two other libraries, RAB-03-G01 and RAB-04-G01, were constructed using a method similar to the procedure above, as described previously in international patent application WO 2005/118644.

Example 2

Construction of scFv Phage Display Libraries Using RNA Extracted from Memory B Cells Peripheral blood was collected from normal healthy donors, convalescent donors or vaccinated donors by venapunction using EDTA anti-coagulation sample tubes. A blood sample (45 ml) was diluted twice with PBS and 30 ml aliquots were underlayed with 10 ml Ficoll-Hypaque (Pharmacia) and centrifuged at 900×g for 20 minutes at room temperature without breaks. The supernatant was removed carefully to just above the white layer containing the lymphocytic and thrombocytic fraction. Next, this layer was carefully removed (~10 ml), transferred to a fresh 50 ml tube and washed three times with 40 ml PBS and spun at 400×g for 10 minutes at room temperature to remove thrombocytes. The obtained pellet containing lymphocytes was resuspended in RPMI medium containing 2% FBS and the cell number was determined by cell counting. Approximately $1\times10^8$ lymphocytes were stained for fluorescent cell sorting using CD24, CD27 and surface IgM as markers for the isolation of switched and IgM memory B cells. A Becton Dickinson Digital Vantage apparatus set in Yield Mode was used for physical memory B cell sorting and isolation. Lymphocytes were gated as the small compact population from the FSC/SSC window. Memory B cells (CD24+/CD27+) were subsequently separated from naive B cells (CD24+/CD27−) and memory T cells (CD24−/CD27+). In a next step, IgM memory B cells (IgM+) were separated from switch memory B cells (IgM−) using IgM expression. In this step IgM memory B cells and switch memory B cells were sorted in separate sample tubes. $1\times10^5$ to $1\times10^6$ cells of each population were collected in DMEM/50% FBS and after completion of the sort they were each centrifuged at 400×g for 10 minutes. The sorted IgM memory B cells were then used as starting material for library construction according to the method described in Example 1, using primer HuCIgM in the first round amplification of heavy chain immunoglobulin sequences. The various libraries obtained were named MEM-05-M01, MEM-05-M02, MEM-05-M03, MEM-05-M04, MEM-05-M05, MEM-05-M06, MEM-05-M07, MEM-05-M08, MEM-05-M09 and MEM-05-M10.

Example 3

Selection of Phages Carrying Single Chain Fv Fragments Specifically Binding to Staphylococci Antibody fragments were selected using antibody phage display libraries, general phage display technology and MABSTRACT® technology, essentially as described in U.S. Pat. No. 6,265,150 and in WO 98/15833 (both of which are incorporated by reference herein). The antibody phage libraries used were screened donor libraries prepared as described in Example 1, IgM memory libraries prepared as described in Example 2 and a semi-synthetic scFv phage library (JK1994) which has been described in de Kruif et al., 1995b. The methods and helper phages as described in WO 02/103012 (incorporated by reference herein) were used herein. For identifying phage antibodies recognizing staphylococci, phage selection experiments were performed using live bacteria in suspension. The clinical isolates used for selection and screening are described in Table 8. The isolates are different based on RFLP-typing.

Bacteria were grown overnight at 37° C. on blood agar plates and scraped into RPMI buffer containing 1 mg/ml of Rabbit IgG and 1% BSA at a concentration of $5\times10^9$ bacteria/ml and incubated for 60 minutes at room temperature. An aliquot of a phage library (approximately $10^{13}$ cfu, amplified using CT helper phage (see WO 02/103012)) was blocked in blocking buffer (2% ELK in PBS) for 1 to 2 hours at room temperature. The blocked phage library was added to the blocked bacterial suspension making a total volume of 1.5 ml and incubated for 2 hours at room temperature in an end-over-end rotor (5 rpm). The suspension was centrifuged at 6800×g for 3 minutes at room temperature and the supernatant was discarded. Bacteria were washed five times with RPMI buffer containing 1% BSA and 0.05% v/v TWEEN-20™, then five times with RPMI buffer containing 1% BSA to remove unbound phages. Bound phages were eluted from the antigen by incubation with 1 ml of 0.1 M triethylamine for 10 minutes at room temperature in an end-over-end rotor (5 rpm). The entire content of the tube was then mixed with 0.5 ml of 1 M Tris-HCl pH 7.5 to neutralize the pH. This mixture was used to infect 5 ml of an XL1-Blue *E. coli* culture that had been grown at 37° C. to an OD 600 nm of approximately 0.3. The phages were allowed to infect the XL1-Blue bacteria for 30 minutes at 37° C. Then, the mixture was centrifuged for 10 minutes at 3200*g at room temperature and the bacterial pellet was resuspended in 0.5 ml 2-trypton yeast extract (2TY) medium. The obtained bacterial suspension was divided over two 2TY agar plates supplemented with tetracyclin, ampicillin and glucose. After overnight incubation of the plates at 37° C., the colonies were scraped from the plates and used to prepare an enriched phage library, essentially as described by De Kruif et al. (1995a) and WO 02/103012. Briefly, scraped bacteria were used to inoculate 2TY medium containing ampicillin, tetracycline and glucose and grown at a temperature of 37° C. to an OD 600 nm of ~0.3. CT helper phages were added and allowed to infect the bacteria after which the medium was changed to 2TY containing ampicillin, tetracycline and kanamycin. Incubation was continued overnight at 30° C. The next day, the bacteria were removed from the 2TY medium by centrifugation after which the phages in the medium were precipitated using polyethylene glycol (PEG) 6000/NaCl Finally, the phages were dissolved in 2 ml of PBS with 1% bovine serum albumin (BSA), filter-sterilized and used for the next round of selection.

Typically, two rounds of selections were performed before isolation of individual phage antibodies. Selection was carried out twice on the same strain of bacteria or different strains were used sequentially (see Table 8 for selection strains). After the second round of selection, individual *E. coli* colonies were used to prepare monoclonal phage antibodies. Essentially, individual colonies were grown to log-phase in 96-well plate format and infected with CT helper phages after which phage antibody production was allowed to proceed overnight. The produced phage antibodies were PEG/NaCl-precipitated and filter-sterilized and tested in ELISA and/or FACS for binding to *Staphylococcus* prepared as described supra.

Example 4

Validation of the Staphylococci Specific Single-Chain Phage Antibodies

Selected single-chain phage antibodies that were obtained in the screens described above were validated in FACS for specific staphylococcal binding activity, i.e., binding to one or more staphylococcal strain prepared as described supra but lacking binding to *Enterococcus* as measured by a FACS-based *enterococcus* binding assay. Phage antibodies were blocked with FACS buffer (20 mM HEPES buffer pH 7.5, 100 mM NaCl, 1% BSA) for 20 minutes on ice. For each staining, $1\times10^9$ bacterial cells, scraped from blood agar plates and washed in FACS buffer, were added to each eppendorf tube. The bacteria were blocked with FACS buffer containing 15% human serum (Biowhittaker) for 30 minutes at room temperature. The bacteria were pelleted by centrifugation at 1700×g for 3 minutes at 4° C. and resuspended with the blocked phage antibodies and incubated for 1.5 hours on ice. The bacteria were then washed with FACS buffer and sequentially incubated with murine biotinylated anti-M13 antibodies (RDI) followed by strepavidin-PE. The cells were fixed in buffered 4% formaldehyde and analyzed on a FACS caliber. SC05-132 and SC05-133 (both selected from RAB-03-G01 on strain Cowan in suspension) showed staining on all clinical isolates tested indicating that they recognize a pan-staphylococcal target. SC02-430 (selected from JK1994 on strain Cowan in suspension) showed specific binding to the staphylococcal strain Cowan (see Table 9). In further selections, the single-chain phage antibodies called SC06-166, SC06-171, SC06-176, SC06-187, SC06-193, SC06-249, SC06-273, SC06-389, SC06-403, SC06-406, SC06-410, SC06-446, SC06-450, SC06-452, SC06-453, SC06-464, SC06-471, SC06-516, SC06-517, SC06-526, SC06-528, SC06-531, SC06-533, SC06-536, SC06-537, SC06-538, SC06-540, SC06-544, SC06-566, SC06-625 were obtained. These antibodies bound at least one of the clinical isolates tested (see Table 9). SC06-166, SC06-171, SC06-176 and SC06-187 were selected from immune libraries, while the other phage antibodies were selected from IgM memory B cell libraries.

To test for non-specific reactivity against non-bacterial antigens, an ELISA assay was used. The complex antigens 5% FBS, 2% ELK and 1% BSA were coated overnight to MAXISORP™ ELISA plates. Selected single-chain phage antibodies were incubated for 15 minutes in an equal volume of PBS containing 1% BSA to obtain blocked phage antibodies. The plates were emptied, and the blocked single-chain phage antibodies were added to the wells. Incubation was allowed to proceed for two hours at room temperature, the plates were washed in PBS containing 0.1% v/v TWEEN-20™ and bound phage antibodies were detected by means of OD 492 nm measurement using an anti-M13 antibody conjugated to peroxidase. As a control, the procedure was performed simultaneously without single-chain phage antibody, with a negative control single-chain phage antibody directed against West Nile virus envelope protein (SC04-374). As shown in Table 10, the selected phage antibodies called SC02-430, SC05-132 and SC05-133, did not display any detectable binding to the negative control antigens FBS, ELK and BSA.

Example 5

Characterization of the Staphylococci Specific scFvs

From the selected specific single-chain phage antibody (scFv) clones, plasmid DNA was obtained and nucleotide sequences were determined according to standard techniques. The nucleotide sequences of the scFvs (including restriction sites for cloning) called SC02-430, SC05-132, and SC05-133 are shown in SEQ ID NO:19, SEQ ID NO:21 and SEQ ID NO:23, respectively. The amino acid sequences of the scFvs called SC02-430, SC05-132 and SC05-133 are shown in SEQ ID NO:20, SEQ ID NO:22 and SEQ ID NO:24, respectively.

The VH and VL gene identity (see I. M. Tomlinson, S. C. Williams, O. Ignatovitch, S. J. Corbett, G. Winter, *VBASE Sequence Directory*, Cambridge United Kingdom: MRC Centre for Protein Engineering (1997)) and the CDR sequences of the scFvs specifically binding staphylococci are depicted in Tables 11 and 12, respectively.

Similar to the single-chain phage antibodies disclosed above, the nucleotide and amino acid sequence, VL and VH gene identity and CDR sequences of the single-chain phage antibodies called SC06-166, SC06-171, SC06-176, SC06-187, SC06-193, SC06-249, SC06-273, SC06-389, SC06-403, SC06-406, SC06-410, SC06-446, SC06-450, SC06-452, SC06-453, SC06-464, SC06-471, SC06-516, SC06-517, SC06-526, SC06-528, SC06-531, SC06-533, SC06-536, SC06-537, SC06-538, SC06-540, SC06-544, SC06-566 and SC06-625 were determined (data not shown).

Example 6

Construction of Fully Human Immunoglobulin Molecules (Human Monoclonal Anti-Staphylococci Antibodies) from the Selected Anti-Staphylococci Single Chain Fvs The heavy and light chain variable region of SC02-430 was PCR-amplified using oligonucleotides to append restriction sites and/or sequences for expression in the IgG expression vectors pSyn-C03-HCγ1 (SEQ ID NO:43) and pSyn-C04-Cλ (SEQ ID NO:44). The heavy chain variable region of SC02-430 was cloned into the vector pSyn-C03-HCγ1; the light chain variable region of SC02-430 was cloned into the vector pSyn-004-Cλ. The VL lambda gene was first amplified using the following oligonucleotides set; 5L-B (SEQ ID NO:45) and sy3L-A (SEQ ID NO:46) and the PCR product was cloned into vector pSyn-004-Cλ. The nucleotide sequence of the construct was verified according to standard techniques known to the skilled artisan. The VH gene was first amplified using the following oligonucleotide set: 5H-F (SEQ ID NO:47) and sy3H-A (SEQ ID NO:48). Thereafter, the PCR product was cloned into vector pSyn-C03-HCγ1 and the nucleotide sequence was verified according to standard techniques known to the skilled person in the art.

Heavy and light chain variable regions of the scFv called SC05-132, SC05-133, SC06-166, SC06-171, SC06-176, SC06-187, SC06-193, SC06-249, SC06-273, SC06-389, SC06-403, SC06-406, SC06-410, SC06-446, SC06-450, SC06-452, SC06-453, SC06-464, SC06-471, SC06-516, SC06-517, SC06-526, SC06-528, SC06-531, SC06-533, SC06-536, SC06-537, SC06-538, SC06-540, SC06-544, SC06-566, SC06-625 were cloned directly by restriction digest for expression in the IgG expression vectors pIg-C911-HCgamma1 (SEQ ID NO:49) and pIg-C909-Ckappa (SEQ ID NO:50) or pIg-C910-Clambda (SEQ ID NO:115). The heavy chain variable regions of the scFvs called SC05-132, SC05-133, SC06-166, SC06-171, SC06-176, SC06-187, SC06-193, SC06-249, SC06-273, SC06-389, SC06-403, SC06-406, SC06-410, SC06-446, SC06-450, SC06-452, SC06-453, SC06-464, SC06-471, SC06-516, SC06-517, SC06-526, SC06-528, SC06-531, SC06-533, SC06-536, SC06-537, SC06-538, SC06-540, SC06-544, SC06-566 and SC06-625 were cloned into the vector pIg-C911-HCgamma1 by restriction digest using the enzymes SfiI and XhoI and the light chain variable regions of the scFvs called SC05-132, SC05-133, SC06-166, SC06-171, SC06-176, SC06-187, SC06-193, SC06-249, SC06-273, SC06-389, SC06-403, SC06-406, SC06-410, SC06-446, SC06-450, SC06-452, SC06-453, SC06-464, SC06-471, SC06-516, SC06-517, SC06-526, SC06-528, SC06-531, SC06-533, SC06-536, SC06-537, SC06-538, SC06-540, SC06-544, SC06-566 and SC06-625 were cloned into the vector pIg-C909-Ckappa or pIg-C910-Clambda by restriction digest using the enzymes SalI and NotI. Thereafter the nucleotide sequences were verified according to standard techniques known to the person skilled in the art.

The resulting expression plasmids pgG102-430C03, pgG105-132C911, pgG105-133C911, pgG106-166C911, pgG106-171C911, pgG106-176C911, pgG106-187C911, pgG106-193C911, pgG106-249C911, pgG106-273C911, pgG106-389C911, pgG106-403C911, pgG106-406C911, pgG106-410C911, pgG106-446C911, pgG106-450C911, pgG106-452C911, pgG106-453C911, pgG106-464C911, pgG106-471C911, pgG106-516C911, pgG106-517C911, pgG106-526C911, pgG106-528C911, pgG106-531C911, pgG106-533C911, pgG106-536C911, pgG106-537C911, pgG106-538C911, pgG106-540C911, pgG106-544C911, pgG106-566C911, and pgG106-625C911 encoding the anti-staphylococci human IgG1 heavy chains and pSyn-004-V12, pgG105-132C909, pgG105-133C909, pgG106-166C910, pgG106-171C910, pgG106-176C909, pgG106-187C909, pgG106-193C910, pgG106-249C910, pgG106-273C910, pgG106-389C910, pgG106-403C910, pgG106-406C910, pgG106-410C910, pgG106-446C910, pgG106-450C910, pgG106-452C909, pgG106-453C909, pgG106-464C910, pgG106-471C910, pgG106-516C909, pgG106-517C910, pgG106-526C910, pgG106-528C910, pgG106-531C910, pgG106-533C909, pgG106-536C909, pgG106-537C910, pgG106-538C910, pgG106-540C910, pgG106-544C910, pgG106-566C910, pgG106-625C910 encoding the anti-staphylococci human Ig light chains were transiently expressed in combination in 293T cells and supernatants containing human IgG1 antibodies were obtained. The nucleotide sequences of the heavy chains of the antibodies called CR2430, CR5132, CR5133, CR6166, CR6171, CR6176, CR6187, CR6193, CR6249, CR6273, CR6389, CR6403, CR6406, CR6410, CR6446, CR6450, CR6452, CR6453, CR6464, CR6471, CR6516, CR6517, CR6526, CR6528, CR6531, CR6533, CR6536, CR6537, CR6538, CR6540, CR6544, CR6566, and CR6625 are shown in SEQ ID NO:25, SEQ ID NO:27, SEQ ID NO:29, SEQ ID NO:116, SEQ ID NO:118, SEQ ID NO:120, SEQ ID NO:122, SEQ ID NO:124, SEQ ID NO:126, SEQ ID NO:128, SEQ ID NO:130, SEQ ID NO:132, SEQ ID NO:134, SEQ ID NO:136, SEQ ID NO:138, SEQ ID NO:140, SEQ ID NO:142, SEQ ID NO:144, SEQ ID NO:146, SEQ ID NO:148, SEQ ID NO:150, SEQ ID NO:152, SEQ ID NO:154, SEQ ID NO:156, SEQ ID NO:158, SEQ ID NO:160, SEQ ID NO:162, SEQ ID NO:164, SEQ ID NO:166, SEQ ID NO:168, SEQ ID NO:170, SEQ ID NO:172 and SEQ ID NO:174, respectively. The amino acid sequences of the heavy chains of the antibodies called CR2430, CR5132, CR5133, CR6166, CR6171, CR6176, CR6187, CR6193, CR6249, CR6273, CR6389, CR6403, CR6406, CR6410, CR6446, CR6450, CR6452, CR6453, CR6464, CR6471, CR6516, CR6517, CR6526, CR6528, CR6531, CR6533, CR6536, CR6537, CR6538, CR6540, CR6544, CR6566, and CR6625 are shown in SEQ ID NO:26, SEQ ID NO:28, SEQ ID NO:30, SEQ ID NO:117, SEQ ID NO:119, SEQ ID NO:121, SEQ ID NO:123, SEQ ID NO:125, SEQ ID NO:127, SEQ ID NO:129, SEQ ID NO:131, SEQ ID NO:133, SEQ ID NO:135, SEQ ID NO:137, SEQ ID NO:139, SEQ ID NO:141, SEQ ID NO:143, SEQ ID NO:145, SEQ ID NO:147, SEQ ID NO:149, SEQ ID NO:151, SEQ ID NO:153, SEQ ID NO:155, SEQ ID NO:157, SEQ ID NO:159, SEQ ID NO:161, SEQ ID NO:163, SEQ ID NO:165, SEQ ID NO:167, SEQ ID NO:169, SEQ ID NO:171, SEQ ID NO:173 and SEQ ID NO:175, respectively. The nucleotide sequences of the light chain of antibodies CR2430, CR5132, CR5133, CR6166, CR6171, CR6176, CR6187, CR6193, CR6249, CR6273, CR6389, CR6403, CR6406, CR6410, CR6446, CR6450, CR6452, CR6453, CR6464, CR6471, CR6516, CR6517, CR6526, CR6528, CR6531, CR6533, CR6536, CR6537, CR6538, CR6540, CR6544, CR6566, and CR6625 are shown in SEQ ID NO:31, SEQ ID NO:33, SEQ ID NO:35, SEQ ID NO:176, SEQ ID NO:178, SEQ ID NO:180, SEQ ID NO:182, SEQ ID NO:184, SEQ ID NO:186, SEQ ID NO:188, SEQ ID NO:190, SEQ ID NO:192, SEQ ID NO:194, SEQ ID NO:196, SEQ ID NO:198, SEQ ID NO:200, SEQ ID NO:202, SEQ ID NO:204, SEQ ID NO:206, SEQ ID NO:208, SEQ ID NO:210, SEQ ID NO:212, SEQ ID NO:214, SEQ ID NO:216, SEQ ID NO:218, SEQ ID NO:220, SEQ ID NO:222, SEQ ID NO:224, SEQ ID NO:226, SEQ ID NO:228, SEQ ID NO:230, SEQ ID NO:232 and SEQ ID NO:234, respectively. The amino acid sequences of the light chain of antibodies CR2430, CR5132, CR5133 CR6166, CR6171, CR6176, CR6187, CR6193, CR6249, CR6273, CR6389, CR6403, CR6406, CR6410, CR6446, CR6450, CR6452, CR6453, CR6464, CR6471, CR6516, CR6517, CR6526, CR6528, CR6531, CR6533, CR6536, CR6537, CR6538, CR6540, CR6544, CR6566, and CR6625 are shown in SEQ ID NO:32, SEQ ID NO:34, SEQ ID NO:36, SEQ ID NO:177, SEQ ID NO:179, SEQ ID NO:181, SEQ ID NO:183, SEQ ID NO:185, SEQ ID NO:187, SEQ ID NO:189, SEQ ID NO:191, SEQ ID NO:193, SEQ ID NO:195, SEQ ID NO:197, SEQ ID NO:199, SEQ ID NO:201, SEQ ID NO:203, SEQ ID NO:205, SEQ ID NO:207, SEQ ID NO:209, SEQ ID NO:211, SEQ ID NO:213, SEQ ID NO:215, SEQ ID NO:217, SEQ ID NO:219, SEQ ID NO:221, SEQ ID NO:223, SEQ ID NO:225, SEQ ID NO:227, SEQ ID NO:229, SEQ ID NO:231, SEQ ID NO:233 and SEQ ID NO:235, respectively. A person skilled in the art can determine the variable regions of the heavy and light chains of the above antibodies and single chain phage antibodies by following Kabat et al. (1991) as described in *Sequences of Proteins of Immunological Interest*, U.S. Dept. Health and Human Services, NIH, USA (fifth edition). A person skilled in the art can determine the CDR regions of the heavy and light chains of the above antibodies and single chain phage antibodies by following Kabat et al. (1991), Chothia and Lesk (1987) or a combination of both. Alternatively, the variable and CDR regions can be determined using the VBASE database, a database well known to persons skilled in the art of antibodies. Sequences of the antibodies hereof can be compared with immunoglobulin sequences in the VBASE database (see I. M. Tomlinson, S. C. Williams, O. Ignatovitch, S. J. Corbett, G. Winter, *VBASE Sequence Directory*, Cambridge United Kingdom: MRC Centre for Protein Engineering (1997)) available on the world-wide web at: vbase.mrc-cpe.cam.ac.uk/; MRC Centre for Protein Engineering) and on the basis thereof variable regions and CDR regions can be determined. The variable regions of the some of the antibodies are given in Table 13. Human anti-staphylococci IgG1 antibodies were validated for their ability to bind to staphylococci by FACS essentially as described for scFvs (see Table 14). The negative control was an anti-West Nile virus antibody (CR4374). Alternatively, batches of greater than 1 mg of each antibody were produced and purified using standard procedures.

Example 7

In Vitro Opsonic Phagocytic Activity of Staphylococcal Specific IgGs as Measured by FACS The opsonic activity of anti-staphylococcal IgGs was measured in an opsonophagocytotic (OPA) assay using freshly differentiated HL-60 cells. During the OPA assay fluorescent bacteria were mixed with differentiated HL-60 cells and serially diluted IgGs. Bacteria were grown to stationary or to logarithmic (log) phase prior to labeling. To grow the bacteria to stationary phase different staphylococcal isolates were incubated overnight on sheep blood agar plates at 37° C. The bacteria were resuspended in 5 ml of bicarbonate buffer (0.1 M $NaHCO_3$, pH 8.0), harvested by centrifugation at 800×g for 10 minutes at room temperature and diluted until a concentration of $2.9\times10^9$ bacteria/ml. Bacteria that were grown until logarithmic phase were first cultured overnight in LB medium at 37° C., then the culture was diluted 10 times and grown for an additional 3 hours in LB medium at 37° C. Bacteria were harvested by centrifugation at 800×g for 10 minutes and resuspended in bicarbonate buffer washed until a concentration of $2.9\times10^9$ bacteria/ml Fifty microliters of a 5,6-carboxyfluorescein, succinimidyl ester solution ((FAM-SE; Molecular Probes, Eugene, Oreg.); 10 mg/ml in dimethyl sulfoxide (Fisher Scientific Co., Fair Lawn, N.J.)) was added to 1 ml of $2.9\times10^9$ bacteria and the mixture was incubated for 1 hour at 37° C. without shaking. The labeled bacteria were washed three times in 20 ml opsonophagocytosis buffer (Hanks balanced salt solution with $Ca^{2+}$ and $Mg^{2+}$ and 0.2% bovine serum albumin), until no free dye in the supernatant was observed. FAM-SE-labeled bacteria were resuspended in 8 ml OPA buffer and stored in aliquots of 500 µl at −20° C. under protection from light.

HL-60 cells (human promyelocytic leukemia cells; ECACC NO 98070106) were grown in cell densities of 1-9×$10^5$ cells/ml in RPMI 1640 medium containing 2 mM L-glutamine supplemented with 10% heat-inactivated fetal bovine serum (HyClone Laboratories, Logan, Utah) and penicillin/streptomycin. Cells between passage 6 and 35 were used for differentiation. The cells were differentiated into granulocytes by culturing in the same medium supplemented with $5\times10^{-7}$ M all-trans-retinoic acid (Sigma), $6\times10^{-12}$ M vitamin-D3 (Sigma) and 30 ng/ml human recombinant G-CSF (R&D). HL-60 cells were harvested by centrifugation at 160×g for 10 minutes and washed twice in 15 ml of wash buffer (Hanks balanced salt solution, without $Ca^{2+}$ and $Mg^{2+}$, containing 0.2% bovine serum albumin). The cells were washed once in opsonophagocytosis buffer, resuspended in 4 ml opsonophagocytosis buffer and counted in a hemocytometer. The cell concentration was adjusted to $5\times10^6$ cells/ml.

Figure 2:
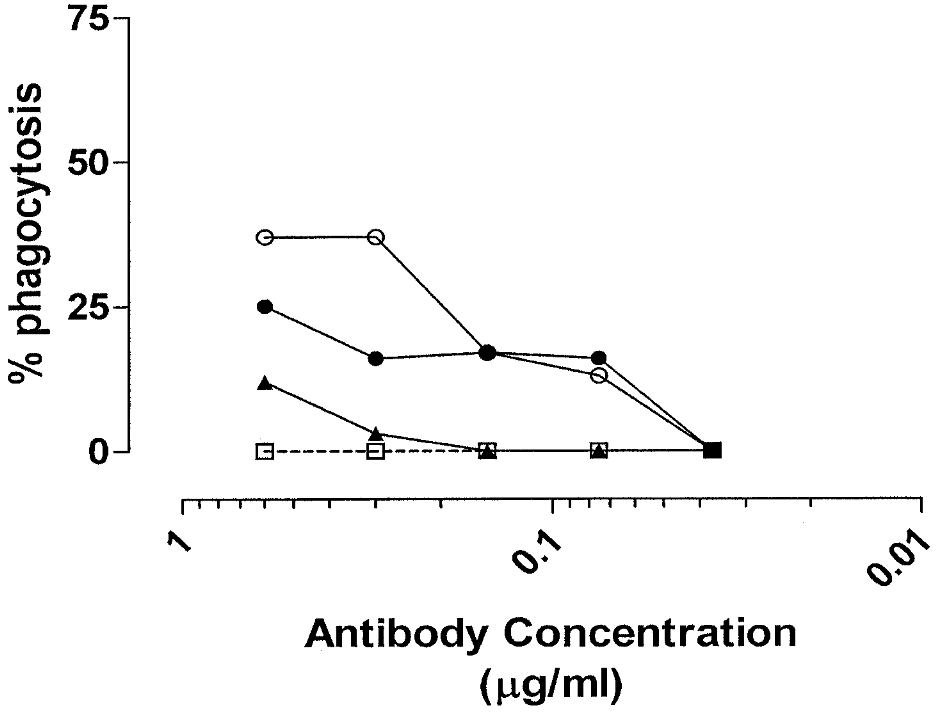
FIG. 2 shows antibody-mediated phagocytosis of *S. aureus* strain Cowan harvested during the stationary phase of growth in the absence of complement with the antibodies CR2430 (white dot), CR5132 (black triangle), CR5133 (black dot), and a negative control monoclonal antibody (white square).
Figure 3:
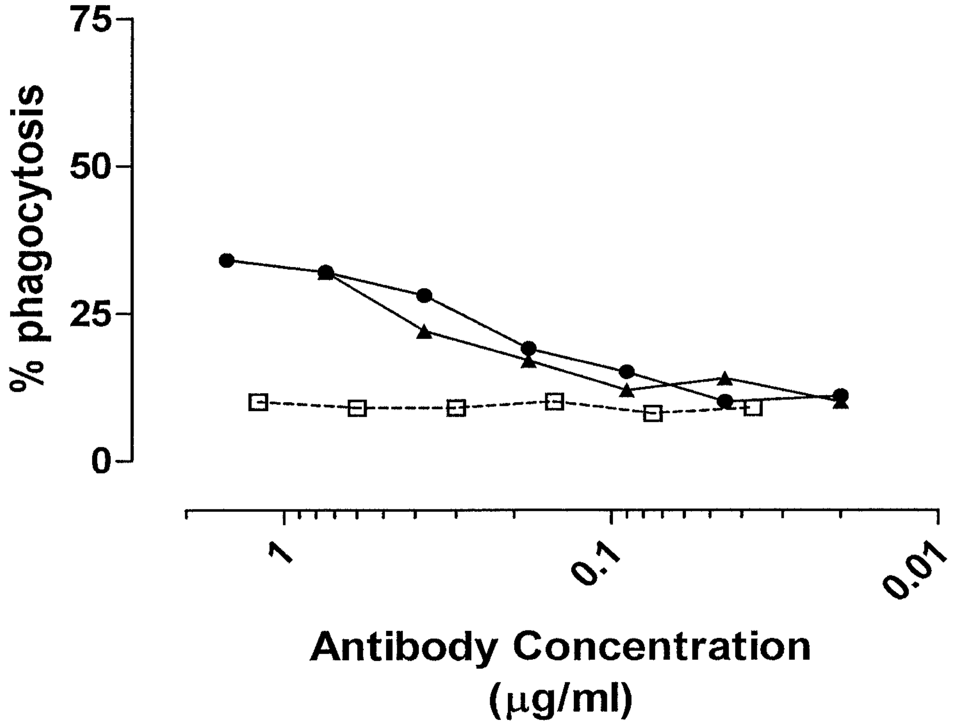
FIG. 3 shows antibody-mediated phagocytosis of *S. aureus* strain SA125 harvested during the stationary phase of growth in the absence of complement with the antibodies CR5132 (black triangle), CR5133 (black dot), and a negative control monoclonal antibody (white square).
Figure 4:
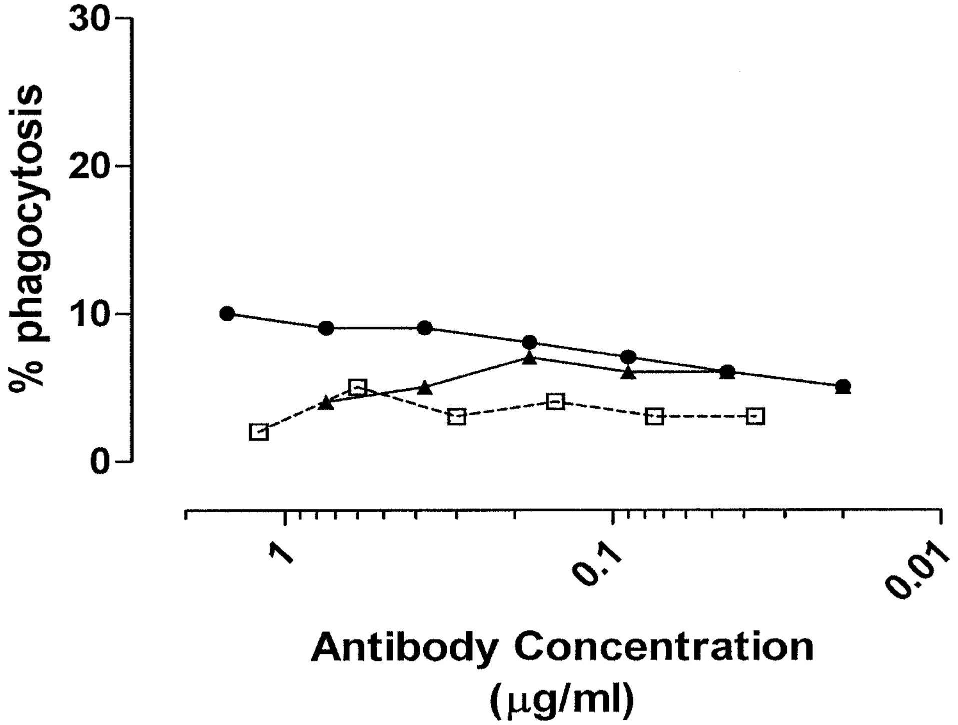
FIG. 4 shows antibody-mediated phagocytosis of *S. epidermidis* strain SE131 harvested during the stationary phase of growth in the absence of complement with the antibodies CR5132 (black triangle), CR5133 (black dot), and a negative control monoclonal antibody (white square).

The anti-staphylococal IgGs and a control IgG (CR4374) were serially diluted in opsonophagocytosis buffer in a total volume of 20 µl to obtain dilutions having an IgG concentration of 2.50 µg/ml, 1.20 µg/ml, 0.60 µg/ml, 0.30 µg/ml, 0.15 µg/ml, 0.075 µg/ml, 0.0375 µg/ml and 0.019 µg/ml. Opsonic activity of dilutions was measured in the OPA assay in a round bottom plate that was blocked with 1% BSA in PBS. As a control, the assay was performed with no IgG. A 15 µl aliquot of a bacterial suspension containing $5.4\times10^6$ cells was added to each well of the plate. When a bacterial suspension from *S. aureus* strain Cowan or *S. epidermidis* was used, the IgG/bacterium suspension was first incubated for 30 minutes at 37° C. while the plate was horizontally shaking (1300 rpm) in a Heidolph titramax 1000. Next, 15 μl of the differentiated HL-60 cells (total: $75\times10^3$ cells) were added to each well of the plate and the plate was incubated while shaking at 37° C. for 30-45 minutes. The final volume in the well was 50 μl. The reaction was stopped by adding 50 μl of wash buffer containing 4% v/v formaldehyde. The content in each well was resuspended and transferred to polystyrene disposable tubes for flow cytometric analysis. The samples were stored in the dark at 4° C. until analyzation. The tubes were vortexed for three seconds before sampling in the flow cytometer. To control the differentiation of the HL-60 cells the expression of the complement receptor CD11b was measured. Fc-receptors of differentiated and non-differentiated cells were first blocked with rabbit IgG for 15 minutes on ice and the cells were subsequently labeled with CD11bAPC (BD) for 15 minutes on ice. Cells were considered properly differentiated when the mean fluorescent intensity (MFI) analyzed was at least between 10- to 100-fold higher compared to that of non-differentiated cells. Samples were assayed with a FACSCalibur immunocytometry system (Becton Dickinson and Co., Paramus, N.J.) and were analyzed with CELLQuest software (version 1.2 for Apple system 7.1; Becton Dickinson). 7,000 gated HL-60 granulocytes were analyzed per tube. FAM-SE was excited at a wavelength of 488 nm and the FAM-SE fluorescence signal of gated viable HL-60 cells was measured for each antibody dilution. IgGs were defined as positive in the phagocytic assay when concentration dependent phagocytosis could be observed greater or equal to two times that of the control IgG. IgGs CR2430, CR5132 and CR5133 demonstrated opsonic activity against *S. aureus* strain Cowan in both the log (see FIG. 1) and stationary growth phase (see FIG. 2). The three IgGs where more effective in enhancing phagocytic activity during the log phase of growth. IgGs CR5132 and CR5133 enhanced phagocytosis of *S. aureus* strain SA125 compared to the negative control antibody (see FIG. 3) and antibody CR5133 significantly enhanced phagocytic activity of the differentiated HL60 cells against *S. epidermidis* strain SE131, when compared to the negative control antibody (see FIG. 4).

Example 8

Breadth of Staphylococci Specific IgG1 Binding Activity

To determine the extent to which the targets of selected human anti-staphylococcal IgG1 antibodies were conserved on staphylococci and other gram positive bacteria FACS assays were carried out on a extended panel of clinical bacterial isolates essentially as described before for scFvs (see Table 15). From the assay was deducted that CR5132 and CR5133 bound to all strains tested. CR5140 did bind all strains tested with the exception of *S. hominis* KV111, *S. warneri* KV112, *S. warneri* KV114, *S. epidermidis* KV115, *S. haemolyticus* KV117, *S. warneri* vd65, *S. warneri* vd66, *S. warneri* vd732, *S. hominis* vd136, *S. hominis* vd139, and *S. hominis* K136. CR6171 did bind all strains tested with the exception of *S. epidermidis* KV110, *S. hominis* KV111, *S. warneri* KV112, *S. saprophytocis* KV113, *S. warneri* KV114, *S. haemolyticus* KV117, *S. hominis* KV118, *S. haemolyticus* K119, *S. warneri* vd65, *S. warneri* vd66, *S. warneri* vd732, *S. hominis* vd136, *S. hominis* vd139, and *S. hominis* K136. Finally, CR6453 did bind all strains tested with the exception of *S. hominis* vd136 and *S. hominis* K136.

In addition, using the same FACS based approach antibodies from the panel were demonstrated to bind to other gram-positive bacteria. The antibodies CR5132 and CR6453 were shown to bind *Listeria monocytogenes, Bacillus cereus* and *Streptococcus* group A and CR5132 also bound to *Propionibacterium* spp. The antibodies CR5133, CR5140 and CR6171 were shown to bind *Streptococcus* group A and CR5140 was also shown to bind *Enterococcus faecalis* (data not shown).

Example 9

In Vitro Opsonic Phagocytic Activity of Staphylococcal Specific IgGs Measured by Opsonophagocytic Killing Assay (OPKA)

To better determine the functional activity of the antibody panel an opsonophagocytic assay was conducted to quantify the killing activity of anti-staphylococcal human IgG1 against the *Staphylococcus aureus* strains 502, Mn8 and Newman and *Staphylococcus epidermidis* strain M187. Freshly drawn human blood (10 to 30 ml) was mixed with an equal volume of dextran-heparin buffer (4.5 g of dextran, Sigma Chemical, St. Louis; 28.4 mg of heparin sodium in 500 ml of distilled water), and the mixture was incubated at 37° C. for 1 hour. The upper layer containing the leukocytes was collected by centrifugation, and hypotonic lysis of the remaining erythrocytes was accomplished by suspension of the cell pellet in 1% (w/v) $NH_4Cl$. The leukocyte population was subsequently washed in RPMI with 15% (v/v) fetal bovine serum. Trypan blue staining and counting in a hemocytometer were used to determine the concentration of live leukocytes, and the final leukocyte concentration was adjusted to $2\times10^7$ cells/ml. The phagocytosis assay was performed in duplicate with or without 100 μl of leukocyte suspension added to 100 μl of bacteria (concentration adjusted spectrophotometrically to $2\times10^7$ per ml and confirmed by viable counts), 100 μl of anti-staphylococcal human IgG1 diluted in RPMI, and 100 μl of baby rabbit complement. The reaction mixture was incubated on a rotor rack at 37° C. for 90 minutes; samples were taken at time 0 and after 90 minutes, diluted in 1% Proteose Peptone (Difco Laboratories, Detroit, Mich.), and plated onto tryptic soy agar plates. The killing activity (%) of the antibodies was calculated as the mean number of CFU surviving in the sample containing leukocytes subtracted from the mean number of CFU surviving in the sample without leukocytes, divided by the latter and amplified by 100. The killing activity of the anti-staphylococcal human IgG1 was tested at two concentrations 1250 and 12.5 ng/ml (see Table 16).

The results show that antibodies CR5132, CR5133, CR6446, CR6453, and CR6566 have more than 20% killing activity against *S. epidermidis* strain M187, even at a low concentration of 12.5 ng/ml.

Example 10

IgG1 Competition Assay

To establish whether antibodies in the panel competed for binding to the same target a competition ELISA was developed. The *S. epidermidis* strain SE132 was streaked onto a blood agar plate and incubated overnight at 37° C. Colonies were scraped from the plate using 5 ml of 50 mM carbonate buffer (8 volumes of 0.2 M $Na_2CO_3$, 17 volumes of 0.2 M $NaHCO_3$ and 75 volumes of distilled water) and centrifuged for 3 minutes at 4000 rpm. The obtained pellet was resuspended in 500 μl of carbonate buffer, centrifuged again and the pellet was resuspended in 500 μl carbonate buffer. Cell density was determined by measuring OD600 of a dilution series of the bacteria. The *S. epidermidis* strain was diluted to a density of $5\times10^9$ cells/ml and 100 μl ($5\times10^8$ cells) per well was coated overnight at 4° C. on Nunc-Immuno MAXISORP™ F96 plates. After incubation, the wells were washed three times with PBS and blocked for one hour at room temperature with 300 μl 2% (v/v) ELK in PBS per well. In separate tubes 25 μl of each scFv-phage maxiprep (produced as above) diluted to subsaturating levels (as determined by ELISA above) was mixed with 25 μl blocking buffer (4% (v/v) ELK/PBS) and 50 μl of IgG1 supernatant diluted to 10 μg/ml in PBS and incubated for 20 minutes on ice. After removing the blocking solution, 100 μl of the blocked phages and IgG1 mixture was added to each well and incubated for one hour at room temperature. The wells were washed three times with PBS/0.01% (v/v) TWEEN™ and once with PBS. After washing, 100 μl of anti-M13 HRP (1:5000 in 2% (v/v) ELK in PBS) was added per well and incubated for 60 minutes at room temperature. The wells were washed again and staining was visualized by adding 100 μl OPD-solution to each well. Reaction was stopped after 5-10 minutes by adding 50 μl 1 M $H_2SO_4$ to each well and OD measured at 492 nm. The experiment was repeated twice with the entire panel of antibodies and a control IgG1 CR4374. The results showed that the antibodies fell into five distinct groups. Group A consisted of CR5132, CR5133, CR6187 and CR6453; Group B consisted of CR5140 and CR6171; Group C consisted of CR6176; Group D consisted of CR6526; and Group E consisted of the rest of the panel CR6166, CR6193, CR6249, CR6273, CR6403, CR6406, CR6410, CR6446, CR6450, CR6452, CR6464, CR6471, CR6516, CR6517, CR6528, CR6531, CR6533, CR6536, CR6537, CR6538, CR6540, CR6544, CR6566, CR6625. The binding activity and functional activity of the antibodies was consistent with the grouping.

Example 11

Target Identification of IgG1 in Group A

To determine the binding target of the panel antibodies, representatives of each of the groups determined above (within each group the most potent antibody based on opsonic activity was chosen) was incubated with LTA extracted from *S. aureus* in a solid phase ELISA (see Table 17). A solution of 1 μg/ml lipoteichoic acid (Sigma) in PBS was coated on wells overnight at room temperature. Plates were washed once with PBS and blocked with 400 μl 2% (v/v) ELK in PBS. A serial dilution of each anti-staphylococcal IgG1 supernatant and negative control supernatant CR4374 and positive control anti-LTA murine mAb 12248 (Abcam) was incubated per well for one hour at room temperature. Wells were washed five times with PBS and 100 μl of anti-human HRP (1/2000) or anti-mouse HRP (1/2000) diluted in PBSE was added and incubated for one hour at room temperature. Wells were visualized and read as above. The results clearly demonstrate that CR5133 from group A binds strongly to LTA. The positive control murine monoclonal 12248 showed similar results. In contrast, none of the antibodies from the other groups nor the negative control antibody showed significant reactivity with LTA. Antibodies CR5132 and CR6453 from Group A were consistently shown to bind LTA, CR6187 however did not show binding reactivity to LTA (data not shown). This may be due to a lower affinity of CR6187 compared to the other antibodies in the group.

Example 12

In Vitro Opsonic Phagocytic Activity of Staphylococcal Specific IgGs Against *Staphylococcus Epidermidis* and *Staphylococcus aureus* Grown Under Different Culture Conditions and Measured by Opsonophagocytic Killing Assay (OPKA)

Figure 5:
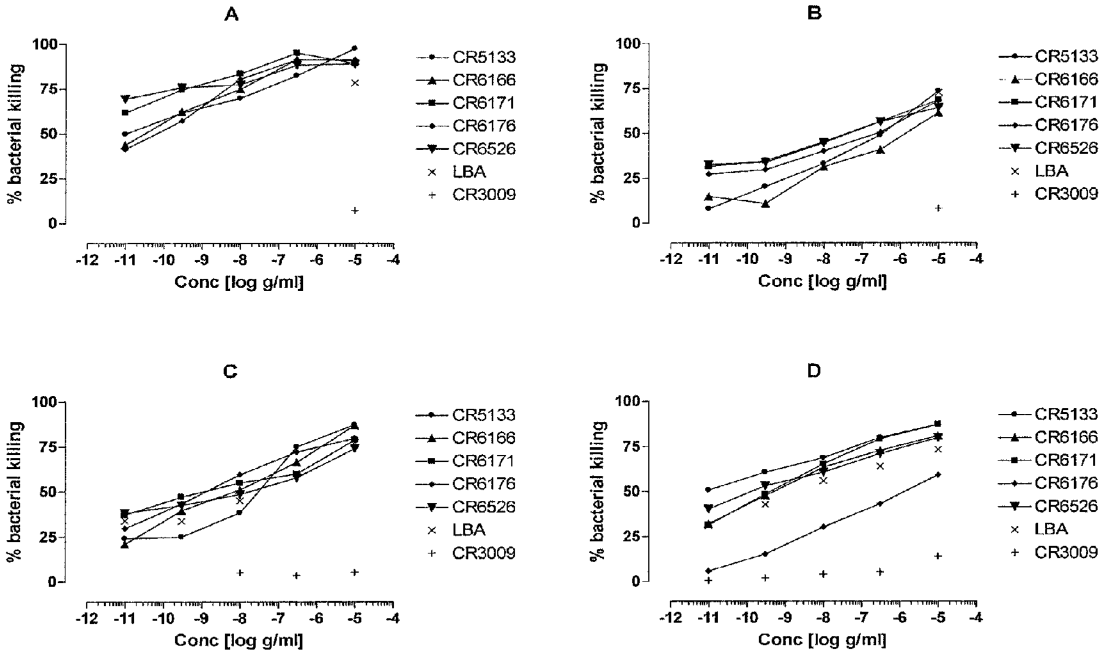
FIG. 5 shows the killing activity of the anti-staphylococcal human IgG1 tested at five concentrations against *Staphylococcus aureus* strain Newman and *Staphylococcus epidermidis* strain RP62A, either grown to mid logarithmic phase (FIGS. 5A and 5B) or to static phase (FIGS. 5G and 5H), or in medium consisting of 1% glucose (FIGS. 5C and 5D) or 100% human plasma (FIGS. 5E and 5F).
Figure 5:
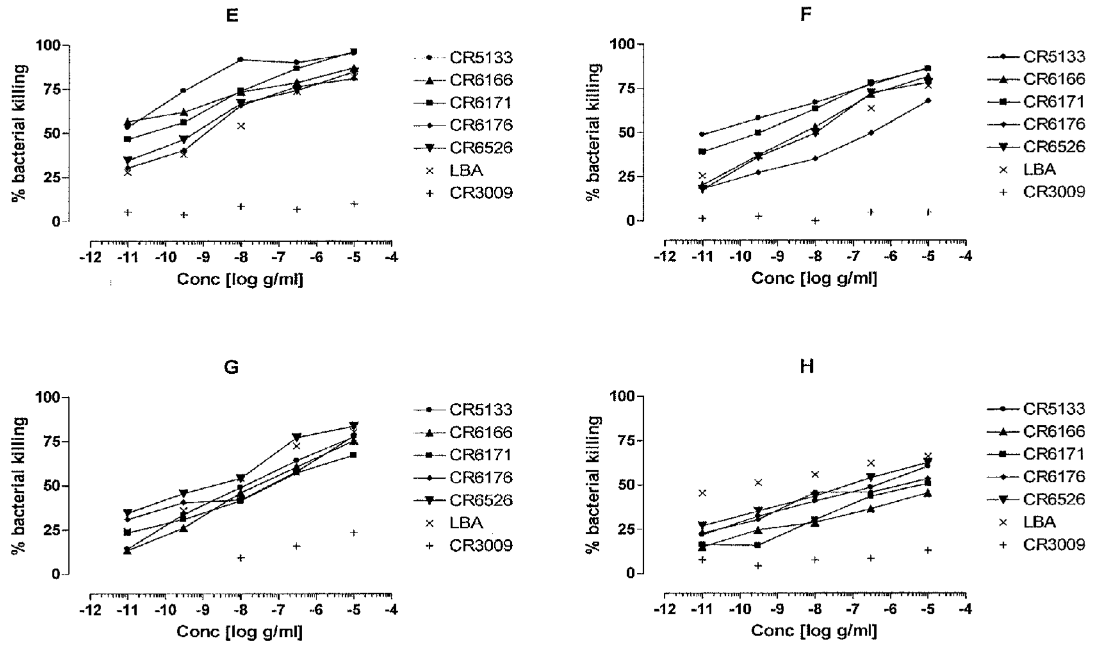

To determine if the bacterial killing activity of the most potent and non-competitive opsonophagocytic anti-staphylococcal IgG1 antibodies identified above is affected by different bacterial growth conditions, the opsonophagocytic assay described above was conducted against the *Staphylococcus aureus* strain Newman and *Staphylococcus epidermidis* strain RP62A grown in different media and under different conditions. LBA is immune serum taken from an infected patient and served as a positive control. The killing activity of the anti-staphylococcal human IgG1 was tested at five concentrations 10,000, 300, 10, 0.3, 0.01 ng/ml or −5, −6.5, −8, −9.5, −11 log [g/ml] against both staphylococcal strains either grown to mid logarithmic phase (FIG. 5 A, B) or to static phase (FIG. 5 G, H) or in medium consisting of 1% glucose (FIG. 5 C, D) or 100% human plasma (FIG. 5 E, F).

The results show that the antibodies CR5133, CR6166, CR6171, CR6176 and CR6526 have robust opsonophagocytic activity against the two staphylococcal strains under all the growth conditions tested. Importantly, they were significantly different from the negative control antibody CR3009, which showed little or no activity. This suggests that the targets of the antibody panel are stably expressed under a variety of bacterial growth conditions, a factor potentially important for therapeutic application where the target bacteria may be present in nutrient poor conditions.

Example 13

In Vivo Protective Activity of Staphylococcal Specific IgGs in a Lethal *Staphylococcus Aureus* Challenge Model A bacterial titration experiment in mice is carried out to determine the optimal inoculation dose to produce 80%-100% lethality. Animals are inoculated i.p. with *S. aureus* strains Mn8 at doses of 5×109 and $5\times10^8$. Animals are observed for 5 days and survival is used as an endpoint. The dose that results in 0% survival after five days is chosen as the challenge dose for further experiments.

Using the dose determined above for the bacterial inoculum, a set of challenge experiments is conducted to assess the protective activity of the panel of Staphylococcal binding mAb (CR5133, CR6166, CR6171, CR6176 and CR6526) that have demonstrated in vitro opsonic phagocytic activity. For each experiment, purified mAbs (one isotype control IgG1 and five test IgG1) are injected i.p. (0.5-1 ml in PBS), at a dose of 15 mg/kg. 5 mAb are tested against *S. aureus* Mn8.

After 24 hours, animals are inoculated i.p. with the *S. aureus* strain at the inoculation dose determined above. Immediately prior to inoculation, a small amount of blood (~50-100 ml) is collected (using the tail cut method) to measure circulating antibody levels. The blood is kept at room temperature between 30 minutes and 2 hours, to allow the blood to clot, then centrifuged at 4° C. for 5 minutes. The serum is removed and stored at −20° C. A human IgG1 ELISA is performed on all blood samples prior to inoculation and after sacrifice. Animals with no measurable antibody in their blood prior to inoculation are excluded from further analysis.

Mice are observed daily for five days and sacrificed when showing signs of severe distress. Survival is scored in each group at the end of five days. To validate each experiment there must be less than 20% survival in the negative control IgG1 group.

Further experiments are carried out in the model described above where the antibodies are titrated at half-log doses from 10 mg/kg to determine their protective potency in vivo.

TABLE 1

Human lambda chain variable region primers (sense).

| Primer name | Primer nucleotide sequence | SEQ ID NO: |
|---|---|---|
| HuVL1A-Back | 5'-CAGTCTGTGCTGACTCAGCCACC-3' | SEQ ID NO: 51 |
| HuVL1B-Back | 5'-CAGTCTGTGYTGACGCAGCCGCC-3' | SEQ ID NO: 52 |
| HuVL1C-Back | 5'-CAGTCTGTCGTGACGCAGCCGCC-3' | SEQ ID NO: 53 |
| HuVL2B-Back | 5'-CAGTCTGCCCTGACTCAGCC-3' | SEQ ID NO: 54 |
| HuVL3A-Back | 5'-TCCTATGWGCTGACTCAGCCACC-3' | SEQ ID NO: 55 |
| HuVL3B-Back | 5'-TCTTCTGAGCTGACTCAGGACCC-3' | SEQ ID NO: 56 |
| HuVL4B-Back | 5'-CAGCYTGTGCTGACTCAATC-3' | SEQ ID NO: 57 |
| HuVL5-Back | 5'-CAGGCTGTGCTGACTCAGCCGTC-3' | SEQ ID NO: 58 |
| HuVL6-Back | 5'-AATTTTATGCTGACTCAGCCCCA-3' | SEQ ID NO: 59 |

TABLE 1-continued

Human lambda chain variable region primers (sense).

| Primer name | Primer nucleotide sequence | SEQ ID NO: |
|---|---|---|
| HuVL7/8-Back | 5'-CAGRCTGTGGTGACYCAGGAGCC-3' | SEQ ID NO: 60 |
| HuVL9-Back | 5'-CWGCCTGTGCTGACTCAGCCMCC-3' | SEQ ID NO: 61 |
| HuVL10-Back | 5'-CAGGCAGGGCTGACTCAG-3' | SEQ ID NO: 62 |

TABLE 2

Human kappa chain variable region primers (sense).

| Primer name | Primer nucleotide sequence | SEQ ID NO: |
|---|---|---|
| HuVK1B-Back | 5'-GACATCCAGWTGACCCAGTCTCC-3' | SEQ ID NO: 63 |
| HuVK2-Back | 5'-GATGTTGTGATGACTCAGTCTCC-3' | SEQ ID NO: 64 |
| HuVK2B2 | 5'-GATATTGTGATGACCCAGACTCC-3' | SEQ ID NO: 65 |
| HuVK3B-Back | 5'-GAAATTGTGWTGACRCAGTCTCC-3' | SEQ ID NO: 66 |
| HuVK5-Back | 5'-GAAACGACACTCACGCAGTCTCC-3' | SEQ ID NO: 67 |
| HuVK6-Back | 5'-GAAATTGTGCTGACTCAGTCTCC-3' | SEQ ID NO: 68 |

TABLE 3

Human kappa chain variable region primers extended with SalI restriction sites (sense), human kappa chain J-region primers extended with NotI restriction sites (anti-sense), human lambda chain variable region primers extended with SalI restriction sites (sense) and human lambda chain J-region primers extended with NotI restriction sites (anti-sense).

| Primer name | Primer nucleotide sequence | SEQ ID NO |
|---|---|---|
| HuVK1B-Back-SAL | 5'-TGAGCACACAGGTCGACGGACATCCAGWTGACCCAGTCTCC-3' | SEQ ID NO: 69 |
| HuVK2-Back-SAL | 5'-TGAGCACACAGGTCGACGGATGTTGTGATGACTCAGTCTCC-3' | SEQ ID NO: 70 |
| HuVK2B2-SAL | 5'-TGAGCACACAGGTCGACGGATATTGTGATGACCCAGACTCC-3' | SEQ ID NO: 71 |
| HuVK3B-Back-SAL | 5'-TGAGCACACAGGTCGACGGAAATTGTGWTGACRCAGTCTCC-3' | SEQ ID NO: 72 |
| HuVK5-Back-SAL | 5'-TGAGCACACAGGTCGACGGAAACGACACTCACGCAGTCTCC-3' | SEQ ID NO: 73 |
| HuVK6-Back-SAL | 5'-TGAGCACACAGGTCGACGGAAATTGTGCTGACTCAGTCTCC-3' | SEQ ID NO: 74 |
| HuJK1-FOR-NOT | 5'-GAGTCATTCTCGACTTGCGGCCGCACGTTTGATTTCCACCTTGGTCCC-3' | SEQ ID NO: 75 |

TABLE 3-continued

Human kappa chain variable region primers extended with SalI restriction sites (sense), human kappa chain J-region primers extended with NotI restriction sites (anti-sense), human lambda chain variable region primers extended with SalI restriction sites (sense) and human lambda chain J-region primers extended with NotI restriction sites (anti-sense).

| Primer name | Primer nucleotide sequence | SEQ ID NO |
|---|---|---|
| HuJK2-FOR-NOT | 5'-GAGTCATTCTCGACTTGCGGCCGCACGTT TGATCTCCAGCTTGGTCCC-3' | SEQ ID NO: 76 |
| HuJK3-FOR-NOT | 5'-GAGTCATTCTCGACTTGCGGCCGCACGTT TGATATCCACTTTGGTCCC-3' | SEQ ID NO: 77 |
| HuJK4-FOR-NOT | 5'-GAGTCATTCTCGACTTGCGGCCGACGTTT GATCTCCACCTTGGTCCC-3' | SEQ ID NO: 78 |
| HuJK5-FOR-NOT | 5'-GAGTCATTCTCGACTTGCGGCCGCACGTT TAATCTCCAGTCGTGTCCC-3' | SEQ ID NO: 79 |
| HuVL1A-Back-SAL | 5'-TGAGCACACAGGTCGACGCAGTCTGTGCT GACTCAGCCACC-3' | SEQ ID NO: 80 |
| HuVL1B-Back-SAL | 5'-TGAGCACACAGGTCGACGCAGTCTGTGYT GACGCAGCCGCC-3' | SEQ ID NO: 81 |
| HuVL1C-Back-SAL | 5'-TGAGCACACAGGTCGACGCAGTCTGTCGT GACGCAGCCGCC-3' | SEQ ID NO: 82 |
| HuVL2B-Back-SAL | 5'-TGAGCACACAGGTCGACGCAGTCTGCCCT GACTCAGCC-3' | SEQ ID NO: 83 |
| HuVL3A-Back-SAL | 5'-TGAGCACACAGGTCGACGTCCTATGWGC TGACTCAGCCACC-3' | SEQ ID NO: 84 |
| HuVL3B-Back-SAL | 5'-TGAGCACACAGGTCGACGTCTTCTGAGCT GACTCAGGACCC-3' | SEQ ID NO: 85 |
| HuVL4B-Back-SAL | 5'-TGAGCACACAGGTCGACGCAGCYTGTGC TGACTCAATC-3' | SEQ ID NO: 86 |
| HuVL5-Back-SAL | 5'-TGAGCACACAGGTCGACGCAGGCTGTGC TGACTCAGCCGTC-3' | SEQ ID NO: 87 |
| HuVL6-Back- SAL | 5'-TGAGCACACAGGTCGACGAATTTTATGCT GACTCAGCCCCA-3' | SEQ ID NO: 88 |
| HuVL7/8-Back-SAL | 5'-TGAGCACACAGGTCGACGCAGRCTGTGG TGACYCAGGAGCC-3' | SEQ ID NO: 89 |
| HuVL9-Back-SAL | 5'-TGAGCACACAGGTCGACGCWGCCTGTGC TGACTCAGCCMCC-3' | SEQ ID NO: 90 |
| HuVL10-Back-SAL | 5'-TGAGCACACAGGTCGACGCAGGCAGGGC TGACTCAG-3' | SEQ ID NO: 91 |
| HuJL1-FOR-NOT | 5'-GAGTCATTCTCGACTTGCGGCCGCACCTA GGACGGTGACCTTGGTCCC-3' | SEQ ID NO: 92 |
| HuJL2/3-FOR-NOT | 5'-GAGTCATTCTCGACTTGCGGCCGCACCTA GGACGGTCAGCTTGGTCCC-3' | SEQ ID NO: 93 |
| HuJL7-FOR-NOT | 5'-GAGTCATTCTCGACTTGCGGCCGCACCGA GGACGGTCAGCTGGGTGCC-3' | SEQ ID NO: 94 |

TABLE 4

Percentage of the different light chain products in the final mixture, based on concentrations determined by agarose gel analysis.

| Sense primer | Antisense primer | Product | Percentage |
|---|---|---|---|
| HuVL1A-Back-SAL + | HuJL1-FOR-NOT | L1J1 | 4.20% |
| HuVL1B-Back-SAL + | HuJL2/3-FOR-NOT | L1J2 | 8.40% |
| HuVL1C-Back-SAL | HuJL7-FOR-NOT | L1J3 | 1.40% |

TABLE 4-continued

Percentage of the different light chain products in the final mixture, based on concentrations determined by agarose gel analysis.

| Sense primer | Antisense primer | Product | Percentage |
|---|---|---|---|
| HuVL2B-Back-SAL | HuJL1-FOR-NOT | L2J1 | 3.00% |
| | HuJL2/3-FOR-NOT | L2J2 | 6.00% |
| | HuJL7-FOR-NOT | L2J3 | 1.00% |

TABLE 4-continued

Percentage of the different light chain products in the final mixture, based on concentrations determined by agarose gel analysis.

| Sense primer | Antisense primer | Product | Percentage |
|---|---|---|---|
| HuVL3A-Back-SAL | HuJL1-FOR-NOT | L3J1 | 3.00% |
| | HuJL2/3-FOR-NOT | L3J2 | 6.00% |
| | HuJL7-FOR-NOT | L3J3 | 1.00% |
| HuVL3B-Back-SAL | HuJL1-FOR-NOT | L4J1 | 0.30% |
| | HuJL2/3-FOR-NOT | L4J2 | 0.60% |
| | HuJL7-FOR-NOT | L4J3 | 0.10% |
| HuVL4B-Back-SAL | HuJL1-FOR-NOT | L5J1 | 0.30% |
| | HuJL2/3-FOR-NOT | L5J2 | 0.60% |
| | HuJL7-FOR-NOT | L5J3 | 0.10% |
| HuVL5-Back-SAL | HuJL1-FOR-NOT | L6J1 | 0.30% |
| | HuJL2/3-FOR-NOT | L6J2 | 0.60% |
| | HuJL7-FOR-NOT | L6J3 | 0.10% |
| HuVL6-Back-SAL | HuJL1-FOR-NOT | L7J1 | 0.30% |
| | HuJL2/3-FOR-NOT | L7J2 | 0.60% |
| | HuJL7-FOR-NOT | L7J3 | 0.10% |
| HuVL7/8-Back-SAL | HuJL1-FOR-NOT | L8J1 | 0.30% |
| | HuJL2/3-FOR-NOT | L8J2 | 0.60% |
| | HuJL7-FOR-NOT | L8J3 | 0.10% |
| HuVL9-Back-SAL + | HuJL1-FOR-NOT | L9J1 | 0.30% |
| HuVL10-Back-SAL | HuJL2/3-FOR-NOT | L9J2 | 0.60% |
| | HuJL7-FOR-NOT | L9J3 | 0.10% |
| HuVK1B-Back-SAL | HuJK1-FOR-NOT | K1J1 | 7.50% |
| | HuJK2-FOR-NOT | K1J2 | 7.50% |
| | HuJK3-FOR-NOT | K1J3 | 3.00% |
| | HuJK4-FOR-NOT | K1J4 | 7.50% |
| | HuJK5-FOR-NOT | K1J5 | 4.50% |

TABLE 4-continued

Percentage of the different light chain products in the final mixture, based on concentrations determined by agarose gel analysis.

| Sense primer | Antisense primer | Product | Percentage |
|---|---|---|---|
| HuVK2-Back-SAL | HuJK1-FOR-NOT | K2J1 | 1.00% |
| | HuJK2-FOR-NOT | K2J2 | 1.00% |
| | HuJK3-FOR-NOT | K2J3 | 0.40% |
| | HuJK4-FOR-NOT | K2J4 | 1.00% |
| | HuJK5-FOR-NOT | K2J5 | 0.60% |
| HuVK2B2-SAL | HuJK1-FOR-NOT | K3J1 | 0.25% |
| | HuJK2-FOR-NOT | K3J2 | 0.25% |
| | HuJK3-FOR-NOT | K3J3 | 0.10% |
| | HuJK4-FOR-NOT | K3J4 | 0.25% |
| | HuJK5-FOR-NOT | K3J5 | 0.15% |
| HuVK3B-Back-SAL | HuJK1-FOR-NOT | K4J1 | 4.75% |
| | HuJK2-FOR-NOT | K4J2 | 4.75% |
| | HuJK3-FOR-NOT | K4J3 | 1.90% |
| | HuJK4-FOR-NOT | K4J4 | 4.75% |
| | HuJK5-FOR-NOT | K4J5 | 2.85% |
| HuVK5-Back-SAL | HuJK1-FOR-NOT | K5J1 | 0.25% |
| | HuJK2-FOR-NOT | K5J2 | 0.25% |
| | HuJK3-FOR-NOT | K5J3 | 0.10% |
| | HuJK4-FOR-NOT | K5J4 | 0.25% |
| | HuJK5-FOR-NOT | K5J5 | 0.15% |
| HuVK6-Back-SAL | HuJK1-FOR-NOT | K6J1 | 1.25% |
| | HuJK2-FOR-NOT | K6J2 | 1.25% |
| | HuJK3-FOR-NOT | K6J3 | 0.50% |
| | HuJK4-FOR-NOT | K6J4 | 1.25% |
| | HuJK5-FOR-NOT | K6J5 | 0.75% |

TABLE 5

Human IgG heavy chain variable region primers (sense).

| Primer name | Primer nucleotide sequence | SEQ ID NO |
|---|---|---|
| HuVH1B/7A-Back | 5'-CAGRTGCAGCTGGTG CARTCTGG-3' | SEQ ID NO: 95 |
| HuVH1C-Back | 5'-SAGGTCCAGCTGGTR CAGTCTGG-3' | SEQ ID NO: 96 |
| HuVH2B-Back | 5'-CAGRTCACCTTGAAG GAGTCTGG-3' | SEQ ID NO: 97 |
| HuVH3A-Back | 5'-GAGGTGCAGCTGGTG GAG-3' | SEQ ID NO: 98 |
| HuVH3C-Back | 5'-GAGGTGCAGCTGGTG GAGWCYGG-3' | SEQ ID NO: 99 |
| HuVH4B-Back | 5'-CAGGTGCAGCTACAG CAGTGGGG-3' | SEQ ID NO: 100 |
| HuVH4C-Back | 5'-CAGSTGCAGCTGCAG GAGTCSGG-3' | SEQ ID NO: 101 |
| HuVH6A-Back | 5'-CAGGTACAGCTGCAG CAGTCAGG-3' | SEQ ID NO: 102 |

TABLE 6

Human IgG heavy chain variable region primers extended with SfiI/NcoI restriction sites (sense) and human IgG heavy chain J-region primers extended with XhoI/BstEII restriction sites (anti-sense).

| Primer name | Primer nucleotide sequence | SEQ ID NO |
|---|---|---|
| HuVH1B/7A-Back-Sfi | 5'-GTCCTCGCAACTGCG GCCCAGCCGGCCATGGCC CAGRTGCAGCTGGTGCAR TCTGG-3' | SEQ ID NO: 103 |

TABLE 6-continued

Human IgG heavy chain variable region primers extended with SfiI/NcoI restriction sites (sense) and human IgG heavy chain J-region primers extended with XhoI/BstEII restriction sites (anti-sense).

| Primer name | Primer nucleotide sequence | SEQ ID NO |
|---|---|---|
| HuVH1C-Back-Sfi | 5'-GTCCTCGCAACTGCG GCCCAGCCGGCCATGGCC SAGGTCCAGCTGGTRCAG TCTGG-3' | SEQ ID NO: 104 |
| HuVH2B-Back-Sfi | 5'-GTCCTCGCAACTGCG GCCCAGCCGGCCATGGCC CAGRTCACCTTGAAGGAG TCTGG-3' | SEQ ID NO: 105 |
| HuVH3A-Back-Sfi | 5'-GTCCTCGCAACTGCGGCC CAGCCGGCCATGGCCGAGGTG CAGCTGGTGGAG-3' | SEQ ID NO: 106 |
| HuVH3C-Back-Sfi | 5'-GTCCTCGCAACTGCG GCCCAGCCGGCCATGGCC GAGGTGCAGCTGGTGGAG WCYGG-3' | SEQ ID NO: 107 |
| HuVH4B-Back-Sfi | 5'-GTCCTCGCAACTGCG GCCCAGCCGGCCATGGCC CAGGTGCAGCTACAGCAG TGGGG-3' | SEQ ID NO: 108 |
| HuVH4C-Back-Sfi | 5'-GTCCTCGCAACTGCGGCC CAGCCGGCCATGGCCCAGSTG CAGCTGCAGGAGTCSGG-3' | SEQ ID NO: 109 |
| HuVH6A-Back-Sfi | 5'-GTCCTCGCAACTGCG GCCCAGCCGGCCATGGCC CAGGTACAGCTGCAGCA TCAGG-3' | SEQ ID NO: 110 |
| HuJH1/2-FOR-XhoIB | 5'-GAGTCATTCTCGACTCGA GACRGTGACCAGGGTGCC-3' | SEQ ID NO: 111 |
| HuJH3-FOR-Xho | 5'-GAGTCATTCTCGACT CGAGACGGTGACCATTGTCCC-3' | SEQ ID NO: 112 |
| HuJH4/5-FOR-Xho | 5'-GAGTCATTCTCGACT CGAGACGGTGACCAGGGT TCC-3' | SEQ ID NO: 113 |
| HuJH6-FOR-Xho | 5'-GAGTCATTCTCGACTCGA GACGGTGACCGTGGTCCC-3' | SEQ ID NO: 114 |

TABLE 7

Percentage of the different heavy chain products in the final mixture.

| Sense primer | Antisense primer | Product | Percentage |
|---|---|---|---|
| HuVH1B/7A-Back-Sfi + HuVH1C-Back-Sfi | HuJH1/2-FOR-XhoIB | H1J1 | 2.5% |
| | HuJH3-FOR-Xho | H1J2 | 2.5% |
| | HuJH4/5-FOR-Xho | H1J3 | 15.0% |
| | HuJH6-FOR-Xho | H1J4 | 5.0% |
| HuVH2B-Back-Sfi | HuJH1/2-FOR-XhoIB | H2J1 | 0.2% |
| | HuJH3-FOR-Xho | H2J2 | 0.2% |
| | HuJH4/5-FOR-Xho | H2J3 | 1.2% |
| | HuJH6-FOR-Xho | H2J4 | 0.4% |
| HuVH3A-Back-Sfi | HuJH1/2-FOR-XhoIB | H3J1 | 2.5% |
| | HuJH3-FOR-Xho | H3J2 | 2.5% |
| | HuJH4/5-FOR-Xho | H3J3 | 15.0% |
| | HuJH6-FOR-Xho | H3J4 | 5.0% |
| HuVH3C-Back-Sfi | HuJH1/2-FOR-XhoIB | H4J1 | 2.5% |
| | HuJH3-FOR-Xho | H4J2 | 2.5% |
| | HuJH4/5-FOR-Xho | H4J3 | 15.0% |
| | HuJH6-FOR-Xho | H4J4 | 5.0% |

TABLE 7-continued

Percentage of the different heavy chain products in the final mixture.

| Sense primer | Antisense primer | Product | Percentage |
|---|---|---|---|
| HuVH4B-Back-Sfi | HuJH1/2-FOR-XhoIB | H5J1 | 0.2% |
| | HuJH3-FOR-Xho | H5J2 | 0.2% |
| | HuJH4/5-FOR-Xho | H5J3 | 1.2% |
| | HuJH6-FOR-Xho | H5J4 | 0.4% |
| HuVH4C-Back-Sfi | HuJH1/2-FOR-XhoIB | H6J1 | 2.0% |
| | HuJH3-FOR-Xho | H6J2 | 2.0% |
| | HuJH4/5-FOR-Xho | H6J3 | 12.0% |
| | HuJH6-FOR-Xho | H6J4 | 4.0% |
| HuVH6A-Back-Sfi | HuJH1/2-FOR-XhoIB | H7J1 | 0.1% |
| | HuJH3-FOR-Xho | H7J2 | 0.1% |
| | HuJH4/5-FOR-Xho | H7J3 | 0.6% |
| | HuJH6-FOR-Xho | H7J4 | 0.2% |

TABLE 8 staphylococcal clinical isolates used for selection and screening of anti-staphylococcal single-chain (scFv) phage antibodies.

| ID | Strain | Hospital Code | Site of Isolation |
|---|---|---|---|
| Cowan | *S. aureus* | NA | NA |
| SA099 | *S. aureus* | D3 | Anterior Nares |
| SA100 | *S. aureus* | D8 | Anterior Nares |
| SA101 | *S. aureus* | D13 | Anterior Nares |
| SA102 | *S. aureus* | D15 | Anterior Nares |
| SA103 | *S. aureus* | D16 | Anterior Nares |
| SA104 | *S. aureus* | D17 | Anterior Nares |
| SA105 | *S. aureus* | D18 | Anterior Nares |
| SA108 | *S. aureus* | D20 | Anterior Nares |
| SA109 | *S. aureus* | D21 | Anterior Nares |
| SA110 | *S. aureus* | D23 | Anterior Nares |
| SA111 | *S. aureus* | D26 | Anterior Nares |
| SA112 | *S. aureus* | D34 | Anterior Nares |
| SA113 | *S. aureus* | D43 | Anterior Nares |
| SA114 | *S. aureus* | D44 | Anterior Nares |
| SA115 | *S. aureus* | Kv2 | Renal Dialysis |
| SA116 | *S. aureus* | Kv3 | Renal Dialysis |
| SA117 | *S. aureus* | Kv5 | Blood |
| SA118 | *S. aureus* | Kv6 | Blood |
| SA119 | *S. aureus* | Kv7 | Blood |
| SA120 | *S. aureus* | Kv8 | Wound |

TABLE 8-continued staphylococcal clinical isolates used for selection and screening of anti-staphylococcal single-chain (scFv) phage antibodies.

| ID | Strain | Hospital Code | Site of Isolation |
|---|---|---|---|
| SA121 | *S. aureus* | Kv9 | Wound |
| SA122 | *S. aureus* | Kv11 | Wound |
| SA123 | *S. aureus* | Kv24 | CSF |
| SA124 | *S. aureus* | Kv25 | CSF |
| SA125 | *S. aureus* | Kv27 | Lung Pleura |
| SA126 | *S. aureus* | Kv28 | Lung Pleura |
| SA127 | *S. aureus* | Kv30 | Pericardiac |
| SA128 | *S. aureus* | Kv31 | Joint |
| SA129 | *S. aureus* | Kv32 | Joint |
| SE130 | *S. epidermidis* | 1587/29 | Blood |
| SE131 | *S. epidermidis* | 1688/35 | Blood |
| SE132 | *S. epidermidis* | 1724/42 | Blood |
| SE133 | *S. epidermidis* | 1587 (Kv110) | Unknown |
| SE134 | *S. epidermidis* | V48 (Kv115) | Unknown |
| SE135 | *S. epidermidis* | 354 (Kv118) | Unknown |
| SE136 | *S. epidermidis* | V16 | Renal Dialysis |
| SE137 | *S. epidermidis* | V29 | Renal Dialysis |
| SE138 | *S. epidermidis* | V33 | Renal Dialysis |
| SE139 | *S. epidermidis* | V65 | Renal Dialysis |
| SE140 | *S. epidermidis* | V75 | Renal Dialysis |

TABLE 9

*Staphylococcal* specific binding activity of single-chain (scFv) phage antibodies as measured by FACS.

| Name phage | *Staphylococcal* strains (% positive) | | | | | | | | |
|---|---|---|---|---|---|---|---|---|---|
| antibody | Cowan | SA102 | SA103 | SA120 | SA124 | SA125 | SE130 | SA131 | SA132 |
| SC02-430 | 89.0 | ND | 30.0 | 13.0 | ND | ND | ND | ND | ND |
| SC05-132 | 21.9 | ND | 82.7 | 86.5 | ND | 84.2 | ND | ND | ND |
| SC05-133 | 48.2 | ND | 77.9 | 83.4 | ND | 76.2 | ND | ND | ND |
| sc06-166 | 31.2 | 51.4 | 48.1 | ND | 58.4 | 59.0 | 22.0 | 53.3 | 43.2 |
| sc06-171 | 32.1 | 69.7 | 67.4 | ND | 71.7 | 71.2 | 5.0 | 39.3 | 29.2 |
| sc06-176 | 30.1 | 11.7 | 30.1 | ND | 29.9 | 27.2 | 1.9 | 27.6 | 15.1 |
| sc06-187 | 24.5 | 72.5 | 65.5 | ND | 67.8 | 63.8 | 36.6 | 31.4 | 43.7 |
| sc06-193 | 12.0 | 27.7 | 37.2 | ND | 50.3 | 56.2 | 2.9 | 17.0 | 8.9 |
| sc06-249 | 10.4 | ND | ND | ND | ND | ND | ND | ND | 7.6 |
| sc06-273 | 5.1 | 10.1 | 33.2 | ND | 36.9 | 44.0 | 2.2 | 12.4 | 8.0 |
| sc06-389 | 7.3 | 12.9 | 35.7 | ND | 46.4 | 44.2 | 3.0 | 14.4 | 2.3 |
| sc06-403 | 6.3 | 8.8 | 7.7 | ND | 10.4 | 11.5 | 0.7 | 5.4 | 2.7 |
| sc06-406 | 6.8 | 14.7 | 28.5 | ND | 36.7 | 48.3 | 5.3 | 14.4 | 8.0 |
| sc06-410 | 13.3 | ND | ND | ND | ND | ND | ND | ND | 8.1 |
| sc06-446 | 9.5 | 16.9 | 14.6 | ND | 14.3 | 26.8 | 1.0 | 7.3 | 2.0 |
| sc06-450 | 46.7 | 61.1 | 58.4 | ND | 63.9 | 55.1 | 1.3 | 14.0 | 6.4 |
| sc06-452 | 9.6 | ND | ND | ND | ND | ND | 1.2 | 18.5 | 2.5 |
| sc06-453 | 41.0 | 26.2 | 33.6 | ND | 56.7 | 59.3 | 36.0 | 55.8 | 42.0 |
| sc06-464 | 20.4 | 33.2 | 19.6 | ND | 45.2 | 47.2 | 6.2 | 25.7 | 7.2 |
| sc06-471 | 2.1 | 53.5 | 46.0 | ND | 64.4 | 62.8 | 0.4 | 10.7 | 1.0 |
| sc06-516 | 12.2 | ND | ND | ND | ND | ND | 3.7 | 22.3 | 10.0 |
| sc06-517 | 26.5 | 21.6 | 17.7 | ND | 24.4 | 24.9 | 12.4 | 14.3 | 13.8 |
| sc06-526 | 8.5 | 8.1 | 3.4 | ND | 15.7 | 16.3 | 3.6 | 6.7 | 6.3 |
| sc06-528 | 29.9 | 19.6 | 10.1 | ND | 31.3 | 28.4 | 15.5 | 17.6 | 24.3 |
| sc06-531 | 10.4 | 10.2 | 10.2 | ND | 15.6 | 12.0 | 0.8 | 5.3 | 1.7 |
| sc06-533 | 15.7 | 3.9 | 8.6 | ND | 15.8 | 8.3 | ND | 6.0 | 0.8 |
| sc06-536 | 14.5 | 9.8 | 12.6 | ND | 20.1 | 10.9 | 2.0 | 7.5 | 3.1 |
| sc06-537 | 38.0 | 5.5 | 10.0 | ND | 9.2 | 22.4 | 2.6 | 23.5 | 8.3 |
| sc06-538 | 14.3 | 6.2 | 9.6 | ND | 7.9 | 16.4 | 0.4 | 9.1 | 2.1 |
| sc06-540 | 9.3 | 7.3 | 10.5 | ND | 22.7 | 23.4 | 0.6 | 6.4 | 1.7 |
| sc06-544 | 22.6 | 8.5 | 12.1 | ND | 7.6 | 17.2 | 1.6 | 13.8 | 11.7 |
| sc06-566 | 8.00 | 13.5 | 22.6 | ND | 37.1 | 39.4 | 1.0 | 13.4 | 1.7 |
| sc06-625 | 9.00 | 8.00 | 15.4 | ND | 21.4 | 24.2 | 0.9 | 8.00 | 1.9 |
| Neg. Ctrl | 13.2 | 1.5 | 2.5 | ND | 5.8 | 20.8 | 0.9 | 1.4 | 0.5 |

ND not determined

TABLE 10

Non-specific binding activity of staphylococci reactive single-chain (scFv) phage antibodies measured by ELISA at 492 nm.

| Name phage antibody | Negative controls ELISA (OD 492 nm) BSA (1%) | FBS (5%) | ELK (2%) |
|---|---|---|---|
| SC02-430 | 0.04 | 0.04 | 0.05 |
| SC05-132 | 0.04 | 0.04 | 0.04 |
| SC05-133 | 0.04 | 0.04 | 0.04 |
| No phage antibody | 0.04 | 0.04 | 0.04 |
| Negative control | 0.04 | 0.06 | 0.16 |

TABLE 11

Data of the *Staphylococcus* specific single-chain Fvs.

| Name scFv | SEQ ID NO of nucl. sequence | SEQ ID NO of amino acid sequence* | VH-locus | VL-locus |
|---|---|---|---|---|
| SC02-430 | 19 | 20 (Vh 1-118; Vl 134-242) | VH4 (4-31) | Vl 2 (2b2) |
| SC05-132 | 21 | 22 (Vh 1-118; Vl 135-242) | VH3 (3-07) | VkI (L12) |
| SC05-133 | 23 | 24 (Vh 1-120; Vl 137-244) | VH3 (3-11) | VkIII (A27) |

*between brackets the amino acids making up the heavy chain variable region (VH) and the light chain variable region (VL) is shown

TABLE 12

Data of the CDR regions of the *Staphylococcus* specific single-chain Fvs.

| Name scFv | HCDR1 (SEQ ID NO:) | HCDR2 (SEQ ID NO:) | HCDR3 (SEQ ID NO:) | LCDR1 (SEQ ID NO:) | LCDR2 (SEQ ID NO:) | LCDR3 (SEQ ID NO:) |
|---|---|---|---|---|---|---|
| SC02-430 | 1 | 2 | 3 | 4 | 5 | 6 |
| SC05-132 | 7 | 8 | 9 | 10 | 11 | 12 |
| SC05-133 | 13 | 14 | 15 | 16 | 17 | 18 |

TABLE 13

Data of the *Staphylococcus* specific IgGs.

| Name IgG | SEQ ID NO of nucl. sequence heavy chain | SEQ ID NO of amino acid sequence* heavy chain | SEQ ID NO of nucl. sequence light chain | SEQ ID NO of amino acid sequence* light chain |
|---|---|---|---|---|
| CR2430 | 25 | 26 (Vh 1-118) | 31 | 32 (Vl 1-109) |
| CR5132 | 27 | 28 (Vh 1-118) | 33 | 34 (Vl 1-110) |
| CR5133 | 29 | 30 (Vh 1-120) | 35 | 36 (Vl 1-110) |

*between brackets the amino acids making up the heavy chain variable region (VH) and the light chain variable region (VL) is shown

TABLE 14

Staphylococcal specific binding activity of IgG1 molecules as measured by FACS.

| Name phage antibody | Staphylococcal strains (MFI) Cowan | SA102 | SA103 | SA124 | SA125 | SE130 | SA131 | SA132 |
|---|---|---|---|---|---|---|---|---|
| CR2430 | 281.4 | ND | ND | ND | ND | ND | ND | ND |
| CR5132 | 192.4 | 9.7 | 9.3 | 20.1 | 13.7 | 222.5 | 141.5 | 128.5 |
| CR5133 | 285.8 | ND | ND | ND | ND | 229.9 | 203.3 | 252.6 |
| Neg. Ctrl | 3.6 | 3.2 | 3.0 | 3.3 | 3.5 | 2.5 | 3.1 | 2.7 |

ND not determined

TABLE 15

*Staphylococcal* binding activity of IgG1 antibodies as measured by FACS.

| Strain | Isolation site/ resistance | Name | IgG1 binding activity (MFI) Ctrl | CR5132 | CR5133 | CR5140 | CR6171 | CR6453 |
|---|---|---|---|---|---|---|---|---|
| *S. aureus* | CAPD/ND | KV01 | 4.05 | 1064 | 850 | 756 | 2 | 564 |
| *S. aureus* | CAPD/ND | KV02 | 16.63 | 919 | 558 | 433 | 147 | 552 |
| *S. aureus* | CAPD/ND | KV03 | 36.3 | 949 | 583 | 358 | 164 | 668 |
| *S. aureus* | CAPD/ND | KV04 | 11.64 | 1123 | 629 | 546 | 197 | 752 |
| *S. aureus* | Blood/ND | KV05 | 12.33 | 564 | 652 | 447 | 134.2 | 525 |
| *S. aureus* | Blood/ND | KV06 | 10.41 | 634 | 526 | 386 | 142.2 | 439 |
| *S. aureus* | Blood/ND | KV07 | 21.04 | 881 | 705 | 441 | 168.4 | 614 |
| *S. aureus* | Wound/ND | KV09 | 23.83 | 754 | 483 | 305 | 134.7 | 515 |
| *S. aureus* | Wound/ND | KV11 | 16.12 | 363 | 280 | 226 | 106.7 | 362 |
| *S. aureus* | Wound/ND | KV12 | 27.55 | 571 | 381 | 224 | 127.4 | 457 |
| *S. aureus* | Blood/ND | KV13 | 23.19 | 576 | 403 | 278 | 141.8 | 503 |
| *S. aureus* | NA/ND | Newman | 8.01 | 655 | 430 | 384 | 153.1 | 387 |
| *S. aureus* | CAPD/ND | KV15 | 22.1 | 674 | 311 | 232 | 99.8 | 481 |
| *S. aureus* | CAPD/ND | KV16 | 9.09 | 458 | 291 | 248 | 97.9 | 334 |
| *S. aureus* | CAPD/ND | KV17 | 8.4 | 226 | 184.5 | 161.1 | 57.4 | 154.5 |

TABLE 15-continued

*Staphylococcal* binding activity of IgG1 antibodies as measured by FACS.

| Strain | Isolation site/ resistance | Name | IgG1 binding activity (MFI) Ctrl | CR5132 | CR5133 | CR5140 | CR6171 | CR6453 |
|---|---|---|---|---|---|---|---|---|
| *S. aureus* | CAPD/ND | KV18 | 13.91 | 269 | 203 | 166.2 | 62.4 | 158.7 |
| *S. aureus* | Blood/ND | KV19 | 2.66 | 190.9 | 194.6 | 203 | 44.6 | 83.3 |
| *S. aureus* | Blood/ND | KV20 | 5.12 | 311 | 298 | 251 | 64.9 | 95 |
| *S. aureus* | Blood/ND | KV21 | 3.67 | 353 | 266 | 290 | 73.9 | 140 |
| *S. aureus* | Liquor/ND | KV24 | 4.28 | 320.2 | 242 | 223 | 69.9 | 102 |
| *S. aureus* | Liquor/ND | KV25 | 3.37 | 269 | 219 | 188.5 | 53.3 | 105.5 |
| *S. aureus* | Liquor/ND | KV26 | 10.03 | 217 | 183.7 | 162.9 | 38.6 | 86.4 |
| *S. aureus* | Pleura/ND | KV27 | 4.03 | 348 | 235 | 239 | 52.9 | 129.4 |
| *S. aureus* | Pleura/ND | KV28 | 6.98 | 217.4 | 184.6 | 203 | 46.7 | 74.1 |
| *S. aureus* | Pleura/ND | KV29 | 2.99 | 183.4 | 182.6 | 147.9 | 38.5 | 110.2 |
| *S. aureus* | Pericard/ND | KV30 | 3.55 | 357 | 358 | 372 | 77.7 | 152.1 |
| *S. aureus* | Joint/ND | KV31 | 4.89 | 200 | 192.3 | 178.7 | 38.1 | 106.5 |
| *S. aureus* | Joint/ND | KV33 | 5.88 | 222 | 232 | 177 | 58.5 | 174.4 |
| *S. aureus* | Wound/ND | KV34 | 7.45 | 286 | 199 | 160.8 | 59.6 | 183.5 |
| *S. aureus* | Wound/ND | KV35 | 4.02 | 237 | 213 | 232 | 70.2 | 190.9 |
| *S. aureus* | Wound/ND | KV36 | 3.44 | 285 | 247 | 229 | 76.4 | 218 |
| *S. aureus* | Wound/ND | KV37 | 4.05 | 217 | 215 | 212 | 42.6 | 125.5 |
| *S. aureus* | ND/MRSA | KV38 | 6.1 | 920 | 642 | 192.3 | 20.4 | 683 |
| *S. aureus* | ND/MRSA | KV39 | 6.06 | 953 | 657 | 615 | 173 | 604 |
| *S. aureus* | ND/MRSA | KV41 | 6.8 | 1038 | 854 | 732 | 226 | 739 |
| *S. aureus* | ND/MRSA | KV42 | 12.41 | 1340 | 950 | 678 | 221 | 973 |
| *S. aureus* | ND/MRSA | KV43 | 5.55 | 1084 | 711 | 480 | 129.6 | 772 |
| *S. aureus* | Enterotoxin-/ND | KV46 | 18.38 | 1144 | 607 | 247 | 79 | 776 |
| *S. aureus* | enterotoxin-/ND | KV47 | 8.58 | 809 | 513 | 353 | 102.1 | 436 |
| *S. aureus* | Blood pediatric/ND | KV48 | 5.29 | 306 | 271 | 210 | 34.5 | 153 |
| *S. aureus* | Blood pediatric/ND | KV49 | 6.53 | 747 | 562 | 522 | 99.7 | 388 |
| *S. aureus* | Blood pediatric/ND | KV50 | 15.86 | 939 | 539 | 397 | 117.8 | 864 |
| *S. aureus* | Blood pediatric/ND | KV51 | 10.25 | 818 | 680 | 510 | 111.9 | 410 |
| *S. aureus* | NA/ND | MW2 | 9.15 | 1080 | 1021 | 774 | 210 | 818 |
| *S. aureus* | NA/ND | COL | 19.62 | 471 | 542 | 192 | 61.7 | 339 |
| *S. epidermidis* | NA/ND | KV110 | 9.01 | 438 | 1221 | 499 | 7.04 | 1210 |
| *S. hominis* | NA/ND | KV111 | 4.57 | 16.91 | 39.1 | 4.11 | 4.01 | 13.43 |
| *S. warneri* | NA/ND | KV112 | 2.95 | 126.4 | 11.7 | 5.44 | 4.39 | 105.6 |
| *S. saprof.* | NA/ND | KV113 | 6.35 | 186.2 | 17.34 | 136.6 | 9.16 | 118.8 |
| *S. warneri* | NA/ND | KV114 | 8.67 | 292 | 303 | 8.63 | 9.17 | 113.4 |
| *S. epidermidis* | NA/ND | KV115 | 12.58 | 886 | 1577 | 11.76 | 90.2 | 369 |
| *S. haemolyticus* | NA/ND | KV117 | 7.23 | 111.8 | 79.5 | 9.89 | 6.44 | 79.9 |
| *S. hominis* | NA/ND | KV118 | 11 | 1334 | 2085 | 97.8 | 9.02 | 1750 |
| *S. haemolyticus* | NA/ND | K119 | 16.71 | 816 | 888 | 103.9 | 11.71 | 371 |
| *S. warneri* | NA/ND | vd65 | 8.24 | 419 | 192.2 | 5.08 | 4.78 | 73.4 |
| *S. warneri* | NA/ND | vd66 | 5.77 | 237 | 104.9 | 6.23 | 5.57 | 80.5 |
| *S. warneri* | NA/ND | vd732 | 7.82 | 285 | 289 | 7.62 | 4.32 | 100.6 |
| *S. warneri* | NA/ND | K706 | 4.21 | 214 | 225 | 14.62 | 10.3 | 68.7 |
| *S. hominis* | NA/ND | vd136 | 4.54 | 25.4 | 815 | 7.37 | 4.13 | 6.4 |
| *S. hominis* | NA/ND | vd139 | 5.64 | 90.3 | 211 | 5.47 | 4.4 | 133.7 |
| *S. hominis* | NA/ND | K136 | 6.48 | 25.3 | 842 | 10.57 | 6.83 | 6.02 |

TABLE 16

*Staphylococcal* killing activity of IgG1 antibodies as measured by OPKA.

| | Mean *staphylococcal* killing activity (%) Strain | | | | | | | |
|---|---|---|---|---|---|---|---|---|
| | 502 [ng/ml] | | Mn8 | | Newman | | M187 | |
| IgG1 antibody | 1250 | 12.5 | 1250 | 12.5 | 1250 | 12.5 | 1250 | 12.5 |
| CR5132 | 83.9 | 43.2 | 85.0 | 37.3 | 70.4 | 47.5 | 80.9 | 64.0 |
| CR5133 | 92.1 | 62.5 | 84.5 | 46.4 | 72.4 | 53.1 | 78.1 | 54.9 |
| CR6166 | 71.6 | 35.1 | 52.1 | 5.5 | 64.8 | 35.1 | 19.3 | 3.3 |
| CR6171 | 81.9 | 40.1 | 88.8 | 52.7 | 62.8 | 39.9 | 29.0 | 14.7 |
| CR6176 | 78.4 | 38.2 | 70.7 | 31.9 | 74.3 | 55.8 | 31.9 | 11.0 |
| CR6187 | 78.1 | 47.1 | 70.3 | 39.0 | 47.3 | 24.7 | 5.9 | 3.7 |
| CR6193 | 61.0 | 37.6 | 81.1 | 44.1 | 61.5 | 28.5 | 6.0 | −0.8 |
| CR6249 | 82.2 | 30.3 | 90.4 | 46.5 | 51.6 | 26.4 | 4.0 | 1.2 |
| CR6273 | 91.5 | 58.2 | 64.0 | 9.1 | 58.8 | 39.9 | 14.8 | 4.7 |
| CR6403 | 85.4 | 35.9 | 62.1 | 21.7 | 59.8 | 35.6 | 22.7 | 7.6 |

TABLE 16-continued

*Staphylococcal* killing activity of IgG1 antibodies as measured by OPKA.

| | Mean *staphylococcal* killing activity (%) Strain | | | | | | | |
|---|---|---|---|---|---|---|---|---|
| | 502 [ng/ml] | | Mn8 | | Newman | | M187 | |
| IgG1 antibody | 1250 | 12.5 | 1250 | 12.5 | 1250 | 12.5 | 1250 | 12.5 |
| CR6406 | 84.0 | 51.3 | 78.5 | 35.8 | 58.0 | 26.1 | 30.3 | 14.1 |
| CR6410 | 81.9 | 46.9 | 56.6 | 24.4 | 54.1 | 27.6 | 48.6 | 18.4 |
| CR6446 | 69.5 | 41.3 | 54.6 | 33.6 | 64.1 | 41.2 | 59.1 | 48.6 |
| CR6450 | 76.3 | 21.9 | 67.0 | 28.4 | 60.6 | 35.4 | 2.0 | −0.7 |
| CR6452 | 83.9 | 30.6 | 91.6 | 41.3 | 57.5 | 36.0 | 7.9 | 2.6 |
| CR6453 | 85.9 | 46.0 | 67.0 | 21.0 | 74.1 | 49.7 | 83.2 | 57.5 |
| CR6464 | 85.9 | 36.7 | 55.5 | 11.4 | 57.2 | 30.7 | 6.8 | 1.4 |
| CR6471 | 96.0 | 68.2 | 44.2 | 7.1 | 62.6 | 34.7 | 8.0 | 0.0 |
| CR6516 | 85.9 | 49.4 | 68.1 | 36.1 | 59.9 | 23.2 | 8.5 | 3.9 |
| CR6517 | 79.4 | 36.1 | 59.8 | 18.4 | 54.8 | 21.5 | 5.8 | 5.1 |

TABLE 16-continued

*Staphylococcal* killing activity of IgG1 antibodies as measured by OPKA.

| | Mean *staphylococcal* killing activity (%) Strain | | | | | | | |
|---|---|---|---|---|---|---|---|---|
| | 502 | | Mn8 | | Newman | | M187 | |
| | [ng/ml] | | | | | | | |
| IgG1 antibody | 1250 | 12.5 | 1250 | 12.5 | 1250 | 12.5 | 1250 | 12.5 |
| CR6526 | 88.8 | 55.3 | 51.1 | 16.7 | 56.5 | 23.7 | 35.2 | 9.4 |
| CR6528 | 89.6 | 47.0 | 49.0 | 16.4 | 55.7 | 27.0 | 6.4 | 1.8 |
| CR6531 | 77.5 | 35.6 | 61.2 | 37.5 | 62.1 | 23.0 | 7.9 | −0.7 |
| CR6533 | 73.6 | 38.4 | 53.6 | 28.9 | 67.2 | 37.8 | 7.1 | 3.3 |
| CR6536 | 91.1 | 59.6 | 46.3 | 17.5 | 69.1 | 48.3 | 4.6 | −1.4 |
| CR6537 | 70.3 | 28.9 | 69.1 | 21.5 | 60.4 | 23.3 | 2.5 | 3.9 |
| CR6538 | 64.9 | 22.6 | 63.9 | 15.2 | 66.3 | 35.2 | 3.3 | 2.0 |
| CR6540 | 92.6 | 53.0 | 63.9 | 16.4 | 61.1 | 38.2 | 8.9 | 4.4 |
| CR6544 | 79.8 | 28.8 | 59.3 | 22.5 | 62.3 | 25.4 | 3.2 | 2.0 |
| CR6566 | 20.9 | 14.2 | 21.3 | 8.7 | 6.3 | −1.6 | 54.3 | 30.4 |
| CR6625 | 20.2 | 9.7 | 8.6 | −0.8 | 51.0 | 23.3 | 43.8 | 19.1 |
| Neg. Ctrl | ND | ND | ND | ND | 4.0 | ND | 4.5 | 0.0 |

TABLE 17

LTA binding activity of IgG1 antibodies as measured by ELISA.

| | ELISA binding to LTA (OD492 nm) | | | | | | |
|---|---|---|---|---|---|---|---|
| IgG1 | 10 | 3 | 1 | 0.3 | 0.1 | 0.03 | 0.01 |
| CR5133 | 3.3 | 2.58 | 2.093 | 1.429 | 0.631 | 0.356 | 0.171 |
| CR6166 | 0.052 | 0.051 | 0.051 | 0.049 | 0.054 | 0.052 | 0.049 |
| CR6171 | 0.133 | 0.127 | 0.121 | 0.116 | 0.091 | 0.073 | 0.065 |
| CR6176 | 0.048 | 0.053 | 0.05 | 0.046 | 0.046 | 0.062 | 0.111 |
| CR6526 | 0.049 | 0.053 | 0.05 | 0.049 | 0.048 | 0.053 | 0.052 |
| CR4374 | 0.093 | 0.099 | 0.084 | 0.073 | 0.07 | 0.07 | 0.069 |
| 12248 | 2.574 | 2.297 | 2.054 | 1.457 | 0.799 | 0.402 | 0.26 |
| PBS | 0.113 | 0.124 | 0.098 | 0.094 | 0.09 | 0.108 | 0.094 |

REFERENCES

Boel E., S. Verlaan, M. J. Poppelier, N. A. Westerdaal, J. A. Van Strijp, and T. Logtenberg (2000), Functional human monoclonal antibodies of all isotypes constructed from phage display library-derived single-chain Fv antibody fragments. *J. Immunol. Methods* 239:153-166.

Burton D. R. and C. F. Barbas (1994), Human antibodies from combinatorial libraries. *Adv. Immunol.* 57:191-280.

Cantinieaux B., C. Hariga, P. Courtoy, J. Hupin and P. Fondu (1989), *Staphylococcus aureus* phagocytosis. A new cytofluorometric method using FITC and paraformaldehyde. *J. Immunol. Methods* 121:203-208.

Chothia and Lesk (1987), Canonical structures for the hypervariable regions of immunoglobulins. *J. Mol. Biol.* 196: 901-917.

Chou T. C. and P. Talalay (1984), Quantitative analysis of dose-effect relationships: the combined effects of multiple drugs or enzyme inhibitors. *Adv. Enzyme Regul.* 22:27-55.

De Kruif J., L. Terstappen, E. Boel and T. Logtenberg (1995a), Rapid selection of cell subpopulation-specific human monoclonal antibodies from a synthetic phage antibody library. *Proc. Natl. Acad. Sci. USA* 92:3938.

De Kruif J., E. Boel and T. Logtenberg (1995b), Selection and application of human single-chain Fv antibody fragments from a semi-synthetic phage antibody display library with designed CDR3 regions. *J. Mol. Biol.* 248:97-105.

Huls G., I. J. Heijnen, E. Cuomo, J. van der Linden, E. Boel, J. van de Winkel and T. Logtenberg (1999), Antitumor immune effector mechanisms recruited by phage display-derived fully human IgG1 and IgA1 monoclonal antibodies. *Cancer Res.* 59:5778-5784.

Slootstra J. W., W. C. Puijk, G. J. Ligtvoet, J. P. Langeveld, and R. H. Meloen (1996), Structural aspects of antibody-antigen interaction revealed through small random peptide libraries. *Mol. Divers.* 1:87-96.

What is claimed is:

1. An isolated human monoclonal antibody having opsonic phagocytic killing activity against at least two different *Staphylococcus* species and against at least three different strains of *Staphylococcus aureus*, wherein the antibody is selected from the group consisting of:

i) an antibody with a heavy chain comprising the variable region of SEQ ID NO:30 and a light chain comprising the variable region of SEQ ID NO:36;

ii) an antibody with a heavy chain comprising the variable region of SEQ ID NO:117 and a light chain comprising the variable region of SEQ ID NO:177;

iii) an antibody with a heavy chain comprising the variable region of SEQ ID NO:119 and a light chain comprising the variable region of SEQ ID NO:179;

iv) an antibody with a heavy chain comprising the variable region of SEQ ID NO:121 and a light chain comprising the variable region of SEQ ID NO:181; and v) an antibody with a heavy chain comprising the variable region of SEQ ID NO:155 and a light chain comprising the variable region of SEQ ID NO:215.

2. The human monoclonal antibody of claim 1, characterized in having opsonic phagocytic killing activity when the *Staphylococcus* species are in logarithmic growth phase and in static phase.

3. The human monoclonal antibody of claim 1, wherein the *Staphylococcus* species comprise *S. aureus* and *S. epidermidis*.

4. The human monoclonal antibody of claim 2, wherein the *Staphylococcus* species comprise *S. aureus* and *S. epidermidis*.

5. An immunoconjugate comprising: the human monoclonal antibody of claim 1 and at least one tag.

6. An immunoconjugate comprising: the human monoclonal antibody of claim 2 and at least one tag.

7. An immunoconjugate comprising: the human monoclonal antibody of claim 3 and at least one tag.

8. An immunoconjugate comprising: the human monoclonal antibody of claim 4 and at least one tag.

9. A composition comprising the human monoclonal antibody of claim 1, and at least one pharmaceutically acceptable excipient.

10. A composition comprising the human monoclonal antibody of claim 2, and at least one pharmaceutically acceptable excipient.

11. A composition comprising the human monoclonal antibody of claim 3, and at least one pharmaceutically acceptable excipient.

12. A composition comprising the human monoclonal antibody of claim 4, and at least one pharmaceutically acceptable excipient.

13. The composition of claim 9, further comprising at least one other therapeutic agent.

14. The composition of claim 10, further comprising at least one other therapeutic agent.

15. A method of diagnosing, prophylaxing, and/or treating a staphylococcal disease in a subject, wherein the method comprises utilizing the human monoclonal antibody of claim 1 for the diagnosis, prophylaxis, treatment, or combination thereof, of the staphylococcal disease.

* * * * *

SEQUENCE LISTING

```
<160> NUMBER OF SEQ ID NOS: 235

<210> SEQ ID NO 1
<211> LENGTH: 7
<212> TYPE: PRT
<213> ORGANISM: Homo sapiens

<400> SEQUENCE: 1

Ser Gly Gly Tyr Tyr Trp Ser
1               5


<210> SEQ ID NO 2
<211> LENGTH: 16
<212> TYPE: PRT
<213> ORGANISM: Homo sapiens

<400> SEQUENCE: 2

Tyr Ile Tyr Tyr Ser Gly Ser Thr Tyr Tyr Asn Ser Ser Leu Lys Ser
1               5                   10                  15


<210> SEQ ID NO 3
<211> LENGTH: 8
<212> TYPE: PRT
<213> ORGANISM: Homo sapiens

<400> SEQUENCE: 3
```

Thr Val Met Asn Ser Phe Phe Asp
1 5

<210> SEQ ID NO 4
<211> LENGTH: 14
<212> TYPE: PRT
<213> ORGANISM: Homo sapiens

<400> SEQUENCE: 4

Thr Gly Thr Ser Ser Asp Val Gly Ser Tyr Asn Leu Val Ser
1 5 10

<210> SEQ ID NO 5
<211> LENGTH: 7
<212> TYPE: PRT
<213> ORGANISM: Homo sapiens

<400> SEQUENCE: 5

Glu Val Ser Lys Arg Pro Ser
1 5

<210> SEQ ID NO 6
<211> LENGTH: 9
<212> TYPE: PRT
<213> ORGANISM: Homo sapiens

<400> SEQUENCE: 6

Cys Ser Tyr Ala Gly Ser Ser Trp Val
1 5

<210> SEQ ID NO 7
<211> LENGTH: 5
<212> TYPE: PRT
<213> ORGANISM: Homo sapiens

<400> SEQUENCE: 7

Asn Tyr Trp Met Thr
1 5

<210> SEQ ID NO 8
<211> LENGTH: 17
<212> TYPE: PRT
<213> ORGANISM: Homo sapiens

<400> SEQUENCE: 8

Asn Ile Asn Arg Asp Gly Ser Asp Lys Tyr His Val Asp Ser Val Glu
1 5 10 15

Gly

<210> SEQ ID NO 9
<211> LENGTH: 11
<212> TYPE: PRT
<213> ORGANISM: Homo sapiens

<400> SEQUENCE: 9

Gly Gly Arg Thr Thr Ser Trp Tyr Trp Arg Asn
1 5 10

<210> SEQ ID NO 10
<211> LENGTH: 11
<212> TYPE: PRT
<213> ORGANISM: Homo sapiens

<400> SEQUENCE: 10

Arg Ala Ser Gln Ser Ile Ser Ser Trp Leu Ala
1 5 10

<210> SEQ ID NO 11
<211> LENGTH: 7
<212> TYPE: PRT
<213> ORGANISM: Homo sapiens

<400> SEQUENCE: 11

Lys Ala Ser Ser Leu Glu Ser
1 5

<210> SEQ ID NO 12
<211> LENGTH: 9
<212> TYPE: PRT
<213> ORGANISM: Homo sapiens

<400> SEQUENCE: 12

Gln Gln Tyr Asn Ser Tyr Pro Leu Thr
1 5

<210> SEQ ID NO 13
<211> LENGTH: 5
<212> TYPE: PRT
<213> ORGANISM: Homo sapiens

<400> SEQUENCE: 13

Asp Tyr Tyr Met Thr
1 5

<210> SEQ ID NO 14
<211> LENGTH: 17
<212> TYPE: PRT
<213> ORGANISM: Homo sapiens

<400> SEQUENCE: 14

His Ile Ser Gly Ser Gly Ser Thr Ile Tyr Tyr Ala Asp Ser Val Arg
1 5 10 15

Gly

<210> SEQ ID NO 15
<211> LENGTH: 11
<212> TYPE: PRT
<213> ORGANISM: Homo sapiens

<400> SEQUENCE: 15

Gly Gly Arg Ala Thr Ser Tyr Tyr Trp Val His
1 5 10

<210> SEQ ID NO 16
<211> LENGTH: 11
<212> TYPE: PRT
<213> ORGANISM: Homo sapiens

<400> SEQUENCE: 16

Arg Ala Ser Gln Ser Val Ser Gly Tyr Leu Gly
1 5 10

<210> SEQ ID NO 17
<211> LENGTH: 7
<212> TYPE: PRT
<213> ORGANISM: Homo sapiens

<400> SEQUENCE: 17

Gly Ala Ser Ser Arg Ala Thr 1 5

<210> SEQ ID NO 18
<211> LENGTH: 9
<212> TYPE: PRT
<213> ORGANISM: Homo sapiens

<400> SEQUENCE: 18

Gln Gln Tyr Gly Ser Ser Pro Leu Thr
1 5

<210> SEQ ID NO 19
<211> LENGTH: 726
<212> TYPE: DNA
<213> ORGANISM: Artificial sequence
<220> FEATURE:
<223> OTHER INFORMATION: SC02-430

<400> SEQUENCE: 19
taggtgcagc tgcaggagtc gggcccagga ctggtgaagc cttcacagac cctgtccctc 60
acctgcactg tctctggtgg ctccatcagc agtggtggtt actactggag ctggatccgg 120
cagcccccag ggaagggact ggagtggatt gggtacatct attacagtgg gagcacctac 180
tacaactcgt ccctcaagag tcgagttacc atatcagtag acacgtctaa gaaccagttc 240
tccctgaagc tgagctctgt gactgccgcg gacacggccg tgtattactg tgcaaagacg 300
gttatgaatt cgttctttga ctggggccaa ggtaccctgg tcaccgtctc gagtggtgga 360
ggcggttcag gcggaggtgg ctctggcggt ggcggatcgg aaattgagct cacgcagccg 420
ccctccgtgt ctgggtctcc tggacagtcg atcaccatct cctgcactgg aaccagcagt 480
gatgttggga gttataacct tgtctcctgg taccaacagc acccaggcaa agcccccaaa 540
ctcatgattt atgaggtcag taagcggccc tcaggggttt ctaatcgctt ctctggctcc 600
aagtctggca acacggcctc cctgacaatc tctgggctcc aggctgagga cgaggctgat 660
tattactgct gctcatatgc aggtagtagc tgggtgttcg gcggagggac caagctgacc 720
gtccta 726

<210> SEQ ID NO 20
<211> LENGTH: 242
<212> TYPE: PRT
<213> ORGANISM: Artificial sequence
<220> FEATURE:
<223> OTHER INFORMATION: SC02-430

<400> SEQUENCE: 20

Gln Val Gln Leu Gln Glu Ser Gly Pro Gly Leu Val Lys Pro Ser Gln
1 5 10 15

Thr Leu Ser Leu Thr Cys Thr Val Ser Gly Gly Ser Ile Ser Ser Gly
20 25 30

Gly Tyr Tyr Trp Ser Trp Ile Arg Gln Pro Pro Gly Lys Gly Leu Glu
35 40 45

Trp Ile Gly Tyr Ile Tyr Tyr Ser Gly Ser Thr Tyr Tyr Asn Ser Ser
50 55 60

Leu Lys Ser Arg Val Thr Ile Ser Val Asp Thr Ser Lys Asn Gln Phe
65 70 75 80

Ser Leu Lys Leu Ser Ser Val Thr Ala Ala Asp Thr Ala Val Tyr Tyr
85 90 95

Cys Ala Lys Thr Val Met Asn Ser Phe Phe Asp Trp Gly Gln Gly Thr
100 105 110

```
Leu Val Thr Val Ser Ser Gly Gly Gly Gly Ser Gly Gly Gly Gly Ser
        115                 120                 125

Gly Gly Gly Gly Ser Glu Ile Glu Leu Thr Gln Pro Pro Ser Val Ser
    130                 135                 140

Gly Ser Pro Gly Gln Ser Ile Thr Ile Ser Cys Thr Gly Thr Ser Ser
145                 150                 155                 160

Asp Val Gly Ser Tyr Asn Leu Val Ser Trp Tyr Gln Gln His Pro Gly
                165                 170                 175

Lys Ala Pro Lys Leu Met Ile Tyr Glu Val Ser Lys Arg Pro Ser Gly
            180                 185                 190

Val Ser Asn Arg Phe Ser Gly Ser Lys Ser Gly Asn Thr Ala Ser Leu
        195                 200                 205

Thr Ile Ser Gly Leu Gln Ala Glu Asp Glu Ala Asp Tyr Tyr Cys Cys
    210                 215                 220

Ser Tyr Ala Gly Ser Ser Trp Val Phe Gly Gly Gly Thr Lys Leu Thr
225                 230                 235                 240

Val Leu


<210> SEQ ID NO 21
<211> LENGTH: 726
<212> TYPE: DNA
<213> ORGANISM: Artificial sequence
<220> FEATURE:
<223> OTHER INFORMATION: SC05-132

<400> SEQUENCE: 21

gaggtgctgg agtctggggg aggcttggtc cagccggggg ggtccctgag actgtcctgt      60

tcagactctg gattctcctt taataactat tggatgacct gggtccgcca ggctccgggg     120

aaggggctgg agtgggtggc caacataaat cgagatggaa gtgacaagta ccatgtagac     180

tctgtggagg gccgattcac catctccaga gacaactcca agaactcact atacctgcaa     240

atgaacaacc tgagagccga cgacgcggcg gtatattttt gtgcgagagg cggccggact     300

actagctggt attggagaaa ctggggccag ggaaccctgg tcaccgtctc gagcggtacg     360

ggcggttcag gcggaaccgg cagcggcact ggcgggtcga cggacatcca gatgacccag     420

tctccttcca ccctgtctgc atctgtagga gacagagtca ccatcacttg ccgggccagt     480

cagagtatta gtagctggtt ggcctggtat cagcagaaac cagggaaagc ccctaagctc     540

ctgatctata aggcgtctag tttagaaagt ggggtcccat caaggttcag cggcagtgga     600

tctgggacag aattcactct caccatcagc agcctgcagc ctgatgattt tgcaacttat     660

tactgccaac agtataatag ttacccccctc actttcggcg gagggaccaa gctggagatc     720

aaacgt                                                                726


<210> SEQ ID NO 22
<211> LENGTH: 242
<212> TYPE: PRT
<213> ORGANISM: Artificial sequence
<220> FEATURE:
<223> OTHER INFORMATION: SC05-132

<400> SEQUENCE: 22

Glu Val Leu Glu Ser Gly Gly Gly Leu Val Gln Pro Gly Gly Ser Leu
1               5                   10                  15

Arg Leu Ser Cys Ser Asp Ser Gly Phe Ser Phe Asn Asn Tyr Trp Met
            20                  25                  30

Thr Trp Val Arg Gln Ala Pro Gly Lys Gly Leu Glu Trp Val Ala Asn
        35                  40                  45
```

```
Ile Asn Arg Asp Gly Ser Asp Lys Tyr His Val Asp Ser Val Glu Gly
    50                  55                  60

Arg Phe Thr Ile Ser Arg Asp Asn Ser Lys Asn Ser Leu Tyr Leu Gln
65                  70                  75                  80

Met Asn Asn Leu Arg Ala Asp Asp Ala Ala Val Tyr Phe Cys Ala Arg
                85                  90                  95

Gly Gly Arg Thr Thr Ser Trp Tyr Trp Arg Asn Trp Gly Gln Gly Thr
            100                 105                 110

Leu Val Thr Val Ser Ser Gly Thr Gly Gly Ser Gly Gly Thr Gly Ser
        115                 120                 125

Gly Thr Gly Gly Ser Thr Asp Ile Gln Met Thr Gln Ser Pro Ser Thr
    130                 135                 140

Leu Ser Ala Ser Val Gly Asp Arg Val Thr Ile Thr Cys Arg Ala Ser
145                 150                 155                 160

Gln Ser Ile Ser Ser Trp Leu Ala Trp Tyr Gln Gln Lys Pro Gly Lys
                165                 170                 175

Ala Pro Lys Leu Leu Ile Tyr Lys Ala Ser Ser Leu Glu Ser Gly Val
            180                 185                 190

Pro Ser Arg Phe Ser Gly Ser Gly Ser Gly Thr Glu Phe Thr Leu Thr
        195                 200                 205

Ile Ser Ser Leu Gln Pro Asp Asp Phe Ala Thr Tyr Tyr Cys Gln Gln
    210                 215                 220

Tyr Asn Ser Tyr Pro Leu Thr Phe Gly Gly Gly Thr Lys Leu Glu Ile
225                 230                 235                 240

Lys Arg
```

<210> SEQ ID NO 23
<211> LENGTH: 732
<212> TYPE: DNA
<213> ORGANISM: Artificial sequence
<220> FEATURE:
<223> OTHER INFORMATION: SC05-133

<400> SEQUENCE: 23

```
gaggtgcagc tggtggagac tgggggaggc ttggtcaagc ctggagggtc cctgagactc     60

tcctgctcag cctctagatt cagcttcagg gactactaca tgacgtggat ccgccaggct    120

ccagggaagg ggccggaatg ggtttcacac ataagtggca gtggcagtac gatttactac    180

gcagactctg tgaggggccg attcaccatc tccagggaca acgccaagag ctccttgtat    240

ctgcaaatgg atagcctaca ggccgacgac acggccgtat attactgtgc gagagggggt    300

cgcgccacca gttactactg ggtccactgg ggcccgggaa ccctggtcac cgtctcgagc    360

ggtacgggcg gttcaggcgg aaccggcagc ggcactggcg ggtcgacgga aattgtgttg    420

acgcagtctc cagccaccct gtctttgtct ccaggggaaa gagccaccct ctcctgcagg    480

gccagtcaga gtgttagcgg ctacttaggc tggtaccaac agaaacctgg ccaggctccc    540

aggctcctca tctatggtgc atccagcagg gccactggca tcccagacag gttcagtggc    600

agtgggtctg ggacagactt cactctcacc atcagccggc tggagcctga agattttgca    660

gtgtattact gtcagcagta tggtagctca ccgctcactt tcggcggagg gaccaagctg    720

gagatcaaac gt                                                        732
```

<210> SEQ ID NO 24
<211> LENGTH: 244
<212> TYPE: PRT
<213> ORGANISM: Artificial sequence

<220> FEATURE:
<223> OTHER INFORMATION: SC05-133

<400> SEQUENCE: 24

```
Glu Val Gln Leu Val Glu Thr Gly Gly Gly Leu Val Lys Pro Gly Gly
1               5                   10                  15

Ser Leu Arg Leu Ser Cys Ser Ala Ser Arg Phe Ser Phe Arg Asp Tyr
            20                  25                  30

Tyr Met Thr Trp Ile Arg Gln Ala Pro Gly Lys Gly Pro Glu Trp Val
        35                  40                  45

Ser His Ile Ser Gly Ser Gly Ser Thr Ile Tyr Tyr Ala Asp Ser Val
    50                  55                  60

Arg Gly Arg Phe Thr Ile Ser Arg Asp Asn Ala Lys Ser Ser Leu Tyr
65                  70                  75                  80

Leu Gln Met Asp Ser Leu Gln Ala Asp Asp Thr Ala Val Tyr Tyr Cys
                85                  90                  95

Ala Arg Gly Gly Arg Ala Thr Ser Tyr Tyr Trp Val His Trp Gly Pro
            100                 105                 110

Gly Thr Leu Val Thr Val Ser Ser Gly Thr Gly Gly Ser Gly Gly Thr
        115                 120                 125

Gly Ser Gly Thr Gly Gly Ser Thr Glu Ile Val Leu Thr Gln Ser Pro
    130                 135                 140

Ala Thr Leu Ser Leu Ser Pro Gly Glu Arg Ala Thr Leu Ser Cys Arg
145                 150                 155                 160

Ala Ser Gln Ser Val Ser Gly Tyr Leu Gly Trp Tyr Gln Gln Lys Pro
                165                 170                 175

Gly Gln Ala Pro Arg Leu Leu Ile Tyr Gly Ala Ser Ser Arg Ala Thr
            180                 185                 190

Gly Ile Pro Asp Arg Phe Ser Gly Ser Gly Ser Gly Thr Asp Phe Thr
        195                 200                 205

Leu Thr Ile Ser Arg Leu Glu Pro Glu Asp Phe Ala Val Tyr Tyr Cys
    210                 215                 220

Gln Gln Tyr Gly Ser Ser Pro Leu Thr Phe Gly Gly Gly Thr Lys Leu
225                 230                 235                 240

Glu Ile Lys Arg
```

<210> SEQ ID NO 25
<211> LENGTH: 1344
<212> TYPE: DNA
<213> ORGANISM: Homo sapiens
<220> FEATURE:
<221> NAME/KEY: CDS
<222> LOCATION: (1)..(1344)

<400> SEQUENCE: 25

```
cag gtg cag ctg cag gag tcc ggc cca gga ctg gtg aag cct tca cag       48
Gln Val Gln Leu Gln Glu Ser Gly Pro Gly Leu Val Lys Pro Ser Gln
1               5                   10                  15

acc ctg tcc ctc acc tgc act gtc tct ggt ggc tcc atc agc agt ggt       96
Thr Leu Ser Leu Thr Cys Thr Val Ser Gly Gly Ser Ile Ser Ser Gly
            20                  25                  30

ggt tac tac tgg agc tgg atc cgg cag ccc cca ggg aag gga ctg gag      144
Gly Tyr Tyr Trp Ser Trp Ile Arg Gln Pro Pro Gly Lys Gly Leu Glu
        35                  40                  45

tgg att ggg tac atc tat tac agt ggg agc acc tac tac aac tcg tcc      192
Trp Ile Gly Tyr Ile Tyr Tyr Ser Gly Ser Thr Tyr Tyr Asn Ser Ser
    50                  55                  60

ctc aag agt cga gtt acc ata tca gta gac acg tct aag aac cag ttc      240
```

-continued

```
Leu Lys Ser Arg Val Thr Ile Ser Val Asp Thr Ser Lys Asn Gln Phe
65                  70                  75                  80

tcc ctg aag ctg agc tct gtg act gcc gcg gac acg gcc gtg tat tac      288
Ser Leu Lys Leu Ser Ser Val Thr Ala Ala Asp Thr Ala Val Tyr Tyr
                85                  90                  95

tgt gca aag acg gtt atg aat tcg ttc ttt gac tgg ggc cag ggc acc      336
Cys Ala Lys Thr Val Met Asn Ser Phe Phe Asp Trp Gly Gln Gly Thr
            100                 105                 110

ctg gtg acc gtc tcc agc gct agc acc aag ggc ccc agc gtg ttc ccc      384
Leu Val Thr Val Ser Ser Ala Ser Thr Lys Gly Pro Ser Val Phe Pro
        115                 120                 125

ctg gcc ccc agc agc aag agc acc agc ggc ggc aca gcc gcc ctg ggc      432
Leu Ala Pro Ser Ser Lys Ser Thr Ser Gly Gly Thr Ala Ala Leu Gly
    130                 135                 140

tgc ctg gtg aag gac tac ttc ccc gag ccc gtg acc gtg agc tgg aac      480
Cys Leu Val Lys Asp Tyr Phe Pro Glu Pro Val Thr Val Ser Trp Asn
145                 150                 155                 160

agc ggc gcc ttg acc agc ggc gtg cac acc ttc ccc gcc gtg ctg cag      528
Ser Gly Ala Leu Thr Ser Gly Val His Thr Phe Pro Ala Val Leu Gln
                165                 170                 175

agc agc ggc ctg tac agc ctg agc agc gtg gtg acc gtg ccc agc agc      576
Ser Ser Gly Leu Tyr Ser Leu Ser Ser Val Val Thr Val Pro Ser Ser
            180                 185                 190

agc ctg ggc acc cag acc tac atc tgc aac gtg aac cac aag ccc agc      624
Ser Leu Gly Thr Gln Thr Tyr Ile Cys Asn Val Asn His Lys Pro Ser
        195                 200                 205

aac acc aag gtg gac aaa cgc gtg gag ccc aag agc tgc gac aag acc      672
Asn Thr Lys Val Asp Lys Arg Val Glu Pro Lys Ser Cys Asp Lys Thr
    210                 215                 220

cac acc tgc ccc ccc tgc cct gcc ccc gag ctg ctg ggc gga ccc tcc      720
His Thr Cys Pro Pro Cys Pro Ala Pro Glu Leu Leu Gly Gly Pro Ser
225                 230                 235                 240

gtg ttc ctg ttc ccc ccc aag ccc aag gac acc ctc atg atc agc cgg      768
Val Phe Leu Phe Pro Pro Lys Pro Lys Asp Thr Leu Met Ile Ser Arg
                245                 250                 255

acc ccc gag gtg acc tgc gtg gtg gtg gac gtg agc cac gag gac ccc      816
Thr Pro Glu Val Thr Cys Val Val Val Asp Val Ser His Glu Asp Pro
            260                 265                 270

gag gtg aag ttc aac tgg tac gtg gac ggc gtg gag gtg cac aac gcc      864
Glu Val Lys Phe Asn Trp Tyr Val Asp Gly Val Glu Val His Asn Ala
        275                 280                 285

aag acc aag ccc cgg gag gag cag tac aac agc acc tac cgg gtg gtg      912
Lys Thr Lys Pro Arg Glu Glu Gln Tyr Asn Ser Thr Tyr Arg Val Val
    290                 295                 300

agc gtg ctc acc gtg ctg cac cag gac tgg ctg aac ggc aag gag tac      960
Ser Val Leu Thr Val Leu His Gln Asp Trp Leu Asn Gly Lys Glu Tyr
305                 310                 315                 320

aag tgc aag gtg agc aac aag gcc ctg cct gcc ccc atc gag aag acc     1008
Lys Cys Lys Val Ser Asn Lys Ala Leu Pro Ala Pro Ile Glu Lys Thr
                325                 330                 335

atc agc aag gcc aag ggc cag ccc cgg gag ccc cag gtg tac acc ctg     1056
Ile Ser Lys Ala Lys Gly Gln Pro Arg Glu Pro Gln Val Tyr Thr Leu
            340                 345                 350

ccc ccc agc cgg gag gag atg acc aag aac cag gtg tcc ctc acc tgt     1104
Pro Pro Ser Arg Glu Glu Met Thr Lys Asn Gln Val Ser Leu Thr Cys
        355                 360                 365

ctg gtg aag ggc ttc tac ccc agc gac atc gcc gtg gag tgg gag agc     1152
Leu Val Lys Gly Phe Tyr Pro Ser Asp Ile Ala Val Glu Trp Glu Ser
    370                 375                 380

aac ggc cag ccc gag aac aac tac aag acc acc ccc cct gtg ctg gac     1200
```

```
Asn Gly Gln Pro Glu Asn Asn Tyr Lys Thr Thr Pro Pro Val Leu Asp
385                 390                 395                 400

agc gac ggc agc ttc ttc ctg tac agc aag ctc acc gtg gac aag agc      1248
Ser Asp Gly Ser Phe Phe Leu Tyr Ser Lys Leu Thr Val Asp Lys Ser
                405                 410                 415

cgg tgg cag cag ggc aac gtg ttc agc tgc agc gtg atg cac gag gcc      1296
Arg Trp Gln Gln Gly Asn Val Phe Ser Cys Ser Val Met His Glu Ala
            420                 425                 430

ctg cac aac cac tac acc cag aag agc ctg agc ctg agc ccc ggc aag      1344
Leu His Asn His Tyr Thr Gln Lys Ser Leu Ser Leu Ser Pro Gly Lys
        435                 440                 445


<210> SEQ ID NO 26
<211> LENGTH: 448
<212> TYPE: PRT
<213> ORGANISM: Homo sapiens

<400> SEQUENCE: 26

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln Pro Pro Gly Lys Gly Leu Glu
        35                  40                  45

Trp Ile Gly Tyr Ile Tyr Tyr Ser Gly Ser Thr Tyr Tyr Asn Ser Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Lys Thr Val Met Asn Ser Phe Phe Asp Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300
```

```
Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445


<210> SEQ ID NO 27
<211> LENGTH: 1344
<212> TYPE: DNA
<213> ORGANISM: Homo sapiens
<220> FEATURE:
<221> NAME/KEY: CDS
<222> LOCATION: (1)..(1344)

<400> SEQUENCE: 27

gag gtg ctg gag tct ggg gga ggc ttg gtc cag ccg ggg ggg tcc ctg       48
Glu Val Leu Glu Ser Gly Gly Gly Leu Val Gln Pro Gly Gly Ser Leu
1               5                   10                  15

aga ctg tcc tgt tca gac tct gga ttc tcc ttt aat aac tat tgg atg       96
Arg Leu Ser Cys Ser Asp Ser Gly Phe Ser Phe Asn Asn Tyr Trp Met
            20                  25                  30

acc tgg gtc cgc cag gct ccg ggg aag ggg ctg gag tgg gtg gcc aac      144
Thr Trp Val Arg Gln Ala Pro Gly Lys Gly Leu Glu Trp Val Ala Asn
        35                  40                  45

ata aat cga gat gga agt gac aag tac cat gta gac tct gtg gag ggc      192
Ile Asn Arg Asp Gly Ser Asp Lys Tyr His Val Asp Ser Val Glu Gly
    50                  55                  60

cga ttc acc atc tcc aga gac aac tcc aag aac tca cta tac ctg caa      240
Arg Phe Thr Ile Ser Arg Asp Asn Ser Lys Asn Ser Leu Tyr Leu Gln
65                  70                  75                  80

atg aac aac ctg aga gcc gac gac gcg gcg gta tat ttt tgt gcg aga      288
Met Asn Asn Leu Arg Ala Asp Asp Ala Ala Val Tyr Phe Cys Ala Arg
                85                  90                  95

ggc ggc cgg act act agc tgg tat tgg aga aac tgg ggc cag gga acc      336
Gly Gly Arg Thr Thr Ser Trp Tyr Trp Arg Asn Trp Gly Gln Gly Thr
            100                 105                 110

ctg gtc acc gtc tcg agt gct agc acc aag ggc ccc agc gtg ttc ccc      384
Leu Val Thr Val Ser Ser Ala Ser Thr Lys Gly Pro Ser Val Phe Pro
        115                 120                 125

ctg gcc ccc agc agc aag agc acc agc ggc ggc aca gcc gcc ctg ggc      432
Leu Ala Pro Ser Ser Lys Ser Thr Ser Gly Gly Thr Ala Ala Leu Gly
    130                 135                 140

tgc ctg gtg aag gac tac ttc ccc gag ccc gtg acc gtg agc tgg aac      480
Cys Leu Val Lys Asp Tyr Phe Pro Glu Pro Val Thr Val Ser Trp Asn
145                 150                 155                 160

agc ggc gcc ttg acc agc ggc gtg cac acc ttc ccc gcc gtg ctg cag      528
Ser Gly Ala Leu Thr Ser Gly Val His Thr Phe Pro Ala Val Leu Gln
```

```
                165                 170                 175

agc agc ggc ctg tac agc ctg agc agc gtg gtg acc gtg ccc agc agc      576
Ser Ser Gly Leu Tyr Ser Leu Ser Ser Val Val Thr Val Pro Ser Ser
            180                 185                 190

agc ctg ggc acc cag acc tac atc tgc aac gtg aac cac aag ccc agc      624
Ser Leu Gly Thr Gln Thr Tyr Ile Cys Asn Val Asn His Lys Pro Ser
        195                 200                 205

aac acc aag gtg gac aaa cgc gtg gag ccc aag agc tgc gac aag acc      672
Asn Thr Lys Val Asp Lys Arg Val Glu Pro Lys Ser Cys Asp Lys Thr
    210                 215                 220

cac acc tgc ccc ccc tgc cct gcc ccc gag ctg ctg ggc gga ccc tcc      720
His Thr Cys Pro Pro Cys Pro Ala Pro Glu Leu Leu Gly Gly Pro Ser
225                 230                 235                 240

gtg ttc ctg ttc ccc ccc aag ccc aag gac acc ctc atg atc agc cgg      768
Val Phe Leu Phe Pro Pro Lys Pro Lys Asp Thr Leu Met Ile Ser Arg
                245                 250                 255

acc ccc gag gtg acc tgc gtg gtg gtg gac gtg agc cac gag gac ccc      816
Thr Pro Glu Val Thr Cys Val Val Val Asp Val Ser His Glu Asp Pro
            260                 265                 270

gag gtg aag ttc aac tgg tac gtg gac ggc gtg gag gtg cac aac gcc      864
Glu Val Lys Phe Asn Trp Tyr Val Asp Gly Val Glu Val His Asn Ala
        275                 280                 285

aag acc aag ccc cgg gag gag cag tac aac agc acc tac cgg gtg gtg      912
Lys Thr Lys Pro Arg Glu Glu Gln Tyr Asn Ser Thr Tyr Arg Val Val
    290                 295                 300

agc gtg ctc acc gtg ctg cac cag gac tgg ctg aac ggc aag gag tac      960
Ser Val Leu Thr Val Leu His Gln Asp Trp Leu Asn Gly Lys Glu Tyr
305                 310                 315                 320

aag tgc aag gtg agc aac aag gcc ctg cct gcc ccc atc gag aag acc     1008
Lys Cys Lys Val Ser Asn Lys Ala Leu Pro Ala Pro Ile Glu Lys Thr
                325                 330                 335

atc agc aag gcc aag ggc cag ccc cgg gag ccc cag gtg tac acc ctg     1056
Ile Ser Lys Ala Lys Gly Gln Pro Arg Glu Pro Gln Val Tyr Thr Leu
            340                 345                 350

ccc ccc agc cgg gag gag atg acc aag aac cag gtg tcc ctc acc tgt     1104
Pro Pro Ser Arg Glu Glu Met Thr Lys Asn Gln Val Ser Leu Thr Cys
        355                 360                 365

ctg gtg aag ggc ttc tac ccc agc gac atc gcc gtg gag tgg gag agc     1152
Leu Val Lys Gly Phe Tyr Pro Ser Asp Ile Ala Val Glu Trp Glu Ser
    370                 375                 380

aac ggc cag ccc gag aac aac tac aag acc acc ccc cct gtg ctg gac     1200
Asn Gly Gln Pro Glu Asn Asn Tyr Lys Thr Thr Pro Pro Val Leu Asp
385                 390                 395                 400

agc gac ggc agc ttc ttc ctg tac agc aag ctc acc gtg gac aag agc     1248
Ser Asp Gly Ser Phe Phe Leu Tyr Ser Lys Leu Thr Val Asp Lys Ser
                405                 410                 415

cgg tgg cag cag ggc aac gtg ttc agc tgc agc gtg atg cac gag gcc     1296
Arg Trp Gln Gln Gly Asn Val Phe Ser Cys Ser Val Met His Glu Ala
            420                 425                 430

ctg cac aac cac tac acc cag aag agc ctg agc ctg agc ccc ggc aag     1344
Leu His Asn His Tyr Thr Gln Lys Ser Leu Ser Leu Ser Pro Gly Lys
        435                 440                 445


<210> SEQ ID NO 28
<211> LENGTH: 448
<212> TYPE: PRT
<213> ORGANISM: Homo sapiens

<400> SEQUENCE: 28

Glu Val Leu Glu Ser Gly Gly Gly Leu Val Gln Pro Gly Gly Ser Leu
1               5                   10                  15
```

-continued

```
Arg Leu Ser Cys Ser Asp Ser Gly Phe Ser Phe Asn Asn Tyr Trp Met
            20                  25                  30

Thr Trp Val Arg Gln Ala Pro Gly Lys Gly Leu Glu Trp Val Ala Asn
        35                  40                  45

Ile Asn Arg Asp Gly Ser Asp Lys Tyr His Val Asp Ser Val Glu Gly
    50                  55                  60

Arg Phe Thr Ile Ser Arg Asp Asn Ser Lys Asn Ser Leu Tyr Leu Gln
65                  70                  75                  80

Met Asn Asn Leu Arg Ala Asp Asp Ala Ala Val Tyr Phe Cys Ala Arg
                85                  90                  95

Gly Gly Arg Thr Thr Ser Trp Tyr Trp Arg Asn Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
```

-continued

```
        435                 440                 445

<210> SEQ ID NO 29
<211> LENGTH: 1350
<212> TYPE: DNA
<213> ORGANISM: Homo sapiens
<220> FEATURE:
<221> NAME/KEY: CDS
<222> LOCATION: (1)..(1350)

<400> SEQUENCE: 29

gag gtg cag ctg gtg gag act ggg gga ggc ttg gtc aag cct gga ggg       48
Glu Val Gln Leu Val Glu Thr Gly Gly Gly Leu Val Lys Pro Gly Gly
1               5                   10                  15

tcc ctg aga ctc tcc tgc tca gcc tct aga ttc agc ttc agg gac tac       96
Ser Leu Arg Leu Ser Cys Ser Ala Ser Arg Phe Ser Phe Arg Asp Tyr
            20                  25                  30

tac atg acg tgg atc cgc cag gct cca ggg aag ggg ccg gaa tgg gtt      144
Tyr Met Thr Trp Ile Arg Gln Ala Pro Gly Lys Gly Pro Glu Trp Val
        35                  40                  45

tca cac ata agt ggc agt ggc agt acg att tac tac gca gac tct gtg      192
Ser His Ile Ser Gly Ser Gly Ser Thr Ile Tyr Tyr Ala Asp Ser Val
    50                  55                  60

agg ggc cga ttc acc atc tcc agg gac aac gcc aag agc tcc ttg tat      240
Arg Gly Arg Phe Thr Ile Ser Arg Asp Asn Ala Lys Ser Ser Leu Tyr
65                  70                  75                  80

ctg caa atg gat agc cta cag gcc gac gac acg gcc gta tat tac tgt      288
Leu Gln Met Asp Ser Leu Gln Ala Asp Asp Thr Ala Val Tyr Tyr Cys
                85                  90                  95

gcg aga ggg ggt cgc gcc acc agt tac tac tgg gtc cac tgg ggc ccg      336
Ala Arg Gly Gly Arg Ala Thr Ser Tyr Tyr Trp Val His Trp Gly Pro
            100                 105                 110

gga acc ctg gtc acc gtc tcg agt gct agc acc aag ggc ccc agc gtg      384
Gly Thr Leu Val Thr Val Ser Ser Ala Ser Thr Lys Gly Pro Ser Val
        115                 120                 125

ttc ccc ctg gcc ccc agc agc aag agc acc agc ggc ggc aca gcc gcc      432
Phe Pro Leu Ala Pro Ser Ser Lys Ser Thr Ser Gly Gly Thr Ala Ala
    130                 135                 140

ctg ggc tgc ctg gtg aag gac tac ttc ccc gag ccc gtg acc gtg agc      480
Leu Gly Cys Leu Val Lys Asp Tyr Phe Pro Glu Pro Val Thr Val Ser
145                 150                 155                 160

tgg aac agc ggc gcc ttg acc agc ggc gtg cac acc ttc ccc gcc gtg      528
Trp Asn Ser Gly Ala Leu Thr Ser Gly Val His Thr Phe Pro Ala Val
                165                 170                 175

ctg cag agc agc ggc ctg tac agc ctg agc agc gtg gtg acc gtg ccc      576
Leu Gln Ser Ser Gly Leu Tyr Ser Leu Ser Ser Val Val Thr Val Pro
            180                 185                 190

agc agc agc ctg ggc acc cag acc tac atc tgc aac gtg aac cac aag      624
Ser Ser Ser Leu Gly Thr Gln Thr Tyr Ile Cys Asn Val Asn His Lys
        195                 200                 205

ccc agc aac acc aag gtg gac aaa cgc gtg gag ccc aag agc tgc gac      672
Pro Ser Asn Thr Lys Val Asp Lys Arg Val Glu Pro Lys Ser Cys Asp
    210                 215                 220

aag acc cac acc tgc ccc ccc tgc cct gcc ccc gag ctg ctg ggc gga      720
Lys Thr His Thr Cys Pro Pro Cys Pro Ala Pro Glu Leu Leu Gly Gly
225                 230                 235                 240

ccc tcc gtg ttc ctg ttc ccc ccc aag ccc aag gac acc ctc atg atc      768
Pro Ser Val Phe Leu Phe Pro Pro Lys Pro Lys Asp Thr Leu Met Ile
                245                 250                 255

agc cgg acc ccc gag gtg acc tgc gtg gtg gtg gac gtg agc cac gag      816
Ser Arg Thr Pro Glu Val Thr Cys Val Val Val Asp Val Ser His Glu
            260                 265                 270
```

```
gac ccc gag gtg aag ttc aac tgg tac gtg gac ggc gtg gag gtg cac      864
Asp Pro Glu Val Lys Phe Asn Trp Tyr Val Asp Gly Val Glu Val His
        275                 280                 285

aac gcc aag acc aag ccc cgg gag gag cag tac aac agc acc tac cgg      912
Asn Ala Lys Thr Lys Pro Arg Glu Glu Gln Tyr Asn Ser Thr Tyr Arg
    290                 295                 300

gtg gtg agc gtg ctc acc gtg ctg cac cag gac tgg ctg aac ggc aag      960
Val Val Ser Val Leu Thr Val Leu His Gln Asp Trp Leu Asn Gly Lys
305                 310                 315                 320

gag tac aag tgc aag gtg agc aac aag gcc ctg cct gcc ccc atc gag     1008
Glu Tyr Lys Cys Lys Val Ser Asn Lys Ala Leu Pro Ala Pro Ile Glu
                325                 330                 335

aag acc atc agc aag gcc aag ggc cag ccc cgg gag ccc cag gtg tac     1056
Lys Thr Ile Ser Lys Ala Lys Gly Gln Pro Arg Glu Pro Gln Val Tyr
            340                 345                 350

acc ctg ccc ccc agc cgg gag gag atg acc aag aac cag gtg tcc ctc     1104
Thr Leu Pro Pro Ser Arg Glu Glu Met Thr Lys Asn Gln Val Ser Leu
        355                 360                 365

acc tgt ctg gtg aag ggc ttc tac ccc agc gac atc gcc gtg gag tgg     1152
Thr Cys Leu Val Lys Gly Phe Tyr Pro Ser Asp Ile Ala Val Glu Trp
    370                 375                 380

gag agc aac ggc cag ccc gag aac aac tac aag acc acc ccc cct gtg     1200
Glu Ser Asn Gly Gln Pro Glu Asn Asn Tyr Lys Thr Thr Pro Pro Val
385                 390                 395                 400

ctg gac agc gac ggc agc ttc ttc ctg tac agc aag ctc acc gtg gac     1248
Leu Asp Ser Asp Gly Ser Phe Phe Leu Tyr Ser Lys Leu Thr Val Asp
                405                 410                 415

aag agc cgg tgg cag cag ggc aac gtg ttc agc tgc agc gtg atg cac     1296
Lys Ser Arg Trp Gln Gln Gly Asn Val Phe Ser Cys Ser Val Met His
            420                 425                 430

gag gcc ctg cac aac cac tac acc cag aag agc ctg agc ctg agc ccc     1344
Glu Ala Leu His Asn His Tyr Thr Gln Lys Ser Leu Ser Leu Ser Pro
        435                 440                 445

ggc aag                                                             1350
Gly Lys
    450


<210> SEQ ID NO 30
<211> LENGTH: 450
<212> TYPE: PRT
<213> ORGANISM: Homo sapiens

<400> SEQUENCE: 30

Glu Val Gln Leu Val Glu Thr Gly Gly Gly Leu Val Lys Pro Gly Gly
1               5                   10                  15

Ser Leu Arg Leu Ser Cys Ser Ala Ser Arg Phe Ser Phe Arg Asp Tyr
            20                  25                  30

Tyr Met Thr Trp Ile Arg Gln Ala Pro Gly Lys Gly Pro Glu Trp Val
        35                  40                  45

Ser His Ile Ser Gly Ser Gly Ser Thr Ile Tyr Tyr Ala Asp Ser Val
    50                  55                  60

Arg Gly Arg Phe Thr Ile Ser Arg Asp Asn Ala Lys Ser Ser Leu Tyr
65                  70                  75                  80

Leu Gln Met Asp Ser Leu Gln Ala Asp Asp Thr Ala Val Tyr Tyr Cys
                85                  90                  95

Ala Arg Gly Gly Arg Ala Thr Ser Tyr Tyr Trp Val His Trp Gly Pro
            100                 105                 110

Gly Thr Leu Val Thr Val Ser Ser Ala Ser Thr Lys Gly Pro Ser Val
        115                 120                 125
```

-continued

```
Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 31
<211> LENGTH: 660
<212> TYPE: DNA
<213> ORGANISM: Homo sapiens
<220> FEATURE:
<221> NAME/KEY: CDS
<222> LOCATION: (1)..(660)

<400> SEQUENCE: 31

cag tcc gcc ctg acc cag ccc cgc tca gtg tct ggg tct cct gga cag       48
Gln Ser Ala Leu Thr Gln Pro Arg Ser Val Ser Gly Ser Pro Gly Gln
1               5                   10                  15

tcg atc acc atc tcc tgc act gga acc agc agt gat gtt ggg agt tat       96
```

-continued

```
Ser Ile Thr Ile Ser Cys Thr Gly Thr Ser Ser Asp Val Gly Ser Tyr
            20                  25                  30

aac ctt gtc tcc tgg tac caa cag cac cca ggc aaa gcc ccc aaa ctc      144
Asn Leu Val Ser Trp Tyr Gln Gln His Pro Gly Lys Ala Pro Lys Leu
        35                  40                  45

atg att tat gag gtc agt aag cgg ccc tca ggg gtt tct aat cgc ttc      192
Met Ile Tyr Glu Val Ser Lys Arg Pro Ser Gly Val Ser Asn Arg Phe
    50                  55                  60

tct ggc tcc aag tct ggc aac acg gcc tcc ctg aca atc tct ggg ctc      240
Ser Gly Ser Lys Ser Gly Asn Thr Ala Ser Leu Thr Ile Ser Gly Leu
65                  70                  75                  80

cag gct gag gac gag gct gat tat tac tgc tgc tca tat gca ggt agt      288
Gln Ala Glu Asp Glu Ala Asp Tyr Tyr Cys Cys Ser Tyr Ala Gly Ser
                85                  90                  95

agc tgg gtg ttc gga act ggc acc aag gtg acc gtg ctg aag ctt acc      336
Ser Trp Val Phe Gly Thr Gly Thr Lys Val Thr Val Leu Lys Leu Thr
            100                 105                 110

gtg ctg ggc cag ccc aag gcc gct ccc agc gtg acc ctg ttc ccc ccc      384
Val Leu Gly Gln Pro Lys Ala Ala Pro Ser Val Thr Leu Phe Pro Pro
        115                 120                 125

tcc tcc gag gag ctg cag gcc aac aag gcc acc ctg gtg tgc ctc atc      432
Ser Ser Glu Glu Leu Gln Ala Asn Lys Ala Thr Leu Val Cys Leu Ile
    130                 135                 140

agc gac ttc tac cct ggc gcc gtg acc gtg gcc tgg aag gcc gac agc      480
Ser Asp Phe Tyr Pro Gly Ala Val Thr Val Ala Trp Lys Ala Asp Ser
145                 150                 155                 160

agc ccc gtg aag gcc ggc gtg gag acc acc acc ccc agc aag cag agc      528
Ser Pro Val Lys Ala Gly Val Glu Thr Thr Thr Pro Ser Lys Gln Ser
                165                 170                 175

aac aac aag tac gcc gcc agc agc tac ctg agc ctc acc ccc gag cag      576
Asn Asn Lys Tyr Ala Ala Ser Ser Tyr Leu Ser Leu Thr Pro Glu Gln
            180                 185                 190

tgg aag agc cac cgg agc tac agc tgc cag gtg acc cac gag ggc agc      624
Trp Lys Ser His Arg Ser Tyr Ser Cys Gln Val Thr His Glu Gly Ser
        195                 200                 205

acc gtg gag aag acc gtg gcc ccc acc gag tgc agc                      660
Thr Val Glu Lys Thr Val Ala Pro Thr Glu Cys Ser
    210                 215                 220


<210> SEQ ID NO 32
<211> LENGTH: 220
<212> TYPE: PRT
<213> ORGANISM: Homo sapiens

<400> SEQUENCE: 32

Gln Ser Ala Leu Thr Gln Pro Arg Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Leu Val Ser Trp Tyr Gln Gln His Pro Gly Lys Ala Pro Lys Leu
        35                  40                  45

Met Ile Tyr Glu Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Ser Trp Val Phe Gly Thr Gly Thr Lys Val Thr Val Leu Lys Leu Thr
            100                 105                 110
```

-continued

```
Val Leu Gly Gln Pro Lys Ala Ala Pro Ser Val Thr Leu Phe Pro Pro
        115                 120                 125

Ser Ser Glu Glu Leu Gln Ala Asn Lys Ala Thr Leu Val Cys Leu Ile
    130                 135                 140

Ser Asp Phe Tyr Pro Gly Ala Val Thr Val Ala Trp Lys Ala Asp Ser
145                 150                 155                 160

Ser Pro Val Lys Ala Gly Val Glu Thr Thr Thr Pro Ser Lys Gln Ser
                165                 170                 175

Asn Asn Lys Tyr Ala Ala Ser Ser Tyr Leu Ser Leu Thr Pro Glu Gln
            180                 185                 190

Trp Lys Ser His Arg Ser Tyr Ser Cys Gln Val Thr His Glu Gly Ser
        195                 200                 205

Thr Val Glu Lys Thr Val Ala Pro Thr Glu Cys Ser
    210                 215                 220


<210> SEQ ID NO 33
<211> LENGTH: 645
<212> TYPE: DNA
<213> ORGANISM: Homo sapiens
<220> FEATURE:
<221> NAME/KEY: CDS
<222> LOCATION: (1)..(645)

<400> SEQUENCE: 33

tcg acg gac atc cag atg acc cag tct cct tcc acc ctg tct gca tct       48
Ser Thr Asp Ile Gln Met Thr Gln Ser Pro Ser Thr Leu Ser Ala Ser
1               5                   10                  15

gta gga gac aga gtc acc atc act tgc cgg gcc agt cag agt att agt       96
Val Gly Asp Arg Val Thr Ile Thr Cys Arg Ala Ser Gln Ser Ile Ser
            20                  25                  30

agc tgg ttg gcc tgg tat cag cag aaa cca ggg aaa gcc cct aag ctc      144
Ser Trp Leu Ala Trp Tyr Gln Gln Lys Pro Gly Lys Ala Pro Lys Leu
        35                  40                  45

ctg atc tat aag gcg tct agt tta gaa agt ggg gtc cca tca agg ttc      192
Leu Ile Tyr Lys Ala Ser Ser Leu Glu Ser Gly Val Pro Ser Arg Phe
    50                  55                  60

agc ggc agt gga tct ggg aca gaa ttc act ctc acc atc agc agc ctg      240
Ser Gly Ser Gly Ser Gly Thr Glu Phe Thr Leu Thr Ile Ser Ser Leu
65                  70                  75                  80

cag cct gat gat ttt gca act tat tac tgc caa cag tat aat agt tac      288
Gln Pro Asp Asp Phe Ala Thr Tyr Tyr Cys Gln Gln Tyr Asn Ser Tyr
                85                  90                  95

ccc ctc act ttc ggc gga ggg acc aag ctg gag atc aaa cgt gcg gcc      336
Pro Leu Thr Phe Gly Gly Gly Thr Lys Leu Glu Ile Lys Arg Ala Ala
            100                 105                 110

gca ccc agc gtg ttc atc ttc ccc ccc tcc gac gag cag ctg aag agc      384
Ala Pro Ser Val Phe Ile Phe Pro Pro Ser Asp Glu Gln Leu Lys Ser
        115                 120                 125

ggc acc gcc agc gtg gtg tgc ctg ctg aac aac ttc tac ccc cgg gag      432
Gly Thr Ala Ser Val Val Cys Leu Leu Asn Asn Phe Tyr Pro Arg Glu
    130                 135                 140

gcc aag gtg cag tgg aag gtg gac aac gcc ctg cag agc ggc aac agc      480
Ala Lys Val Gln Trp Lys Val Asp Asn Ala Leu Gln Ser Gly Asn Ser
145                 150                 155                 160

cag gag agc gtg acc gag cag gac agc aag gac tcc acc tac agc ctg      528
Gln Glu Ser Val Thr Glu Gln Asp Ser Lys Asp Ser Thr Tyr Ser Leu
                165                 170                 175

agc agc acc ctc acc ctg agc aag gcc gac tac gag aag cac aag gtg      576
Ser Ser Thr Leu Thr Leu Ser Lys Ala Asp Tyr Glu Lys His Lys Val
            180                 185                 190
```

```
tac gcc tgc gag gtg acc cac cag ggc ctg agc agc ccc gtg acc aag      624
Tyr Ala Cys Glu Val Thr His Gln Gly Leu Ser Ser Pro Val Thr Lys
        195                 200                 205

agc ttc aac cgg ggc gag tgt                                          645
Ser Phe Asn Arg Gly Glu Cys
    210                 215


<210> SEQ ID NO 34
<211> LENGTH: 215
<212> TYPE: PRT
<213> ORGANISM: Homo sapiens

<400> SEQUENCE: 34

Ser Thr Asp Ile Gln Met Thr Gln Ser Pro Ser Thr Leu Ser Ala Ser
1               5                   10                  15

Val Gly Asp Arg Val Thr Ile Thr Cys Arg Ala Ser Gln Ser Ile Ser
            20                  25                  30

Ser Trp Leu Ala Trp Tyr Gln Gln Lys Pro Gly Lys Ala Pro Lys Leu
        35                  40                  45

Leu Ile Tyr Lys Ala Ser Ser Leu Glu Ser Gly Val Pro Ser Arg Phe
    50                  55                  60

Ser Gly Ser Gly Ser Gly Thr Glu Phe Thr Leu Thr Ile Ser Ser Leu
65                  70                  75                  80

Gln Pro Asp Asp Phe Ala Thr Tyr Tyr Cys Gln Gln Tyr Asn Ser Tyr
                85                  90                  95

Pro Leu Thr Phe Gly Gly Gly Thr Lys Leu Glu Ile Lys Arg Ala Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215


<210> SEQ ID NO 35
<211> LENGTH: 645
<212> TYPE: DNA
<213> ORGANISM: Homo sapiens
<220> FEATURE:
<221> NAME/KEY: CDS
<222> LOCATION: (1)..(645)

<400> SEQUENCE: 35

tcg acg gaa att gtg ttg acg cag tct cca gcc acc ctg tct ttg tct       48
Ser Thr Glu Ile Val Leu Thr Gln Ser Pro Ala Thr Leu Ser Leu Ser
1               5                   10                  15

cca ggg gaa aga gcc acc ctc tcc tgc agg gcc agt cag agt gtt agc       96
Pro Gly Glu Arg Ala Thr Leu Ser Cys Arg Ala Ser Gln Ser Val Ser
            20                  25                  30

ggc tac tta ggc tgg tac caa cag aaa cct ggc cag gct ccc agg ctc      144
Gly Tyr Leu Gly Trp Tyr Gln Gln Lys Pro Gly Gln Ala Pro Arg Leu
        35                  40                  45
```

```
ctc atc tat ggt gca tcc agc agg gcc act ggc atc cca gac agg ttc      192
Leu Ile Tyr Gly Ala Ser Ser Arg Ala Thr Gly Ile Pro Asp Arg Phe
    50                  55                  60

agt ggc agt ggg tct ggg aca gac ttc act ctc acc atc agc cgg ctg      240
Ser Gly Ser Gly Ser Gly Thr Asp Phe Thr Leu Thr Ile Ser Arg Leu
65                  70                  75                  80

gag cct gaa gat ttt gca gtg tat tac tgt cag cag tat ggt agc tca      288
Glu Pro Glu Asp Phe Ala Val Tyr Tyr Cys Gln Gln Tyr Gly Ser Ser
                85                  90                  95

ccg ctc act ttc ggc gga ggg acc aag ctg gag atc aaa cgt gcg gcc      336
Pro Leu Thr Phe Gly Gly Gly Thr Lys Leu Glu Ile Lys Arg Ala Ala
            100                 105                 110

gca ccc agc gtg ttc atc ttc ccc ccc tcc gac gag cag ctg aag agc      384
Ala Pro Ser Val Phe Ile Phe Pro Pro Ser Asp Glu Gln Leu Lys Ser
        115                 120                 125

ggc acc gcc agc gtg gtg tgc ctg ctg aac aac ttc tac ccc cgg gag      432
Gly Thr Ala Ser Val Val Cys Leu Leu Asn Asn Phe Tyr Pro Arg Glu
    130                 135                 140

gcc aag gtg cag tgg aag gtg gac aac gcc ctg cag agc ggc aac agc      480
Ala Lys Val Gln Trp Lys Val Asp Asn Ala Leu Gln Ser Gly Asn Ser
145                 150                 155                 160

cag gag agc gtg acc gag cag gac agc aag gac tcc acc tac agc ctg      528
Gln Glu Ser Val Thr Glu Gln Asp Ser Lys Asp Ser Thr Tyr Ser Leu
                165                 170                 175

agc agc acc ctc acc ctg agc aag gcc gac tac gag aag cac aag gtg      576
Ser Ser Thr Leu Thr Leu Ser Lys Ala Asp Tyr Glu Lys His Lys Val
            180                 185                 190

tac gcc tgc gag gtg acc cac cag ggc ctg agc agc ccc gtg acc aag      624
Tyr Ala Cys Glu Val Thr His Gln Gly Leu Ser Ser Pro Val Thr Lys
        195                 200                 205

agc ttc aac cgg ggc gag tgt                                          645
Ser Phe Asn Arg Gly Glu Cys
    210                 215


<210> SEQ ID NO 36
<211> LENGTH: 215
<212> TYPE: PRT
<213> ORGANISM: Homo sapiens

<400> SEQUENCE: 36

Ser Thr Glu Ile Val Leu Thr Gln Ser Pro Ala Thr Leu Ser Leu Ser
1               5                   10                  15

Pro Gly Glu Arg Ala Thr Leu Ser Cys Arg Ala Ser Gln Ser Val Ser
            20                  25                  30

Gly Tyr Leu Gly Trp Tyr Gln Gln Lys Pro Gly Gln Ala Pro Arg Leu
        35                  40                  45

Leu Ile Tyr Gly Ala Ser Ser Arg Ala Thr Gly Ile Pro Asp Arg Phe
    50                  55                  60

Ser Gly Ser Gly Ser Gly Thr Asp Phe Thr Leu Thr Ile Ser Arg Leu
65                  70                  75                  80

Glu Pro Glu Asp Phe Ala Val Tyr Tyr Cys Gln Gln Tyr Gly Ser Ser
                85                  90                  95

Pro Leu Thr Phe Gly Gly Gly Thr Lys Leu Glu Ile Lys Arg Ala Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140
```

```
Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215


<210> SEQ ID NO 37
<211> LENGTH: 24
<212> TYPE: DNA
<213> ORGANISM: Artificial sequence
<220> FEATURE:
<223> OTHER INFORMATION: Anti-sense primer HuCK-FOR

<400> SEQUENCE: 37

acactctccc ctgttgaagc tctt                                              24


<210> SEQ ID NO 38
<211> LENGTH: 23
<212> TYPE: DNA
<213> ORGANISM: Artificial sequence
<220> FEATURE:
<223> OTHER INFORMATION: Anti-sense primer HuCL2-FOR

<400> SEQUENCE: 38

tgaacattct gtaggggcca ctg                                               23


<210> SEQ ID NO 39
<211> LENGTH: 23
<212> TYPE: DNA
<213> ORGANISM: Artificial sequence
<220> FEATURE:
<223> OTHER INFORMATION: Anti-sense primer HuCL7-FOR

<400> SEQUENCE: 39

agagcattct gcaggggcca ctg                                               23


<210> SEQ ID NO 40
<211> LENGTH: 4941
<212> TYPE: DNA
<213> ORGANISM: Artificial sequence
<220> FEATURE:
<223> OTHER INFORMATION: Vector PDV-C06

<400> SEQUENCE: 40

aagcttgcat gcaaattcta tttcaaggag acagtcataa tgaaatacct attgcctacg      60

gcagccgctg gattgttatt actcgcggcc cagccggcca tggccgaggt gtttgactaa     120

tggggcgcgc ctcagggaac cctggtcacc gtctcgagcg gtacgggcgg ttcaggcgga     180

accggcagcg gcactggcgg gtcgacggaa attgtgctca cacagtctcc agccaccctg     240

tctttgtctc caggggaaag agccaccctc tcctgcaggg ccagtcagag tgttagcagc     300

tacttagcct ggtaccaaca gaaacctggc caggctccca ggctcctcat ctatgatgca     360

tccaacaggg ccactggcat cccagccagg ttcagtggca gtgggtctgg gacagacttc     420

actctcacca tcagcagcct agagcctgaa gattttgcag tttattactg tcagcagcgt     480

agcaactggc ctccggcttt cggcggaggg accaaggtgg agatcaaacg tgcggccgca     540

catcatcatc accatcacgg ggccgcatat accgatattg aaatgaaccg cctgggcaaa     600
```

-continued

```
ggggccgcat agactgttga aagttgttta gcaaaacctc atacagaaaa ttcatttact    660
aacgtctgga aagacgacaa aactttagat cgttacgcta actatgaggg ctgtctgtgg    720
aatgctacag gcgttgtggt ttgtactggt gacgaaactc agtgttacgg tacatgggtt    780
cctattgggc ttgctatccc tgaaaatgag ggtggtggct ctgagggtgg cggttctgag    840
ggtggcggtt ctgagggtgg cggtactaaa cctcctgagt acggtgatac acctattccg    900
ggctatactt atatcaaccc tctcgacggc acttatccgc ctggtactga gcaaaacccc    960
gctaatccta atccttctct tgaggagtct cagcctctta atactttcat gtttcagaat   1020
aataggttcc gaaataggca gggtgcatta actgtttata cgggcactgt tactcaaggc   1080
actgaccccg ttaaaactta ttaccagtac actcctgtat catcaaaagc catgtatgac   1140
gcttactgga acggtaaatt cagagactgc gctttccatt ctggctttaa tgaggatcca   1200
ttcgtttgtg aatatcaagg ccaatcgtct gacctgcctc aacctcctgt caatgctggc   1260
ggcggctctg gtggtggttc tggtggcggc tctgagggtg gcggctctga gggtggcggt   1320
tctgagggtg gcggctctga gggtggcggt tccggtggcg gctccggttc cggtgatttt   1380
gattatgaaa aaatggcaaa cgctaataag ggggctatga ccgaaaatgc cgatgaaaac   1440
gcgctacagt ctgacgctaa aggcaaactt gattctgtcg ctactgatta cggtgctgct   1500
atcgatggtt tcattggtga cgtttccggc cttgctaatg gtaatggtgc tactggtgat   1560
tttgctggct ctaattccca aatggctcaa gtcggtgacg gtgataattc acctttaatg   1620
aataatttcc gtcaatattt accttctttg cctcagtcgg ttgaatgtcg cccttatgtc   1680
tttggcgctg gtaaaccata tgaattttct attgattgtg acaaaataaa cttattccgt   1740
ggtgtctttg cgtttctttt atatgttgcc acctttatgt atgtattttc gacgtttgct   1800
aacatactgc gtaataagga gtcttaataa gaattcactg gccgtcgttt tacaacgtcg   1860
tgactgggaa aaccctggcg ttacccaact taatcgcctt gcagcacatc ccccttttcgc  1920
cagctggcgt aatagcgaag aggcccgcac cgatcgccct tcccaacagt tgcgcagcct   1980
gaatggcgaa tggcgcctga tgcggtattt tctccttacg catctgtgcg gtatttcaca   2040
ccgcatacgt caaagcaacc atagtacgcg ccctgtagcg gcgcattaag cgcggcgggt   2100
gtggtggtta cgcgcagcgt gaccgctaca cttgccagcg ccctagcgcc cgctcctttc   2160
gctttcttcc cttcctttct cgccacgttc gccggctttc cccgtcaagc tctaaatcgg   2220
gggctccctt tagggttccg atttagtgct ttacggcacc tcgaccccaa aaaacttgat   2280
ttgggtgatg gttcacgtag tgggccatcg ccctgataga cggtttttcg ccctttgacg   2340
ttggagtcca cgttctttaa tagtggactc ttgttccaaa ctggaacaac actcaaccct   2400
atctcgggct attcttttga tttataaggg attttgccga tttcggccta ttggttaaaa   2460
aatgagctga tttaacaaaa atttaacgcg aattttaaca aaatattaac gtttacaatt   2520
ttatggtgca ctctcagtac aatctgctct gatgccgcat agttaagcca gccccgacac   2580
ccgccaacac ccgctgacgc gccctgacgg gcttgtctgc tcccggcatc cgcttacaga   2640
caagctgtga ccgtctccgg gagctgcatg tgtcagaggt tttcaccgtc atcaccgaaa   2700
cgcgcgagac gaaagggcct cgtgatacgc ctatttttat aggttaatgt catgataata   2760
atggtttctt agacgtcagg tggcactttt cggggaaatg tgcgcggaac ccctatttgt   2820
ttatttttct aaatacattc aaatatgtat ccgctcatga gacaataacc ctgataaatg   2880
cttcaataat attgaaaaag gaagagtatg agtattcaac atttccgtgt cgcccttatt   2940
cccttttttg cggcattttg ccttcctgtt tttgctcacc cagaaacgct ggtgaaagta   3000
```

```
aaagatgctg aagatcagtt gggtgcacga gtgggttaca tcgaactgga tctcaacagc   3060

ggtaagatcc ttgagagttt tcgccccgaa gaacgttttc caatgatgag cacttttaaa   3120

gttctgctat gtggcgcggt attatcccgt attgacgccg ggcaagagca actcggtcgc   3180

cgcatacact attctcagaa tgacttggtt gagtactcac cagtcacaga aaagcatctt   3240

acggatggca tgacagtaag agaattatgc agtgctgcca taaccatgag tgataacact   3300

gcggccaact tacttctgac aacgatcgga ggaccgaagg agctaaccgc tttttgcac   3360

aacatggggg atcatgtaac tcgccttgat cgttgggaac cggagctgaa tgaagccata   3420

ccaaacgacg agcgtgacac cacgatgcct gtagcaatgg caacaacgtt gcgcaaacta   3480

ttaactggcg aactacttac tctagcttcc cggcaacaat taatagactg gatggaggcg   3540

gataaagttg caggaccact tctgcgctcg gcccttccgg ctggctggtt tattgctgat   3600

aaatctggag ccggtgagcg tgggtctcgc ggtatcattg cagcactggg gccagatggt   3660

aagccctccc gtatcgtagt tatctacacg acggggagtc aggcaactat ggatgaacga   3720

aatagacaga tcgctgagat aggtgcctca ctgattaagc attggtaact gtcagaccaa   3780

gtttactcat atatacttta gattgattta aaacttcatt tttaatttaa aaggatctag   3840

gtgaagatcc tttttgataa tctcatgacc aaaatccctt aacgtgagtt ttcgttccac   3900

tgagcgtcag accccgtaga aaagatcaaa ggatcttctt gagatccttt ttttctgcgc   3960

gtaatctgct gcttgcaaac aaaaaaacca ccgctaccag cggtggtttg tttgccggat   4020

caagagctac caactctttt tccgaaggta actggcttca gcagagcgca gataccaaat   4080

actgtccttc tagtgtagcc gtagttaggc caccacttca agaactctgt agcaccgcct   4140

acatacctcg ctctgctaat cctgttacca gtggctgctg ccagtggcga taagtcgtgt   4200

cttaccgggt tggactcaag acgatagtta ccggataagg cgcagcggtc gggctgaacg   4260

gggggttcgt gcacacagcc cagcttggag cgaacgacct acaccgaact gagataccta   4320

cagcgtgagc tatgagaaag cgccacgctt cccgaaggga gaaaggcgga caggtatccg   4380

gtaagcggca gggtcggaac aggagagcgc acgagggagc ttccaggggg aaacgcctgg   4440

tatctttata gtcctgtcgg gtttcgccac ctctgacttg agcgtcgatt tttgtgatgc   4500

tcgtcagggg ggcggagcct atggaaaaac gccagcaacg cggccttttt acggttcctg   4560

gccttttgct ggccttttgc tcacatgttc tttcctgcgt tatcccctga ttctgtggat   4620

aaccgtatta ccgcctttga gtgagctgat accgctcgcc gcagccgaac gaccgagcgc   4680

agcgagtcag tgagcgagga agcggaagag cgcccaatac gcaaaccgcc tctccccgcg   4740

cgttggccga ttcattaatg cagctggcac gacaggtttc ccgactggaa agcgggcagt   4800

gagcgcaacg caattaatgt gagttagctc actcattagg caccccaggc tttacacttt   4860

atgcttccgg ctcgtatgtt gtgtggaatt gtgagcggat aacaatttca cacaggaaac   4920

agctatgacc atgattacgc c                                             4941
```

<210> SEQ ID NO 41
<211> LENGTH: 24
<212> TYPE: DNA
<213> ORGANISM: Artificial sequence
<220> FEATURE:
<223> OTHER INFORMATION: Anti-sense primer HuCIgG

<400> SEQUENCE: 41

```
gtccaccttg gtgttgctgg gctt                                          24
```

<210> SEQ ID NO 42
<211> LENGTH: 24
<212> TYPE: DNA
<213> ORGANISM: Artificial sequence
<220> FEATURE:
<223> OTHER INFORMATION: Anti-sense primer HuCIgM

<400> SEQUENCE: 42
tggaagaggc acgttctttt cttt 24

<210> SEQ ID NO 43
<211> LENGTH: 6778
<212> TYPE: DNA
<213> ORGANISM: Artificial sequence
<220> FEATURE:
<223> OTHER INFORMATION: Vector pSyn-C03-HCgamma1

<400> SEQUENCE: 43
gacggatcgg gagatctccc gatcccctat ggtgcactct cagtacaatc tgctctgatg 60
ccgcatagtt aagccagtat ctgctccctg cttgtgtgtt ggaggtcgct gagtagtgcg 120
cgagcaaaat ttaagctaca acaaggcaag gcttgaccga caattgcatg aagaatctgc 180
ttagggttag gcgttttgcg ctgcttcgct aggtggtcaa tattggccat tagccatatt 240
attcattggt tatatagcat aaatcaatat tggctattgg ccattgcata cgttgtatcc 300
atatcataat atgtacattt atattggctc atgtccaaca ttaccgccat gttgacattg 360
attattgact agttattaat agtaatcaat tacggggtca ttagttcata gcccatatat 420
ggagttccgc gttacataac ttacggtaaa tggcccgcct ggctgaccgc ccaacgaccc 480
ccgcccattg acgtcaataa tgacgtatgt tcccatagta acgccaatag ggactttcca 540
ttgacgtcaa tgggtggagt atttacggta aactgcccac ttggcagtac atcaagtgta 600
tcatatgcca agtacgcccc ctattgacgt caatgacggt aaatggcccg cctggcatta 660
tgcccagtac atgaccttat gggactttcc tacttggcag tacatctacg tattagtcat 720
cgctattacc atggtgatgc ggttttggca gtacatcaat gggcgtggat agcggtttga 780
ctcacgggga tttccaagtc tccaccccat tgacgtcaat gggagtttgt tttggcacca 840
aaatcaacgg gactttccaa aatgtcgtaa caactccgcc ccattgacgc aaatgggcgg 900
taggcgtgta cggtgggagg tctatataag cagagctcgt ttagtgaacc gtcagatcgc 960
ctggagacgc catccacgct gttttgacct ccatagaaga caccgggacc gatccagcct 1020
ccgcggccgg gaacggtgca ttggaagctg gcctggatgg cctgactctc ttaggtagcc 1080
ttgcagaagt tggtcgtgag gcactgggca ggtaagtatc aaggttacaa gacaggttta 1140
aggagatcaa tagaaactgg gcttgtcgag acagagaaga ctcttgcgtt tctgataggc 1200
acctattggt cttactgaca tccactttgc ctttctctcc acaggtgtcc actcccagtt 1260
caattacagc tcgccaccat ggcctgcccc ggcttcctgt gggccctggt gatcagcacc 1320
tgcctggaat tcagcatgag cagcgctagc accaagggcc ccagcgtgtt ccccctggcc 1380
cccagcagca agagcaccag cggcggcaca gccgccctgg gctgcctggt gaaggactac 1440
ttccccgagc ccgtgaccgt gagctggaac agcggcgcct tgaccagcgg cgtgcacacc 1500
ttccccgccg tgctgcagag cagcggcctg tacagcctga gcagcgtggt gaccgtgccc 1560
agcagcagcc tgggcaccca gacctacatc tgcaacgtga accacaagcc cagcaacacc 1620
aaggtggaca aacgcgtgga gcccaagagc tgcgacaaga cccacacctg ccccccctgc 1680
cctgcccccg agctgctggg cggaccctcc gtgttcctgt tccccccaa gcccaaggac 1740 accctcatga tcagccggac ccccgaggtg acctgcgtgg tggtggacgt gagccacgag 1800

-continued

```
gaccccgagg tgaagttcaa ctggtacgtg gacggcgtgg aggtgcacaa cgccaagacc   1860
aagccccggg aggagcagta caacagcacc taccgggtgg tgagcgtgct caccgtgctg   1920
caccaggact ggctgaacgg caaggagtac aagtgcaagg tgagcaacaa ggccctgcct   1980
gcccccatcg agaagaccat cagcaaggcc aagggccagc cccgggagcc ccaggtgtac   2040
accctgcccc ccagccggga ggagatgacc aagaaccagg tgtccctcac ctgtctggtg   2100
aagggcttct accccagcga catcgccgtg gagtgggaga gcaacggcca gcccgagaac   2160
aactacaaga ccaccccccc tgtgctggac agcgacggca gcttcttcct gtacagcaag   2220
ctcaccgtgg acaagagccg gtggcagcag ggcaacgtgt tcagctgcag cgtgatgcac   2280
gaggccctgc acaaccacta cacccagaag agcctgagcc tgagccccgg caagtgataa   2340
tctagagggc ccgtttaaac ccgctgatca gcctcgactg tgccttctag ttgccagcca   2400
tctgttgttt gcccctcccc cgtgccttcc ttgaccctgg aaggtgccac tcccactgtc   2460
ctttcctaat aaaatgagga aattgcatcg cattgtctga gtaggtgtca ttctattctg   2520
gggggtgggg tggggcagga cagcaagggg gaggattggg aagacaatag caggcatgct   2580
ggggatgcgg tgggctctat ggcttctgag gcggaaagaa ccagctgggg ctctaggggg   2640
tatccccacg cgccctgtag cggcgcatta agcgcggcgg gtgtggtggt tacgcgcagc   2700
gtgaccgcta cacttgccag cgccctagcg cccgctcctt tcgctttctt cccttccttt   2760
ctcgccacgt tcgccggctt tccccgtcaa gctctaaatc gggggctccc tttagggttc   2820
cgatttagtg ctttacggca cctcgacccc aaaaaacttg attagggtga tggttcacgt   2880
agtgggccat cgccctgata gacggttttt cgccctttga cgttggagtc cacgttcttt   2940
aatagtggac tcttgttcca aactggaaca acactcaacc ctatctcggt ctattctttt   3000
gatttataag ggattttgcc gatttcggcc tattggttaa aaaatgagct gatttaacaa   3060
aaatttaacg cgaattaatt ctgtggaatg tgtgtcagtt agggtgtgga aagtccccag   3120
gctccccagc aggcagaagt atgcaaagca tgcatctcaa ttagtcagca accaggtgtg   3180
gaaagtcccc aggctcccca gcaggcagaa gtatgcaaag catgcatctc aattagtcag   3240
caaccatagt cccgccccta actccgccca tcccgcccct aactccgccc agttccgccc   3300
attctccgcc ccatggctga ctaatttttt ttatttatgc agaggccgag gccgcctctg   3360
cctctgagct attccagaag tagtgaggag gcttttttgg aggcctaggc ttttgcaaaa   3420
agctcccggg agcttgtata tccattttcg gatctgatca agagacagga tgaggatcgt   3480
ttcgcatgat tgaacaagat ggattgcacg caggttctcc ggccgcttgg gtggagaggc   3540
tattcggcta tgactgggca caacagacaa tcggctgctc tgatgccgcc gtgttccggc   3600
tgtcagcgca ggggcgcccg gttctttttg tcaagaccga cctgtccggt gccctgaatg   3660
aactgcagga cgaggcagcg cggctatcgt ggctggccac gacgggcgtt ccttgcgcag   3720
ctgtgctcga cgttgtcact gaagcgggaa gggactggct gctattgggc gaagtgccgg   3780
ggcaggatct cctgtcatct caccttgctc ctgccgagaa agtatccatc atggctgatg   3840
caatgcggcg gctgcatacg cttgatccgg ctacctgccc attcgaccac caagcgaaac   3900
atcgcatcga gcgagcacgt actcggatgg aagccggtct tgtcgatcag gatgatctgg   3960
acgaagagca tcaggggctc gcgccagccg aactgttcgc caggctcaag gcgcgcatgc   4020
ccgacggcga ggatctcgtc gtgacccatg gcgatgcctg cttgccgaat atcatggtgg   4080
aaaatggccg cttttctgga ttcatcgact gtggccggct gggtgtggcg gatcgctatc   4140
aggacatagc gttggctacc cgtgatattg ctgaagagct tggcggcgaa tgggctgacc   4200
```

gcttcctcgt gctttacggt atcgccgctc ccgattcgca gcgcatcgcc ttctatcgcc 4260
ttcttgacga gttcttctga gcgggactct ggggttcgaa atgaccgacc aagcgacgcc 4320
caacctgcca tcacgagatt tcgattccac cgccgccttc tatgaaaggt tgggcttcgg 4380
aatcgttttc cgggacgccg gctggatgat cctccagcgc ggggatctca tgctggagtt 4440
cttcgcccac cccaacttgt ttattgcagc ttataatggt tacaaataaa gcaatagcat 4500
cacaaatttc acaaataaag catttttttc actgcattct agttgtggtt tgtccaaact 4560
catcaatgta tcttatcatg tctgtatacc gtcgacctct agctagagct tggcgtaatc 4620
atggtcatag ctgtttcctg tgtgaaattg ttatccgctc acaattccac acaacatacg 4680
agccggaagc ataaagtgta aagcctgggg tgcctaatga gtgagctaac tcacattaat 4740
tgcgttgcgc tcactgcccg ctttccagtc gggaaacctg tcgtgccagc tgcattaatg 4800
aatcggccaa cgcgcgggga gaggcggttt gcgtattggg cgctcttccg cttcctcgct 4860
cactgactcg ctgcgctcgg tcgttcggct gcggcgagcg gtatcagctc actcaaaggc 4920
ggtaatacgg ttatccacag aatcagggga taacgcagga aagaacatgt gagcaaaagg 4980
ccagcaaaag gccaggaacc gtaaaaaggc cgcgttgctg gcgtttttcc ataggctccg 5040
cccccctgac gagcatcaca aaaatcgacg ctcaagtcag aggtggcgaa acccgacagg 5100
actataaaga taccaggcgt ttccccctgg aagctccctc gtgcgctctc ctgttccgac 5160
cctgccgctt accggatacc tgtccgcctt tctcccttcg ggaagcgtgg cgctttctca 5220
tagctcacgc tgtaggtatc tcagttcggt gtaggtcgtt cgctccaagc tgggctgtgt 5280
gcacgaaccc cccgttcagc ccgaccgctg cgccttatcc ggtaactatc gtcttgagtc 5340
caacccggta agacacgact tatcgccact ggcagcagcc actggtaaca ggattagcag 5400
agcgaggtat gtaggcggtg ctacagagtt cttgaagtgg tggcctaact acggctacac 5460
tagaagaaca gtatttggta tctgcgctct gctgaagcca gttaccttcg gaaaaagagt 5520
tggtagctct tgatccggca aacaaaccac cgctggtagc ggtttttttg tttgcaagca 5580
gcagattacg cgcagaaaaa aaggatctca agaagatcct ttgatctttt ctacggggtc 5640
tgacgctcag tggaacgaaa actcacgtta agggattttg gtcatgagat tatcaaaaag 5700
gatcttcacc tagatccttt taaattaaaa atgaagtttt aaatcaatct aaagtatata 5760
tgagtaaact tggtctgaca gttaccaatg cttaatcagt gaggcaccta tctcagcgat 5820
ctgtctattt cgttcatcca tagttgcctg actccccgtc gtgtagataa ctacgatacg 5880
ggagggctta ccatctggcc ccagtgctgc aatgataccg cgagacccac gctcaccggc 5940
tccagattta tcagcaataa accagccagc cggaagggcc gagcgcagaa gtggtcctgc 6000
aactttatcc gcctccatcc agtctattaa ttgttgccgg gaagctagag taagtagttc 6060
gccagttaat agtttgcgca acgttgttgc cattgctaca ggcatcgtgg tgtcacgctc 6120
gtcgtttggt atggcttcat tcagctccgg ttcccaacga tcaaggcgag ttacatgatc 6180
ccccatgttg tgcaaaaaag cggttagctc cttcggtcct ccgatcgttg tcagaagtaa 6240
gttggccgca gtgttatcac tcatggttat ggcagcactg cataattctc ttactgtcat 6300
gccatccgta agatgctttt ctgtgactgg tgagtactca accaagtcat tctgagaata 6360
gtgtatgcgg cgaccgagtt gctcttgccc ggcgtcaata cgggataata ccgcgccaca 6420
tagcagaact ttaaaagtgc tcatcattgg aaaacgttct tcggggcgaa aactctcaag 6480
gatcttaccg ctgttgagat ccagttcgat gtaacccact cgtgcaccca actgatcttc 6540
agcatctttt actttcacca gcgtttctgg gtgagcaaaa acaggaaggc aaaatgccgc 6600
aaaaaaggga ataagggcga cacggaaatg ttgaatactc atactcttcc tttttcaata 6660
ttattgaagc atttatcagg gttattgtct catgagcgga tacatatttg aatgtattta 6720
gaaaaataaa caaatagggg ttccgcgcac atttccccga aaagtgccac ctgacgtc 6778

<210> SEQ ID NO 44
<211> LENGTH: 6283
<212> TYPE: DNA
<213> ORGANISM: Artificial sequence
<220> FEATURE:
<223> OTHER INFORMATION: Vector pSyn-C04-Clambda

<400> SEQUENCE: 44
gacggatcgg gagatctccc gatcccctat ggtgcactct cagtacaatc tgctctgatg 60
ccgcatagtt aagccagtat ctgctccctg cttgtgtgtt ggaggtcgct gagtagtgcg 120
cgagcaaaat ttaagctaca acaaggcaag gcttgaccga caattgttaa ttaacatgaa 180
gaatctgctt agggttaggc gttttgcgct gcttcgctag gtggtcaata ttggccatta 240
gccatattat tcattggtta tatagcataa atcaatattg gctattggcc attgcatacg 300
ttgtatccat atcataatat gtacatttat attggctcat gtccaacatt accgccatgt 360
tgacattgat tattgactag ttattaatag taatcaatta cggggtcatt agttcatagc 420
ccatatatgg agttccgcgt tacataactt acggtaaatg gcccgcctgg ctgaccgccc 480
aacgaccccc gcccattgac gtcaataatg acgtatgttc ccatagtaac gccaataggg 540
actttccatt gacgtcaatg ggtggagtat ttacggtaaa ctgcccactt ggcagtacat 600
caagtgtatc atatgccaag tacgccccct attgacgtca atgacggtaa atggcccgcc 660
tggcattatg cccagtacat gaccttatgg gactttccta cttggcagta catctacgta 720
ttagtcatcg ctattaccat ggtgatgcgg ttttggcagt acatcaatgg gcgtggatag 780
cggtttgact cacggggatt tccaagtctc caccccattg acgtcaatgg gagtttgttt 840
tggcaccaaa atcaacggga ctttccaaaa tgtcgtaaca actccgcccc attgacgcaa 900
atgggcggta ggcgtgtacg gtgggaggtc tatataagca gagctcgttt agtgaaccgt 960
cagatcgcct ggagacgcca tccacgctgt tttgacctcc atagaagaca ccgggaccga 1020
tccagcctcc gcggccggga acggtgcatt ggaatcgatg actctcttag gtagccttgc 1080
agaagttggt cgtgaggcac tgggcaggta agtatcaagg ttacaagaca ggtttaagga 1140
gatcaataga aactgggctt gtcgagacag agaagactct tgcgtttctg ataggcacct 1200
attggtctta ctgacatcca ctttgccttt ctctccacag gtgtccactc ccagttcaat 1260
tacagctcgc caccatggcc tgccccggct tcctgtgggc cctggtgatc agcacctgcc 1320
tcgagatccc cggaccgcgg ccgcaagctt accgtgctgg gccagcccaa ggccgctccc 1380
agcgtgaccc tgttcccccc ctcctccgag gagctgcagg ccaacaaggc caccctggtg 1440
tgcctcatca gcgacttcta ccctggcgcc gtgaccgtgg cctggaaggc cgacagcagc 1500
cccgtgaagg ccggcgtgga gaccaccacc cccagcaagc agagcaacaa caagtacgcc 1560
gccagcagct acctgagcct cacccccgag cagtggaaga gccaccggag ctacagctgc 1620
caggtgaccc acgagggcag caccgtggag aagaccgtgg cccccaccga gtgcagctaa 1680
tagacttaag tttaaaccgc tgatcagcct cgactgtgcc ttctagttgc cagccatctg 1740
ttgtttgccc ctcccccgtg ccttccttga ccctggaagg tgccactccc actgtccttt 1800
cctaataaaa tgaggaaatt gcatcgcatt gtctgagtag gtgtcattct attctggggg 1860
gtggggtggg gcaggacagc aagggggagg attgggaaga caatagcagg catgctgggg 1920

-continued

```
atgcggtggg ctctatggct tctgaggcgg aaagaaccag ctggggctct agggggtatc   1980
cccacgcgcc ctgtagcggc gcattaagcg cggcgggtgt ggtggttacg cgcagcgtga   2040
ccgctacact tgccagcgcc ctagcgcccg ctcctttcgc tttcttccct tcctttctcg   2100
ccacgttcgc cggctttccc cgtcaagctc taaatcgggg gctcccttta gggttccgat   2160
ttagtgcttt acggcacctc gaccccaaaa aacttgatta gggtgatggt tcacgtagtg   2220
ggccatcgcc ctgatagacg gtttttcgcc ctttgacgtt ggagtccacg ttctttaata   2280
gtggactctt gttccaaact ggaacaacac tcaaccctat ctcggtctat tcttttgatt   2340
tataagggat tttggccatt tcggcctatt ggttaaaaaa tgagctgatt taacaaaaat   2400
ttaacgcgaa ttaattctgt ggaatgtgtg tcagttaggg tgtggaaagt ccccaggctc   2460
cccagcaggc agaagtatgc aaagcatgca tctcaattag tcagcaacca ggtgtggaaa   2520
gtccccaggc tccccagcag gcagaagtat gcaaagcatg catctcaatt agtcagcaac   2580
catagtcccg cccctaactc cgcccatccc gcccctaact ccgcccagtt ccgcccattc   2640
tccgccccat ggctgactaa ttttttttat ttatgcagag gccgaggccg cctctgcctc   2700
tgagctattc cagaagtagt gaggaggctt ttttggaggc ctaggctttt gcaaaaagct   2760
cccgggagct tgtatatcca ttttcggatc tgatcagcac gtgatgaaaa agcctgaact   2820
caccgcgacg tctgtcgaga agtttctgat cgaaaagttc gacagcgtct ccgacctgat   2880
gcagctctcg gagggcgaag aatctcgtgc tttcagcttc gatgtaggag ggcgtggata   2940
tgtcctgcgg gtaaatagct gcgccgatgg tttctacaaa gatcgttatg tttatcggca   3000
ctttgcatcg gccgcgctcc cgattccgga agtgcttgac attggggaat tcagcgagag   3060
cctgacctat tgcatctccc gccgtgcaca gggtgtcacg ttgcaagacc tgcctgaaac   3120
cgaactgccc gctgttctgc agccggtcgc ggaggccatg gatgcgatcg ctgcggccga   3180
tcttagccag acgagcgggt tcggcccatt cggaccgcaa ggaatcggtc aatacactac   3240
atggcgtgat ttcatatgcg cgattgctga tccccatgtg tatcactggc aaactgtgat   3300
ggacgacacc gtcagtgcgt ccgtcgcgca ggctctcgat gagctgatgc tttgggccga   3360
ggactgcccc gaagtccggc acctcgtgca cgcggatttc ggctccaaca atgtcctgac   3420
ggacaatggc cgcataacag cggtcattga ctggagcgag gcgatgttcg gggattccca   3480
atacgaggtc gccaacatct tcttctggag gccgtggttg gcttgtatgg agcagcagac   3540
gcgctacttc gagcggaggc atccggagct tgcaggatcg ccgcggctcc gggcgtatat   3600
gctccgcatt ggtcttgacc aactctatca gagcttggtt gacggcaatt tcgatgatgc   3660
agcttgggcg cagggtcgat gcgacgcaat cgtccgatcc ggagccggga ctgtcgggcg   3720
tacacaaatc gcccgcagaa gcgcggccgt ctggaccgat ggctgtgtag aagtactcgc   3780
cgatagtgga aaccgacgcc ccagcactcg tccgagggca aaggaatagc acgtgctacg   3840
agatttcgat tccaccgccg ccttctatga aaggttgggc ttcggaatcg ttttccggga   3900
cgccggctgg atgatcctcc agcgcgggga tctcatgctg gagttcttcg cccaccccaa   3960
cttgtttatt gcagcttata atggttacaa ataaagcaat agcatcacaa atttcacaaa   4020
taaagcattt ttttcactgc attctagttg tggtttgtcc aaactcatca atgtatctta   4080
tcatgtctgt ataccgtcga cctctagcta gagcttggcg taatcatggt catagctgtt   4140
tcctgtgtga aattgttatc cgctcacaat tccacacaac atacgagccg gaagcataaa   4200
gtgtaaagcc tggggtgcct aatgagtgag ctaactcaca ttaattgcgt tgcgctcact   4260
gcccgctttc cagtcgggaa acctgtcgtg ccagctgcat taatgaatcg gccaacgcgc   4320
```

-continued

```
ggggagaggc ggtttgcgta ttgggcgctc ttccgcttcc tcgctcactg actcgctgcg   4380

ctcggtcgtt cggctgcggc gagcggtatc agctcactca aaggcggtaa tacggttatc   4440

cacagaatca ggggataacg caggaaagaa catgtgagca aaaggccagc aaaaggccag   4500

gaaccgtaaa aaggccgcgt tgctggcgtt tttccatagg ctccgccccc ctgacgagca   4560

tcacaaaaat cgacgctcaa gtcagaggtg gcgaaacccg acaggactat aaagatacca   4620

ggcgtttccc cctggaagct ccctcgtgcg ctctcctgtt ccgaccctgc cgcttaccgg   4680

atacctgtcc gcctttctcc cttcgggaag cgtggcgctt tctcatagct cacgctgtag   4740

gtatctcagt tcggtgtagg tcgttcgctc caagctgggc tgtgtgcacg aaccccccgt   4800

tcagcccgac cgctgcgcct tatccggtaa ctatcgtctt gagtccaacc cggtaagaca   4860

cgacttatcg ccactggcag cagccactgg taacaggatt agcagagcga ggtatgtagg   4920

cggtgctaca gagttcttga agtggtggcc taactacggc tacactagaa gaacagtatt   4980

tggtatctgc gctctgctga agccagttac cttcggaaaa agagttggta gctcttgatc   5040

cggcaaacaa accaccgctg gtagcggttt ttttgtttgc aagcagcaga ttacgcgcag   5100

aaaaaaagga tctcaagaag atcctttgat cttttctacg gggtctgacg ctcagtggaa   5160

cgaaaactca cgttaaggga ttttggtcat gagattatca aaaaggatct tcacctagat   5220

ccttttaaat taaaaatgaa gttttaaatc aatctaaagt atatatgagt aaacttggtc   5280

tgacagttac caatgcttaa tcagtgaggc acctatctca gcgatctgtc tatttcgttc   5340

atccatagtt gcctgactcc ccgtcgtgta gataactacg atacgggagg gcttaccatc   5400

tggccccagt gctgcaatga taccgcgaga cccacgctca ccggctccag atttatcagc   5460

aataaaccag ccagccggaa gggccgagcg cagaagtggt cctgcaactt tatccgcctc   5520

catccagtct attaattgtt gccgggaagc tagagtaagt agttcgccag ttaatagttt   5580

gcgcaacgtt gttgccattg ctacaggcat cgtggtgtca cgctcgtcgt ttggtatggc   5640

ttcattcagc tccggttccc aacgatcaag gcgagttaca tgatccccca tgttgtgcaa   5700

aaaagcggtt agctccttcg gtcctccgat cgttgtcaga agtaagttgg ccgcagtgtt   5760

atcactcatg gttatggcag cactgcataa ttctcttact gtcatgccat ccgtaagatg   5820

cttttctgtg actggtgagt actcaaccaa gtcattctga gaatagtgta tgcggcgacc   5880

gagttgctct tgcccggcgt caatacggga taataccgcg ccacatagca gaactttaaa   5940

agtgctcatc attggaaaac gttcttcggg gcgaaaactc tcaaggatct taccgctgtt   6000

gagatccagt tcgatgtaac ccactcgtgc acccaactga tcttcagcat cttttacttt   6060

caccagcgtt tctgggtgag caaaaacagg aaggcaaaat gccgcaaaaa agggaataag   6120

ggcgacacgg aaatgttgaa tactcatact cttccttttt caatattatt gaagcattta   6180

tcagggttat tgtctcatga gcggatacat atttgaatgt atttagaaaa ataaacaaat   6240

aggggttccg cgcacatttc cccgaaaagt gccacctgac gtc                     6283
```

<210> SEQ ID NO 45
<211> LENGTH: 52
<212> TYPE: DNA
<213> ORGANISM: Artificial sequence
<220> FEATURE:
<223> OTHER INFORMATION: Oligonucleotide 5L-B

<400> SEQUENCE: 45

```
acctgtctcg agttttccat ggctcagtcc gccctgaccc agccccgctc ag             52
```

-continued

```
<210> SEQ ID NO 46
<211> LENGTH: 43
<212> TYPE: DNA
<213> ORGANISM: Artificial sequence
<220> FEATURE:
<223> OTHER INFORMATION: Oligonucleotide sy3L-A

<400> SEQUENCE: 46

ccagcacggt aagcttcagc acggtcacct tggtgccagt tcc                       43


<210> SEQ ID NO 47
<211> LENGTH: 50
<212> TYPE: DNA
<213> ORGANISM: Artificial sequence
<220> FEATURE:
<223> OTHER INFORMATION: Oligonucleotide 5H-F

<400> SEQUENCE: 47

acctgtcttg aattctccat ggcccaggtg cagctgcagg agtccggccc                50


<210> SEQ ID NO 48
<211> LENGTH: 47
<212> TYPE: DNA
<213> ORGANISM: Artificial sequence
<220> FEATURE:
<223> OTHER INFORMATION: Oligonucleotide sy3H-A

<400> SEQUENCE: 48

gcccttggtg ctagcgctgg agacggtcac cagggtgccc tggcccc                   47


<210> SEQ ID NO 49
<211> LENGTH: 10515
<212> TYPE: DNA
<213> ORGANISM: Artificial sequence
<220> FEATURE:
<223> OTHER INFORMATION: Vector piG-C911-HCgamma1
<220> FEATURE:
<221> NAME/KEY: misc_feature
<222> LOCATION: (1326)..(5076)
<223> OTHER INFORMATION: Stuffer

<400> SEQUENCE: 49

tcgacggatc gggagatctc ccgatcccct atggtgcact ctcagtacaa tctgctctga      60

tgccgcatag ttaagccagt atctgctccc tgcttgtgtg ttggaggtcg ctgagtagtg     120

cgcgagcaaa atttaagcta caacaaggca aggcttgacc gacaattgca tgaagaatct     180

gcttagggtt aggcgttttg cgctgcttcg ctaggtggtc aatattggcc attagccata     240

ttattcattg gttatatagc ataaatcaat attggctatt ggccattgca tacgttgtat     300

ccatatcata atatgtacat ttatattggc tcatgtccaa cattaccgcc atgttgacat     360

tgattattga ctagttatta atagtaatca attacggggt cattagttca tagcccatat     420

atggagttcc gcgttacata acttacggta aatggcccgc ctggctgacc gcccaacgac     480

ccccgcccat tgacgtcaat aatgacgtat gttcccatag taacgccaat agggactttc     540

cattgacgtc aatgggtgga gtatttacgg taaactgccc acttggcagt acatcaagtg     600

tatcatatgc caagtacgcc ccctattgac gtcaatgacg gtaaatggcc cgcctggcat     660

tatgcccagt acatgacctt atgggacttt cctacttggc agtacatcta cgtattagtc     720

atcgctatta ccatggtgat gcggttttgg cagtacatca atgggcgtgg atagcggttt     780

gactcacggg gatttccaag tctccacccc attgacgtca atgggagttt gttttggcac     840

caaaatcaac gggactttcc aaaatgtcgt aacaactccg ccccattgac gcaaatgggc     900

ggtaggcgtg tacggtggga ggtctatata agcagagctc gtttagtgaa ccgtcagatc     960
```

-continued

```
gcctggagac gccatccacg ctgttttgac ctccatagaa gacaccggga ccgatccagc   1020
ctccgcggcc gggaacggtg cattggaagc tggcctggat atcctgactc tcttaggtag   1080
ccttgcagaa gttggtcgtg aggcactggg caggtaagta tcaaggttac aagacaggtt   1140
taaggagatc aatagaaact gggcttgtcg agacagagaa gactcttgcg tttctgatag   1200
gcacctattg gtcttactga catccacttt gcctttctct ccacaggtgt ccactcccag   1260
ttcaattaca gctcgccacc atgggatgga gctgtatcat cctcttcttg gtactgctgc   1320
tggcccagcc ggccagtgac cttgaccggt gcaccacttt tgatgatgtt caagctccta   1380
attacactca acatacttca tctatgaggg gggtttacta tcctgatgaa atttttagat   1440
cggacactct ttatttaact caggatttat ttcttccatt ttattctaat gttacagggt   1500
ttcatactat taatcatacg tttggcaacc ctgtcatacc ttttaaggat ggtatttatt   1560
ttgctgccac agagaaatca aatgttgtcc gtggttgggt tttggttct accatgaaca    1620
acaagtcaca gtcggtgatt attattaaca attctactaa tgttgttata cgagcatgta   1680
actttgaatt gtgtgacaac cctttctttg ctgtttctaa acccatgggt acacagacac   1740
atactatgat attcgataat gcatttaatt gcactttcga gtacatatct gatgcctttt   1800
cgcttgatgt ttcagaaaag tcaggtaatt ttaaacactt acgagagttt gtgtttaaaa   1860
ataaagatgg gtttctctat gtttataagg gctatcaacc tatagatgta gttcgtgatc   1920
taccttctgg ttttaacact ttgaaaccta tttttaagtt gcctcttggt attaacatta   1980
caaattttag agccattctt acagcctttt cacctgctca agacatttgg ggcacgtcag   2040
ctgcagccta ttttgttggc tatttaaagc caactacatt tatgctcaag tatgatgaaa   2100
atggtacaat cacagatgct gttgattgtt ctcaaaatcc acttgctgaa ctcaaatgct   2160
ctgttaagag ctttgagatt gacaaaggaa tttaccagac ctctaatttc agggttgttc   2220
cctcaggaga tgttgtgaga ttccctaata ttacaaactt gtgtcctttt ggagaggttt   2280
ttaatgctac taaattccct tctgtctatg catgggagag aaaaaaaatt tctaattgtg   2340
ttgctgatta ctctgtgctc tacaactcaa catttttttc aacctttaag tgctatggcg   2400
tttctgccac taagttgaat gatctttgct tctccaatgt ctatgcagat tcttttgtag   2460
tcaagggaga tgatgtaaga caaatagcgc caggacaaac tggtgttatt gctgattata   2520
attataaatt gccagatgat ttcatgggtt gtgtccttgc ttggaatact aggaacattg   2580
atgctacttc aactggtaat tataattata aatataggta tcttagacat ggcaagctta   2640
ggccctttga gagagacata tctaatgtgc ctttctcccc tgatggcaaa ccttgcaccc   2700
cacctgctct taattgttat tggccattaa atgattatgg tttttacacc actactggca   2760
ttggctacca accttacaga gttgtagtac tttcttttga acttttaaat gcaccggcca   2820
cggtttgtgg accaaaatta tccactgacc ttattaagaa ccagtgtgtc aattttaatt   2880
ttaatggact cactggtact ggtgtgttaa ctccttcttc aaagagattt caaccatttc   2940
aacaatttgg ccgtgatgtt tctgatttca ctgattccgt tcgagatcct aaaacatctg   3000
aaatattaga catttcacct tgctcttttg gggtgtaag tgtaattaca cctggaacaa    3060
atgcttcatc tgaagttgct gttctatatc aagatgttaa ctgcactgat gtttctacag   3120
caattcatgc agatcaactc acaccagctt ggcgcatata ttctactgga aacaatgtat   3180
tccagactca ggcaggctgt cttataggag ctgagcatgt cgacacttct tatgagtgcg   3240
acattcctat tggagctggc atttgtgcta gttaccatac agtttcttta ttacgtagta   3300
ctagccaaaa atctattgtg gcttatacta tgtctttagg tgctgatagt tcaattgctt   3360
```

-continued actctaataa caccattgct atacctacta acttttcaat tagcattact acagaagtaa 3420
tgcctgtttc tatggctaaa acctccgtag attgtaatat gtacatctgc ggagattcta 3480
ctgaatgtgc taatttgctt ctccaatatg gtagcttttg cacacaacta aatcgtgcac 3540
tctcaggtat tgctgctgaa caggatcgca acacacgtga agtgttcgct caagtcaaac 3600
aaatgtacaa aaccccaact ttgaaatatt ttggtggttt taatttttca caaatattac 3660
ctgaccctct aaagccaact aagaggtctt ttattgagga cttgctcttt aataaggtga 3720
cactcgctga tgctggcttc atgaagcaat atggcgaatg cctaggtgat attaatgcta 3780
gagatctcat ttgtgcgcag aagttcaatg gacttacagt gttgccacct ctgctcactg 3840
atgatatgat tgctgcctac actgctgctc tagttagtgg tactgccact gctggatgga 3900
catttggtgc tggcgctgct cttcaaatac cttttgctat gcaaatggca tataggttca 3960
atggcattgg agttacccaa aatgttctct atgagaacca aaaacaaatc gccaaccaat 4020
ttaacaaggc gattagtcaa attcaagaat cacttacaac aacatcaact gcattgggca 4080
agctgcaaga cgttgttaac cagaatgctc aagcattaaa cacacttgtt aaacaactta 4140
gctctaattt tggtgcaatt tcaagtgtgc taaatgatat cctttcgcga cttgataaag 4200
tcgaggcgga ggtacaaatt gacaggttaa ttacaggcag acttcaaagc cttcaaacct 4260
atgtaacaca acaactaatc agggctgctg aaatcagggc ttctgctaat cttgctgcta 4320
ctaaaatgtc tgagtgtgtt cttggacaat caaaaagagt tgacttttgt ggaaagggct 4380
accaccttat gtccttccca caagcagccc cgcatggtgt tgtcttccta catgtcacgt 4440
atgtgccatc ccaggagagg aacttcacca cagcgccagc aatttgtcat gaaggcaaag 4500
catacttccc tcgtgaaggt gtttttgtgt ttaatggcac ttcttggttt attacacaga 4560
ggaacttctt ttctccacaa ataattacta cagacaatac atttgtctca ggaaattgtg 4620
atgtcgttat tggcatcatt aacaacacag tttatgatcc tctgcaacct gagcttgact 4680
cattcaaaga agagctggac aagtacttca aaaatcatac atcaccagat gttgattttg 4740
gcgacatttc aggcattaac gcttctgtcg tcaacattca aaaagaaatt gaccgcctca 4800
atgaggtcgc taaaaattta aatgaatcac tcattgacct tcaagaactg ggaaaatatg 4860
agcaatatat taaatggcct ctcgacgaac aaaaactcat ctcagaagag gatctgaatg 4920
ctgtgggcca ggacacgcag gaggtcatcg tggtgccaca ctccttgccc tttaaggtgg 4980
tggtgatctc agccatcctg gccctggtgg tgctcaccat catctccctt atcatcctca 5040
tcatgctttg gcagaagaag ccacgttagg cggccgctcg agtgctagca ccaagggccc 5100
cagcgtgttc cccctggccc ccagcagcaa gagcaccagc ggcggcacag ccgccctggg 5160
ctgcctggtg aaggactact tccccgagcc cgtgaccgtg agctggaaca gcggcgcctt 5220
gaccagcggc gtgcacacct tccccgccgt gctgcagagc agcggcctgt acagcctgag 5280
cagcgtggtg accgtgccca gcagcagcct gggcacccag acctacatct gcaacgtgaa 5340
ccacaagccc agcaacacca aggtggacaa acgcgtggag cccaagagct gcgacaagac 5400
ccacacctgc ccccccctgcc ctgcccccga gctgctgggc ggaccctccg tgttcctgtt 5460
ccccccccaag cccaaggaca ccctcatgat cagccggacc cccgaggtga cctgcgtggt 5520
ggtggacgtg agccacgagg accccgaggt gaagttcaac tggtacgtgg acggcgtgga 5580
ggtgcacaac gccaagacca agccccggga ggagcagtac aacagcacct accgggtggt 5640
gagcgtgctc accgtgctgc accaggactg gctgaacggc aaggagtaca agtgcaaggt 5700
gagcaacaag gccctgcctg cccccatcga gaagaccatc agcaaggcca agggccagcc 5760

-continued

```
ccgggagccc caggtgtaca ccctgccccc cagccgggag gagatgacca agaaccaggt   5820
gtccctcacc tgtctggtga agggcttcta ccccagcgac atcgccgtgg agtgggagag   5880
caacggccag cccgagaaca actacaagac caccccccct gtgctggaca gcgacggcag   5940
cttcttcctg tacagcaagc tcaccgtgga caagagccgg tggcagcagg gcaacgtgtt   6000
cagctgcagc gtgatgcacg aggccctgca caaccactac acccagaaga gcctgagcct   6060
gagccccggc aagtgataat ctagagggcc cgtttaaacc cgctgatcag cctcgactgt   6120
gccttctagt tgccagccat ctgttgtttg cccctccccc gtgccttcct tgaccctgga   6180
aggtgccact cccactgtcc tttcctaata aaatgaggaa attgcatcgc attgtctgag   6240
taggtgtcat tctattctgg ggggtggggt ggggcaggac agcaaggggg aggattggga   6300
agacaatagc aggcatgctg gggatgcggt gggctctatg gcttctgagg cggaaagaac   6360
cagctggggc tctagggggt atccccacgc gccctgtagc ggcgcattaa gcgcggcggg   6420
tgtggtggtt acgcgcagcg tgaccgctac acttgccagc gccctagcgc ccgctccttt   6480
cgctttcttc ccttcctttc tcgccacgtt cgccggcttt ccccgtcaag ctctaaatcg   6540
ggggctccct ttagggttcc gatttagtgc tttacggcac ctcgacccca aaaaacttga   6600
ttagggtgat ggttcacgta gtgggccatc gccctgatag acggtttttc gccctttgac   6660
gttggagtcc acgttcttta atagtggact cttgttccaa actggaacaa cactcaaccc   6720
tatctcggtc tattcttttg atttataagg gattttgccg atttcggcct attggttaaa   6780
aaatgagctg atttaacaaa aatttaacgc gaattaattc tgtggaatgt gtgtcagtta   6840
gggtgtggaa agtccccagg ctccccagca ggcagaagta tgcaaagcat gcatctcaat   6900
tagtcagcaa ccaggtgtgg aaagtcccca ggctccccag caggcagaag tatgcaaagc   6960
atgcatctca attagtcagc aaccatagtc ccgcccctaa ctccgcccat cccgccccta   7020
actccgccca gttccgccca ttctccgccc catggctgac taattttttt tatttatgca   7080
gaggccgagg ccgcctctgc ctctgagcta ttccagaagt agtgaggagg cttttttgga   7140
ggcctaggct tttgcaaaaa gctcccggga gcttgtatat ccattttcgg atctgatcaa   7200
gagacaggat gaggatcgtt tcgcatgatt gaacaagatg gattgcacgc aggttctccg   7260
gccgcttggg tggagaggct attcggctat gactgggcac aacagacaat cggctgctct   7320
gatgccgccg tgttccggct gtcagcgcag gggcgcccgg ttctttttgt caagaccgac   7380
ctgtccggtg ccctgaatga actgcaggac gaggcagcgc ggctatcgtg gctggccacg   7440
acgggcgttc cttgcgcagc tgtgctcgac gttgtcactg aagcgggaag ggactggctg   7500
ctattgggcg aagtgccggg gcaggatctc ctgtcatctc accttgctcc tgccgagaaa   7560
gtatccatca tggctgatgc aatgcggcgg ctgcatacgc ttgatccggc tacctgccca   7620
ttcgaccacc aagcgaaaca tcgcatcgag cgagcacgta ctcggatgga agccggtctt   7680
gtcgatcagg atgatctgga cgaagagcat caggggctcg cgccagccga actgttcgcc   7740
aggctcaagg cgcgcatgcc cgacggcgag gatctcgtcg tgacccatgg cgatgcctgc   7800
ttgccgaata tcatggtgga aaatggccgc ttttctggat tcatcgactg tggccggctg   7860
ggtgtggcgg accgctatca ggacatagcg ttggctaccc gtgatattgc tgaagagctt   7920
ggcggcgaat gggctgaccg cttcctcgtg ctttacggta tcgccgctcc cgattcgcag   7980
cgcatcgcct tctatcgcct tcttgacgag ttcttctgag cgggactctg gggttcgaaa   8040
tgaccgacca agcgacgccc aacctgccat cacgagattt cgattccacc gccgccttct   8100
atgaaaggtt gggcttcgga atcgttttcc gggacgccgg ctggatgatc ctccagcgcg   8160
```

```
gggatctcat gctggagttc ttcgcccacc ccaacttgtt tattgcagct tataatggtt   8220
acaaataaag caatagcatc acaaatttca caaataaagc atttttttca ctgcattcta   8280
gttgtggttt gtccaaactc atcaatgtat cttatcatgt ctgtataccg tcgacctcta   8340
gctagagctt ggcgtaatca tggtcatagc tgtttcctgt gtgaaattgt tatccgctca   8400
caattccaca caacatacga gccggaagca taaagtgtaa agcctggggt gcctaatgag   8460
tgagctaact cacattaatt gcgttgcgct cactgcccgc tttccagtcg ggaaacctgt   8520
cgtgccagct gcattaatga atcggccaac gcgcggggag aggcggtttg cgtattgggc   8580
gctcttccgc ttcctcgctc actgactcgc tgcgctcggt cgttcggctg cggcgagcgg   8640
tatcagctca ctcaaaggcg gtaatacggt tatccacaga atcaggggat aacgcaggaa   8700
agaacatgtg agcaaaaggc cagcaaaagg ccaggaaccg taaaaaggcc gcgttgctgg   8760
cgtttttcca taggctccgc ccccctgacg agcatcacaa aaatcgacgc tcaagtcaga   8820
ggtggcgaaa cccgacagga ctataaagat accaggcgtt tccccctgga agctccctcg   8880
tgcgctctcc tgttccgacc ctgccgctta ccggatacct gtccgccttt ctcccttcgg   8940
gaagcgtggc gctttctcat agctcacgct gtaggtatct cagttcggtg taggtcgttc   9000
gctccaagct gggctgtgtg cacgaacccc ccgttcagcc cgaccgctgc gccttatccg   9060
gtaactatcg tcttgagtcc aacccggtaa gacacgactt atcgccactg gcagcagcca   9120
ctggtaacag gattagcaga gcgaggtatg taggcggtgc tacagagttc ttgaagtggt   9180
ggcctaacta cggctacact agaagaacag tatttggtat ctgcgctctg ctgaagccag   9240
ttaccttcgg aaaaagagtt ggtagctctt gatccggcaa acaaaccacc gctggtagcg   9300
gtttttttgt ttgcaagcag cagattacgc gcagaaaaaa aggatctcaa gaagatcctt   9360
tgatcttttc tacggggtct gacgctcagt ggaacgaaaa ctcacgttaa gggattttgg   9420
tcatgagatt atcaaaaagg atcttcacct agatcctttt aaattaaaaa tgaagtttta   9480
aatcaatcta aagtatatat gagtaaactt ggtctgacag ttaccaatgc ttaatcagtg   9540
aggcacctat ctcagcgatc tgtctatttc gttcatccat agttgcctga ctccccgtcg   9600
tgtagataac tacgatacgg gagggcttac catctggccc cagtgctgca atgataccgc   9660
gagacccacg ctcaccggct ccagatttat cagcaataaa ccagccagcc ggaagggccg   9720
agcgcagaag tggtcctgca actttatccg cctccatcca gtctattaat tgttgccggg   9780
aagctagagt aagtagttcg ccagttaata gtttgcgcaa cgttgttgcc attgctacag   9840
gcatcgtggt gtcacgctcg tcgtttggta tggcttcatt cagctccggt tcccaacgat   9900
caaggcgagt tacatgatcc cccatgttgt gcaaaaaagc ggttagctcc ttcggtcctc   9960
cgatcgttgt cagaagtaag ttggccgcag tgttatcact catggttatg gcagcactgc  10020
ataattctct tactgtcatg ccatccgtaa gatgcttttc tgtgactggt gagtactcaa  10080
ccaagtcatt ctgagaatag tgtatgcggc gaccgagttg ctcttgcccg gcgtcaatac  10140
gggataatac cgcgccacat agcagaactt taaaagtgct catcattgga aaacgttctt  10200
cggggcgaaa actctcaagg atcttaccgc tgttgagatc cagttcgatg taacccactc  10260
gtgcacccaa ctgatcttca gcatctttta ctttcaccag cgtttctggg tgagcaaaaa  10320
caggaaggca aaatgccgca aaaaagggaa taagggcgac acggaaatgt tgaatactca  10380
tactcttcct ttttcaatat tattgaagca tttatcaggg ttattgtctc atgagcggat  10440
acatatttga atgtatttag aaaaataaac aaataggggt tccgcgcaca tttccccgaa  10500
aagtgccacc tgacg                                                   10515
```

<210> SEQ ID NO 50
<211> LENGTH: 8777
<212> TYPE: DNA
<213> ORGANISM: Artificial sequence
<220> FEATURE:
<223> OTHER INFORMATION: Vector piG-C909-Ckappa
<220> FEATURE:
<221> NAME/KEY: misc_feature
<222> LOCATION: (1328)..(3860)
<223> OTHER INFORMATION: Stuffer

<400> SEQUENCE: 50
tcgacggatc gggagatctc ccgatcccct atggtgcact ctcagtacaa tctgctctga 60
tgccgcatag ttaagccagt atctgctccc tgcttgtgtg ttggaggtcg ctgagtagtg 120
cgcgagcaaa atttaagcta caacaaggca aggcttgacc gacaattgtt aattaacatg 180
aagaatctgc ttagggttag gcgttttgcg ctgcttcgct aggtggtcaa tattggccat 240
tagccatatt attcattggt tatatagcat aaatcaatat tggctattgg ccattgcata 300
cgttgtatcc atatcataat atgtacattt atattggctc atgtccaaca ttaccgccat 360
gttgacattg attattgact agttattaat agtaatcaat tacggggtca ttagttcata 420
gcccatatat ggagttccgc gttacataac ttacggtaaa tggcccgcct ggctgaccgc 480
ccaacgaccc ccgcccattg acgtcaataa tgacgtatgt tcccatagta acgccaatag 540
ggactttcca ttgacgtcaa tgggtggagt atttacggta aactgcccac ttggcagtac 600
atcaagtgta tcatatgcca agtacgcccc ctattgacgt caatgacggt aaatggcccg 660
cctggcatta tgcccagtac atgaccttat gggactttcc tacttggcag tacatctacg 720
tattagtcat cgctattacc atggtgatgc ggttttggca gtacatcaat gggcgtggat 780
agcggtttga ctcacgggga tttccaagtc tccaccccat tgacgtcaat gggagtttgt 840
tttggcacca aaatcaacgg gactttccaa aatgtcgtaa caactccgcc ccattgacgc 900
aaatgggcgg taggcgtgta cggtgggagg tctatataag cagagctcgt ttagtgaacc 960
gtcagatcgc ctggagacgc catccacgct gttttgacct ccatagaaga caccgggacc 1020
gatccagcct ccgcggccgg gaacggtgca ttggaatcga tgactctctt aggtagcctt 1080
gcagaagttg gtcgtgaggc actgggcagg taagtatcaa ggttacaaga caggtttaag 1140
gagatcaata gaaactgggc ttgtcgagac agagaagact cttgcgtttc tgataggcac 1200
ctattggtct tactgacatc cactttgcct ttctctccac aggtgtccac tcccagttca 1260
attacagctc gccaccatgc ggctgcccgc ccagctgctg ggccttctca tgctgtgggt 1320
gcccgcctcg agatctatcg atgcatgcca tggtaccaag cttgccacca tgagcagcag 1380
ctcttggctg ctgctgagcc tggtggccgt gacagccgcc cagagcacca tcgaggagca 1440
ggccaagacc ttcctggaca agttcaacca cgaggccgag gacctgttct accagagcag 1500
cctggccagc tggaactaca acaccaacat caccgaggag aacgtgcaga acatgaacaa 1560
cgccggcgac aagtggagcg ccttcctgaa ggagcagagc acactggccc agatgtaccc 1620
cctgcaggag atccagaacc tgaccgtgaa gctgcagctg caggccctgc agcagaacgg 1680
cagcagcgtg ctgagcgagg acaagagcaa gcggctgaac accatcctga acaccatgtc 1740
caccatctac agcaccggca aagtgtgcaa ccccgacaac ccccaggagt gcctgctgct 1800
ggagcccggc ctgaacgaga tcatggccaa cagcctggac tacaacgagc ggctgtgggc 1860
ctgggagagc tggcggagcg aagtgggcaa gcagctgcgg cccctgtacg aggagtacgt 1920
ggtgctgaag aacgagatgg ccagggccaa ccactacgag gactacggcg actactggag 1980

-continued

```
aggcgactac gaagtgaacg gcgtggacgg ctacgactac agcagaggcc agctgatcga   2040
ggacgtggag cacaccttcg aggagatcaa gcctctgtac gagcacctgc acgcctacgt   2100
gcgggccaag ctgatgaacg cctaccccag ctacatcagc cccatcggct gcctgcccgc   2160
ccacctgctg ggcgacatgt ggggccggtt ctggaccaac ctgtacagcc tgaccgtgcc   2220
cttcggccag aagcccaaca tcgacgtgac cgacgccatg gtggaccagg cctgggacgc   2280
ccagcggatc ttcaaggagg ccgagaagtt cttcgtgagc gtgggcctgc ccaacatgac   2340
ccagggcttt tgggagaaca gcatgctgac cgaccccggc aatgtgcaga aggccgtgtg   2400
ccaccccacc gcctgggacc tgggcaaggg cgacttccgg atcctgatgt gcaccaaagt   2460
gaccatggac gacttcctga ccgcccacca cgagatgggc cacatccagt acgacatggc   2520
ctacgccgcc cagcccttcc tgctgcggaa cggcgccaac gagggctttc acgaggccgt   2580
gggcgagatc atgagcctga gcgccgccac ccccaagcac ctgaagagca tcggcctgct   2640
gagccccgac ttccaggagg acaacgagac cgagatcaac ttcctgctga agcaggccct   2700
gaccatcgtg ggcaccctgc ccttcaccta catgctggag aagtggcggt ggatggtgtt   2760
taagggcgag atccccaagg accagtggat gaagaagtgg tgggagatga agcgggagat   2820
cgtgggcgtg gtggagcccg tgccccacga cgagacctac tgcgaccccg ccagcctgtt   2880
ccacgtgagc aacgactact ccttcatccg gtactacacc cggaccctgt accagttcca   2940
gttccaggag gccctgtgcc aggccgccaa gcacgagggc cccctgcaca agtgcgacat   3000
cagcaacagc accgaggccg gacagaaact gttcaacatg ctgcggctgg gcaagagcga   3060
gccctggacc ctggccctgg agaatgtggt gggcgccaag aacatgaatg tgcgcccccct   3120
gctgaactac ttcgagcccc tgttcacctg gctgaaggac cagaacaaga acagcttcgt   3180
gggctggagc accgactgga gcccctacgc cgaccagagc atcaaagtgc ggatcagcct   3240
gaagagcgcc ctgggcgaca aggcctacga gtggaacgac aacgagatgt acctgttccg   3300
gagcagcgtg gcctatgcca tgcggcagta cttcctgaaa gtgaagaacc agatgatcct   3360
gttcggcgag gaggacgtga gagtggccaa cctgaagccc cggatcagct tcaacttctt   3420
cgtgaccgcc cccaagaacg tgagcgacat catcccccgg accgaagtgg agaaggccat   3480
ccggatgagc cggagccgga tcaacgacgc cttccggctg aacgacaact ccctggagtt   3540
cctgggcatc cagcccaccc tgggccctcc caaccagccc cccgtgagca tctggctgat   3600
cgtgtttggc gtggtgatgg gcgtgatcgt ggtgggaatc gtgatcctga tcttcaccgg   3660
catccgggac cggaagaaga agaacaaggc ccggagcggc gagaacccct acgccagcat   3720
cgatatcagc aagggcgaga acaaccccgg cttccagaac accgacgacg tgcagaccag   3780
cttctgataa tctagaacga gctcgaattc gaagcttctg cagacgcgtc gacgtcatat   3840
ggatccgata tcgccgtggc ggccgcaccc agcgtgttca tcttcccccc ctccgacgag   3900
cagctgaaga gcggcaccgc cagcgtggtg tgcctgctga acaacttcta cccccgggag   3960
gccaaggtgc agtggaaggt ggacaacgcc ctgcagagcg gcaacagcca ggagagcgtg   4020
accgagcagg acagcaagga ctccacctac agcctgagca gcaccctcac cctgagcaag   4080
gccgactacg agaagcacaa ggtgtacgcc tgcgaggtga cccaccaggg cctgagcagc   4140
cccgtgacca agagcttcaa ccggggcgag tgttaataga cttaagttta aaccgctgat   4200
cagcctcgac tgtgccttct agttgccagc catctgttgt ttgcccctcc cccgtgcctt   4260
ccttgaccct ggaaggtgcc actcccactg tcctttccta ataaaatgag gaaattgcat   4320
cgcattgtct gagtaggtgt cattctattc tggggggtgg ggtggggcag gacagcaagg   4380
```

-continued

```
gggaggattg ggaagacaat agcaggcatg ctggggatgc ggtgggctct atggcttctg   4440
aggcggaaag aaccagctgg ggctctaggg ggtatcccca cgcgccctgt agcggcgcat   4500
taagcgcggc gggtgtggtg gttacgcgca gcgtgaccgc tacacttgcc agcgccctag   4560
cgcccgctcc tttcgctttc ttcccttcct ttctcgccac gttcgccggc tttccccgtc   4620
aagctctaaa tcgggggctc cctttagggt tccgatttag tgctttacgg cacctcgacc   4680
ccaaaaaact tgattagggt gatggttcac gtagtgggcc atcgccctga tagacggttt   4740
ttcgcccttt gacgttggag tccacgttct ttaatagtgg actcttgttc caaactggaa   4800
caacactcaa ccctatctcg gtctattctt ttgatttata agggattttg gccatttcgg   4860
cctattggtt aaaaaatgag ctgatttaac aaaaatttaa cgcgaattaa ttctgtggaa   4920
tgtgtgtcag ttagggtgtg gaaagtcccc aggctcccca gcaggcagaa gtatgcaaag   4980
catgcatctc aattagtcag caaccaggtg tggaaagtcc ccaggctccc cagcaggcag   5040
aagtatgcaa agcatgcatc tcaattagtc agcaaccata gtcccgcccc taactccgcc   5100
catcccgccc ctaactccgc ccagttccgc ccattctccg ccccatggct gactaatttt   5160
ttttatttat gcagaggccg aggccgcctc tgcctctgag ctattccaga agtagtgagg   5220
aggctttttt ggaggcctag gcttttgcaa aaagctcccg ggagcttgta tatccatttt   5280
cggatctgat cagcacgtga tgaaaaagcc tgaactcacc gcgacgtctg tcgagaagtt   5340
tctgatcgaa aagttcgaca gcgtctccga cctgatgcag ctctcggagg gcgaagaatc   5400
tcgtgctttc agcttcgatg taggagggcg tggatatgtc ctgcgggtaa atagctgcgc   5460
cgatggtttc tacaaagatc gttatgttta tcggcacttt gcatcggccg cgctcccgat   5520
tccggaagtg cttgacattg gggaattcag cgagagcctg acctattgca tctcccgccg   5580
tgcacagggt gtcacgttgc aagacctgcc tgaaaccgaa ctgcccgctg ttctgcagcc   5640
ggtcgcggag gccatggatg cgatcgctgc ggccgatctt agccagacga gcgggttcgg   5700
cccattcgga ccacaaggaa tcggtcaata cactacatgg cgtgatttca tatgcgcgat   5760
tgctgatccc catgtgtatc actggcaaac tgtgatggac gacaccgtca gtgcgtccgt   5820
cgcgcaggct ctcgatgagc tgatgctttg ggccgaggac tgccccgaag tccggcacct   5880
cgtgcacgcg gatttcggct ccaacaatgt cctgacggac aatggccgca taacagcggt   5940
cattgactgg agcgaggcga tgttcgggga ttcccaatac gaggtcgcca acatcttctt   6000
ctggaggccg tggttggctt gtatggagca gcagacgcgc tacttcgagc ggaggcatcc   6060
ggagcttgca ggatcgccgc ggctccgggc gtatatgctc cgcattggtc ttgaccaact   6120
ctatcagagc ttggttgacg gcaatttcga tgatgcagct tgggcgcagg gtcgatgcga   6180
cgcaatcgtc cgatccggag ccgggactgt cgggcgtaca caaatcgccc gcagaagcgc   6240
ggccgtctgg accgatggct gtgtagaagt actcgccgat agtggaaacc gacgccccag   6300
cactcgtccg agggcaaagg aatagcacgt gctacgagat ttcgattcca ccgccgcctt   6360
ctatgaaagg ttgggcttcg gaatcgtttt ccgggacgcc ggctggatga tcctccagcg   6420
cggggatctc atgctggagt tcttcgccca ccccaacttg tttattgcag cttataatgg   6480
ttacaaataa agcaatagca tcacaaattt cacaaataaa gcattttttt cactgcattc   6540
tagttgtggt ttgtccaaac tcatcaatgt atcttatcat gtctgtatac cgtcgacctc   6600
tagctagagc ttggcgtaat catggtcata gctgtttcct gtgtgaaatt gttatccgct   6660
cacaattcca cacaacatac gagccggaag cataaagtgt aaagcctggg gtgcctaatg   6720
agtgagctaa ctcacattaa ttgcgttgcg ctcactgccc gctttccagt cgggaaacct   6780
```

-continued

```
gtcgtgccag ctgcattaat gaatcggcca acgcgcgggg agaggcggtt tgcgtattgg   6840

gcgctcttcc gcttcctcgc tcactgactc gctgcgctcg gtcgttcggc tgcggcgagc   6900

ggtatcagct cactcaaagg cggtaatacg gttatccaca gaatcagggg ataacgcagg   6960

aaagaacatg tgagcaaaag gccagcaaaa ggccaggaac cgtaaaaagg ccgcgttgct   7020

ggcgtttttc cataggctcc gcccccctga cgagcatcac aaaaatcgac gctcaagtca   7080

gaggtggcga aacccgacag gactataaag ataccaggcg tttccccctg gaagctccct   7140

cgtgcgctct cctgttccga ccctgccgct taccggatac ctgtccgcct ttctcccttc   7200

gggaagcgtg gcgctttctc atagctcacg ctgtaggtat ctcagttcgg tgtaggtcgt   7260

tcgctccaag ctgggctgtg tgcacgaacc ccccgttcag cccgaccgct gcgccttatc   7320

cggtaactat cgtcttgagt ccaacccggt aagacacgac ttatcgccac tggcagcagc   7380

cactggtaac aggattagca gagcgaggta tgtaggcggt gctacagagt tcttgaagtg   7440

gtggcctaac tacggctaca ctagaagaac agtatttggt atctgcgctc tgctgaagcc   7500

agttaccttc ggaaaaagag ttggtagctc ttgatccggc aaacaaacca ccgctggtag   7560

cggttttttt gtttgcaagc agcagattac gcgcagaaaa aaaggatctc aagaagatcc   7620

tttgatcttt tctacggggt ctgacgctca gtggaacgaa aactcacgtt aagggatttt   7680

ggtcatgaga ttatcaaaaa ggatcttcac ctagatcctt ttaaattaaa aatgaagttt   7740

taaatcaatc taaagtatat atgagtaaac ttggtctgac agttaccaat gcttaatcag   7800

tgaggcacct atctcagcga tctgtctatt tcgttcatcc atagttgcct gactccccgt   7860

cgtgtagata actacgatac gggagggctt accatctggc cccagtgctg caatgatacc   7920

gcgagaccca cgctcaccgg ctccagattt atcagcaata aaccagccag ccggaagggc   7980

cgagcgcaga agtggtcctg caactttatc cgcctccatc cagtctatta attgttgccg   8040

ggaagctaga gtaagtagtt cgccagttaa tagtttgcgc aacgttgttg ccattgctac   8100

aggcatcgtg gtgtcacgct cgtcgtttgg tatggcttca ttcagctccg gttcccaacg   8160

atcaaggcga gttacatgat cccccatgtt gtgcaaaaaa gcggttagct ccttcggtcc   8220

tccgatcgtt gtcagaagta agttggccgc agtgttatca ctcatggtta tggcagcact   8280

gcataattct cttactgtca tgccatccgt aagatgcttt tctgtgactg gtgagtactc   8340

aaccaagtca ttctgagaat agtgtatgcg gcgaccgagt tgctcttgcc cggcgtcaat   8400

acgggataat accgcgccac atagcagaac tttaaaagtg ctcatcattg gaaaacgttc   8460

ttcggggcga aaactctcaa ggatcttacc gctgttgaga tccagttcga tgtaacccac   8520

tcgtgcaccc aactgatctt cagcatcttt tactttcacc agcgtttctg ggtgagcaaa   8580

aacaggaagg caaaatgccg caaaaaaggg aataagggcg acacggaaat gttgaatact   8640

catactcttc ctttttcaat attattgaag catttatcag ggttattgtc tcatgagcgg   8700

atacatattt gaatgtattt agaaaaataa acaaataggg gttccgcgca catttccccg   8760

aaaagtgcca cctgacg                                                  8777

<210> SEQ ID NO 51
<211> LENGTH: 23
<212> TYPE: DNA
<213> ORGANISM: Artificial sequence
<220> FEATURE:
<223> OTHER INFORMATION: Primer HuVL1A-Back

<400> SEQUENCE: 51

cagtctgtgc tgactcagcc acc                                             23
```

<210> SEQ ID NO 52
<211> LENGTH: 23
<212> TYPE: DNA
<213> ORGANISM: Artificial sequence
<220> FEATURE:
<223> OTHER INFORMATION: Primer HuVL1B-Back

<400> SEQUENCE: 52
cagtctgtgy tgacgcagcc gcc 23

<210> SEQ ID NO 53
<211> LENGTH: 23
<212> TYPE: DNA
<213> ORGANISM: Artificial sequence
<220> FEATURE:
<223> OTHER INFORMATION: Primer HuVL1C-Back

<400> SEQUENCE: 53
cagtctgtcg tgacgcagcc gcc 23

<210> SEQ ID NO 54
<211> LENGTH: 20
<212> TYPE: DNA
<213> ORGANISM: Artificial sequence
<220> FEATURE:
<223> OTHER INFORMATION: Primer HuVL2B-Back

<400> SEQUENCE: 54
cagtctgccc tgactcagcc 20

<210> SEQ ID NO 55
<211> LENGTH: 23
<212> TYPE: DNA
<213> ORGANISM: Artificial sequence
<220> FEATURE:
<223> OTHER INFORMATION: Primer HuVL3A-Back

<400> SEQUENCE: 55
tcctatgwgc tgactcagcc acc 23

<210> SEQ ID NO 56
<211> LENGTH: 23
<212> TYPE: DNA
<213> ORGANISM: Artificial sequence
<220> FEATURE:
<223> OTHER INFORMATION: Primer HuVL3B-Back

<400> SEQUENCE: 56
tcttctgagc tgactcagga ccc 23

<210> SEQ ID NO 57
<211> LENGTH: 20
<212> TYPE: DNA
<213> ORGANISM: Artificial sequence
<220> FEATURE:
<223> OTHER INFORMATION: Primer HuVL4B-Back

<400> SEQUENCE: 57
cagcytgtgc tgactcaatc 20

<210> SEQ ID NO 58
<211> LENGTH: 23
<212> TYPE: DNA
<213> ORGANISM: Artificial sequence
<220> FEATURE:
<223> OTHER INFORMATION: Primer HuVL5-Back

<400> SEQUENCE: 58
caggctgtgc tgactcagcc gtc 23

<210> SEQ ID NO 59
<211> LENGTH: 23
<212> TYPE: DNA
<213> ORGANISM: Artificial sequence
<220> FEATURE:
<223> OTHER INFORMATION: Primer HuVL6-Back

<400> SEQUENCE: 59
aattttatgc tgactcagcc cca 23

<210> SEQ ID NO 60
<211> LENGTH: 23
<212> TYPE: DNA
<213> ORGANISM: Artificial sequence
<220> FEATURE:
<223> OTHER INFORMATION: Primer HuVL7/8-Back

<400> SEQUENCE: 60
cagrctgtgg tgacycagga gcc 23

<210> SEQ ID NO 61
<211> LENGTH: 23
<212> TYPE: DNA
<213> ORGANISM: Artificial sequence
<220> FEATURE:
<223> OTHER INFORMATION: Primer HuVL9-Back

<400> SEQUENCE: 61
cwgcctgtgc tgactcagcc mcc 23

<210> SEQ ID NO 62
<211> LENGTH: 18
<212> TYPE: DNA
<213> ORGANISM: Artificial sequence
<220> FEATURE:
<223> OTHER INFORMATION: Primer HuVL10-Back

<400> SEQUENCE: 62
caggcagggc tgactcag 18

<210> SEQ ID NO 63
<211> LENGTH: 23
<212> TYPE: DNA
<213> ORGANISM: Artificial sequence
<220> FEATURE:
<223> OTHER INFORMATION: Primer HuVK1B-Back

<400> SEQUENCE: 63
gacatccagw tgacccagtc tcc 23

<210> SEQ ID NO 64
<211> LENGTH: 23
<212> TYPE: DNA
<213> ORGANISM: Artificial sequence
<220> FEATURE:
<223> OTHER INFORMATION: Primer HuVK2-Back

<400> SEQUENCE: 64
gatgttgtga tgactcagtc tcc 23

<210> SEQ ID NO 65
<211> LENGTH: 23

-continued

<212> TYPE: DNA
<213> ORGANISM: Artificial sequence
<220> FEATURE:
<223> OTHER INFORMATION: Primer HuVK2B2

<400> SEQUENCE: 65
gatattgtga tgacccagac tcc 23

<210> SEQ ID NO 66
<211> LENGTH: 23
<212> TYPE: DNA
<213> ORGANISM: Artificial sequence
<220> FEATURE:
<223> OTHER INFORMATION: Primer HuVK3B-Back

<400> SEQUENCE: 66
gaaattgtgw tgacrcagtc tcc 23

<210> SEQ ID NO 67
<211> LENGTH: 23
<212> TYPE: DNA
<213> ORGANISM: Artificial sequence
<220> FEATURE:
<223> OTHER INFORMATION: Primer HuVK5-Back

<400> SEQUENCE: 67
gaaacgacac tcacgcagtc tcc 23

<210> SEQ ID NO 68
<211> LENGTH: 23
<212> TYPE: DNA
<213> ORGANISM: Artificial sequence
<220> FEATURE:
<223> OTHER INFORMATION: Primer HuVK6-Back

<400> SEQUENCE: 68
gaaattgtgc tgactcagtc tcc 23

<210> SEQ ID NO 69
<211> LENGTH: 41
<212> TYPE: DNA
<213> ORGANISM: Artificial sequence
<220> FEATURE:
<223> OTHER INFORMATION: Primer HuVK1B-Back-SAL

<400> SEQUENCE: 69
tgagcacaca ggtcgacgga catccagwtg acccagtctc c 41

<210> SEQ ID NO 70
<211> LENGTH: 41
<212> TYPE: DNA
<213> ORGANISM: Artificial sequence
<220> FEATURE:
<223> OTHER INFORMATION: Primer HuVK2-Back-SAL

<400> SEQUENCE: 70
tgagcacaca ggtcgacgga tgttgtgatg actcagtctc c 41

<210> SEQ ID NO 71
<211> LENGTH: 41
<212> TYPE: DNA
<213> ORGANISM: Artificial sequence
<220> FEATURE:
<223> OTHER INFORMATION: Primer HuVK2B2-SAL

<400> SEQUENCE: 71
tgagcacaca ggtcgacgga tattgtgatg acccagactc c 41

<210> SEQ ID NO 72
<211> LENGTH: 41
<212> TYPE: DNA
<213> ORGANISM: Artificial sequence
<220> FEATURE:
<223> OTHER INFORMATION: Primer HuVK3B-Back-SAL

<400> SEQUENCE: 72
tgagcacaca ggtcgacgga aattgtgwtg acrcagtctc c 41

<210> SEQ ID NO 73
<211> LENGTH: 41
<212> TYPE: DNA
<213> ORGANISM: Artificial sequence
<220> FEATURE:
<223> OTHER INFORMATION: Primer HuVK5-Back-SAL

<400> SEQUENCE: 73
tgagcacaca ggtcgacgga aacgacactc acgcagtctc c 41

<210> SEQ ID NO 74
<211> LENGTH: 41
<212> TYPE: DNA
<213> ORGANISM: Artificial sequence
<220> FEATURE:
<223> OTHER INFORMATION: Primer HuVK6-Back-SAL

<400> SEQUENCE: 74
tgagcacaca ggtcgacgga aattgtgctg actcagtctc c 41

<210> SEQ ID NO 75
<211> LENGTH: 48
<212> TYPE: DNA
<213> ORGANISM: Artificial sequence
<220> FEATURE:
<223> OTHER INFORMATION: Primer HuJK1-FOR-NOT

<400> SEQUENCE: 75
gagtcattct cgacttgcgg ccgcacgttt gatttccacc ttggtccc 48

<210> SEQ ID NO 76
<211> LENGTH: 48
<212> TYPE: DNA
<213> ORGANISM: Artificial sequence
<220> FEATURE:
<223> OTHER INFORMATION: Primer HuJK2-FOR-NOT

<400> SEQUENCE: 76
gagtcattct cgacttgcgg ccgcacgttt gatctccagc ttggtccc 48

<210> SEQ ID NO 77
<211> LENGTH: 48
<212> TYPE: DNA
<213> ORGANISM: Artificial sequence
<220> FEATURE:
<223> OTHER INFORMATION: Primer HuJK3-FOR-NOT

<400> SEQUENCE: 77
gagtcattct cgacttgcgg ccgcacgttt gatatccact ttggtccc 48

<210> SEQ ID NO 78
<211> LENGTH: 47
<212> TYPE: DNA
<213> ORGANISM: Artificial sequence
<220> FEATURE:
<223> OTHER INFORMATION: Primer HuJK4-FOR-NOT

<400> SEQUENCE: 78
gagtcattct cgacttgcgg ccgacgtttg atctccacct tggtccc 47

<210> SEQ ID NO 79
<211> LENGTH: 48
<212> TYPE: DNA
<213> ORGANISM: Artificial sequence
<220> FEATURE:
<223> OTHER INFORMATION: Primer HuJK5-FOR-NOT

<400> SEQUENCE: 79
gagtcattct cgacttgcgg ccgcacgttt aatctccagt cgtgtccc 48

<210> SEQ ID NO 80
<211> LENGTH: 41
<212> TYPE: DNA
<213> ORGANISM: Artificial sequence
<220> FEATURE:
<223> OTHER INFORMATION: Primer HuVL1A-Back-SAL

<400> SEQUENCE: 80
tgagcacaca ggtcgacgca gtctgtgctg actcagccac c 41

<210> SEQ ID NO 81
<211> LENGTH: 41
<212> TYPE: DNA
<213> ORGANISM: Artificial sequence
<220> FEATURE:
<223> OTHER INFORMATION: Primer HuVL1B-Back-SAL

<400> SEQUENCE: 81
tgagcacaca ggtcgacgca gtctgtgytg acgcagccgc c 41

<210> SEQ ID NO 82
<211> LENGTH: 41
<212> TYPE: DNA
<213> ORGANISM: Artificial sequence
<220> FEATURE:
<223> OTHER INFORMATION: Primer HuVL1C-Back-SAL

<400> SEQUENCE: 82
tgagcacaca ggtcgacgca gtctgtcgtg acgcagccgc c 41

<210> SEQ ID NO 83
<211> LENGTH: 38
<212> TYPE: DNA
<213> ORGANISM: Artificial sequence
<220> FEATURE:
<223> OTHER INFORMATION: Primer HuVL2B-Back-SAL

<400> SEQUENCE: 83
tgagcacaca ggtcgacgca gtctgccctg actcagcc 38

<210> SEQ ID NO 84
<211> LENGTH: 41
<212> TYPE: DNA
<213> ORGANISM: Artificial sequence
<220> FEATURE:
<223> OTHER INFORMATION: Primer HuVL3A-Back-SAL

<400> SEQUENCE: 84
tgagcacaca ggtcgacgtc ctatgwgctg actcagccac c 41

<210> SEQ ID NO 85
<211> LENGTH: 41

<212> TYPE: DNA
<213> ORGANISM: Artificial sequence
<220> FEATURE:
<223> OTHER INFORMATION: Primer HuVL3B-Back-SAL

<400> SEQUENCE: 85
tgagcacaca ggtcgacgtc ttctgagctg actcaggacc c 41

<210> SEQ ID NO 86
<211> LENGTH: 38
<212> TYPE: DNA
<213> ORGANISM: Artificial sequence
<220> FEATURE:
<223> OTHER INFORMATION: Primer HuVL4B-Back-SAL

<400> SEQUENCE: 86
tgagcacaca ggtcgacgca gcytgtgctg actcaatc 38

<210> SEQ ID NO 87
<211> LENGTH: 41
<212> TYPE: DNA
<213> ORGANISM: Artificial sequence
<220> FEATURE:
<223> OTHER INFORMATION: Primer HuVL5-Back-SAL

<400> SEQUENCE: 87
tgagcacaca ggtcgacgca ggctgtgctg actcagccgt c 41

<210> SEQ ID NO 88
<211> LENGTH: 41
<212> TYPE: DNA
<213> ORGANISM: Artificial sequence
<220> FEATURE:
<223> OTHER INFORMATION: Primer HuVL6-Back-SAL

<400> SEQUENCE: 88
tgagcacaca ggtcgacgaa ttttatgctg actcagcccc a 41

<210> SEQ ID NO 89
<211> LENGTH: 41
<212> TYPE: DNA
<213> ORGANISM: Artificial sequence
<220> FEATURE:
<223> OTHER INFORMATION: Primer HuVL7/8-Back-SAL

<400> SEQUENCE: 89
tgagcacaca ggtcgacgca grctgtggtg acycaggagc c 41

<210> SEQ ID NO 90
<211> LENGTH: 41
<212> TYPE: DNA
<213> ORGANISM: Artificial sequence
<220> FEATURE:
<223> OTHER INFORMATION: Primer HuVL9-Back-SAL

<400> SEQUENCE: 90
tgagcacaca ggtcgacgcw gcctgtgctg actcagccmc c 41

<210> SEQ ID NO 91
<211> LENGTH: 36
<212> TYPE: DNA
<213> ORGANISM: Artificial sequence
<220> FEATURE:
<223> OTHER INFORMATION: Primer HuVL10-Back-SAL

<400> SEQUENCE: 91
tgagcacaca ggtcgacgca ggcagggctg actcag 36

<210> SEQ ID NO 92
<211> LENGTH: 48
<212> TYPE: DNA
<213> ORGANISM: Artificial sequence
<220> FEATURE:
<223> OTHER INFORMATION: Primer HuJL1-FOR-NOT

<400> SEQUENCE: 92
gagtcattct cgacttgcgg ccgcacctag gacggtgacc ttggtccc 48

<210> SEQ ID NO 93
<211> LENGTH: 48
<212> TYPE: DNA
<213> ORGANISM: Artificial sequence
<220> FEATURE:
<223> OTHER INFORMATION: Primer HuJL2/3-FOR-NOT

<400> SEQUENCE: 93
gagtcattct cgacttgcgg ccgcacctag gacggtcagc ttggtccc 48

<210> SEQ ID NO 94
<211> LENGTH: 48
<212> TYPE: DNA
<213> ORGANISM: Artificial sequence
<220> FEATURE:
<223> OTHER INFORMATION: Primer HuJL7-FOR-NOT

<400> SEQUENCE: 94
gagtcattct cgacttgcgg ccgcaccgag gacggtcagc tgggtgcc 48

<210> SEQ ID NO 95
<211> LENGTH: 23
<212> TYPE: DNA
<213> ORGANISM: Artificial sequence
<220> FEATURE:
<223> OTHER INFORMATION: Primer HuVH1B/7A-Back

<400> SEQUENCE: 95
cagrtgcagc tggtgcartc tgg 23

<210> SEQ ID NO 96
<211> LENGTH: 23
<212> TYPE: DNA
<213> ORGANISM: Artificial sequence
<220> FEATURE:
<223> OTHER INFORMATION: Primer HuVH1C-Back

<400> SEQUENCE: 96
saggtccagc tggtrcagtc tgg 23

<210> SEQ ID NO 97
<211> LENGTH: 23
<212> TYPE: DNA
<213> ORGANISM: Artificial sequence
<220> FEATURE:
<223> OTHER INFORMATION: Primer HuVH2B-Back

<400> SEQUENCE: 97
cagrtcacct tgaaggagtc tgg 23

<210> SEQ ID NO 98
<211> LENGTH: 18
<212> TYPE: DNA
<213> ORGANISM: Artificial sequence
<220> FEATURE:
<223> OTHER INFORMATION: Primer HuVH3A-Back

<400> SEQUENCE: 98
gaggtgcagc tggtggag 18

<210> SEQ ID NO 99
<211> LENGTH: 23
<212> TYPE: DNA
<213> ORGANISM: Artificial sequence
<220> FEATURE:
<223> OTHER INFORMATION: Primer HuVH3C-Back

<400> SEQUENCE: 99
gaggtgcagc tggtggagwc ygg 23

<210> SEQ ID NO 100
<211> LENGTH: 23
<212> TYPE: DNA
<213> ORGANISM: Artificial sequence
<220> FEATURE:
<223> OTHER INFORMATION: Primer HuVH4B-Back

<400> SEQUENCE: 100
caggtgcagc tacagcagtg ggg 23

<210> SEQ ID NO 101
<211> LENGTH: 23
<212> TYPE: DNA
<213> ORGANISM: Artificial sequence
<220> FEATURE:
<223> OTHER INFORMATION: Primer HuVH4C-Back

<400> SEQUENCE: 101
cagstgcagc tgcaggagtc sgg 23

<210> SEQ ID NO 102
<211> LENGTH: 23
<212> TYPE: DNA
<213> ORGANISM: Artificial sequence
<220> FEATURE:
<223> OTHER INFORMATION: Primer HuVH6A-Back

<400> SEQUENCE: 102
caggtacagc tgcagcagtc agg 23

<210> SEQ ID NO 103
<211> LENGTH: 56
<212> TYPE: DNA
<213> ORGANISM: Artificial sequence
<220> FEATURE:
<223> OTHER INFORMATION: Primer HuVH1B/7A-Back-Sfi

<400> SEQUENCE: 103
gtcctcgcaa ctgcggccca gccggccatg gcccagrtgc agctggtgca rtctgg 56

<210> SEQ ID NO 104
<211> LENGTH: 56
<212> TYPE: DNA
<213> ORGANISM: Artificial sequence
<220> FEATURE:
<223> OTHER INFORMATION: Primer HuVH1C-Back-Sfi

<400> SEQUENCE: 104
gtcctcgcaa ctgcggccca gccggccatg gccsaggtcc agctggtrca gtctgg 56

<210> SEQ ID NO 105
<211> LENGTH: 56

-continued

```
<212> TYPE: DNA
<213> ORGANISM: Artificial sequence
<220> FEATURE:
<223> OTHER INFORMATION: Primer HuVH2B-Back-Sfi

<400> SEQUENCE: 105

gtcctcgcaa ctgcggccca gccggccatg gcccagrtca ccttgaagga gtctgg        56


<210> SEQ ID NO 106
<211> LENGTH: 51
<212> TYPE: DNA
<213> ORGANISM: Artificial sequence
<220> FEATURE:
<223> OTHER INFORMATION: Primer HuVH3A-Back-Sfi

<400> SEQUENCE: 106

gtcctcgcaa ctgcggccca gccggccatg gccgaggtgc agctggtgga g             51


<210> SEQ ID NO 107
<211> LENGTH: 56
<212> TYPE: DNA
<213> ORGANISM: Artificial sequence
<220> FEATURE:
<223> OTHER INFORMATION: Primer HuVH3C-Back-Sfi

<400> SEQUENCE: 107

gtcctcgcaa ctgcggccca gccggccatg gccgaggtgc agctggtgga gwcygg        56


<210> SEQ ID NO 108
<211> LENGTH: 56
<212> TYPE: DNA
<213> ORGANISM: Artificial sequence
<220> FEATURE:
<223> OTHER INFORMATION: Primer HuVH4B-Back-Sfi

<400> SEQUENCE: 108

gtcctcgcaa ctgcggccca gccggccatg gcccaggtgc agctacagca gtgggg        56


<210> SEQ ID NO 109
<211> LENGTH: 56
<212> TYPE: DNA
<213> ORGANISM: Artificial sequence
<220> FEATURE:
<223> OTHER INFORMATION: Primer HuVH4C-Back-Sfi

<400> SEQUENCE: 109

gtcctcgcaa ctgcggccca gccggccatg gcccagstgc agctgcagga gtcsgg        56


<210> SEQ ID NO 110
<211> LENGTH: 56
<212> TYPE: DNA
<213> ORGANISM: Artificial sequence
<220> FEATURE:
<223> OTHER INFORMATION: Primer HuVH6A-Back-Sfi

<400> SEQUENCE: 110

gtcctcgcaa ctgcggccca gccggccatg gcccaggtac agctgcagca gtcagg        56


<210> SEQ ID NO 111
<211> LENGTH: 36
<212> TYPE: DNA
<213> ORGANISM: Artificial sequence
<220> FEATURE:
<223> OTHER INFORMATION: Primer HuJH1/2-FOR-XhoIB

<400> SEQUENCE: 111

gagtcattct cgactcgaga crgtgaccag ggtgcc                              36
```

<210> SEQ ID NO 112
<211> LENGTH: 36
<212> TYPE: DNA
<213> ORGANISM: Artificial sequence
<220> FEATURE:
<223> OTHER INFORMATION: Primer HuJH3-FOR-Xho

<400> SEQUENCE: 112
gagtcattct cgactcgaga cggtgaccat tgtccc 36

<210> SEQ ID NO 113
<211> LENGTH: 36
<212> TYPE: DNA
<213> ORGANISM: Artificial sequence
<220> FEATURE:
<223> OTHER INFORMATION: Primer HuJH4/5-FOR-Xho

<400> SEQUENCE: 113
gagtcattct cgactcgaga cggtgaccag ggttcc 36

<210> SEQ ID NO 114
<211> LENGTH: 36
<212> TYPE: DNA
<213> ORGANISM: Artificial sequence
<220> FEATURE:
<223> OTHER INFORMATION: Primer HuJH6-FOR-Xho

<400> SEQUENCE: 114
gagtcattct cgactcgaga cggtgaccgt ggtccc 36

<210> SEQ ID NO 115
<211> LENGTH: 8792
<212> TYPE: DNA
<213> ORGANISM: Artificial sequence
<220> FEATURE:
<223> OTHER INFORMATION: Vector pIg-C910-Clambda
<220> FEATURE:
<221> NAME/KEY: misc_feature
<222> LOCATION: (1330)..(3869)
<223> OTHER INFORMATION: Stuffer

<400> SEQUENCE: 115
tcgacggatc gggagatctc ccgatcccct atggtgcact ctcagtacaa tctgctctga 60
tgccgcatag ttaagccagt atctgctccc tgcttgtgtg ttggaggtcg ctgagtagtg 120
cgcgagcaaa atttaagcta caacaaggca aggcttgacc gacaattgtt aattaacatg 180
aagaatctgc ttagggttag gcgttttgcg ctgcttcgct aggtggtcaa tattggccat 240
tagccatatt attcattggt tatatagcat aaatcaatat tggctattgg ccattgcata 300
cgttgtatcc atatcataat atgtacattt atattggctc atgtccaaca ttaccgccat 360
gttgacattg attattgact agttattaat agtaatcaat tacggggtca ttagttcata 420
gcccatatat ggagttccgc gttacataac ttacggtaaa tggcccgcct ggctgaccgc 480
ccaacgaccc ccgcccattg acgtcaataa tgacgtatgt tcccatagta acgccaatag 540
ggactttcca ttgacgtcaa tgggtggagt atttacggta aactgcccac ttggcagtac 600
atcaagtgta tcatatgcca agtacgcccc ctattgacgt caatgacggt aaatggcccg 660
cctggcatta tgcccagtac atgaccttat gggactttcc tacttggcag tacatctacg 720
tattagtcat cgctattacc atggtgatgc ggttttggca gtacatcaat gggcgtggat 780
agcggtttga ctcacgggga tttccaagtc tccaccccat tgacgtcaat gggagtttgt 840
tttggcacca aaatcaacgg gactttccaa aatgtcgtaa caactccgcc ccattgacgc 900

-continued

```
aaatgggcgg taggcgtgta cggtgggagg tctatataag cagagctcgt ttagtgaacc    960
gtcagatcgc ctggagacgc catccacgct gttttgacct ccatagaaga caccgggacc   1020
gatccagcct ccgcggccgg gaacggtgca ttggaatcga tgactctctt aggtagcctt   1080
gcagaagttg gtcgtgaggc actgggcagg taagtatcaa ggttacaaga caggtttaag   1140
gagatcaata gaaactgggc ttgtcgagac agagaagact cttgcgtttc tgataggcac   1200
ctattggtct tactgacatc cactttgcct ttctctccac aggtgtccac tcccagttca   1260
attacagctc gccaccatgc ggttctccgc tcagctgctg ggccttctgg tgctgtggat   1320
tcccggcgtc tcgagatcta tcgatgcatg ccatggtacc aagcttgcca ccatgagcag   1380
cagctcttgg ctgctgctga gcctggtggc cgtgacagcc gcccagagca ccatcgagga   1440
gcaggccaag accttcctgg acaagttcaa ccacgaggcc gaggacctgt tctaccagag   1500
cagcctggcc agctggaact acaacaccaa catcaccgag gagaacgtgc agaacatgaa   1560
caacgccggc gacaagtgga gcgccttcct gaaggagcag agcacactgg cccagatgta   1620
cccccctgcag gagatccaga acctgaccgt gaagctgcag ctgcaggccc tgcagcagaa   1680
cggcagcagc gtgctgagcg aggacaagag caagcggctg aacaccatcc tgaacaccat   1740
gtccaccatc tacagcaccg gcaaagtgtg caaccccgac aacccccagg agtgcctgct   1800
gctggagccc ggcctgaacg agatcatggc caacagcctg gactacaacg agcggctgtg   1860
ggcctgggag agctggcgga gcgaagtggg caagcagctg cggcccctgt acgaggagta   1920
cgtggtgctg aagaacgaga tggccagggc caaccactac gaggactacg gcgactactg   1980
gagaggcgac tacgaagtga acggcgtgga cggctacgac tacagcagag gccagctgat   2040
cgaggacgtg gagcacacct tcgaggagat caagcctctg tacgagcacc tgcacgccta   2100
cgtgcgggcc aagctgatga acgcctaccc cagctacatc agccccatcg gctgcctgcc   2160
cgcccacctg ctgggcgaca tgtggggccg gttctggacc aacctgtaca gcctgaccgt   2220
gcccttcggc cagaagccca acatcgacgt gaccgacgcc atggtggacc aggcctggga   2280
cgcccagcgg atcttcaagg aggccgagaa gttcttcgtg agcgtgggcc tgcccaacat   2340
gacccagggc ttttgggaga acagcatgct gaccgacccc ggcaatgtgc agaaggccgt   2400
gtgccacccc accgcctggg acctgggcaa gggcgacttc cggatcctga tgtgcaccaa   2460
agtgaccatg gacgacttcc tgaccgccca ccacgagatg ggccacatcc agtacgacat   2520
ggcctacgcc gcccagccct tcctgctgcg gaacggcgcc aacgagggct ttcacgaggc   2580
cgtgggcgag atcatgagcc tgagcgccgc cacccccaag cacctgaaga gcatcggcct   2640
gctgagcccc gacttccagg aggacaacga gaccgagatc aacttcctgc tgaagcaggc   2700
cctgaccatc gtgggcaccc tgcccttcac ctacatgctg gagaagtggc ggtggatggt   2760
gtttaagggc gagatcccca aggaccagtg gatgaagaag tggtgggaga tgaagcggga   2820
gatcgtgggc gtggtggagc ccgtgcccca cgacgagacc tactgcgacc ccgccagcct   2880
gttccacgtg agcaacgact actccttcat ccggtactac acccggaccc tgtaccagtt   2940
ccagttccag gaggccctgt gccaggccgc caagcacgag ggcccccctgc acaagtgcga   3000
catcagcaac agcaccgagg ccggacagaa actgttcaac atgctgcggc tgggcaagag   3060
cgagccctgg accctggccc tggagaatgt ggtgggcgcc aagaacatga atgtgcgccc   3120
cctgctgaac tacttcgagc ccctgttcac ctggctgaag gaccagaaca agaacagctt   3180
cgtgggctgg agcaccgact ggagccccta cgccgaccag agcatcaaag tgcggatcag   3240
cctgaagagc gccctgggcg acaaggccta cgagtggaac gacaacgaga tgtacctgtt   3300
```

ccggagcagc gtggcctatg ccatgcggca gtacttcctg aaagtgaaga accagatgat 3360
cctgttcggc gaggaggacg tgagagtggc caacctgaag ccccggatca gcttcaactt 3420
cttcgtgacc gcccccaaga acgtgagcga catcatcccc cggaccgaag tggagaaggc 3480
catccggatg agccggagcc ggatcaacga cgccttccgg ctgaacgaca actccctgga 3540
gttcctgggc atccagccca ccctgggccc tcccaaccag ccccccgtga gcatctggct 3600
gatcgtgttt ggcgtggtga tgggcgtgat cgtggtggga atcgtgatcc tgatcttcac 3660
cggcatccgg gaccggaaga agaagaacaa ggcccggagc ggcgagaacc cctacgccag 3720
catcgatatc agcaagggcg agaacaaccc cggcttccag aacaccgacg acgtgcagac 3780
cagcttctga taatctagaa cgagctcgaa ttcgaagctt ctgcagacgc gtcgacgtca 3840
tatggatccg atatcgccgt ggcggccgca ggccagccca aggccgctcc cagcgtgacc 3900
ctgttccccc cctcctccga ggagctgcag gccaacaagg ccaccctggt gtgcctcatc 3960
agcgacttct accctggcgc cgtgaccgtg gcctggaagg ccgacagcag ccccgtgaag 4020
gccggcgtgg agaccaccac ccccagcaag cagagcaaca acaagtacgc cgccagcagc 4080
tacctgagcc tcacccccga gcagtggaag agccaccgga gctacagctg ccaggtgacc 4140
cacgagggca gcaccgtgga gaagaccgtg gcccccaccg agtgcagcta atagacttaa 4200
gtttaaaccg ctgatcagcc tcgactgtgc cttctagttg ccagccatct gttgtttgcc 4260
cctcccccgt gccttccttg accctggaag gtgccactcc cactgtcctt tcctaataaa 4320
atgaggaaat tgcatcgcat tgtctgagta ggtgtcattc tattctgggg ggtggggtgg 4380
ggcaggacag caagggggag gattgggaag acaatagcag gcatgctggg gatgcggtgg 4440
gctctatggc ttctgaggcg gaaagaacca gctggggctc taggggggtat ccccacgcgc 4500 cctgtagcgg cgcattaagc gcggcgggtg tggtggttac gcgcagcgtg accgctacac 4560
ttgccagcgc cctagcgccc gctcctttcg ctttcttccc ttcctttctc gccacgttcg 4620
ccggctttcc ccgtcaagct ctaaatcggg ggctcccttt agggttccga tttagtgctt 4680
tacggcacct cgaccccaaa aaacttgatt agggtgatgg ttcacgtagt gggccatcgc 4740
cctgatagac ggtttttcgc cctttgacgt tggagtccac gttctttaat agtggactct 4800
tgttccaaac tggaacaaca ctcaacccta tctcggtcta ttcttttgat ttataaggga 4860
ttttggccat ttcggcctat tggttaaaaa atgagctgat ttaacaaaaa tttaacgcga 4920
attaattctg tggaatgtgt gtcagttagg gtgtggaaag tccccaggct ccccagcagg 4980
cagaagtatg caaagcatgc atctcaatta gtcagcaacc aggtgtggaa agtccccagg 5040
ctccccagca ggcagaagta tgcaaagcat gcatctcaat tagtcagcaa ccatagtccc 5100
gcccctaact ccgcccatcc cgcccctaac tccgcccagt tccgcccatt ctccgcccca 5160
tggctgacta atttttttta tttatgcaga ggccgaggcc gcctctgcct ctgagctatt 5220
ccagaagtag tgaggaggct tttttggagg cctaggcttt tgcaaaaagc tcccgggagc 5280
ttgtatatcc attttcggat ctgatcagca cgtgatgaaa aagcctgaac tcaccgcgac 5340
gtctgtcgag aagtttctga tcgaaaagtt cgacagcgtc tccgacctga tgcagctctc 5400
ggagggcgaa gaatctcgtg ctttcagctt cgatgtagga gggcgtggat atgtcctgcg 5460
ggtaaatagc tgcgccgatg gtttctacaa agatcgttat gtttatcggc actttgcatc 5520
ggccgcgctc ccgattccgg aagtgcttga cattggggaa ttcagcgaga gcctgaccta 5580
ttgcatctcc cgccgtgcac agggtgtcac gttgcaagac ctgcctgaaa ccgaactgcc 5640
cgctgttctg cagccggtcg cggaggccat ggatgcgatc gctgcggccg atcttagcca 5700
gacgagcggg ttcggcccat tcggaccgca aggaatcggt caatacacta catggcgtga 5760
tttcatatgc gcgattgctg atccccatgt gtatcactgg caaactgtga tggacgacac 5820
cgtcagtgcg tccgtcgcgc aggctctcga tgagctgatg ctttgggccg aggactgccc 5880
cgaagtccgg cacctcgtgc acgcggattt cggctccaac aatgtcctga cggacaatgg 5940
ccgcataaca gcggtcattg actggagcga ggcgatgttc ggggattccc aatacgaggt 6000
cgccaacatc ttcttctgga ggccgtggtt ggcttgtatg gagcagcaga cgcgctactt 6060
cgagcggagg catccggagc ttgcaggatc gccgcggctc cgggcgtata tgctccgcat 6120
tggtcttgac caactctatc agagcttggt tgacggcaat ttcgatgatg cagcttgggc 6180
gcagggtcga tgcgacgcaa tcgtccgatc cggagccggg actgtcgggc gtacacaaat 6240
cgcccgcaga agcgcggccg tctggaccga tggctgtgta gaagtactcg ccgatagtgg 6300
aaaccgacgc cccagcactc gtccgagggc aaaggaatag cacgtgctac gagatttcga 6360
ttccaccgcc gccttctatg aaaggttggg cttcggaatc gttttccggg acgccggctg 6420
gatgatcctc cagcgcgggg atctcatgct ggagttcttc gcccacccca acttgtttat 6480
tgcagcttat aatggttaca aataaagcaa tagcatcaca aatttcacaa ataaagcatt 6540
tttttcactg cattctagtt gtggtttgtc caaactcatc aatgtatctt atcatgtctg 6600
tataccgtcg acctctagct agagcttggc gtaatcatgg tcatagctgt ttcctgtgtg 6660
aaattgttat ccgctcacaa ttccacacaa catacgagcc ggaagcataa agtgtaaagc 6720
ctggggtgcc taatgagtga gctaactcac attaattgcg ttgcgctcac tgcccgcttt 6780
ccagtcggga aacctgtcgt gccagctgca ttaatgaatc ggccaacgcg cggggagagg 6840
cggtttgcgt attgggcgct cttccgcttc ctcgctcact gactcgctgc gctcggtcgt 6900
tcggctgcgg cgagcggtat cagctcactc aaaggcggta atacggttat ccacagaatc 6960
aggggataac gcaggaaaga acatgtgagc aaaaggccag caaaaggcca ggaaccgtaa 7020
aaaggccgcg ttgctggcgt ttttccatag gctccgcccc cctgacgagc atcacaaaaa 7080
tcgacgctca agtcagaggt ggcgaaaccc gacaggacta taaagatacc aggcgtttcc 7140
ccctggaagc tccctcgtgc gctctcctgt tccgaccctg ccgcttaccg gatacctgtc 7200
cgcctttctc ccttcgggaa gcgtggcgct ttctcatagc tcacgctgta ggtatctcag 7260
ttcggtgtag gtcgttcgct ccaagctggg ctgtgtgcac gaaccccccg ttcagcccga 7320
ccgctgcgcc ttatccggta actatcgtct tgagtccaac ccggtaagac acgacttatc 7380
gccactggca gcagccactg gtaacaggat tagcagagcg aggtatgtag gcggtgctac 7440
agagttcttg aagtggtggc ctaactacgg ctacactaga agaacagtat ttggtatctg 7500
cgctctgctg aagccagtta ccttcggaaa aagagttggt agctcttgat ccggcaaaca 7560
aaccaccgct ggtagcggtt tttttgtttg caagcagcag attacgcgca gaaaaaaagg 7620
atctcaagaa gatcctttga tcttttctac ggggtctgac gctcagtgga acgaaaactc 7680
acgttaaggg attttggtca tgagattatc aaaaaggatc ttcacctaga tccttttaaa 7740
ttaaaaatga agttttaaat caatctaaag tatatatgag taaacttggt ctgacagtta 7800
ccaatgctta atcagtgagg cacctatctc agcgatctgt ctatttcgtt catccatagt 7860
tgcctgactc cccgtcgtgt agataactac gatacgggag ggcttaccat ctggccccag 7920
tgctgcaatg ataccgcgag acccacgctc accggctcca gatttatcag caataaacca 7980
gccagccgga agggccgagc gcagaagtgg tcctgcaact ttatccgcct ccatccagtc 8040
tattaattgt tgccgggaag ctagagtaag tagttcgcca gttaatagtt tgcgcaacgt 8100

```
tgttgccatt gctacaggca tcgtggtgtc acgctcgtcg tttggtatgg cttcattcag   8160

ctccggttcc caacgatcaa ggcgagttac atgatccccc atgttgtgca aaaaagcggt   8220

tagctccttc ggtcctccga tcgttgtcag aagtaagttg gccgcagtgt tatcactcat   8280

ggttatggca gcactgcata attctcttac tgtcatgcca tccgtaagat gcttttctgt   8340

gactggtgag tactcaacca agtcattctg agaatagtgt atgcggcgac cgagttgctc   8400

ttgcccggcg tcaatacggg ataataccgc gccacatagc agaactttaa aagtgctcat   8460

cattggaaaa cgttcttcgg ggcgaaaact ctcaaggatc ttaccgctgt tgagatccag   8520

ttcgatgtaa cccactcgtg cacccaactg atcttcagca tcttttactt tcaccagcgt   8580

ttctgggtga gcaaaaacag gaaggcaaaa tgccgcaaaa aagggaataa gggcgacacg   8640

gaaatgttga atactcatac tcttcctttt tcaatattat tgaagcattt atcagggtta   8700

ttgtctcatg agcggataca tatttgaatg tatttagaaa aataaacaaa taggggttcc   8760

gcgcacattt ccccgaaaag tgccacctga cg                                 8792


<210> SEQ ID NO 116
<211> LENGTH: 1353
<212> TYPE: DNA
<213> ORGANISM: Homo sapiens
<220> FEATURE:
<221> NAME/KEY: CDS
<222> LOCATION: (1)..(1353)

<400> SEQUENCE: 116

cag gtc cag ctg gtg cag tct gga gca gag gtg aaa aag ccg ggg gag       48
Gln Val Gln Leu Val Gln Ser Gly Ala Glu Val Lys Lys Pro Gly Glu
1               5                   10                  15

tct ctg aag atc tcc tgt aag ggt tct gga tac agc ttt acc agc tac       96
Ser Leu Lys Ile Ser Cys Lys Gly Ser Gly Tyr Ser Phe Thr Ser Tyr
            20                  25                  30

tgg atc ggc tgg gtg cgc cag atg ccc ggg aaa ggc ctg gag tgg atg      144
Trp Ile Gly Trp Val Arg Gln Met Pro Gly Lys Gly Leu Glu Trp Met
        35                  40                  45

ggg atc atc tat cct ggt gac tct gat acc aga tac agc ccg tcc ttc      192
Gly Ile Ile Tyr Pro Gly Asp Ser Asp Thr Arg Tyr Ser Pro Ser Phe
    50                  55                  60

caa ggc cag gtc acc atc tca gcc gac aag tcc atc agc acc gcc tac      240
Gln Gly Gln Val Thr Ile Ser Ala Asp Lys Ser Ile Ser Thr Ala Tyr
65                  70                  75                  80

ctg cag tgg agc agc ctg aag gcc tcg gac acc gcc atg tat tac tgt      288
Leu Gln Trp Ser Ser Leu Lys Ala Ser Asp Thr Ala Met Tyr Tyr Cys
                85                  90                  95

gcg aga cgc gct agt ata gtg gga gct acc cac ttt gac tac tgg ggc      336
Ala Arg Arg Ala Ser Ile Val Gly Ala Thr His Phe Asp Tyr Trp Gly
            100                 105                 110

cag gga acc ctg gtc acc gtc tcg agt gct agc acc aag ggc ccc agc      384
Gln Gly Thr Leu Val Thr Val Ser Ser Ala Ser Thr Lys Gly Pro Ser
        115                 120                 125

gtg ttc ccc ctg gcc ccc agc agc aag agc acc agc ggc ggc aca gcc      432
Val Phe Pro Leu Ala Pro Ser Ser Lys Ser Thr Ser Gly Gly Thr Ala
    130                 135                 140

gcc ctg ggc tgc ctg gtg aag gac tac ttc ccc gag ccc gtg acc gtg      480
Ala Leu Gly Cys Leu Val Lys Asp Tyr Phe Pro Glu Pro Val Thr Val
145                 150                 155                 160

agc tgg aac agc ggc gcc ttg acc agc ggc gtg cac acc ttc ccc gcc      528
Ser Trp Asn Ser Gly Ala Leu Thr Ser Gly Val His Thr Phe Pro Ala
                165                 170                 175
```

```
gtg ctg cag agc agc ggc ctg tac agc ctg agc agc gtg gtg acc gtg       576
Val Leu Gln Ser Ser Gly Leu Tyr Ser Leu Ser Ser Val Val Thr Val
            180                 185                 190

ccc agc agc agc ctg ggc acc cag acc tac atc tgc aac gtg aac cac       624
Pro Ser Ser Ser Leu Gly Thr Gln Thr Tyr Ile Cys Asn Val Asn His
        195                 200                 205

aag ccc agc aac acc aag gtg gac aaa cgc gtg gag ccc aag agc tgc       672
Lys Pro Ser Asn Thr Lys Val Asp Lys Arg Val Glu Pro Lys Ser Cys
    210                 215                 220

gac aag acc cac acc tgc ccc ccc tgc cct gcc ccc gag ctg ctg ggc       720
Asp Lys Thr His Thr Cys Pro Pro Cys Pro Ala Pro Glu Leu Leu Gly
225                 230                 235                 240

gga ccc tcc gtg ttc ctg ttc ccc ccc aag ccc aag gac acc ctc atg       768
Gly Pro Ser Val Phe Leu Phe Pro Pro Lys Pro Lys Asp Thr Leu Met
                245                 250                 255

atc agc cgg acc ccc gag gtg acc tgc gtg gtg gtg gac gtg agc cac       816
Ile Ser Arg Thr Pro Glu Val Thr Cys Val Val Val Asp Val Ser His
            260                 265                 270

gag gac ccc gag gtg aag ttc aac tgg tac gtg gac ggc gtg gag gtg       864
Glu Asp Pro Glu Val Lys Phe Asn Trp Tyr Val Asp Gly Val Glu Val
        275                 280                 285

cac aac gcc aag acc aag ccc cgg gag gag cag tac aac agc acc tac       912
His Asn Ala Lys Thr Lys Pro Arg Glu Glu Gln Tyr Asn Ser Thr Tyr
    290                 295                 300

cgg gtg gtg agc gtg ctc acc gtg ctg cac cag gac tgg ctg aac ggc       960
Arg Val Val Ser Val Leu Thr Val Leu His Gln Asp Trp Leu Asn Gly
305                 310                 315                 320

aag gag tac aag tgc aag gtg agc aac aag gcc ctg cct gcc ccc atc      1008
Lys Glu Tyr Lys Cys Lys Val Ser Asn Lys Ala Leu Pro Ala Pro Ile
                325                 330                 335

gag aag acc atc agc aag gcc aag ggc cag ccc cgg gag ccc cag gtg      1056
Glu Lys Thr Ile Ser Lys Ala Lys Gly Gln Pro Arg Glu Pro Gln Val
            340                 345                 350

tac acc ctg ccc ccc agc cgg gag gag atg acc aag aac cag gtg tcc      1104
Tyr Thr Leu Pro Pro Ser Arg Glu Glu Met Thr Lys Asn Gln Val Ser
        355                 360                 365

ctc acc tgt ctg gtg aag ggc ttc tac ccc agc gac atc gcc gtg gag      1152
Leu Thr Cys Leu Val Lys Gly Phe Tyr Pro Ser Asp Ile Ala Val Glu
    370                 375                 380

tgg gag agc aac ggc cag ccc gag aac aac tac aag acc acc ccc cct      1200
Trp Glu Ser Asn Gly Gln Pro Glu Asn Asn Tyr Lys Thr Thr Pro Pro
385                 390                 395                 400

gtg ctg gac agc gac ggc agc ttc ttc ctg tac agc aag ctc acc gtg      1248
Val Leu Asp Ser Asp Gly Ser Phe Phe Leu Tyr Ser Lys Leu Thr Val
                405                 410                 415

gac aag agc cgg tgg cag cag ggc aac gtg ttc agc tgc agc gtg atg      1296
Asp Lys Ser Arg Trp Gln Gln Gly Asn Val Phe Ser Cys Ser Val Met
            420                 425                 430

cac gag gcc ctg cac aac cac tac acc cag aag agc ctg agc ctg agc      1344
His Glu Ala Leu His Asn His Tyr Thr Gln Lys Ser Leu Ser Leu Ser
        435                 440                 445

ccc ggc aag                                                          1353
Pro Gly Lys
    450
```

<210> SEQ ID NO 117
<211> LENGTH: 451
<212> TYPE: PRT
<213> ORGANISM: Homo sapiens

<400> SEQUENCE: 117

```
Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Arg Ala Ser Ile Val Gly Ala Thr His Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430
```

```
His Glu Ala Leu His Asn His Tyr Thr Gln Lys Ser Leu Ser Leu Ser
        435                 440                 445

Pro Gly Lys
    450


<210> SEQ ID NO 118
<211> LENGTH: 1353
<212> TYPE: DNA
<213> ORGANISM: Homo sapiens
<220> FEATURE:
<221> NAME/KEY: CDS
<222> LOCATION: (1)..(1353)

<400> SEQUENCE: 118

gag gtg cag ctg gtg gag act ggg gga gtc gcg gtc cag cct ggg agg       48
Glu Val Gln Leu Val Glu Thr Gly Gly Val Ala Val Gln Pro Gly Arg
1               5                   10                  15

tcc ctg aga ctc tcc tgt gcg gcg tct gga ttc agt ttc aga gat tat       96
Ser Leu Arg Leu Ser Cys Ala Ala Ser Gly Phe Ser Phe Arg Asp Tyr
            20                  25                  30

ggc atg cac tgg gtc cgc cag gct gca ggc aag ggg ctg gag tgg gtg      144
Gly Met His Trp Val Arg Gln Ala Ala Gly Lys Gly Leu Glu Trp Val
        35                  40                  45

gca ttt ata tgg cct cat gga gta aat agg ttt tat gca gac tca atg      192
Ala Phe Ile Trp Pro His Gly Val Asn Arg Phe Tyr Ala Asp Ser Met
    50                  55                  60

gag ggc cga ttc acc atc tcc aga gac gat tcc aag aat atg ttg tat      240
Glu Gly Arg Phe Thr Ile Ser Arg Asp Asp Ser Lys Asn Met Leu Tyr
65                  70                  75                  80

cta gaa atg aat aat ctg aga acc gaa gac acg gct cta tat tac tgt      288
Leu Glu Met Asn Asn Leu Arg Thr Glu Asp Thr Ala Leu Tyr Tyr Cys
                85                  90                  95

aca aga gat caa gac tat gtc ccg aga aag tac ttc gat ctt tgg ggc      336
Thr Arg Asp Gln Asp Tyr Val Pro Arg Lys Tyr Phe Asp Leu Trp Gly
            100                 105                 110

cgt ggc acc ctg gtc acc gtc tcg agt gct agc acc aag ggc ccc agc      384
Arg Gly Thr Leu Val Thr Val Ser Ser Ala Ser Thr Lys Gly Pro Ser
        115                 120                 125

gtg ttc ccc ctg gcc ccc agc agc aag agc acc agc ggc ggc aca gcc      432
Val Phe Pro Leu Ala Pro Ser Ser Lys Ser Thr Ser Gly Gly Thr Ala
    130                 135                 140

gcc ctg ggc tgc ctg gtg aag gac tac ttc ccc gag ccc gtg acc gtg      480
Ala Leu Gly Cys Leu Val Lys Asp Tyr Phe Pro Glu Pro Val Thr Val
145                 150                 155                 160

agc tgg aac agc ggc gcc ttg acc agc ggc gtg cac acc ttc ccc gcc      528
Ser Trp Asn Ser Gly Ala Leu Thr Ser Gly Val His Thr Phe Pro Ala
                165                 170                 175

gtg ctg cag agc agc ggc ctg tac agc ctg agc agc gtg gtg acc gtg      576
Val Leu Gln Ser Ser Gly Leu Tyr Ser Leu Ser Ser Val Val Thr Val
            180                 185                 190

ccc agc agc agc ctg ggc acc cag acc tac atc tgc aac gtg aac cac      624
Pro Ser Ser Ser Leu Gly Thr Gln Thr Tyr Ile Cys Asn Val Asn His
        195                 200                 205

aag ccc agc aac acc aag gtg gac aaa cgc gtg gag ccc aag agc tgc      672
Lys Pro Ser Asn Thr Lys Val Asp Lys Arg Val Glu Pro Lys Ser Cys
    210                 215                 220

gac aag acc cac acc tgc ccc ccc tgc cct gcc ccc gag ctg ctg ggc      720
Asp Lys Thr His Thr Cys Pro Pro Cys Pro Ala Pro Glu Leu Leu Gly
225                 230                 235                 240

gga ccc tcc gtg ttc ctg ttc ccc ccc aag ccc aag gac acc ctc atg      768
Gly Pro Ser Val Phe Leu Phe Pro Pro Lys Pro Lys Asp Thr Leu Met
```

```
                245                 250                 255

atc agc cgg acc ccc gag gtg acc tgc gtg gtg gtg gac gtg agc cac      816
Ile Ser Arg Thr Pro Glu Val Thr Cys Val Val Val Asp Val Ser His
            260                 265                 270

gag gac ccc gag gtg aag ttc aac tgg tac gtg gac ggc gtg gag gtg      864
Glu Asp Pro Glu Val Lys Phe Asn Trp Tyr Val Asp Gly Val Glu Val
        275                 280                 285

cac aac gcc aag acc aag ccc cgg gag gag cag tac aac agc acc tac      912
His Asn Ala Lys Thr Lys Pro Arg Glu Glu Gln Tyr Asn Ser Thr Tyr
    290                 295                 300

cgg gtg gtg agc gtg ctc acc gtg ctg cac cag gac tgg ctg aac ggc      960
Arg Val Val Ser Val Leu Thr Val Leu His Gln Asp Trp Leu Asn Gly
305                 310                 315                 320

aag gag tac aag tgc aag gtg agc aac aag gcc ctg cct gcc ccc atc     1008
Lys Glu Tyr Lys Cys Lys Val Ser Asn Lys Ala Leu Pro Ala Pro Ile
                325                 330                 335

gag aag acc atc agc aag gcc aag ggc cag ccc cgg gag ccc cag gtg     1056
Glu Lys Thr Ile Ser Lys Ala Lys Gly Gln Pro Arg Glu Pro Gln Val
            340                 345                 350

tac acc ctg ccc ccc agc cgg gag gag atg acc aag aac cag gtg tcc     1104
Tyr Thr Leu Pro Pro Ser Arg Glu Glu Met Thr Lys Asn Gln Val Ser
        355                 360                 365

ctc acc tgt ctg gtg aag ggc ttc tac ccc agc gac atc gcc gtg gag     1152
Leu Thr Cys Leu Val Lys Gly Phe Tyr Pro Ser Asp Ile Ala Val Glu
    370                 375                 380

tgg gag agc aac ggc cag ccc gag aac aac tac aag acc acc ccc cct     1200
Trp Glu Ser Asn Gly Gln Pro Glu Asn Asn Tyr Lys Thr Thr Pro Pro
385                 390                 395                 400

gtg ctg gac agc gac ggc agc ttc ttc ctg tac agc aag ctc acc gtg     1248
Val Leu Asp Ser Asp Gly Ser Phe Phe Leu Tyr Ser Lys Leu Thr Val
                405                 410                 415

gac aag agc cgg tgg cag cag ggc aac gtg ttc agc tgc agc gtg atg     1296
Asp Lys Ser Arg Trp Gln Gln Gly Asn Val Phe Ser Cys Ser Val Met
            420                 425                 430

cac gag gcc ctg cac aac cac tac acc cag aag agc ctg agc ctg agc     1344
His Glu Ala Leu His Asn His Tyr Thr Gln Lys Ser Leu Ser Leu Ser
        435                 440                 445

ccc ggc aag                                                         1353
Pro Gly Lys
    450


<210> SEQ ID NO 119
<211> LENGTH: 451
<212> TYPE: PRT
<213> ORGANISM: Homo sapiens

<400> SEQUENCE: 119

Glu Val Gln Leu Val Glu Thr Gly Gly Val Ala Val Gln Pro Gly Arg
1               5                   10                  15

Ser Leu Arg Leu Ser Cys Ala Ala Ser Gly Phe Ser Phe Arg Asp Tyr
            20                  25                  30

Gly Met His Trp Val Arg Gln Ala Ala Gly Lys Gly Leu Glu Trp Val
        35                  40                  45

Ala Phe Ile Trp Pro His Gly Val Asn Arg Phe Tyr Ala Asp Ser Met
    50                  55                  60

Glu Gly Arg Phe Thr Ile Ser Arg Asp Asp Ser Lys Asn Met Leu Tyr
65                  70                  75                  80

Leu Glu Met Asn Asn Leu Arg Thr Glu Asp Thr Ala Leu Tyr Tyr Cys
                85                  90                  95
```

-continued

```
Thr Arg Asp Gln Asp Tyr Val Pro Arg Lys Tyr Phe Asp Leu Trp Gly
            100                 105                 110

Arg Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450
```

<210> SEQ ID NO 120
<211> LENGTH: 1377
<212> TYPE: DNA
<213> ORGANISM: Homo sapiens
<220> FEATURE:
<221> NAME/KEY: CDS
<222> LOCATION: (1)..(1377)

<400> SEQUENCE: 120

```
cag gtg cag ctg cag gag tcg ggc ccg aga ctg gtg aag cct tcg gag       48
Gln Val Gln Leu Gln Glu Ser Gly Pro Arg Leu Val Lys Pro Ser Glu
1               5                   10                  15

acc ctg tcc ctc act tgc aat gtc tct gat gac tcc atc acg agt tat       96
Thr Leu Ser Leu Thr Cys Asn Val Ser Asp Asp Ser Ile Thr Ser Tyr
            20                  25                  30

ggt tac tat tgg ggc tgg atc cgc cag ccc cca ggg gag gca ctg gag      144
Gly Tyr Tyr Trp Gly Trp Ile Arg Gln Pro Pro Gly Glu Ala Leu Glu
        35                  40                  45

tgg att ggc aat gtc ttt tac agt ggc atg gct tat tac aac ccg tcc      192
Trp Ile Gly Asn Val Phe Tyr Ser Gly Met Ala Tyr Tyr Asn Pro Ser
    50                  55                  60

ctc aag agt cga gtc acc ata tta ata gac aca tcg aag aaa cag ttt      240
Leu Lys Ser Arg Val Thr Ile Leu Ile Asp Thr Ser Lys Lys Gln Phe
65                  70                  75                  80

tcc ctg aga ctc aac tcc gtg acc gcc gcg gac acg gcc att tat tac      288
Ser Leu Arg Leu Asn Ser Val Thr Ala Ala Asp Thr Ala Ile Tyr Tyr
                85                  90                  95

tgt gcg aga gtg ccc ttt ctg atg ttt aga gtg aaa att gta cag ggg      336
Cys Ala Arg Val Pro Phe Leu Met Phe Arg Val Lys Ile Val Gln Gly
            100                 105                 110

acg ggt gct ttt gat atc tgg ggc caa ggg aca atg gtc acc gtc tcg      384
Thr Gly Ala Phe Asp Ile Trp Gly Gln Gly Thr Met Val Thr Val Ser
        115                 120                 125

agt gct agc acc aag ggc ccc agc gtg ttc ccc ctg gcc ccc agc agc      432
Ser Ala Ser Thr Lys Gly Pro Ser Val Phe Pro Leu Ala Pro Ser Ser
    130                 135                 140

aag agc acc agc ggc ggc aca gcc gcc ctg ggc tgc ctg gtg aag gac      480
Lys Ser Thr Ser Gly Gly Thr Ala Ala Leu Gly Cys Leu Val Lys Asp
145                 150                 155                 160

tac ttc ccc gag ccc gtg acc gtg agc tgg aac agc ggc gcc ttg acc      528
Tyr Phe Pro Glu Pro Val Thr Val Ser Trp Asn Ser Gly Ala Leu Thr
                165                 170                 175

agc ggc gtg cac acc ttc ccc gcc gtg ctg cag agc agc ggc ctg tac      576
Ser Gly Val His Thr Phe Pro Ala Val Leu Gln Ser Ser Gly Leu Tyr
            180                 185                 190

agc ctg agc agc gtg gtg acc gtg ccc agc agc agc ctg ggc acc cag      624
Ser Leu Ser Ser Val Val Thr Val Pro Ser Ser Ser Leu Gly Thr Gln
        195                 200                 205

acc tac atc tgc aac gtg aac cac aag ccc agc aac acc aag gtg gac      672
Thr Tyr Ile Cys Asn Val Asn His Lys Pro Ser Asn Thr Lys Val Asp
    210                 215                 220

aaa cgc gtg gag ccc aag agc tgc gac aag acc cac acc tgc ccc ccc      720
Lys Arg Val Glu Pro Lys Ser Cys Asp Lys Thr His Thr Cys Pro Pro
225                 230                 235                 240

tgc cct gcc ccc gag ctg ctg ggc gga ccc tcc gtg ttc ctg ttc ccc      768
Cys Pro Ala Pro Glu Leu Leu Gly Gly Pro Ser Val Phe Leu Phe Pro
                245                 250                 255

ccc aag ccc aag gac acc ctc atg atc agc cgg acc ccc gag gtg acc      816
Pro Lys Pro Lys Asp Thr Leu Met Ile Ser Arg Thr Pro Glu Val Thr
            260                 265                 270

tgc gtg gtg gtg gac gtg agc cac gag gac ccc gag gtg aag ttc aac      864
Cys Val Val Val Asp Val Ser His Glu Asp Pro Glu Val Lys Phe Asn
        275                 280                 285

tgg tac gtg gac ggc gtg gag gtg cac aac gcc aag acc aag ccc cgg      912
Trp Tyr Val Asp Gly Val Glu Val His Asn Ala Lys Thr Lys Pro Arg
    290                 295                 300

gag gag cag tac aac agc acc tac cgg gtg gtg agc gtg ctc acc gtg      960
Glu Glu Gln Tyr Asn Ser Thr Tyr Arg Val Val Ser Val Leu Thr Val
305                 310                 315                 320
```

```
ctg cac cag gac tgg ctg aac ggc aag gag tac aag tgc aag gtg agc      1008
Leu His Gln Asp Trp Leu Asn Gly Lys Glu Tyr Lys Cys Lys Val Ser
                325                 330                 335

aac aag gcc ctg cct gcc ccc atc gag aag acc atc agc aag gcc aag      1056
Asn Lys Ala Leu Pro Ala Pro Ile Glu Lys Thr Ile Ser Lys Ala Lys
            340                 345                 350

ggc cag ccc cgg gag ccc cag gtg tac acc ctg ccc ccc agc cgg gag      1104
Gly Gln Pro Arg Glu Pro Gln Val Tyr Thr Leu Pro Pro Ser Arg Glu
        355                 360                 365

gag atg acc aag aac cag gtg tcc ctc acc tgt ctg gtg aag ggc ttc      1152
Glu Met Thr Lys Asn Gln Val Ser Leu Thr Cys Leu Val Lys Gly Phe
    370                 375                 380

tac ccc agc gac atc gcc gtg gag tgg gag agc aac ggc cag ccc gag      1200
Tyr Pro Ser Asp Ile Ala Val Glu Trp Glu Ser Asn Gly Gln Pro Glu
385                 390                 395                 400

aac aac tac aag acc acc ccc cct gtg ctg gac agc gac ggc agc ttc      1248
Asn Asn Tyr Lys Thr Thr Pro Pro Val Leu Asp Ser Asp Gly Ser Phe
                405                 410                 415

ttc ctg tac agc aag ctc acc gtg gac aag agc cgg tgg cag cag ggc      1296
Phe Leu Tyr Ser Lys Leu Thr Val Asp Lys Ser Arg Trp Gln Gln Gly
            420                 425                 430

aac gtg ttc agc tgc agc gtg atg cac gag gcc ctg cac aac cac tac      1344
Asn Val Phe Ser Cys Ser Val Met His Glu Ala Leu His Asn His Tyr
        435                 440                 445

acc cag aag agc ctg agc ctg agc ccc ggc aag                          1377
Thr Gln Lys Ser Leu Ser Leu Ser Pro Gly Lys
    450                 455
```

<210> SEQ ID NO 121
<211> LENGTH: 459
<212> TYPE: PRT
<213> ORGANISM: Homo sapiens

<400> SEQUENCE: 121

```
Gln Val Gln Leu Gln Glu Ser Gly Pro Arg Leu Val Lys Pro Ser Glu
1               5                   10                  15

Thr Leu Ser Leu Thr Cys Asn Val Ser Asp Asp Ser Ile Thr Ser Tyr
            20                  25                  30

Gly Tyr Tyr Trp Gly Trp Ile Arg Gln Pro Pro Gly Glu Ala Leu Glu
        35                  40                  45

Trp Ile Gly Asn Val Phe Tyr Ser Gly Met Ala Tyr Tyr Asn Pro Ser
    50                  55                  60

Leu Lys Ser Arg Val Thr Ile Leu Ile Asp Thr Ser Lys Lys Gln Phe
65                  70                  75                  80

Ser Leu Arg Leu Asn Ser Val Thr Ala Ala Asp Thr Ala Ile Tyr Tyr
                85                  90                  95

Cys Ala Arg Val Pro Phe Leu Met Phe Arg Val Lys Ile Val Gln Gly
            100                 105                 110

Thr Gly Ala Phe Asp Ile Trp Gly Gln Gly Thr Met Val Thr Val Ser
        115                 120                 125

Ser Ala Ser Thr Lys Gly Pro Ser Val Phe Pro Leu Ala Pro Ser Ser
    130                 135                 140

Lys Ser Thr Ser Gly Gly Thr Ala Ala Leu Gly Cys Leu Val Lys Asp
145                 150                 155                 160

Tyr Phe Pro Glu Pro Val Thr Val Ser Trp Asn Ser Gly Ala Leu Thr
                165                 170                 175

Ser Gly Val His Thr Phe Pro Ala Val Leu Gln Ser Ser Gly Leu Tyr
            180                 185                 190
```

-continued

```
Ser Leu Ser Ser Val Val Thr Val Pro Ser Ser Ser Leu Gly Thr Gln
        195                 200                 205

Thr Tyr Ile Cys Asn Val Asn His Lys Pro Ser Asn Thr Lys Val Asp
    210                 215                 220

Lys Arg Val Glu Pro Lys Ser Cys Asp Lys Thr His Thr Cys Pro Pro
225                 230                 235                 240

Cys Pro Ala Pro Glu Leu Leu Gly Gly Pro Ser Val Phe Leu Phe Pro
                245                 250                 255

Pro Lys Pro Lys Asp Thr Leu Met Ile Ser Arg Thr Pro Glu Val Thr
            260                 265                 270

Cys Val Val Val Asp Val Ser His Glu Asp Pro Glu Val Lys Phe Asn
        275                 280                 285

Trp Tyr Val Asp Gly Val Glu Val His Asn Ala Lys Thr Lys Pro Arg
    290                 295                 300

Glu Glu Gln Tyr Asn Ser Thr Tyr Arg Val Val Ser Val Leu Thr Val
305                 310                 315                 320

Leu His Gln Asp Trp Leu Asn Gly Lys Glu Tyr Lys Cys Lys Val Ser
                325                 330                 335

Asn Lys Ala Leu Pro Ala Pro Ile Glu Lys Thr Ile Ser Lys Ala Lys
            340                 345                 350

Gly Gln Pro Arg Glu Pro Gln Val Tyr Thr Leu Pro Pro Ser Arg Glu
        355                 360                 365

Glu Met Thr Lys Asn Gln Val Ser Leu Thr Cys Leu Val Lys Gly Phe
    370                 375                 380

Tyr Pro Ser Asp Ile Ala Val Glu Trp Glu Ser Asn Gly Gln Pro Glu
385                 390                 395                 400

Asn Asn Tyr Lys Thr Thr Pro Pro Val Leu Asp Ser Asp Gly Ser Phe
                405                 410                 415

Phe Leu Tyr Ser Lys Leu Thr Val Asp Lys Ser Arg Trp Gln Gln Gly
            420                 425                 430

Asn Val Phe Ser Cys Ser Val Met His Glu Ala Leu His Asn His Tyr
        435                 440                 445

Thr Gln Lys Ser Leu Ser Leu Ser Pro Gly Lys
    450                 455


<210> SEQ ID NO 122
<211> LENGTH: 1350
<212> TYPE: DNA
<213> ORGANISM: Homo sapiens
<220> FEATURE:
<221> NAME/KEY: CDS
<222> LOCATION: (1)..(1350)

<400> SEQUENCE: 122

gag gtg cag ctg gtg gag tct ggg gga gac ttg gta cag ccg ggg ggg       48
Glu Val Gln Leu Val Glu Ser Gly Gly Asp Leu Val Gln Pro Gly Gly
1               5                   10                  15

tcc ctg cga ctc tcc tgt gta ggc tct gga ttc acc ttt ggc cgc tat       96
Ser Leu Arg Leu Ser Cys Val Gly Ser Gly Phe Thr Phe Gly Arg Tyr
            20                  25                  30

gcc atg agt tgg gtc cgc cag gct cca ggg aag ggg ctg gag tgg gtc      144
Ala Met Ser Trp Val Arg Gln Ala Pro Gly Lys Gly Leu Glu Trp Val
        35                  40                  45

gcg tct att aac aat aat gga aat cca tac tac gca gac tcc gtg aag      192
Ala Ser Ile Asn Asn Asn Gly Asn Pro Tyr Tyr Ala Asp Ser Val Lys
    50                  55                  60

ggc cga ttc acc atc tcc gca gac aat tcc aag agc aca gtt tat ctg      240
Gly Arg Phe Thr Ile Ser Ala Asp Asn Ser Lys Ser Thr Val Tyr Leu
```

-continued

```
65                  70                  75                  80

caa atg aat agc ctg aga gcc gaa gac acg gcc atg tat tac tgt gcg      288
Gln Met Asn Ser Leu Arg Ala Glu Asp Thr Ala Met Tyr Tyr Cys Ala
                85                  90                  95

aaa gac cac tat agc agt ggc tgg ccc gcg ttt gac cac tgg ggc cag      336
Lys Asp His Tyr Ser Ser Gly Trp Pro Ala Phe Asp His Trp Gly Gln
            100                 105                 110

gga acc ctg gtc acc gtc tcg agt gct agc acc aag ggc ccc agc gtg      384
Gly Thr Leu Val Thr Val Ser Ser Ala Ser Thr Lys Gly Pro Ser Val
        115                 120                 125

ttc ccc ctg gcc ccc agc agc aag agc acc agc ggc ggc aca gcc gcc      432
Phe Pro Leu Ala Pro Ser Ser Lys Ser Thr Ser Gly Gly Thr Ala Ala
    130                 135                 140

ctg ggc tgc ctg gtg aag gac tac ttc ccc gag ccc gtg acc gtg agc      480
Leu Gly Cys Leu Val Lys Asp Tyr Phe Pro Glu Pro Val Thr Val Ser
145                 150                 155                 160

tgg aac agc ggc gcc ttg acc agc ggc gtg cac acc ttc ccc gcc gtg      528
Trp Asn Ser Gly Ala Leu Thr Ser Gly Val His Thr Phe Pro Ala Val
                165                 170                 175

ctg cag agc agc ggc ctg tac agc ctg agc agc gtg gtg acc gtg ccc      576
Leu Gln Ser Ser Gly Leu Tyr Ser Leu Ser Ser Val Val Thr Val Pro
            180                 185                 190

agc agc agc ctg ggc acc cag acc tac atc tgc aac gtg aac cac aag      624
Ser Ser Ser Leu Gly Thr Gln Thr Tyr Ile Cys Asn Val Asn His Lys
        195                 200                 205

ccc agc aac acc aag gtg gac aaa cgc gtg gag ccc aag agc tgc gac      672
Pro Ser Asn Thr Lys Val Asp Lys Arg Val Glu Pro Lys Ser Cys Asp
    210                 215                 220

aag acc cac acc tgc ccc ccc tgc cct gcc ccc gag ctg ctg ggc gga      720
Lys Thr His Thr Cys Pro Pro Cys Pro Ala Pro Glu Leu Leu Gly Gly
225                 230                 235                 240

ccc tcc gtg ttc ctg ttc ccc ccc aag ccc aag gac acc ctc atg atc      768
Pro Ser Val Phe Leu Phe Pro Pro Lys Pro Lys Asp Thr Leu Met Ile
                245                 250                 255

agc cgg acc ccc gag gtg acc tgc gtg gtg gtg gac gtg agc cac gag      816
Ser Arg Thr Pro Glu Val Thr Cys Val Val Val Asp Val Ser His Glu
            260                 265                 270

gac ccc gag gtg aag ttc aac tgg tac gtg gac ggc gtg gag gtg cac      864
Asp Pro Glu Val Lys Phe Asn Trp Tyr Val Asp Gly Val Glu Val His
        275                 280                 285

aac gcc aag acc aag ccc cgg gag gag cag tac aac agc acc tac cgg      912
Asn Ala Lys Thr Lys Pro Arg Glu Glu Gln Tyr Asn Ser Thr Tyr Arg
    290                 295                 300

gtg gtg agc gtg ctc acc gtg ctg cac cag gac tgg ctg aac ggc aag      960
Val Val Ser Val Leu Thr Val Leu His Gln Asp Trp Leu Asn Gly Lys
305                 310                 315                 320

gag tac aag tgc aag gtg agc aac aag gcc ctg cct gcc ccc atc gag     1008
Glu Tyr Lys Cys Lys Val Ser Asn Lys Ala Leu Pro Ala Pro Ile Glu
                325                 330                 335

aag acc atc agc aag gcc aag ggc cag ccc cgg gag ccc cag gtg tac     1056
Lys Thr Ile Ser Lys Ala Lys Gly Gln Pro Arg Glu Pro Gln Val Tyr
            340                 345                 350

acc ctg ccc ccc agc cgg gag gag atg acc aag aac cag gtg tcc ctc     1104
Thr Leu Pro Pro Ser Arg Glu Glu Met Thr Lys Asn Gln Val Ser Leu
        355                 360                 365

acc tgt ctg gtg aag ggc ttc tac ccc agc gac atc gcc gtg gag tgg     1152
Thr Cys Leu Val Lys Gly Phe Tyr Pro Ser Asp Ile Ala Val Glu Trp
    370                 375                 380

gag agc aac ggc cag ccc gag aac aac tac aag acc acc ccc cct gtg     1200
Glu Ser Asn Gly Gln Pro Glu Asn Asn Tyr Lys Thr Thr Pro Pro Val
```

```
385                 390                 395                 400

ctg gac agc gac ggc agc ttc ttc ctg tac agc aag ctc acc gtg gac      1248
Leu Asp Ser Asp Gly Ser Phe Phe Leu Tyr Ser Lys Leu Thr Val Asp
                405                 410                 415

aag agc cgg tgg cag cag ggc aac gtg ttc agc tgc agc gtg atg cac      1296
Lys Ser Arg Trp Gln Gln Gly Asn Val Phe Ser Cys Ser Val Met His
            420                 425                 430

gag gcc ctg cac aac cac tac acc cag aag agc ctg agc ctg agc ccc      1344
Glu Ala Leu His Asn His Tyr Thr Gln Lys Ser Leu Ser Leu Ser Pro
        435                 440                 445

ggc aag                                                              1350
Gly Lys
    450


<210> SEQ ID NO 123
<211> LENGTH: 450
<212> TYPE: PRT
<213> ORGANISM: Homo sapiens

<400> SEQUENCE: 123

Glu Val Gln Leu Val Glu Ser Gly Gly Asp Leu Val Gln Pro Gly Gly
1               5                   10                  15

Ser Leu Arg Leu Ser Cys Val Gly Ser Gly Phe Thr Phe Gly Arg Tyr
            20                  25                  30

Ala Met Ser Trp Val Arg Gln Ala Pro Gly Lys Gly Leu Glu Trp Val
        35                  40                  45

Ala Ser Ile Asn Asn Asn Gly Asn Pro Tyr Tyr Ala Asp Ser Val Lys
    50                  55                  60

Gly Arg Phe Thr Ile Ser Ala Asp Asn Ser Lys Ser Thr Val Tyr Leu
65                  70                  75                  80

Gln Met Asn Ser Leu Arg Ala Glu Asp Thr Ala Met Tyr Tyr Cys Ala
                85                  90                  95

Lys Asp His Tyr Ser Ser Gly Trp Pro Ala Phe Asp His Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285
```

```
Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 124
<211> LENGTH: 1344
<212> TYPE: DNA
<213> ORGANISM: Homo sapiens
<220> FEATURE:
<221> NAME/KEY: CDS
<222> LOCATION: (1)..(1344)

<400> SEQUENCE: 124

gag gtg cag ctg gtg gag tct gga gca gag gtg aaa aag ccc ggg gag       48
Glu Val Gln Leu Val Glu Ser Gly Ala Glu Val Lys Lys Pro Gly Glu
1               5                   10                  15

tct ctg aag atc tcc tgt aag ggt tct gga tac agc ttt acc agc tac       96
Ser Leu Lys Ile Ser Cys Lys Gly Ser Gly Tyr Ser Phe Thr Ser Tyr
            20                  25                  30

tgg atc ggc tgg gtg cgc cag atg ccc ggg aaa ggc ctg gag tgg atg      144
Trp Ile Gly Trp Val Arg Gln Met Pro Gly Lys Gly Leu Glu Trp Met
        35                  40                  45

ggg atc atc tat cct ggt gac tct gat acc aga tac agc ccg tcc ttc      192
Gly Ile Ile Tyr Pro Gly Asp Ser Asp Thr Arg Tyr Ser Pro Ser Phe
    50                  55                  60

caa ggc cag gtc acc atc tca gcc gac aag tcc atc agc acc gcc tac      240
Gln Gly Gln Val Thr Ile Ser Ala Asp Lys Ser Ile Ser Thr Ala Tyr
65                  70                  75                  80

ctg cag tgg agc agc ctg aag gcc tcg gac acc gcc atg tat tac tgt      288
Leu Gln Trp Ser Ser Leu Lys Ala Ser Asp Thr Ala Met Tyr Tyr Cys
                85                  90                  95

gcg agg tac agt aac tcc caa ggt atg gac gtc tgg ggc caa ggg acc      336
Ala Arg Tyr Ser Asn Ser Gln Gly Met Asp Val Trp Gly Gln Gly Thr
            100                 105                 110

acg gtc acc gtc tcg agt gct agc acc aag ggc ccc agc gtg ttc ccc      384
Thr Val Thr Val Ser Ser Ala Ser Thr Lys Gly Pro Ser Val Phe Pro
        115                 120                 125

ctg gcc ccc agc agc aag agc acc agc ggc ggc aca gcc gcc ctg ggc      432
Leu Ala Pro Ser Ser Lys Ser Thr Ser Gly Gly Thr Ala Ala Leu Gly
    130                 135                 140
```

```
tgc ctg gtg aag gac tac ttc ccc gag ccc gtg acc gtg agc tgg aac      480
Cys Leu Val Lys Asp Tyr Phe Pro Glu Pro Val Thr Val Ser Trp Asn
145                 150                 155                 160

agc ggc gcc ttg acc agc ggc gtg cac acc ttc ccc gcc gtg ctg cag      528
Ser Gly Ala Leu Thr Ser Gly Val His Thr Phe Pro Ala Val Leu Gln
                165                 170                 175

agc agc ggc ctg tac agc ctg agc agc gtg gtg acc gtg ccc agc agc      576
Ser Ser Gly Leu Tyr Ser Leu Ser Ser Val Val Thr Val Pro Ser Ser
            180                 185                 190

agc ctg ggc acc cag acc tac atc tgc aac gtg aac cac aag ccc agc      624
Ser Leu Gly Thr Gln Thr Tyr Ile Cys Asn Val Asn His Lys Pro Ser
        195                 200                 205

aac acc aag gtg gac aaa cgc gtg gag ccc aag agc tgc gac aag acc      672
Asn Thr Lys Val Asp Lys Arg Val Glu Pro Lys Ser Cys Asp Lys Thr
    210                 215                 220

cac acc tgc ccc ccc tgc cct gcc ccc gag ctg ctg ggc gga ccc tcc      720
His Thr Cys Pro Pro Cys Pro Ala Pro Glu Leu Leu Gly Gly Pro Ser
225                 230                 235                 240

gtg ttc ctg ttc ccc ccc aag ccc aag gac acc ctc atg atc agc cgg      768
Val Phe Leu Phe Pro Pro Lys Pro Lys Asp Thr Leu Met Ile Ser Arg
                245                 250                 255

acc ccc gag gtg acc tgc gtg gtg gtg gac gtg agc cac gag gac ccc      816
Thr Pro Glu Val Thr Cys Val Val Val Asp Val Ser His Glu Asp Pro
            260                 265                 270

gag gtg aag ttc aac tgg tac gtg gac ggc gtg gag gtg cac aac gcc      864
Glu Val Lys Phe Asn Trp Tyr Val Asp Gly Val Glu Val His Asn Ala
        275                 280                 285

aag acc aag ccc cgg gag gag cag tac aac agc acc tac cgg gtg gtg      912
Lys Thr Lys Pro Arg Glu Glu Gln Tyr Asn Ser Thr Tyr Arg Val Val
    290                 295                 300

agc gtg ctc acc gtg ctg cac cag gac tgg ctg aac ggc aag gag tac      960
Ser Val Leu Thr Val Leu His Gln Asp Trp Leu Asn Gly Lys Glu Tyr
305                 310                 315                 320

aag tgc aag gtg agc aac aag gcc ctg cct gcc ccc atc gag aag acc     1008
Lys Cys Lys Val Ser Asn Lys Ala Leu Pro Ala Pro Ile Glu Lys Thr
                325                 330                 335

atc agc aag gcc aag ggc cag ccc cgg gag ccc cag gtg tac acc ctg     1056
Ile Ser Lys Ala Lys Gly Gln Pro Arg Glu Pro Gln Val Tyr Thr Leu
            340                 345                 350

ccc ccc agc cgg gag gag atg acc aag aac cag gtg tcc ctc acc tgt     1104
Pro Pro Ser Arg Glu Glu Met Thr Lys Asn Gln Val Ser Leu Thr Cys
        355                 360                 365

ctg gtg aag ggc ttc tac ccc agc gac atc gcc gtg gag tgg gag agc     1152
Leu Val Lys Gly Phe Tyr Pro Ser Asp Ile Ala Val Glu Trp Glu Ser
    370                 375                 380

aac ggc cag ccc gag aac aac tac aag acc acc ccc cct gtg ctg gac     1200
Asn Gly Gln Pro Glu Asn Asn Tyr Lys Thr Thr Pro Pro Val Leu Asp
385                 390                 395                 400

agc gac ggc agc ttc ttc ctg tac agc aag ctc acc gtg gac aag agc     1248
Ser Asp Gly Ser Phe Phe Leu Tyr Ser Lys Leu Thr Val Asp Lys Ser
                405                 410                 415

cgg tgg cag cag ggc aac gtg ttc agc tgc agc gtg atg cac gag gcc     1296
Arg Trp Gln Gln Gly Asn Val Phe Ser Cys Ser Val Met His Glu Ala
            420                 425                 430

ctg cac aac cac tac acc cag aag agc ctg agc ctg agc ccc ggc aag     1344
Leu His Asn His Tyr Thr Gln Lys Ser Leu Ser Leu Ser Pro Gly Lys
        435                 440                 445
```

<210> SEQ ID NO 125
<211> LENGTH: 448
<212> TYPE: PRT

<213> ORGANISM: Homo sapiens

<400> SEQUENCE: 125

```
Glu Val Gln Leu Val Glu Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Tyr Ser Asn Ser Gln Gly Met Asp Val Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
```

```
            405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445


<210> SEQ ID NO 126
<211> LENGTH: 1356
<212> TYPE: DNA
<213> ORGANISM: Homo sapiens
<220> FEATURE:
<221> NAME/KEY: CDS
<222> LOCATION: (1)..(1356)

<400> SEQUENCE: 126

cag gtc cag ctg gta cag tct gga gca gag gtg aaa aag ccg ggg gag       48
Gln Val Gln Leu Val Gln Ser Gly Ala Glu Val Lys Lys Pro Gly Glu
1               5                   10                  15

tct ctg aag atc tcc tgt aag ggt tct aga tac agc tct acc agc tac       96
Ser Leu Lys Ile Ser Cys Lys Gly Ser Arg Tyr Ser Ser Thr Ser Tyr
            20                  25                  30

tgg atc ggc tgg gtg cgc cag atg ccc ggg gaa ggc ctg gag tgg atg      144
Trp Ile Gly Trp Val Arg Gln Met Pro Gly Glu Gly Leu Glu Trp Met
        35                  40                  45

ggg atc atc tat cct ggt gac tct gat acc aga tac agc ccg tcc ttc      192
Gly Ile Ile Tyr Pro Gly Asp Ser Asp Thr Arg Tyr Ser Pro Ser Phe
    50                  55                  60

caa ggc cag gtc acc atc tca gcc gac aag tcc atc agc acc gcc tac      240
Gln Gly Gln Val Thr Ile Ser Ala Asp Lys Ser Ile Ser Thr Ala Tyr
65                  70                  75                  80

ctg cag tgg agt agc ctg aag gcc tcg gac agc gcc tta tat tac tgt      288
Leu Gln Trp Ser Ser Leu Lys Ala Ser Asp Ser Ala Leu Tyr Tyr Cys
                85                  90                  95

gcg aga ggg gcc gtg gct gga acg gtc ggc aat ggt ttt gat gtc tgg      336
Ala Arg Gly Ala Val Ala Gly Thr Val Gly Asn Gly Phe Asp Val Trp
            100                 105                 110

ggc caa ggg aca atg gtc acc gtc tcg agt gct agc acc aag ggc ccc      384
Gly Gln Gly Thr Met Val Thr Val Ser Ser Ala Ser Thr Lys Gly Pro
        115                 120                 125

agc gtg ttc ccc ctg gcc ccc agc agc aag agc acc agc ggc ggc aca      432
Ser Val Phe Pro Leu Ala Pro Ser Ser Lys Ser Thr Ser Gly Gly Thr
    130                 135                 140

gcc gcc ctg ggc tgc ctg gtg aag gac tac ttc ccc gag ccc gtg acc      480
Ala Ala Leu Gly Cys Leu Val Lys Asp Tyr Phe Pro Glu Pro Val Thr
145                 150                 155                 160

gtg agc tgg aac agc ggc gcc ttg acc agc ggc gtg cac acc ttc ccc      528
Val Ser Trp Asn Ser Gly Ala Leu Thr Ser Gly Val His Thr Phe Pro
                165                 170                 175

gcc gtg ctg cag agc agc ggc ctg tac agc ctg agc agc gtg gtg acc      576
Ala Val Leu Gln Ser Ser Gly Leu Tyr Ser Leu Ser Ser Val Val Thr
            180                 185                 190

gtg ccc agc agc agc ctg ggc acc cag acc tac atc tgc aac gtg aac      624
Val Pro Ser Ser Ser Leu Gly Thr Gln Thr Tyr Ile Cys Asn Val Asn
        195                 200                 205

cac aag ccc agc aac acc aag gtg gac aaa cgc gtg gag ccc aag agc      672
His Lys Pro Ser Asn Thr Lys Val Asp Lys Arg Val Glu Pro Lys Ser
    210                 215                 220

tgc gac aag acc cac acc tgc ccc ccc tgc cct gcc ccc gag ctg ctg      720
Cys Asp Lys Thr His Thr Cys Pro Pro Cys Pro Ala Pro Glu Leu Leu
225                 230                 235                 240

ggc gga ccc tcc gtg ttc ctg ttc ccc ccc aag ccc aag gac acc ctc      768
```

```
Gly Gly Pro Ser Val Phe Leu Phe Pro Pro Lys Pro Lys Asp Thr Leu
                245                 250                 255

atg atc agc cgg acc ccc gag gtg acc tgc gtg gtg gtg gac gtg agc      816
Met Ile Ser Arg Thr Pro Glu Val Thr Cys Val Val Val Asp Val Ser
            260                 265                 270

cac gag gac ccc gag gtg aag ttc aac tgg tac gtg gac ggc gtg gag      864
His Glu Asp Pro Glu Val Lys Phe Asn Trp Tyr Val Asp Gly Val Glu
        275                 280                 285

gtg cac aac gcc aag acc aag ccc cgg gag gag cag tac aac agc acc      912
Val His Asn Ala Lys Thr Lys Pro Arg Glu Glu Gln Tyr Asn Ser Thr
    290                 295                 300

tac cgg gtg gtg agc gtg ctc acc gtg ctg cac cag gac tgg ctg aac      960
Tyr Arg Val Val Ser Val Leu Thr Val Leu His Gln Asp Trp Leu Asn
305                 310                 315                 320

ggc aag gag tac aag tgc aag gtg agc aac aag gcc ctg cct gcc ccc     1008
Gly Lys Glu Tyr Lys Cys Lys Val Ser Asn Lys Ala Leu Pro Ala Pro
                325                 330                 335

atc gag aag acc atc agc aag gcc aag ggc cag ccc cgg gag ccc cag     1056
Ile Glu Lys Thr Ile Ser Lys Ala Lys Gly Gln Pro Arg Glu Pro Gln
            340                 345                 350

gtg tac acc ctg ccc ccc agc cgg gag gag atg acc aag aac cag gtg     1104
Val Tyr Thr Leu Pro Pro Ser Arg Glu Glu Met Thr Lys Asn Gln Val
        355                 360                 365

tcc ctc acc tgt ctg gtg aag ggc ttc tac ccc agc gac atc gcc gtg     1152
Ser Leu Thr Cys Leu Val Lys Gly Phe Tyr Pro Ser Asp Ile Ala Val
    370                 375                 380

gag tgg gag agc aac ggc cag ccc gag aac aac tac aag acc acc ccc     1200
Glu Trp Glu Ser Asn Gly Gln Pro Glu Asn Asn Tyr Lys Thr Thr Pro
385                 390                 395                 400

cct gtg ctg gac agc gac ggc agc ttc ttc ctg tac agc aag ctc acc     1248
Pro Val Leu Asp Ser Asp Gly Ser Phe Phe Leu Tyr Ser Lys Leu Thr
                405                 410                 415

gtg gac aag agc cgg tgg cag cag ggc aac gtg ttc agc tgc agc gtg     1296
Val Asp Lys Ser Arg Trp Gln Gln Gly Asn Val Phe Ser Cys Ser Val
            420                 425                 430

atg cac gag gcc ctg cac aac cac tac acc cag aag agc ctg agc ctg     1344
Met His Glu Ala Leu His Asn His Tyr Thr Gln Lys Ser Leu Ser Leu
        435                 440                 445

agc ccc ggc aag                                                     1356
Ser Pro Gly Lys
    450


<210> SEQ ID NO 127
<211> LENGTH: 452
<212> TYPE: PRT
<213> ORGANISM: Homo sapiens

<400> SEQUENCE: 127

Gln Val Gln Leu Val Gln Ser Gly Ala Glu Val Lys Lys Pro Gly Glu
1               5                   10                  15

Ser Leu Lys Ile Ser Cys Lys Gly Ser Arg Tyr Ser Ser Thr Ser Tyr
            20                  25                  30

Trp Ile Gly Trp Val Arg Gln Met Pro Gly Glu Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Ser Ala Leu Tyr Tyr Cys
                85                  90                  95
```

```
Ala Arg Gly Ala Val Ala Gly Thr Val Gly Asn Gly Phe Asp Val Trp
            100                 105                 110

Gly Gln Gly Thr Met Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450
```

<210> SEQ ID NO 128
<211> LENGTH: 1353
<212> TYPE: DNA
<213> ORGANISM: Homo sapiens
<220> FEATURE:
<221> NAME/KEY: CDS
<222> LOCATION: (1)..(1353)

<400> SEQUENCE: 128

-continued

```
gag gtg cag ctg gtg gag act gga gca gag gtg aaa aag ccc ggg gag         48
Glu Val Gln Leu Val Glu Thr Gly Ala Glu Val Lys Lys Pro Gly Glu
1               5                   10                  15

tct ctg aag atc tcc tgt aag ggt tct gga tac agc ttt acc agc tac         96
Ser Leu Lys Ile Ser Cys Lys Gly Ser Gly Tyr Ser Phe Thr Ser Tyr
            20                  25                  30

tgg atc ggc tgg gtg cgc cag atg ccc ggg aaa ggc ctg gag tgg gtg        144
Trp Ile Gly Trp Val Arg Gln Met Pro Gly Lys Gly Leu Glu Trp Val
        35                  40                  45

ggg atc atc tat cct ggt gac tct gat acc aga tac agc ccg tcc ttc        192
Gly Ile Ile Tyr Pro Gly Asp Ser Asp Thr Arg Tyr Ser Pro Ser Phe
    50                  55                  60

caa ggc cag gtc acc atc tca gcc gac aag tcc atc agc acc gcc tac        240
Gln Gly Gln Val Thr Ile Ser Ala Asp Lys Ser Ile Ser Thr Ala Tyr
65                  70                  75                  80

ctg cag tgg agc agc ctg aag gcc tcg gac acc gcc atg tat tac tgt        288
Leu Gln Trp Ser Ser Leu Lys Ala Ser Asp Thr Ala Met Tyr Tyr Cys
                85                  90                  95

gcg aga cgc cgt ggt tct acc agc tcc acg gac ttt gac tac tgg ggc        336
Ala Arg Arg Arg Gly Ser Thr Ser Ser Thr Asp Phe Asp Tyr Trp Gly
            100                 105                 110

cag gga acc ctg gtc acc gtc tcg agt gct agc acc aag ggc ccc agc        384
Gln Gly Thr Leu Val Thr Val Ser Ser Ala Ser Thr Lys Gly Pro Ser
        115                 120                 125

gtg ttc ccc ctg gcc ccc agc agc aag agc acc agc ggc ggc aca gcc        432
Val Phe Pro Leu Ala Pro Ser Ser Lys Ser Thr Ser Gly Gly Thr Ala
    130                 135                 140

gcc ctg ggc tgc ctg gtg aag gac tac ttc ccc gag ccc gtg acc gtg        480
Ala Leu Gly Cys Leu Val Lys Asp Tyr Phe Pro Glu Pro Val Thr Val
145                 150                 155                 160

agc tgg aac agc ggc gcc ttg acc agc ggc gtg cac acc ttc ccc gcc        528
Ser Trp Asn Ser Gly Ala Leu Thr Ser Gly Val His Thr Phe Pro Ala
                165                 170                 175

gtg ctg cag agc agc ggc ctg tac agc ctg agc agc gtg gtg acc gtg        576
Val Leu Gln Ser Ser Gly Leu Tyr Ser Leu Ser Ser Val Val Thr Val
            180                 185                 190

ccc agc agc agc ctg ggc acc cag acc tac atc tgc aac gtg aac cac        624
Pro Ser Ser Ser Leu Gly Thr Gln Thr Tyr Ile Cys Asn Val Asn His
        195                 200                 205

aag ccc agc aac acc aag gtg gac aaa cgc gtg gag ccc aag agc tgc        672
Lys Pro Ser Asn Thr Lys Val Asp Lys Arg Val Glu Pro Lys Ser Cys
    210                 215                 220

gac aag acc cac acc tgc ccc ccc tgc cct gcc ccc gag ctg ctg ggc        720
Asp Lys Thr His Thr Cys Pro Pro Cys Pro Ala Pro Glu Leu Leu Gly
225                 230                 235                 240

gga ccc tcc gtg ttc ctg ttc ccc ccc aag ccc aag gac acc ctc atg        768
Gly Pro Ser Val Phe Leu Phe Pro Pro Lys Pro Lys Asp Thr Leu Met
                245                 250                 255

atc agc cgg acc ccc gag gtg acc tgc gtg gtg gtg gac gtg agc cac        816
Ile Ser Arg Thr Pro Glu Val Thr Cys Val Val Val Asp Val Ser His
            260                 265                 270

gag gac ccc gag gtg aag ttc aac tgg tac gtg gac ggc gtg gag gtg        864
Glu Asp Pro Glu Val Lys Phe Asn Trp Tyr Val Asp Gly Val Glu Val
        275                 280                 285

cac aac gcc aag acc aag ccc cgg gag gag cag tac aac agc acc tac        912
His Asn Ala Lys Thr Lys Pro Arg Glu Glu Gln Tyr Asn Ser Thr Tyr
    290                 295                 300

cgg gtg gtg agc gtg ctc acc gtg ctg cac cag gac tgg ctg aac ggc        960
Arg Val Val Ser Val Leu Thr Val Leu His Gln Asp Trp Leu Asn Gly
305                 310                 315                 320
```

```
aag gag tac aag tgc aag gtg agc aac aag gcc ctg cct gcc ccc atc      1008
Lys Glu Tyr Lys Cys Lys Val Ser Asn Lys Ala Leu Pro Ala Pro Ile
                325                 330                 335

gag aag acc atc agc aag gcc aag ggc cag ccc cgg gag ccc cag gtg      1056
Glu Lys Thr Ile Ser Lys Ala Lys Gly Gln Pro Arg Glu Pro Gln Val
            340                 345                 350

tac acc ctg ccc ccc agc cgg gag gag atg acc aag aac cag gtg tcc      1104
Tyr Thr Leu Pro Pro Ser Arg Glu Glu Met Thr Lys Asn Gln Val Ser
        355                 360                 365

ctc acc tgt ctg gtg aag ggc ttc tac ccc agc gac atc gcc gtg gag      1152
Leu Thr Cys Leu Val Lys Gly Phe Tyr Pro Ser Asp Ile Ala Val Glu
    370                 375                 380

tgg gag agc aac ggc cag ccc gag aac aac tac aag acc acc ccc cct      1200
Trp Glu Ser Asn Gly Gln Pro Glu Asn Asn Tyr Lys Thr Thr Pro Pro
385                 390                 395                 400

gtg ctg gac agc gac ggc agc ttc ttc ctg tac agc aag ctc acc gtg      1248
Val Leu Asp Ser Asp Gly Ser Phe Phe Leu Tyr Ser Lys Leu Thr Val
                405                 410                 415

gac aag agc cgg tgg cag cag ggc aac gtg ttc agc tgc agc gtg atg      1296
Asp Lys Ser Arg Trp Gln Gln Gly Asn Val Phe Ser Cys Ser Val Met
            420                 425                 430

cac gag gcc ctg cac aac cac tac acc cag aag agc ctg agc ctg agc      1344
His Glu Ala Leu His Asn His Tyr Thr Gln Lys Ser Leu Ser Leu Ser
        435                 440                 445

ccc ggc aag                                                          1353
Pro Gly Lys
    450


<210> SEQ ID NO 129
<211> LENGTH: 451
<212> TYPE: PRT
<213> ORGANISM: Homo sapiens

<400> SEQUENCE: 129

Glu Val Gln Leu Val Glu Thr Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Val
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Arg Arg Gly Ser Thr Ser Ser Thr Asp Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190
```

```
Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450


<210> SEQ ID NO 130
<211> LENGTH: 1353
<212> TYPE: DNA
<213> ORGANISM: Homo sapiens
<220> FEATURE:
<221> NAME/KEY: CDS
<222> LOCATION: (1)..(1353)

<400> SEQUENCE: 130

cag gtc cag ctg gta cag tct gga gca gag gtg aaa aag ccc ggg gag       48
Gln Val Gln Leu Val Gln Ser Gly Ala Glu Val Lys Lys Pro Gly Glu
1               5                   10                  15

tct ctg aag atc tcc tgt aag ggt tct gga tac agc ttt agt aca tac       96
Ser Leu Lys Ile Ser Cys Lys Gly Ser Gly Tyr Ser Phe Ser Thr Tyr
            20                  25                  30

tgg atc ggc tgg gtg cgc cag atg ccc ggg aaa ggc ctg gag tgg atg      144
Trp Ile Gly Trp Val Arg Gln Met Pro Gly Lys Gly Leu Glu Trp Met
        35                  40                  45

ggg atc att tat cct ggt gac tct gat acc agg tac agc ccg tcc ttc      192
Gly Ile Ile Tyr Pro Gly Asp Ser Asp Thr Arg Tyr Ser Pro Ser Phe
    50                  55                  60

caa ggc cag gtc acc atc tca gcc gac aag tcc atc agc acc gcc cac      240
```

```
Gln Gly Gln Val Thr Ile Ser Ala Asp Lys Ser Ile Ser Thr Ala His
65                  70                  75                  80

ctg cag tgg agc agc ctg aag gcc tcg gac acc gcc atg tat tac tgt      288
Leu Gln Trp Ser Ser Leu Lys Ala Ser Asp Thr Ala Met Tyr Tyr Cys
                85                  90                  95

gcg agg cca gga ccc cgt gga tac aac cat ggc ttt gac tac tgg ggc      336
Ala Arg Pro Gly Pro Arg Gly Tyr Asn His Gly Phe Asp Tyr Trp Gly
            100                 105                 110

cag gga acc ctg gtc acc gtc tcg agt gct agc acc aag ggc ccc agc      384
Gln Gly Thr Leu Val Thr Val Ser Ser Ala Ser Thr Lys Gly Pro Ser
        115                 120                 125

gtg ttc ccc ctg gcc ccc agc agc aag agc acc agc ggc ggc aca gcc      432
Val Phe Pro Leu Ala Pro Ser Ser Lys Ser Thr Ser Gly Gly Thr Ala
    130                 135                 140

gcc ctg ggc tgc ctg gtg aag gac tac ttc ccc gag ccc gtg acc gtg      480
Ala Leu Gly Cys Leu Val Lys Asp Tyr Phe Pro Glu Pro Val Thr Val
145                 150                 155                 160

agc tgg aac agc ggc gcc ttg acc agc ggc gtg cac acc ttc ccc gcc      528
Ser Trp Asn Ser Gly Ala Leu Thr Ser Gly Val His Thr Phe Pro Ala
                165                 170                 175

gtg ctg cag agc agc ggc ctg tac agc ctg agc agc gtg gtg acc gtg      576
Val Leu Gln Ser Ser Gly Leu Tyr Ser Leu Ser Ser Val Val Thr Val
            180                 185                 190

ccc agc agc agc ctg ggc acc cag acc tac atc tgc aac gtg aac cac      624
Pro Ser Ser Ser Leu Gly Thr Gln Thr Tyr Ile Cys Asn Val Asn His
        195                 200                 205

aag ccc agc aac acc aag gtg gac aaa cgc gtg gag ccc aag agc tgc      672
Lys Pro Ser Asn Thr Lys Val Asp Lys Arg Val Glu Pro Lys Ser Cys
    210                 215                 220

gac aag acc cac acc tgc ccc ccc tgc cct gcc ccc gag ctg ctg ggc      720
Asp Lys Thr His Thr Cys Pro Pro Cys Pro Ala Pro Glu Leu Leu Gly
225                 230                 235                 240

gga ccc tcc gtg ttc ctg ttc ccc ccc aag ccc aag gac acc ctc atg      768
Gly Pro Ser Val Phe Leu Phe Pro Pro Lys Pro Lys Asp Thr Leu Met
                245                 250                 255

atc agc cgg acc ccc gag gtg acc tgc gtg gtg gtg gac gtg agc cac      816
Ile Ser Arg Thr Pro Glu Val Thr Cys Val Val Val Asp Val Ser His
            260                 265                 270

gag gac ccc gag gtg aag ttc aac tgg tac gtg gac ggc gtg gag gtg      864
Glu Asp Pro Glu Val Lys Phe Asn Trp Tyr Val Asp Gly Val Glu Val
        275                 280                 285

cac aac gcc aag acc aag ccc cgg gag gag cag tac aac agc acc tac      912
His Asn Ala Lys Thr Lys Pro Arg Glu Glu Gln Tyr Asn Ser Thr Tyr
    290                 295                 300

cgg gtg gtg agc gtg ctc acc gtg ctg cac cag gac tgg ctg aac ggc      960
Arg Val Val Ser Val Leu Thr Val Leu His Gln Asp Trp Leu Asn Gly
305                 310                 315                 320

aag gag tac aag tgc aag gtg agc aac aag gcc ctg cct gcc ccc atc     1008
Lys Glu Tyr Lys Cys Lys Val Ser Asn Lys Ala Leu Pro Ala Pro Ile
                325                 330                 335

gag aag acc atc agc aag gcc aag ggc cag ccc cgg gag ccc cag gtg     1056
Glu Lys Thr Ile Ser Lys Ala Lys Gly Gln Pro Arg Glu Pro Gln Val
            340                 345                 350

tac acc ctg ccc ccc agc cgg gag gag atg acc aag aac cag gtg tcc     1104
Tyr Thr Leu Pro Pro Ser Arg Glu Glu Met Thr Lys Asn Gln Val Ser
        355                 360                 365

ctc acc tgt ctg gtg aag ggc ttc tac ccc agc gac atc gcc gtg gag     1152
Leu Thr Cys Leu Val Lys Gly Phe Tyr Pro Ser Asp Ile Ala Val Glu
    370                 375                 380

tgg gag agc aac ggc cag ccc gag aac aac tac aag acc acc ccc cct     1200
```

-continued

```
Trp Glu Ser Asn Gly Gln Pro Glu Asn Asn Tyr Lys Thr Thr Pro Pro
385                 390                 395                 400

gtg ctg gac agc gac ggc agc ttc ttc ctg tac agc aag ctc acc gtg     1248
Val Leu Asp Ser Asp Gly Ser Phe Phe Leu Tyr Ser Lys Leu Thr Val
                405                 410                 415

gac aag agc cgg tgg cag cag ggc aac gtg ttc agc tgc agc gtg atg     1296
Asp Lys Ser Arg Trp Gln Gln Gly Asn Val Phe Ser Cys Ser Val Met
            420                 425                 430

cac gag gcc ctg cac aac cac tac acc cag aag agc ctg agc ctg agc     1344
His Glu Ala Leu His Asn His Tyr Thr Gln Lys Ser Leu Ser Leu Ser
        435                 440                 445

ccc ggc aag                                                         1353
Pro Gly Lys
    450


<210> SEQ ID NO 131
<211> LENGTH: 451
<212> TYPE: PRT
<213> ORGANISM: Homo sapiens

<400> SEQUENCE: 131

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Ser Thr Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala His
65                  70                  75                  80

Leu Gln Trp Ser Ser Leu Lys Ala Ser Asp Thr Ala Met Tyr Tyr Cys
                85                  90                  95

Ala Arg Pro Gly Pro Arg Gly Tyr Asn His Gly Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285
```

-continued

```
His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450


<210> SEQ ID NO 132
<211> LENGTH: 1347
<212> TYPE: DNA
<213> ORGANISM: Homo sapiens
<220> FEATURE:
<221> NAME/KEY: CDS
<222> LOCATION: (1)..(1347)

<400> SEQUENCE: 132

gag gtg cag ctg gtg gag tct gga gca gag gtg aaa gag ccg ggg gag       48
Glu Val Gln Leu Val Glu Ser Gly Ala Glu Val Lys Glu Pro Gly Glu
1               5                   10                  15

tct ctg aag atc tcc tgt aag ggt tct gga tac acc ttt gcc agc tat       96
Ser Leu Lys Ile Ser Cys Lys Gly Ser Gly Tyr Thr Phe Ala Ser Tyr
            20                  25                  30

tgg gtc gcc tgg gtg cgc cag atg ccc ggg aaa ggc ctg gag tgg atg      144
Trp Val Ala Trp Val Arg Gln Met Pro Gly Lys Gly Leu Glu Trp Met
        35                  40                  45

ggg atc atc tat cct ggt gac tct gat acc aga tac agc ccg tcc ttc      192
Gly Ile Ile Tyr Pro Gly Asp Ser Asp Thr Arg Tyr Ser Pro Ser Phe
    50                  55                  60

caa ggc cag gtc acc gtc tca gcc gac aag tcc atc agc acc gcc tac      240
Gln Gly Gln Val Thr Val Ser Ala Asp Lys Ser Ile Ser Thr Ala Tyr
65                  70                  75                  80

ctg cag tgg agc agc ctg aag gcc tcg gac acc gcc atg tat tac tgt      288
Leu Gln Trp Ser Ser Leu Lys Ala Ser Asp Thr Ala Met Tyr Tyr Cys
                85                  90                  95

gcg aga tgg tgg ggc agc ttg cat gct ttt gat atc tgg ggc caa ggg      336
Ala Arg Trp Trp Gly Ser Leu His Ala Phe Asp Ile Trp Gly Gln Gly
            100                 105                 110

aca atg gtc acc gtc tcg agt gct agc acc aag ggc ccc agc gtg ttc      384
Thr Met Val Thr Val Ser Ser Ala Ser Thr Lys Gly Pro Ser Val Phe
        115                 120                 125

ccc ctg gcc ccc agc agc aag agc acc agc ggc ggc aca gcc gcc ctg      432
Pro Leu Ala Pro Ser Ser Lys Ser Thr Ser Gly Gly Thr Ala Ala Leu
    130                 135                 140
```

-continued

```
ggc tgc ctg gtg aag gac tac ttc ccc gag ccc gtg acc gtg agc tgg      480
Gly Cys Leu Val Lys Asp Tyr Phe Pro Glu Pro Val Thr Val Ser Trp
145                 150                 155                 160

aac agc ggc gcc ttg acc agc ggc gtg cac acc ttc ccc gcc gtg ctg      528
Asn Ser Gly Ala Leu Thr Ser Gly Val His Thr Phe Pro Ala Val Leu
                165                 170                 175

cag agc agc ggc ctg tac agc ctg agc agc gtg gtg acc gtg ccc agc      576
Gln Ser Ser Gly Leu Tyr Ser Leu Ser Ser Val Val Thr Val Pro Ser
            180                 185                 190

agc agc ctg ggc acc cag acc tac atc tgc aac gtg aac cac aag ccc      624
Ser Ser Leu Gly Thr Gln Thr Tyr Ile Cys Asn Val Asn His Lys Pro
        195                 200                 205

agc aac acc aag gtg gac aaa cgc gtg gag ccc aag agc tgc gac aag      672
Ser Asn Thr Lys Val Asp Lys Arg Val Glu Pro Lys Ser Cys Asp Lys
    210                 215                 220

acc cac acc tgc ccc ccc tgc cct gcc ccc gag ctg ctg ggc gga ccc      720
Thr His Thr Cys Pro Pro Cys Pro Ala Pro Glu Leu Leu Gly Gly Pro
225                 230                 235                 240

tcc gtg ttc ctg ttc ccc ccc aag ccc aag gac acc ctc atg atc agc      768
Ser Val Phe Leu Phe Pro Pro Lys Pro Lys Asp Thr Leu Met Ile Ser
                245                 250                 255

cgg acc ccc gag gtg acc tgc gtg gtg gtg gac gtg agc cac gag gac      816
Arg Thr Pro Glu Val Thr Cys Val Val Val Asp Val Ser His Glu Asp
            260                 265                 270

ccc gag gtg aag ttc aac tgg tac gtg gac ggc gtg gag gtg cac aac      864
Pro Glu Val Lys Phe Asn Trp Tyr Val Asp Gly Val Glu Val His Asn
        275                 280                 285

gcc aag acc aag ccc cgg gag gag cag tac aac agc acc tac cgg gtg      912
Ala Lys Thr Lys Pro Arg Glu Glu Gln Tyr Asn Ser Thr Tyr Arg Val
    290                 295                 300

gtg agc gtg ctc acc gtg ctg cac cag gac tgg ctg aac ggc aag gag      960
Val Ser Val Leu Thr Val Leu His Gln Asp Trp Leu Asn Gly Lys Glu
305                 310                 315                 320

tac aag tgc aag gtg agc aac aag gcc ctg cct gcc ccc atc gag aag     1008
Tyr Lys Cys Lys Val Ser Asn Lys Ala Leu Pro Ala Pro Ile Glu Lys
                325                 330                 335

acc atc agc aag gcc aag ggc cag ccc cgg gag ccc cag gtg tac acc     1056
Thr Ile Ser Lys Ala Lys Gly Gln Pro Arg Glu Pro Gln Val Tyr Thr
            340                 345                 350

ctg ccc ccc agc cgg gag gag atg acc aag aac cag gtg tcc ctc acc     1104
Leu Pro Pro Ser Arg Glu Glu Met Thr Lys Asn Gln Val Ser Leu Thr
        355                 360                 365

tgt ctg gtg aag ggc ttc tac ccc agc gac atc gcc gtg gag tgg gag     1152
Cys Leu Val Lys Gly Phe Tyr Pro Ser Asp Ile Ala Val Glu Trp Glu
    370                 375                 380

agc aac ggc cag ccc gag aac aac tac aag acc acc ccc cct gtg ctg     1200
Ser Asn Gly Gln Pro Glu Asn Asn Tyr Lys Thr Thr Pro Pro Val Leu
385                 390                 395                 400

gac agc gac ggc agc ttc ttc ctg tac agc aag ctc acc gtg gac aag     1248
Asp Ser Asp Gly Ser Phe Phe Leu Tyr Ser Lys Leu Thr Val Asp Lys
                405                 410                 415

agc cgg tgg cag cag ggc aac gtg ttc agc tgc agc gtg atg cac gag     1296
Ser Arg Trp Gln Gln Gly Asn Val Phe Ser Cys Ser Val Met His Glu
            420                 425                 430

gcc ctg cac aac cac tac acc cag aag agc ctg agc ctg agc ccc ggc     1344
Ala Leu His Asn His Tyr Thr Gln Lys Ser Leu Ser Leu Ser Pro Gly
        435                 440                 445

aag                                                                 1347
Lys
```

<210> SEQ ID NO 133
<211> LENGTH: 449
<212> TYPE: PRT
<213> ORGANISM: Homo sapiens

<400> SEQUENCE: 133

Glu Val Gln Leu Val Glu Ser Gly Ala Glu Val Lys Glu Pro Gly Glu
1               5                   10                  15

Ser Leu Lys Ile Ser Cys Lys Gly Ser Gly Tyr Thr Phe Ala Ser Tyr
            20                  25                  30

Trp Val Ala Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Val Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Trp Trp Gly Ser Leu His Ala Phe Asp Ile Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

```
Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 134
<211> LENGTH: 1359
<212> TYPE: DNA
<213> ORGANISM: Homo sapiens
<220> FEATURE:
<221> NAME/KEY: CDS
<222> LOCATION: (1)..(1359)

<400> SEQUENCE: 134

gag gtg cag ctg gtg gag acc gga gca gag gtg caa aag ccc ggg gag       48
Glu Val Gln Leu Val Glu Thr Gly Ala Glu Val Gln Lys Pro Gly Glu
1               5                   10                  15

tct ctg aag atc tcc tgt aag ggt tct gga tac acc ttt acc aac tac       96
Ser Leu Lys Ile Ser Cys Lys Gly Ser Gly Tyr Thr Phe Thr Asn Tyr
            20                  25                  30

tgg atc gcc tgg gtg cgc cag aag ccc ggg aaa ggc ctg gag tgg atg      144
Trp Ile Ala Trp Val Arg Gln Lys Pro Gly Lys Gly Leu Glu Trp Met
        35                  40                  45

ggg atc atc tat cct ggt gac tct gat acc aga tac agc ccg tcc ttc      192
Gly Ile Ile Tyr Pro Gly Asp Ser Asp Thr Arg Tyr Ser Pro Ser Phe
    50                  55                  60

caa ggc cag gtc acc atc tca gcc gac aag tcc atc agc acc gcc tac      240
Gln Gly Gln Val Thr Ile Ser Ala Asp Lys Ser Ile Ser Thr Ala Tyr
65                  70                  75                  80

ctg cag tgg agc agc ctg aag gcc tcg gac acc gcc atg tat tac tgt      288
Leu Gln Trp Ser Ser Leu Lys Ala Ser Asp Thr Ala Met Tyr Tyr Cys
                85                  90                  95

gcg aga cga tat tgt act act acc agc tgc agt gct ggg ttc gac ccc      336
Ala Arg Arg Tyr Cys Thr Thr Thr Ser Cys Ser Ala Gly Phe Asp Pro
            100                 105                 110

tgg ggc cag gga acc ctg gtc acc gtc tcg agt gct agc acc aag ggc      384
Trp Gly Gln Gly Thr Leu Val Thr Val Ser Ser Ala Ser Thr Lys Gly
        115                 120                 125

ccc agc gtg ttc ccc ctg gcc ccc agc agc aag agc acc agc ggc ggc      432
Pro Ser Val Phe Pro Leu Ala Pro Ser Ser Lys Ser Thr Ser Gly Gly
    130                 135                 140

aca gcc gcc ctg ggc tgc ctg gtg aag gac tac ttc ccc gag ccc gtg      480
Thr Ala Ala Leu Gly Cys Leu Val Lys Asp Tyr Phe Pro Glu Pro Val
145                 150                 155                 160

acc gtg agc tgg aac agc ggc gcc ttg acc agc ggc gtg cac acc ttc      528
Thr Val Ser Trp Asn Ser Gly Ala Leu Thr Ser Gly Val His Thr Phe
                165                 170                 175

ccc gcc gtg ctg cag agc agc ggc ctg tac agc ctg agc agc gtg gtg      576
Pro Ala Val Leu Gln Ser Ser Gly Leu Tyr Ser Leu Ser Ser Val Val
            180                 185                 190

acc gtg ccc agc agc agc ctg ggc acc cag acc tac atc tgc aac gtg      624
Thr Val Pro Ser Ser Ser Leu Gly Thr Gln Thr Tyr Ile Cys Asn Val
        195                 200                 205

aac cac aag ccc agc aac acc aag gtg gac aaa cgc gtg gag ccc aag      672
Asn His Lys Pro Ser Asn Thr Lys Val Asp Lys Arg Val Glu Pro Lys
    210                 215                 220
```

```
agc tgc gac aag acc cac acc tgc ccc ccc tgc cct gcc ccc gag ctg      720
Ser Cys Asp Lys Thr His Thr Cys Pro Pro Cys Pro Ala Pro Glu Leu
225                 230                 235                 240

ctg ggc gga ccc tcc gtg ttc ctg ttc ccc ccc aag ccc aag gac acc      768
Leu Gly Gly Pro Ser Val Phe Leu Phe Pro Pro Lys Pro Lys Asp Thr
                245                 250                 255

ctc atg atc agc cgg acc ccc gag gtg acc tgc gtg gtg gtg gac gtg      816
Leu Met Ile Ser Arg Thr Pro Glu Val Thr Cys Val Val Val Asp Val
            260                 265                 270

agc cac gag gac ccc gag gtg aag ttc aac tgg tac gtg gac ggc gtg      864
Ser His Glu Asp Pro Glu Val Lys Phe Asn Trp Tyr Val Asp Gly Val
        275                 280                 285

gag gtg cac aac gcc aag acc aag ccc cgg gag gag cag tac aac agc      912
Glu Val His Asn Ala Lys Thr Lys Pro Arg Glu Glu Gln Tyr Asn Ser
    290                 295                 300

acc tac cgg gtg gtg agc gtg ctc acc gtg ctg cac cag gac tgg ctg      960
Thr Tyr Arg Val Val Ser Val Leu Thr Val Leu His Gln Asp Trp Leu
305                 310                 315                 320

aac ggc aag gag tac aag tgc aag gtg agc aac aag gcc ctg cct gcc     1008
Asn Gly Lys Glu Tyr Lys Cys Lys Val Ser Asn Lys Ala Leu Pro Ala
                325                 330                 335

ccc atc gag aag acc atc agc aag gcc aag ggc cag ccc cgg gag ccc     1056
Pro Ile Glu Lys Thr Ile Ser Lys Ala Lys Gly Gln Pro Arg Glu Pro
            340                 345                 350

cag gtg tac acc ctg ccc ccc agc cgg gag gag atg acc aag aac cag     1104
Gln Val Tyr Thr Leu Pro Pro Ser Arg Glu Glu Met Thr Lys Asn Gln
        355                 360                 365

gtg tcc ctc acc tgt ctg gtg aag ggc ttc tac ccc agc gac atc gcc     1152
Val Ser Leu Thr Cys Leu Val Lys Gly Phe Tyr Pro Ser Asp Ile Ala
    370                 375                 380

gtg gag tgg gag agc aac ggc cag ccc gag aac aac tac aag acc acc     1200
Val Glu Trp Glu Ser Asn Gly Gln Pro Glu Asn Asn Tyr Lys Thr Thr
385                 390                 395                 400

ccc cct gtg ctg gac agc gac ggc agc ttc ttc ctg tac agc aag ctc     1248
Pro Pro Val Leu Asp Ser Asp Gly Ser Phe Phe Leu Tyr Ser Lys Leu
                405                 410                 415

acc gtg gac aag agc cgg tgg cag cag ggc aac gtg ttc agc tgc agc     1296
Thr Val Asp Lys Ser Arg Trp Gln Gln Gly Asn Val Phe Ser Cys Ser
            420                 425                 430

gtg atg cac gag gcc ctg cac aac cac tac acc cag aag agc ctg agc     1344
Val Met His Glu Ala Leu His Asn His Tyr Thr Gln Lys Ser Leu Ser
        435                 440                 445

ctg agc ccc ggc aag                                                 1359
Leu Ser Pro Gly Lys
    450
```

<210> SEQ ID NO 135
<211> LENGTH: 453
<212> TYPE: PRT
<213> ORGANISM: Homo sapiens

<400> SEQUENCE: 135

```
Glu Val Gln Leu Val Glu Thr Gly Ala Glu Val Gln Lys Pro Gly Glu
1               5                   10                  15

Ser Leu Lys Ile Ser Cys Lys Gly Ser Gly Tyr Thr Phe Thr Asn Tyr
            20                  25                  30

Trp Ile Ala Trp Val Arg Gln Lys Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60
```

```
Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Arg Tyr Cys Thr Thr Thr Ser Cys Ser Ala Gly Phe Asp Pro
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450
```

<210> SEQ ID NO 136
<211> LENGTH: 1350
<212> TYPE: DNA

```
<213> ORGANISM: Homo sapiens
<220> FEATURE:
<221> NAME/KEY: CDS
<222> LOCATION: (1)..(1350)

<400> SEQUENCE: 136

gag gtg cag ctg gtg gag tct ggg gca gag gtg aaa aag ccg ggg gag       48
Glu Val Gln Leu Val Glu Ser Gly Ala Glu Val Lys Lys Pro Gly Glu
1               5                   10                  15

tct ctg aag atc tcc tgt aag ggt tct gga tac agc ttt acc aag tac       96
Ser Leu Lys Ile Ser Cys Lys Gly Ser Gly Tyr Ser Phe Thr Lys Tyr
            20                  25                  30

tgg atc ggc tgg gtg cgc cag aag ccc ggg aaa ggc ctg gag tgg atg      144
Trp Ile Gly Trp Val Arg Gln Lys Pro Gly Lys Gly Leu Glu Trp Met
        35                  40                  45

ggg atc atc tat cct ggt gac tct gat acc aga tac agc ccg tcc ttc      192
Gly Ile Ile Tyr Pro Gly Asp Ser Asp Thr Arg Tyr Ser Pro Ser Phe
    50                  55                  60

caa ggc cag gtc acc atc tca acc gac aag tcc atc agc acc gcc tac      240
Gln Gly Gln Val Thr Ile Ser Thr Asp Lys Ser Ile Ser Thr Ala Tyr
65                  70                  75                  80

ctg cag tgg agc agc ctg aag gcc tcg gac acc gcc atg tat tac tgt      288
Leu Gln Trp Ser Ser Leu Lys Ala Ser Asp Thr Ala Met Tyr Tyr Cys
                85                  90                  95

gcg aga ctg ggg ggg ggg ata gca gca gca ttt gac tac tgg ggc cag      336
Ala Arg Leu Gly Gly Gly Ile Ala Ala Ala Phe Asp Tyr Trp Gly Gln
            100                 105                 110

gga acc ctg gtc acc gtc tcg agt gct agc acc aag ggc ccc agc gtg      384
Gly Thr Leu Val Thr Val Ser Ser Ala Ser Thr Lys Gly Pro Ser Val
        115                 120                 125

ttc ccc ctg gcc ccc agc agc aag agc acc agc ggc ggc aca gcc gcc      432
Phe Pro Leu Ala Pro Ser Ser Lys Ser Thr Ser Gly Gly Thr Ala Ala
    130                 135                 140

ctg ggc tgc ctg gtg aag gac tac ttc ccc gag ccc gtg acc gtg agc      480
Leu Gly Cys Leu Val Lys Asp Tyr Phe Pro Glu Pro Val Thr Val Ser
145                 150                 155                 160

tgg aac agc ggc gcc ttg acc agc ggc gtg cac acc ttc ccc gcc gtg      528
Trp Asn Ser Gly Ala Leu Thr Ser Gly Val His Thr Phe Pro Ala Val
                165                 170                 175

ctg cag agc agc ggc ctg tac agc ctg agc agc gtg gtg acc gtg ccc      576
Leu Gln Ser Ser Gly Leu Tyr Ser Leu Ser Ser Val Val Thr Val Pro
            180                 185                 190

agc agc agc ctg ggc acc cag acc tac atc tgc aac gtg aac cac aag      624
Ser Ser Ser Leu Gly Thr Gln Thr Tyr Ile Cys Asn Val Asn His Lys
        195                 200                 205

ccc agc aac acc aag gtg gac aaa cgc gtg gag ccc aag agc tgc gac      672
Pro Ser Asn Thr Lys Val Asp Lys Arg Val Glu Pro Lys Ser Cys Asp
    210                 215                 220

aag acc cac acc tgc ccc ccc tgc cct gcc ccc gag ctg ctg ggc gga      720
Lys Thr His Thr Cys Pro Pro Cys Pro Ala Pro Glu Leu Leu Gly Gly
225                 230                 235                 240

ccc tcc gtg ttc ctg ttc ccc ccc aag ccc aag gac acc ctc atg atc      768
Pro Ser Val Phe Leu Phe Pro Pro Lys Pro Lys Asp Thr Leu Met Ile
                245                 250                 255

agc cgg acc ccc gag gtg acc tgc gtg gtg gtg gac gtg agc cac gag      816
Ser Arg Thr Pro Glu Val Thr Cys Val Val Val Asp Val Ser His Glu
            260                 265                 270

gac ccc gag gtg aag ttc aac tgg tac gtg gac ggc gtg gag gtg cac      864
Asp Pro Glu Val Lys Phe Asn Trp Tyr Val Asp Gly Val Glu Val His
        275                 280                 285

aac gcc aag acc aag ccc cgg gag gag cag tac aac agc acc tac cgg      912
```

```
Asn Ala Lys Thr Lys Pro Arg Glu Glu Gln Tyr Asn Ser Thr Tyr Arg
    290                 295                 300

gtg gtg agc gtg ctc acc gtg ctg cac cag gac tgg ctg aac ggc aag      960
Val Val Ser Val Leu Thr Val Leu His Gln Asp Trp Leu Asn Gly Lys
305                 310                 315                 320

gag tac aag tgc aag gtg agc aac aag gcc ctg cct gcc ccc atc gag     1008
Glu Tyr Lys Cys Lys Val Ser Asn Lys Ala Leu Pro Ala Pro Ile Glu
                325                 330                 335

aag acc atc agc aag gcc aag ggc cag ccc cgg gag ccc cag gtg tac     1056
Lys Thr Ile Ser Lys Ala Lys Gly Gln Pro Arg Glu Pro Gln Val Tyr
            340                 345                 350

acc ctg ccc ccc agc cgg gag gag atg acc aag aac cag gtg tcc ctc     1104
Thr Leu Pro Pro Ser Arg Glu Glu Met Thr Lys Asn Gln Val Ser Leu
        355                 360                 365

acc tgt ctg gtg aag ggc ttc tac ccc agc gac atc gcc gtg gag tgg     1152
Thr Cys Leu Val Lys Gly Phe Tyr Pro Ser Asp Ile Ala Val Glu Trp
    370                 375                 380

gag agc aac ggc cag ccc gag aac aac tac aag acc acc ccc cct gtg     1200
Glu Ser Asn Gly Gln Pro Glu Asn Asn Tyr Lys Thr Thr Pro Pro Val
385                 390                 395                 400

ctg gac agc gac ggc agc ttc ttc ctg tac agc aag ctc acc gtg gac     1248
Leu Asp Ser Asp Gly Ser Phe Phe Leu Tyr Ser Lys Leu Thr Val Asp
                405                 410                 415

aag agc cgg tgg cag cag ggc aac gtg ttc agc tgc agc gtg atg cac     1296
Lys Ser Arg Trp Gln Gln Gly Asn Val Phe Ser Cys Ser Val Met His
            420                 425                 430

gag gcc ctg cac aac cac tac acc cag aag agc ctg agc ctg agc ccc     1344
Glu Ala Leu His Asn His Tyr Thr Gln Lys Ser Leu Ser Leu Ser Pro
        435                 440                 445

ggc aag                                                             1350
Gly Lys
    450


<210> SEQ ID NO 137
<211> LENGTH: 450
<212> TYPE: PRT
<213> ORGANISM: Homo sapiens

<400> SEQUENCE: 137

Glu Val Gln Leu Val Glu Ser Gly Ala Glu Val Lys Lys Pro Gly Glu
1               5                   10                  15

Ser Leu Lys Ile Ser Cys Lys Gly Ser Gly Tyr Ser Phe Thr Lys Tyr
            20                  25                  30

Trp Ile Gly Trp Val Arg Gln Lys Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Thr Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu Gly Gly Gly Ile Ala Ala Ala Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160
```

```
Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 138
<211> LENGTH: 1350
<212> TYPE: DNA
<213> ORGANISM: Homo sapiens
<220> FEATURE:
<221> NAME/KEY: CDS
<222> LOCATION: (1)..(1350)

<400> SEQUENCE: 138

gag gtg cag ctg gtg gag tcc gga gca gag gtg aaa aag ccg ggg gag       48
Glu Val Gln Leu Val Glu Ser Gly Ala Glu Val Lys Lys Pro Gly Glu
1               5                   10                  15

tct ctg aag atc tcc tgt aag ggt tct gga tac acc ttt acc cgc tac       96
Ser Leu Lys Ile Ser Cys Lys Gly Ser Gly Tyr Thr Phe Thr Arg Tyr
            20                  25                  30

tgg atc ggc tgg gtg cgc cag atg ccc ggg aaa ggc ctg gag tgg atg      144
Trp Ile Gly Trp Val Arg Gln Met Pro Gly Lys Gly Leu Glu Trp Met
        35                  40                  45
```

-continued

```
gga atc atc tat cct ggt gac tct gat acc aga tac agc ccg tcc ttc      192
Gly Ile Ile Tyr Pro Gly Asp Ser Asp Thr Arg Tyr Ser Pro Ser Phe
    50                  55                  60

cga ggc cag gtc acc atc tca gcc gac aag tcc atc agc acc gcc tac      240
Arg Gly Gln Val Thr Ile Ser Ala Asp Lys Ser Ile Ser Thr Ala Tyr
65                  70                  75                  80

ctg cag tgg agc agc ctg aag gcc tcg gac acc gcc atg tat tac tgt      288
Leu Gln Trp Ser Ser Leu Lys Ala Ser Asp Thr Ala Met Tyr Tyr Cys
                85                  90                  95

gcg aga cgt atg ggg gct gct tct gcc tac ttt gac aac tgg ggc cag      336
Ala Arg Arg Met Gly Ala Ala Ser Ala Tyr Phe Asp Asn Trp Gly Gln
            100                 105                 110

gga acc ctg gtc acc gtc tcg agt gct agc acc aag ggc ccc agc gtg      384
Gly Thr Leu Val Thr Val Ser Ser Ala Ser Thr Lys Gly Pro Ser Val
        115                 120                 125

ttc ccc ctg gcc ccc agc agc aag agc acc agc ggc ggc aca gcc gcc      432
Phe Pro Leu Ala Pro Ser Ser Lys Ser Thr Ser Gly Gly Thr Ala Ala
    130                 135                 140

ctg ggc tgc ctg gtg aag gac tac ttc ccc gag ccc gtg acc gtg agc      480
Leu Gly Cys Leu Val Lys Asp Tyr Phe Pro Glu Pro Val Thr Val Ser
145                 150                 155                 160

tgg aac agc ggc gcc ttg acc agc ggc gtg cac acc ttc ccc gcc gtg      528
Trp Asn Ser Gly Ala Leu Thr Ser Gly Val His Thr Phe Pro Ala Val
                165                 170                 175

ctg cag agc agc ggc ctg tac agc ctg agc agc gtg gtg acc gtg ccc      576
Leu Gln Ser Ser Gly Leu Tyr Ser Leu Ser Ser Val Val Thr Val Pro
            180                 185                 190

agc agc agc ctg ggc acc cag acc tac atc tgc aac gtg aac cac aag      624
Ser Ser Ser Leu Gly Thr Gln Thr Tyr Ile Cys Asn Val Asn His Lys
        195                 200                 205

ccc agc aac acc aag gtg gac aaa cgc gtg gag ccc aag agc tgc gac      672
Pro Ser Asn Thr Lys Val Asp Lys Arg Val Glu Pro Lys Ser Cys Asp
    210                 215                 220

aag acc cac acc tgc ccc ccc tgc cct gcc ccc gag ctg ctg ggc gga      720
Lys Thr His Thr Cys Pro Pro Cys Pro Ala Pro Glu Leu Leu Gly Gly
225                 230                 235                 240

ccc tcc gtg ttc ctg ttc ccc ccc aag ccc aag gac acc ctc atg atc      768
Pro Ser Val Phe Leu Phe Pro Pro Lys Pro Lys Asp Thr Leu Met Ile
                245                 250                 255

agc cgg acc ccc gag gtg acc tgc gtg gtg gtg gac gtg agc cac gag      816
Ser Arg Thr Pro Glu Val Thr Cys Val Val Val Asp Val Ser His Glu
            260                 265                 270

gac ccc gag gtg aag ttc aac tgg tac gtg gac ggc gtg gag gtg cac      864
Asp Pro Glu Val Lys Phe Asn Trp Tyr Val Asp Gly Val Glu Val His
        275                 280                 285

aac gcc aag acc aag ccc cgg gag gag cag tac aac agc acc tac cgg      912
Asn Ala Lys Thr Lys Pro Arg Glu Glu Gln Tyr Asn Ser Thr Tyr Arg
    290                 295                 300

gtg gtg agc gtg ctc acc gtg ctg cac cag gac tgg ctg aac ggc aag      960
Val Val Ser Val Leu Thr Val Leu His Gln Asp Trp Leu Asn Gly Lys
305                 310                 315                 320

gag tac aag tgc aag gtg agc aac aag gcc ctg cct gcc ccc atc gag     1008
Glu Tyr Lys Cys Lys Val Ser Asn Lys Ala Leu Pro Ala Pro Ile Glu
                325                 330                 335

aag acc atc agc aag gcc aag ggc cag ccc cgg gag ccc cag gtg tac     1056
Lys Thr Ile Ser Lys Ala Lys Gly Gln Pro Arg Glu Pro Gln Val Tyr
            340                 345                 350

acc ctg ccc ccc agc cgg gag gag atg acc aag aac cag gtg tcc ctc     1104
Thr Leu Pro Pro Ser Arg Glu Glu Met Thr Lys Asn Gln Val Ser Leu
        355                 360                 365
```

```
acc tgt ctg gtg aag ggc ttc tac ccc agc gac atc gcc gtg gag tgg      1152
Thr Cys Leu Val Lys Gly Phe Tyr Pro Ser Asp Ile Ala Val Glu Trp
    370                 375                 380

gag agc aac ggc cag ccc gag aac aac tac aag acc acc ccc cct gtg      1200
Glu Ser Asn Gly Gln Pro Glu Asn Asn Tyr Lys Thr Thr Pro Pro Val
385                 390                 395                 400

ctg gac agc gac ggc agc ttc ttc ctg tac agc aag ctc acc gtg gac      1248
Leu Asp Ser Asp Gly Ser Phe Phe Leu Tyr Ser Lys Leu Thr Val Asp
                405                 410                 415

aag agc cgg tgg cag cag ggc aac gtg ttc agc tgc agc gtg atg cac      1296
Lys Ser Arg Trp Gln Gln Gly Asn Val Phe Ser Cys Ser Val Met His
            420                 425                 430

gag gcc ctg cac aac cac tac acc cag aag agc ctg agc ctg agc ccc      1344
Glu Ala Leu His Asn His Tyr Thr Gln Lys Ser Leu Ser Leu Ser Pro
        435                 440                 445

ggc aag                                                              1350
Gly Lys
    450


<210> SEQ ID NO 139
<211> LENGTH: 450
<212> TYPE: PRT
<213> ORGANISM: Homo sapiens

<400> SEQUENCE: 139

Glu Val Gln Leu Val Glu Ser Gly Ala Glu Val Lys Lys Pro Gly Glu
1               5                   10                  15

Ser Leu Lys Ile Ser Cys Lys Gly Ser Gly Tyr Thr Phe Thr Arg Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Arg Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Arg Met Gly Ala Ala Ser Ala Tyr Phe Asp Asn Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255
```

```
Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 140
<211> LENGTH: 1359
<212> TYPE: DNA
<213> ORGANISM: Homo sapiens
<220> FEATURE:
<221> NAME/KEY: CDS
<222> LOCATION: (1)..(1359)

<400> SEQUENCE: 140

gag gtg cag ctg gtg gag tct ggg gca gag gtg aaa aag ccg ggg gag       48
Glu Val Gln Leu Val Glu Ser Gly Ala Glu Val Lys Lys Pro Gly Glu
1               5                   10                  15

tct ctg aag atc tcc tgt aag ggt tct gga tac agt ttt acc agc tac       96
Ser Leu Lys Ile Ser Cys Lys Gly Ser Gly Tyr Ser Phe Thr Ser Tyr
            20                  25                  30

tgg atc ggc tgg gtg cgc cag atg ccc ggg aaa ggc ctg gag tgg atg      144
Trp Ile Gly Trp Val Arg Gln Met Pro Gly Lys Gly Leu Glu Trp Met
        35                  40                  45

ggg atc atc tat cct ggt gac tct gat acc aga tac agc ccg tcc ttc      192
Gly Ile Ile Tyr Pro Gly Asp Ser Asp Thr Arg Tyr Ser Pro Ser Phe
    50                  55                  60

caa ggc cag gtc acc atc tca gcc gac aag tcc ata agc acc gcc tac      240
Gln Gly Gln Val Thr Ile Ser Ala Asp Lys Ser Ile Ser Thr Ala Tyr
65                  70                  75                  80

ctg cag tgg acc agc ctg aag gcc tcg gac acc gcc gtg tat ttc tgt      288
Leu Gln Trp Thr Ser Leu Lys Ala Ser Asp Thr Ala Val Tyr Phe Cys
                85                  90                  95

gcg aga ctc ggc gaa ttc cgt aga act gga aat agc tac ttt gac tac      336
Ala Arg Leu Gly Glu Phe Arg Arg Thr Gly Asn Ser Tyr Phe Asp Tyr
            100                 105                 110

tgg ggc cag gga acc ctg gtc acc gtc tcg agt gct agc acc aag ggc      384
```

-continued

```
Trp Gly Gln Gly Thr Leu Val Thr Val Ser Ser Ala Ser Thr Lys Gly
        115                 120                 125

ccc agc gtg ttc ccc ctg gcc ccc agc agc aag agc acc agc ggc ggc      432
Pro Ser Val Phe Pro Leu Ala Pro Ser Ser Lys Ser Thr Ser Gly Gly
    130                 135                 140

aca gcc gcc ctg ggc tgc ctg gtg aag gac tac ttc ccc gag ccc gtg      480
Thr Ala Ala Leu Gly Cys Leu Val Lys Asp Tyr Phe Pro Glu Pro Val
145                 150                 155                 160

acc gtg agc tgg aac agc ggc gcc ttg acc agc ggc gtg cac acc ttc      528
Thr Val Ser Trp Asn Ser Gly Ala Leu Thr Ser Gly Val His Thr Phe
                165                 170                 175

ccc gcc gtg ctg cag agc agc ggc ctg tac agc ctg agc agc gtg gtg      576
Pro Ala Val Leu Gln Ser Ser Gly Leu Tyr Ser Leu Ser Ser Val Val
            180                 185                 190

acc gtg ccc agc agc agc ctg ggc acc cag acc tac atc tgc aac gtg      624
Thr Val Pro Ser Ser Ser Leu Gly Thr Gln Thr Tyr Ile Cys Asn Val
        195                 200                 205

aac cac aag ccc agc aac acc aag gtg gac aaa cgc gtg gag ccc aag      672
Asn His Lys Pro Ser Asn Thr Lys Val Asp Lys Arg Val Glu Pro Lys
    210                 215                 220

agc tgc gac aag acc cac acc tgc ccc ccc tgc cct gcc ccc gag ctg      720
Ser Cys Asp Lys Thr His Thr Cys Pro Pro Cys Pro Ala Pro Glu Leu
225                 230                 235                 240

ctg ggc gga ccc tcc gtg ttc ctg ttc ccc ccc aag ccc aag gac acc      768
Leu Gly Gly Pro Ser Val Phe Leu Phe Pro Pro Lys Pro Lys Asp Thr
                245                 250                 255

ctc atg atc agc cgg acc ccc gag gtg acc tgc gtg gtg gtg gac gtg      816
Leu Met Ile Ser Arg Thr Pro Glu Val Thr Cys Val Val Val Asp Val
            260                 265                 270

agc cac gag gac ccc gag gtg aag ttc aac tgg tac gtg gac ggc gtg      864
Ser His Glu Asp Pro Glu Val Lys Phe Asn Trp Tyr Val Asp Gly Val
        275                 280                 285

gag gtg cac aac gcc aag acc aag ccc cgg gag gag cag tac aac agc      912
Glu Val His Asn Ala Lys Thr Lys Pro Arg Glu Glu Gln Tyr Asn Ser
    290                 295                 300

acc tac cgg gtg gtg agc gtg ctc acc gtg ctg cac cag gac tgg ctg      960
Thr Tyr Arg Val Val Ser Val Leu Thr Val Leu His Gln Asp Trp Leu
305                 310                 315                 320

aac ggc aag gag tac aag tgc aag gtg agc aac aag gcc ctg cct gcc     1008
Asn Gly Lys Glu Tyr Lys Cys Lys Val Ser Asn Lys Ala Leu Pro Ala
                325                 330                 335

ccc atc gag aag acc atc agc aag gcc aag ggc cag ccc cgg gag ccc     1056
Pro Ile Glu Lys Thr Ile Ser Lys Ala Lys Gly Gln Pro Arg Glu Pro
            340                 345                 350

cag gtg tac acc ctg ccc ccc agc cgg gag gag atg acc aag aac cag     1104
Gln Val Tyr Thr Leu Pro Pro Ser Arg Glu Glu Met Thr Lys Asn Gln
        355                 360                 365

gtg tcc ctc acc tgt ctg gtg aag ggc ttc tac ccc agc gac atc gcc     1152
Val Ser Leu Thr Cys Leu Val Lys Gly Phe Tyr Pro Ser Asp Ile Ala
    370                 375                 380

gtg gag tgg gag agc aac ggc cag ccc gag aac aac tac aag acc acc     1200
Val Glu Trp Glu Ser Asn Gly Gln Pro Glu Asn Asn Tyr Lys Thr Thr
385                 390                 395                 400

ccc cct gtg ctg gac agc gac ggc agc ttc ttc ctg tac agc aag ctc     1248
Pro Pro Val Leu Asp Ser Asp Gly Ser Phe Phe Leu Tyr Ser Lys Leu
                405                 410                 415

acc gtg gac aag agc cgg tgg cag cag ggc aac gtg ttc agc tgc agc     1296
Thr Val Asp Lys Ser Arg Trp Gln Gln Gly Asn Val Phe Ser Cys Ser
            420                 425                 430

gtg atg cac gag gcc ctg cac aac cac tac acc cag aag agc ctg agc     1344
```

```
Val Met His Glu Ala Leu His Asn His Tyr Thr Gln Lys Ser Leu Ser
        435                 440                 445

ctg agc ccc ggc aag                                             1359
Leu Ser Pro Gly Lys
    450


<210> SEQ ID NO 141
<211> LENGTH: 453
<212> TYPE: PRT
<213> ORGANISM: Homo sapiens

<400> SEQUENCE: 141

Glu Val Gln Leu Val Glu Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Thr Ser Leu Lys Ala Ser Asp Thr Ala Val Tyr Phe Cys
                85                  90                  95

Ala Arg Leu Gly Glu Phe Arg Arg Thr Gly Asn Ser Tyr Phe Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350
```

```
Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450


<210> SEQ ID NO 142
<211> LENGTH: 1335
<212> TYPE: DNA
<213> ORGANISM: Homo sapiens
<220> FEATURE:
<221> NAME/KEY: CDS
<222> LOCATION: (1)..(1335)

<400> SEQUENCE: 142

gag gtg cag ctg gtg gag act ggg gga gac ttg gta cag cct ggg ggg       48
Glu Val Gln Leu Val Glu Thr Gly Gly Asp Leu Val Gln Pro Gly Gly
1               5                   10                  15

tcc ctg aga ctc tcc tgt gca gcc tct gga ttc acc ttt agc agc tat       96
Ser Leu Arg Leu Ser Cys Ala Ala Ser Gly Phe Thr Phe Ser Ser Tyr
            20                  25                  30

gcc atg ggc tgg gtc cgc cag gct cca ggg aag ggg ctg gag tgg ctt      144
Ala Met Gly Trp Val Arg Gln Ala Pro Gly Lys Gly Leu Glu Trp Leu
        35                  40                  45

tcg tac att cgg aat gat ggt agt gtc atc tat tac gca gac tct gtg      192
Ser Tyr Ile Arg Asn Asp Gly Ser Val Ile Tyr Tyr Ala Asp Ser Val
    50                  55                  60

aag ggt cga ttc acc atc tcc aga gac aat gcc aag aac tca ctg tat      240
Lys Gly Arg Phe Thr Ile Ser Arg Asp Asn Ala Lys Asn Ser Leu Tyr
65                  70                  75                  80

ctg caa atg aac agc cta aga gcc gag gac acg gct gtg tat tac tgt      288
Leu Gln Met Asn Ser Leu Arg Ala Glu Asp Thr Ala Val Tyr Tyr Cys
                85                  90                  95

gcg aga aga ggg tac ctc gat ctc tgg ggc cgt gga acc ctg gtc acc      336
Ala Arg Arg Gly Tyr Leu Asp Leu Trp Gly Arg Gly Thr Leu Val Thr
            100                 105                 110

gtc tcg agt gct agc acc aag ggc ccc agc gtg ttc ccc ctg gcc ccc      384
Val Ser Ser Ala Ser Thr Lys Gly Pro Ser Val Phe Pro Leu Ala Pro
        115                 120                 125

agc agc aag agc acc agc ggc ggc aca gcc gcc ctg ggc tgc ctg gtg      432
Ser Ser Lys Ser Thr Ser Gly Gly Thr Ala Ala Leu Gly Cys Leu Val
    130                 135                 140

aag gac tac ttc ccc gag ccc gtg acc gtg agc tgg aac agc ggc gcc      480
Lys Asp Tyr Phe Pro Glu Pro Val Thr Val Ser Trp Asn Ser Gly Ala
145                 150                 155                 160

ttg acc agc ggc gtg cac acc ttc ccc gcc gtg ctg cag agc agc ggc      528
Leu Thr Ser Gly Val His Thr Phe Pro Ala Val Leu Gln Ser Ser Gly
                165                 170                 175

ctg tac agc ctg agc agc gtg gtg acc gtg ccc agc agc agc ctg ggc      576
Leu Tyr Ser Leu Ser Ser Val Val Thr Val Pro Ser Ser Ser Leu Gly
            180                 185                 190
```

```
acc cag acc tac atc tgc aac gtg aac cac aag ccc agc aac acc aag      624
Thr Gln Thr Tyr Ile Cys Asn Val Asn His Lys Pro Ser Asn Thr Lys
        195                 200                 205

gtg gac aaa cgc gtg gag ccc aag agc tgc gac aag acc cac acc tgc      672
Val Asp Lys Arg Val Glu Pro Lys Ser Cys Asp Lys Thr His Thr Cys
    210                 215                 220

ccc ccc tgc cct gcc ccc gag ctg ctg ggc gga ccc tcc gtg ttc ctg      720
Pro Pro Cys Pro Ala Pro Glu Leu Leu Gly Gly Pro Ser Val Phe Leu
225                 230                 235                 240

ttc ccc ccc aag ccc aag gac acc ctc atg atc agc cgg acc ccc gag      768
Phe Pro Pro Lys Pro Lys Asp Thr Leu Met Ile Ser Arg Thr Pro Glu
                245                 250                 255

gtg acc tgc gtg gtg gtg gac gtg agc cac gag gac ccc gag gtg aag      816
Val Thr Cys Val Val Val Asp Val Ser His Glu Asp Pro Glu Val Lys
            260                 265                 270

ttc aac tgg tac gtg gac ggc gtg gag gtg cac aac gcc aag acc aag      864
Phe Asn Trp Tyr Val Asp Gly Val Glu Val His Asn Ala Lys Thr Lys
        275                 280                 285

ccc cgg gag gag cag tac aac agc acc tac cgg gtg gtg agc gtg ctc      912
Pro Arg Glu Glu Gln Tyr Asn Ser Thr Tyr Arg Val Val Ser Val Leu
    290                 295                 300

acc gtg ctg cac cag gac tgg ctg aac ggc aag gag tac aag tgc aag      960
Thr Val Leu His Gln Asp Trp Leu Asn Gly Lys Glu Tyr Lys Cys Lys
305                 310                 315                 320

gtg agc aac aag gcc ctg cct gcc ccc atc gag aag acc atc agc aag     1008
Val Ser Asn Lys Ala Leu Pro Ala Pro Ile Glu Lys Thr Ile Ser Lys
                325                 330                 335

gcc aag ggc cag ccc cgg gag ccc cag gtg tac acc ctg ccc ccc agc     1056
Ala Lys Gly Gln Pro Arg Glu Pro Gln Val Tyr Thr Leu Pro Pro Ser
            340                 345                 350

cgg gag gag atg acc aag aac cag gtg tcc ctc acc tgt ctg gtg aag     1104
Arg Glu Glu Met Thr Lys Asn Gln Val Ser Leu Thr Cys Leu Val Lys
        355                 360                 365

ggc ttc tac ccc agc gac atc gcc gtg gag tgg gag agc aac ggc cag     1152
Gly Phe Tyr Pro Ser Asp Ile Ala Val Glu Trp Glu Ser Asn Gly Gln
    370                 375                 380

ccc gag aac aac tac aag acc acc ccc cct gtg ctg gac agc gac ggc     1200
Pro Glu Asn Asn Tyr Lys Thr Thr Pro Pro Val Leu Asp Ser Asp Gly
385                 390                 395                 400

agc ttc ttc ctg tac agc aag ctc acc gtg gac aag agc cgg tgg cag     1248
Ser Phe Phe Leu Tyr Ser Lys Leu Thr Val Asp Lys Ser Arg Trp Gln
                405                 410                 415

cag ggc aac gtg ttc agc tgc agc gtg atg cac gag gcc ctg cac aac     1296
Gln Gly Asn Val Phe Ser Cys Ser Val Met His Glu Ala Leu His Asn
            420                 425                 430

cac tac acc cag aag agc ctg agc ctg agc ccc ggc aag                 1335
His Tyr Thr Gln Lys Ser Leu Ser Leu Ser Pro Gly Lys
        435                 440                 445


<210> SEQ ID NO 143
<211> LENGTH: 445
<212> TYPE: PRT
<213> ORGANISM: Homo sapiens

<400> SEQUENCE: 143

Glu Val Gln Leu Val Glu Thr Gly Gly Asp Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Gly Trp Val Arg Gln Ala Pro Gly Lys Gly Leu Glu Trp Leu
```

```
        35                  40                  45

Ser Tyr Ile Arg Asn Asp Gly Ser Val Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Gly Tyr Leu Asp Leu Trp Gly Arg Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445
```

<210> SEQ ID NO 144
<211> LENGTH: 1350

```
<212> TYPE: DNA
<213> ORGANISM: Homo sapiens
<220> FEATURE:
<221> NAME/KEY: CDS
<222> LOCATION: (1)..(1350)

<400> SEQUENCE: 144

gag gtg cag ctg gtg gag tct ggg gga ggc ttg gtc cag cct ggg ggg       48
Glu Val Gln Leu Val Glu Ser Gly Gly Gly Leu Val Gln Pro Gly Gly
1               5                   10                  15

tcc ctg aga gtc tcc tgt gca gcc tct gga ttc acg ttt agt agc tat       96
Ser Leu Arg Val Ser Cys Ala Ala Ser Gly Phe Thr Phe Ser Ser Tyr
            20                  25                  30

tgg atg acc tgg gtc cgc cag gct cca gga aag ggg ctg gag tgg gtg      144
Trp Met Thr Trp Val Arg Gln Ala Pro Gly Lys Gly Leu Glu Trp Val
        35                  40                  45

gcc aac ata aag aaa gat gga agt gag aaa tat tat gtg gac tct gtg      192
Ala Asn Ile Lys Lys Asp Gly Ser Glu Lys Tyr Tyr Val Asp Ser Val
    50                  55                  60

aag ggc cga ttc agc atc tcc aga gac aac gcc aag gat tca ctg tat      240
Lys Gly Arg Phe Ser Ile Ser Arg Asp Asn Ala Lys Asp Ser Leu Tyr
65                  70                  75                  80

ctg caa atg agc agc ctg aga gcc gag gac acg gct gtg tat tac tgt      288
Leu Gln Met Ser Ser Leu Arg Ala Glu Asp Thr Ala Val Tyr Tyr Cys
                85                  90                  95

gcg agg ggg ggc agc agc tcg tcg ttt tat tgg tgg ctc tgg ggc aaa      336
Ala Arg Gly Gly Ser Ser Ser Ser Phe Tyr Trp Trp Leu Trp Gly Lys
            100                 105                 110

ggg acc acg gtc acc gtc tcg agt gct agc acc aag ggc ccc agc gtg      384
Gly Thr Thr Val Thr Val Ser Ser Ala Ser Thr Lys Gly Pro Ser Val
        115                 120                 125

ttc ccc ctg gcc ccc agc agc aag agc acc agc ggc ggc aca gcc gcc      432
Phe Pro Leu Ala Pro Ser Ser Lys Ser Thr Ser Gly Gly Thr Ala Ala
    130                 135                 140

ctg ggc tgc ctg gtg aag gac tac ttc ccc gag ccc gtg acc gtg agc      480
Leu Gly Cys Leu Val Lys Asp Tyr Phe Pro Glu Pro Val Thr Val Ser
145                 150                 155                 160

tgg aac agc ggc gcc ttg acc agc ggc gtg cac acc ttc ccc gcc gtg      528
Trp Asn Ser Gly Ala Leu Thr Ser Gly Val His Thr Phe Pro Ala Val
                165                 170                 175

ctg cag agc agc ggc ctg tac agc ctg agc agc gtg gtg acc gtg ccc      576
Leu Gln Ser Ser Gly Leu Tyr Ser Leu Ser Ser Val Val Thr Val Pro
            180                 185                 190

agc agc agc ctg ggc acc cag acc tac atc tgc aac gtg aac cac aag      624
Ser Ser Ser Leu Gly Thr Gln Thr Tyr Ile Cys Asn Val Asn His Lys
        195                 200                 205

ccc agc aac acc aag gtg gac aaa cgc gtg gag ccc aag agc tgc gac      672
Pro Ser Asn Thr Lys Val Asp Lys Arg Val Glu Pro Lys Ser Cys Asp
    210                 215                 220

aag acc cac acc tgc ccc ccc tgc cct gcc ccc gag ctg ctg ggc gga      720
Lys Thr His Thr Cys Pro Pro Cys Pro Ala Pro Glu Leu Leu Gly Gly
225                 230                 235                 240

ccc tcc gtg ttc ctg ttc ccc ccc aag ccc aag gac acc ctc atg atc      768
Pro Ser Val Phe Leu Phe Pro Pro Lys Pro Lys Asp Thr Leu Met Ile
                245                 250                 255

agc cgg acc ccc gag gtg acc tgc gtg gtg gtg gac gtg agc cac gag      816
Ser Arg Thr Pro Glu Val Thr Cys Val Val Val Asp Val Ser His Glu
            260                 265                 270

gac ccc gag gtg aag ttc aac tgg tac gtg gac ggc gtg gag gtg cac      864
Asp Pro Glu Val Lys Phe Asn Trp Tyr Val Asp Gly Val Glu Val His
        275                 280                 285
```

```
aac gcc aag acc aag ccc cgg gag gag cag tac aac agc acc tac cgg      912
Asn Ala Lys Thr Lys Pro Arg Glu Glu Gln Tyr Asn Ser Thr Tyr Arg
    290                 295                 300

gtg gtg agc gtg ctc acc gtg ctg cac cag gac tgg ctg aac ggc aag      960
Val Val Ser Val Leu Thr Val Leu His Gln Asp Trp Leu Asn Gly Lys
305                 310                 315                 320

gag tac aag tgc aag gtg agc aac aag gcc ctg cct gcc ccc atc gag     1008
Glu Tyr Lys Cys Lys Val Ser Asn Lys Ala Leu Pro Ala Pro Ile Glu
                325                 330                 335

aag acc atc agc aag gcc aag ggc cag ccc cgg gag ccc cag gtg tac     1056
Lys Thr Ile Ser Lys Ala Lys Gly Gln Pro Arg Glu Pro Gln Val Tyr
            340                 345                 350

acc ctg ccc ccc agc cgg gag gag atg acc aag aac cag gtg tcc ctc     1104
Thr Leu Pro Pro Ser Arg Glu Glu Met Thr Lys Asn Gln Val Ser Leu
        355                 360                 365

acc tgt ctg gtg aag ggc ttc tac ccc agc gac atc gcc gtg gag tgg     1152
Thr Cys Leu Val Lys Gly Phe Tyr Pro Ser Asp Ile Ala Val Glu Trp
    370                 375                 380

gag agc aac ggc cag ccc gag aac aac tac aag acc acc ccc cct gtg     1200
Glu Ser Asn Gly Gln Pro Glu Asn Asn Tyr Lys Thr Thr Pro Pro Val
385                 390                 395                 400

ctg gac agc gac ggc agc ttc ttc ctg tac agc aag ctc acc gtg gac     1248
Leu Asp Ser Asp Gly Ser Phe Phe Leu Tyr Ser Lys Leu Thr Val Asp
                405                 410                 415

aag agc cgg tgg cag cag ggc aac gtg ttc agc tgc agc gtg atg cac     1296
Lys Ser Arg Trp Gln Gln Gly Asn Val Phe Ser Cys Ser Val Met His
            420                 425                 430

gag gcc ctg cac aac cac tac acc cag aag agc ctg agc ctg agc ccc     1344
Glu Ala Leu His Asn His Tyr Thr Gln Lys Ser Leu Ser Leu Ser Pro
        435                 440                 445

ggc aag                                                             1350
Gly Lys
    450


<210> SEQ ID NO 145
<211> LENGTH: 450
<212> TYPE: PRT
<213> ORGANISM: Homo sapiens

<400> SEQUENCE: 145

Glu Val Gln Leu Val Glu Ser Gly Gly Gly Leu Val Gln Pro Gly Gly
1               5                   10                  15

Ser Leu Arg Val Ser Cys Ala Ala Ser Gly Phe Thr Phe Ser Ser Tyr
            20                  25                  30

Trp Met Thr Trp Val Arg Gln Ala Pro Gly Lys Gly Leu Glu Trp Val
        35                  40                  45

Ala Asn Ile Lys Lys Asp Gly Ser Glu Lys Tyr Tyr Val Asp Ser Val
    50                  55                  60

Lys Gly Arg Phe Ser Ile Ser Arg Asp Asn Ala Lys Asp Ser Leu Tyr
65                  70                  75                  80

Leu Gln Met Ser Ser Leu Arg Ala Glu Asp Thr Ala Val Tyr Tyr Cys
                85                  90                  95

Ala Arg Gly Gly Ser Ser Ser Ser Phe Tyr Trp Trp Leu Trp Gly Lys
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
```

```
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 146
<211> LENGTH: 1353
<212> TYPE: DNA
<213> ORGANISM: Homo sapiens
<220> FEATURE:
<221> NAME/KEY: CDS
<222> LOCATION: (1)..(1353)

<400> SEQUENCE: 146

cag gtc cag ctg gtg cag tct gga gca gag gtg aaa aag ccg ggg gag       48
Gln Val Gln Leu Val Gln Ser Gly Ala Glu Val Lys Lys Pro Gly Glu
1               5                   10                  15

tct ctg aag atc tcc tgt aag ggt tct gga tac agc ttt acc agc tac       96
Ser Leu Lys Ile Ser Cys Lys Gly Ser Gly Tyr Ser Phe Thr Ser Tyr
            20                  25                  30

tgg atc ggc tgg gtg cgc cag atg ccc ggg aaa ggc ctg gag tgg atg      144
Trp Ile Gly Trp Val Arg Gln Met Pro Gly Lys Gly Leu Glu Trp Met
```

-continued

```
        35                  40                  45

ggg atc atc tat cct ggt gac tct gat acc aga tac agc ccg tcc ttc      192
Gly Ile Ile Tyr Pro Gly Asp Ser Asp Thr Arg Tyr Ser Pro Ser Phe
    50                  55                  60

caa ggc cag gtc acc atc tca gcc gac aag tcc atc agc acc gcc tac      240
Gln Gly Gln Val Thr Ile Ser Ala Asp Lys Ser Ile Ser Thr Ala Tyr
65                  70                  75                  80

ctg cag tgg agc agc ctg aag gcc tcg gac acc gcc atg tat tac tgt      288
Leu Gln Trp Ser Ser Leu Lys Ala Ser Asp Thr Ala Met Tyr Tyr Cys
                85                  90                  95

gcg aga cgc gct agt ata gtg gga gct acc cac ttt gac tac tgg ggc      336
Ala Arg Arg Ala Ser Ile Val Gly Ala Thr His Phe Asp Tyr Trp Gly
            100                 105                 110

cag gga acc ctg gtc acc gtc tcg agt gct agc acc aag ggc ccc agc      384
Gln Gly Thr Leu Val Thr Val Ser Ser Ala Ser Thr Lys Gly Pro Ser
        115                 120                 125

gtg ttc ccc ctg gcc ccc agc agc aag agc acc agc ggc ggc aca gcc      432
Val Phe Pro Leu Ala Pro Ser Ser Lys Ser Thr Ser Gly Gly Thr Ala
    130                 135                 140

gcc ctg ggc tgc ctg gtg aag gac tac ttc ccc gag ccc gtg acc gtg      480
Ala Leu Gly Cys Leu Val Lys Asp Tyr Phe Pro Glu Pro Val Thr Val
145                 150                 155                 160

agc tgg aac agc ggc gcc ttg acc agc ggc gtg cac acc ttc ccc gcc      528
Ser Trp Asn Ser Gly Ala Leu Thr Ser Gly Val His Thr Phe Pro Ala
                165                 170                 175

gtg ctg cag agc agc ggc ctg tac agc ctg agc agc gtg gtg acc gtg      576
Val Leu Gln Ser Ser Gly Leu Tyr Ser Leu Ser Ser Val Val Thr Val
            180                 185                 190

ccc agc agc agc ctg ggc acc cag acc tac atc tgc aac gtg aac cac      624
Pro Ser Ser Ser Leu Gly Thr Gln Thr Tyr Ile Cys Asn Val Asn His
        195                 200                 205

aag ccc agc aac acc aag gtg gac aaa cgc gtg gag ccc aag agc tgc      672
Lys Pro Ser Asn Thr Lys Val Asp Lys Arg Val Glu Pro Lys Ser Cys
    210                 215                 220

gac aag acc cac acc tgc ccc ccc tgc cct gcc ccc gag ctg ctg ggc      720
Asp Lys Thr His Thr Cys Pro Pro Cys Pro Ala Pro Glu Leu Leu Gly
225                 230                 235                 240

gga ccc tcc gtg ttc ctg ttc ccc ccc aag ccc aag gac acc ctc atg      768
Gly Pro Ser Val Phe Leu Phe Pro Pro Lys Pro Lys Asp Thr Leu Met
                245                 250                 255

atc agc cgg acc ccc gag gtg acc tgc gtg gtg gtg gac gtg agc cac      816
Ile Ser Arg Thr Pro Glu Val Thr Cys Val Val Val Asp Val Ser His
            260                 265                 270

gag gac ccc gag gtg aag ttc aac tgg tac gtg gac ggc gtg gag gtg      864
Glu Asp Pro Glu Val Lys Phe Asn Trp Tyr Val Asp Gly Val Glu Val
        275                 280                 285

cac aac gcc aag acc aag ccc cgg gag gag cag tac aac agc acc tac      912
His Asn Ala Lys Thr Lys Pro Arg Glu Glu Gln Tyr Asn Ser Thr Tyr
    290                 295                 300

cgg gtg gtg agc gtg ctc acc gtg ctg cac cag gac tgg ctg aac ggc      960
Arg Val Val Ser Val Leu Thr Val Leu His Gln Asp Trp Leu Asn Gly
305                 310                 315                 320

aag gag tac aag tgc aag gtg agc aac aag gcc ctg cct gcc ccc atc     1008
Lys Glu Tyr Lys Cys Lys Val Ser Asn Lys Ala Leu Pro Ala Pro Ile
                325                 330                 335

gag aag acc atc agc aag gcc aag ggc cag ccc cgg gag ccc cag gtg     1056
Glu Lys Thr Ile Ser Lys Ala Lys Gly Gln Pro Arg Glu Pro Gln Val
            340                 345                 350

tac acc ctg ccc ccc agc cgg gag gag atg acc aag aac cag gtg tcc     1104
Tyr Thr Leu Pro Pro Ser Arg Glu Glu Met Thr Lys Asn Gln Val Ser
```

```
        355                 360                 365

ctc acc tgt ctg gtg aag ggc ttc tac ccc agc gac atc gcc gtg gag      1152
Leu Thr Cys Leu Val Lys Gly Phe Tyr Pro Ser Asp Ile Ala Val Glu
    370                 375                 380

tgg gag agc aac ggc cag ccc gag aac aac tac aag acc acc ccc cct      1200
Trp Glu Ser Asn Gly Gln Pro Glu Asn Asn Tyr Lys Thr Thr Pro Pro
385                 390                 395                 400

gtg ctg gac agc gac ggc agc ttc ttc ctg tac agc aag ctc acc gtg      1248
Val Leu Asp Ser Asp Gly Ser Phe Phe Leu Tyr Ser Lys Leu Thr Val
                405                 410                 415

gac aag agc cgg tgg cag cag ggc aac gtg ttc agc tgc agc gtg atg      1296
Asp Lys Ser Arg Trp Gln Gln Gly Asn Val Phe Ser Cys Ser Val Met
            420                 425                 430

cac gag gcc ctg cac aac cac tac acc cag aag agc ctg agc ctg agc      1344
His Glu Ala Leu His Asn His Tyr Thr Gln Lys Ser Leu Ser Leu Ser
        435                 440                 445

ccc ggc aag                                                          1353
Pro Gly Lys
    450


<210> SEQ ID NO 147
<211> LENGTH: 451
<212> TYPE: PRT
<213> ORGANISM: Homo sapiens

<400> SEQUENCE: 147

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Arg Ala Ser Ile Val Gly Ala Thr His Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
```

```
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450


<210> SEQ ID NO 148
<211> LENGTH: 1353
<212> TYPE: DNA
<213> ORGANISM: Homo sapiens
<220> FEATURE:
<221> NAME/KEY: CDS
<222> LOCATION: (1)..(1353)

<400> SEQUENCE: 148

gag gtg cag ctg gtg gag act ggg gga ggc ttg gtt caa cct ggg ggg       48
Glu Val Gln Leu Val Glu Thr Gly Gly Gly Leu Val Gln Pro Gly Gly
1               5                   10                  15

tcc ctg aga ctc tcc tgt tca gcc tct gga ttc acc ttt agc aac tat       96
Ser Leu Arg Leu Ser Cys Ser Ala Ser Gly Phe Thr Phe Ser Asn Tyr
            20                  25                  30

gcc atg agt tgg gtc cgc cag gct cca ggg aag ggg ctg gag tgg gtc      144
Ala Met Ser Trp Val Arg Gln Ala Pro Gly Lys Gly Leu Glu Trp Val
        35                  40                  45

tca ggt atc agt ggt agt ggt ggt agg aca tac tac gca gac tcc gtg      192
Ser Gly Ile Ser Gly Ser Gly Gly Arg Thr Tyr Tyr Ala Asp Ser Val
    50                  55                  60

aag ggc cgg ttc acc atc tcc aga gac aat tcc aag aac acg ctg tat      240
Lys Gly Arg Phe Thr Ile Ser Arg Asp Asn Ser Lys Asn Thr Leu Tyr
65                  70                  75                  80

ctg caa atg aac agc ctg gga gcc gac gac acg gcc gta tat tac tgt      288
Leu Gln Met Asn Ser Leu Gly Ala Asp Asp Thr Ala Val Tyr Tyr Cys
                85                  90                  95

gcg aaa ggg gta agg gcg gga gtc ccg tat tat ttt gac tct tgg ggc      336
Ala Lys Gly Val Arg Ala Gly Val Pro Tyr Tyr Phe Asp Ser Trp Gly
            100                 105                 110
```

-continued

```
cag gga acc ctg gtc acc gtc tcg agt gct agc acc aag ggc ccc agc      384
Gln Gly Thr Leu Val Thr Val Ser Ser Ala Ser Thr Lys Gly Pro Ser
        115                 120                 125

gtg ttc ccc ctg gcc ccc agc agc aag agc acc agc ggc ggc aca gcc      432
Val Phe Pro Leu Ala Pro Ser Ser Lys Ser Thr Ser Gly Gly Thr Ala
    130                 135                 140

gcc ctg ggc tgc ctg gtg aag gac tac ttc ccc gag ccc gtg acc gtg      480
Ala Leu Gly Cys Leu Val Lys Asp Tyr Phe Pro Glu Pro Val Thr Val
145                 150                 155                 160

agc tgg aac agc ggc gcc ttg acc agc ggc gtg cac acc ttc ccc gcc      528
Ser Trp Asn Ser Gly Ala Leu Thr Ser Gly Val His Thr Phe Pro Ala
                165                 170                 175

gtg ctg cag agc agc ggc ctg tac agc ctg agc agc gtg gtg acc gtg      576
Val Leu Gln Ser Ser Gly Leu Tyr Ser Leu Ser Ser Val Val Thr Val
            180                 185                 190

ccc agc agc agc ctg ggc acc cag acc tac atc tgc aac gtg aac cac      624
Pro Ser Ser Ser Leu Gly Thr Gln Thr Tyr Ile Cys Asn Val Asn His
        195                 200                 205

aag ccc agc aac acc aag gtg gac aaa cgc gtg gag ccc aag agc tgc      672
Lys Pro Ser Asn Thr Lys Val Asp Lys Arg Val Glu Pro Lys Ser Cys
    210                 215                 220

gac aag acc cac acc tgc ccc ccc tgc cct gcc ccc gag ctg ctg ggc      720
Asp Lys Thr His Thr Cys Pro Pro Cys Pro Ala Pro Glu Leu Leu Gly
225                 230                 235                 240

gga ccc tcc gtg ttc ctg ttc ccc ccc aag ccc aag gac acc ctc atg      768
Gly Pro Ser Val Phe Leu Phe Pro Pro Lys Pro Lys Asp Thr Leu Met
                245                 250                 255

atc agc cgg acc ccc gag gtg acc tgc gtg gtg gtg gac gtg agc cac      816
Ile Ser Arg Thr Pro Glu Val Thr Cys Val Val Val Asp Val Ser His
            260                 265                 270

gag gac ccc gag gtg aag ttc aac tgg tac gtg gac ggc gtg gag gtg      864
Glu Asp Pro Glu Val Lys Phe Asn Trp Tyr Val Asp Gly Val Glu Val
        275                 280                 285

cac aac gcc aag acc aag ccc cgg gag gag cag tac aac agc acc tac      912
His Asn Ala Lys Thr Lys Pro Arg Glu Glu Gln Tyr Asn Ser Thr Tyr
    290                 295                 300

cgg gtg gtg agc gtg ctc acc gtg ctg cac cag gac tgg ctg aac ggc      960
Arg Val Val Ser Val Leu Thr Val Leu His Gln Asp Trp Leu Asn Gly
305                 310                 315                 320

aag gag tac aag tgc aag gtg agc aac aag gcc ctg cct gcc ccc atc     1008
Lys Glu Tyr Lys Cys Lys Val Ser Asn Lys Ala Leu Pro Ala Pro Ile
                325                 330                 335

gag aag acc atc agc aag gcc aag ggc cag ccc cgg gag ccc cag gtg     1056
Glu Lys Thr Ile Ser Lys Ala Lys Gly Gln Pro Arg Glu Pro Gln Val
            340                 345                 350

tac acc ctg ccc ccc agc cgg gag gag atg acc aag aac cag gtg tcc     1104
Tyr Thr Leu Pro Pro Ser Arg Glu Glu Met Thr Lys Asn Gln Val Ser
        355                 360                 365

ctc acc tgt ctg gtg aag ggc ttc tac ccc agc gac atc gcc gtg gag     1152
Leu Thr Cys Leu Val Lys Gly Phe Tyr Pro Ser Asp Ile Ala Val Glu
    370                 375                 380

tgg gag agc aac ggc cag ccc gag aac aac tac aag acc acc ccc cct     1200
Trp Glu Ser Asn Gly Gln Pro Glu Asn Asn Tyr Lys Thr Thr Pro Pro
385                 390                 395                 400

gtg ctg gac agc gac ggc agc ttc ttc ctg tac agc aag ctc acc gtg     1248
Val Leu Asp Ser Asp Gly Ser Phe Phe Leu Tyr Ser Lys Leu Thr Val
                405                 410                 415

gac aag agc cgg tgg cag cag ggc aac gtg ttc agc tgc agc gtg atg     1296
Asp Lys Ser Arg Trp Gln Gln Gly Asn Val Phe Ser Cys Ser Val Met
            420                 425                 430
```

```
cac gag gcc ctg cac aac cac tac acc cag aag agc ctg agc ctg agc      1344
His Glu Ala Leu His Asn His Tyr Thr Gln Lys Ser Leu Ser Leu Ser
        435                 440                 445

ccc ggc aag                                                          1353
Pro Gly Lys
    450


<210> SEQ ID NO 149
<211> LENGTH: 451
<212> TYPE: PRT
<213> ORGANISM: Homo sapiens

<400> SEQUENCE: 149

Glu Val Gln Leu Val Glu Thr Gly Gly Gly Leu Val Gln Pro Gly Gly
1               5                   10                  15

Ser Leu Arg Leu Ser Cys Ser Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Gly Ile Ser Gly Ser Gly Gly Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Gly Ala Asp Asp Thr Ala Val Tyr Tyr Cys
                85                  90                  95

Ala Lys Gly Val Arg Ala Gly Val Pro Tyr Tyr Phe Asp Ser Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
```

```
        340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450


<210> SEQ ID NO 150
<211> LENGTH: 1368
<212> TYPE: DNA
<213> ORGANISM: Homo sapiens
<220> FEATURE:
<221> NAME/KEY: CDS
<222> LOCATION: (1)..(1368)

<400> SEQUENCE: 150

gag gtc cag ctg gta cag tct gga gca gag gtg aaa aag ccg ggg gag       48
Glu Val Gln Leu Val Gln Ser Gly Ala Glu Val Lys Lys Pro Gly Glu
1               5                   10                  15

tct ctg aag atc tcc tgt aag gct tct gga tac agt ttt acc agc tac       96
Ser Leu Lys Ile Ser Cys Lys Ala Ser Gly Tyr Ser Phe Thr Ser Tyr
            20                  25                  30

tgg atc ggc tgg gtg cgc cag atg ccc ggg aaa ggc ctg gag tgg atg      144
Trp Ile Gly Trp Val Arg Gln Met Pro Gly Lys Gly Leu Glu Trp Met
        35                  40                  45

gga atc atc tat ccc ggt gac tct gat acc aga tac agc ccg tcc ttc      192
Gly Ile Ile Tyr Pro Gly Asp Ser Asp Thr Arg Tyr Ser Pro Ser Phe
    50                  55                  60

caa ggc cag gtc atc atc tca gcc gac aag tcc atc agc acc gcc tac      240
Gln Gly Gln Val Ile Ile Ser Ala Asp Lys Ser Ile Ser Thr Ala Tyr
65                  70                  75                  80

ctg cag tgg agc agc ctg aag gcc tcg gac acc gcc atg tat tac tgt      288
Leu Gln Trp Ser Ser Leu Lys Ala Ser Asp Thr Ala Met Tyr Tyr Cys
                85                  90                  95

gcg aga ttt aag aag agc tca gct gct agg ggc tac tac tac tac tac      336
Ala Arg Phe Lys Lys Ser Ser Ala Ala Arg Gly Tyr Tyr Tyr Tyr Tyr
            100                 105                 110

atg gac gtc tgg ggc aaa ggg acc acg gtc acc gtc tcg agt gct agc      384
Met Asp Val Trp Gly Lys Gly Thr Thr Val Thr Val Ser Ser Ala Ser
        115                 120                 125

acc aag ggc ccc agc gtg ttc ccc ctg gcc ccc agc agc aag agc acc      432
Thr Lys Gly Pro Ser Val Phe Pro Leu Ala Pro Ser Ser Lys Ser Thr
    130                 135                 140

agc ggc ggc aca gcc gcc ctg ggc tgc ctg gtg aag gac tac ttc ccc      480
Ser Gly Gly Thr Ala Ala Leu Gly Cys Leu Val Lys Asp Tyr Phe Pro
145                 150                 155                 160

gag ccc gtg acc gtg agc tgg aac agc ggc gcc ttg acc agc ggc gtg      528
Glu Pro Val Thr Val Ser Trp Asn Ser Gly Ala Leu Thr Ser Gly Val
                165                 170                 175

cac acc ttc ccc gcc gtg ctg cag agc agc ggc ctg tac agc ctg agc      576
His Thr Phe Pro Ala Val Leu Gln Ser Ser Gly Leu Tyr Ser Leu Ser
```

```
            180                 185                 190

agc gtg gtg acc gtg ccc agc agc agc ctg ggc acc cag acc tac atc      624
Ser Val Val Thr Val Pro Ser Ser Ser Leu Gly Thr Gln Thr Tyr Ile
        195                 200                 205

tgc aac gtg aac cac aag ccc agc aac acc aag gtg gac aaa cgc gtg      672
Cys Asn Val Asn His Lys Pro Ser Asn Thr Lys Val Asp Lys Arg Val
    210                 215                 220

gag ccc aag agc tgc gac aag acc cac acc tgc ccc ccc tgc cct gcc      720
Glu Pro Lys Ser Cys Asp Lys Thr His Thr Cys Pro Pro Cys Pro Ala
225                 230                 235                 240

ccc gag ctg ctg ggc gga ccc tcc gtg ttc ctg ttc ccc ccc aag ccc      768
Pro Glu Leu Leu Gly Gly Pro Ser Val Phe Leu Phe Pro Pro Lys Pro
                245                 250                 255

aag gac acc ctc atg atc agc cgg acc ccc gag gtg acc tgc gtg gtg      816
Lys Asp Thr Leu Met Ile Ser Arg Thr Pro Glu Val Thr Cys Val Val
            260                 265                 270

gtg gac gtg agc cac gag gac ccc gag gtg aag ttc aac tgg tac gtg      864
Val Asp Val Ser His Glu Asp Pro Glu Val Lys Phe Asn Trp Tyr Val
        275                 280                 285

gac ggc gtg gag gtg cac aac gcc aag acc aag ccc cgg gag gag cag      912
Asp Gly Val Glu Val His Asn Ala Lys Thr Lys Pro Arg Glu Glu Gln
    290                 295                 300

tac aac agc acc tac cgg gtg gtg agc gtg ctc acc gtg ctg cac cag      960
Tyr Asn Ser Thr Tyr Arg Val Val Ser Val Leu Thr Val Leu His Gln
305                 310                 315                 320

gac tgg ctg aac ggc aag gag tac aag tgc aag gtg agc aac aag gcc     1008
Asp Trp Leu Asn Gly Lys Glu Tyr Lys Cys Lys Val Ser Asn Lys Ala
                325                 330                 335

ctg cct gcc ccc atc gag aag acc atc agc aag gcc aag ggc cag ccc     1056
Leu Pro Ala Pro Ile Glu Lys Thr Ile Ser Lys Ala Lys Gly Gln Pro
            340                 345                 350

cgg gag ccc cag gtg tac acc ctg ccc ccc agc cgg gag gag atg acc     1104
Arg Glu Pro Gln Val Tyr Thr Leu Pro Pro Ser Arg Glu Glu Met Thr
        355                 360                 365

aag aac cag gtg tcc ctc acc tgt ctg gtg aag ggc ttc tac ccc agc     1152
Lys Asn Gln Val Ser Leu Thr Cys Leu Val Lys Gly Phe Tyr Pro Ser
    370                 375                 380

gac atc gcc gtg gag tgg gag agc aac ggc cag ccc gag aac aac tac     1200
Asp Ile Ala Val Glu Trp Glu Ser Asn Gly Gln Pro Glu Asn Asn Tyr
385                 390                 395                 400

aag acc acc ccc cct gtg ctg gac agc gac ggc agc ttc ttc ctg tac     1248
Lys Thr Thr Pro Pro Val Leu Asp Ser Asp Gly Ser Phe Phe Leu Tyr
                405                 410                 415

agc aag ctc acc gtg gac aag agc cgg tgg cag cag ggc aac gtg ttc     1296
Ser Lys Leu Thr Val Asp Lys Ser Arg Trp Gln Gln Gly Asn Val Phe
            420                 425                 430

agc tgc agc gtg atg cac gag gcc ctg cac aac cac tac acc cag aag     1344
Ser Cys Ser Val Met His Glu Ala Leu His Asn His Tyr Thr Gln Lys
        435                 440                 445

agc ctg agc ctg agc ccc ggc aag                                     1368
Ser Leu Ser Leu Ser Pro Gly Lys
    450                 455


<210> SEQ ID NO 151
<211> LENGTH: 456
<212> TYPE: PRT
<213> ORGANISM: Homo sapiens

<400> SEQUENCE: 151

Glu Val Gln Leu Val Gln Ser Gly Ala Glu Val Lys Lys Pro Gly Glu
1               5                   10                  15
```

```
Ser Leu Lys Ile Ser Cys Lys Ala Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Ile Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Phe Lys Lys Ser Ser Ala Ala Arg Gly Tyr Tyr Tyr Tyr Tyr
            100                 105                 110

Met Asp Val Trp Gly Lys Gly Thr Thr Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Arg Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Glu Glu Met Thr
        355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
```

```
        435                 440                 445

Ser Leu Ser Leu Ser Pro Gly Lys
    450                 455


<210> SEQ ID NO 152
<211> LENGTH: 1347
<212> TYPE: DNA
<213> ORGANISM: Homo sapiens
<220> FEATURE:
<221> NAME/KEY: CDS
<222> LOCATION: (1)..(1347)

<400> SEQUENCE: 152

gag gtc cag ctg gtg cag tct gga gca gag gtg aaa aag ccc ggg gag       48
Glu Val Gln Leu Val Gln Ser Gly Ala Glu Val Lys Lys Pro Gly Glu
1               5                   10                  15

tct ctg aag atc tcc tgt aag ggt tcc gga tac acc ttt agc agc tac       96
Ser Leu Lys Ile Ser Cys Lys Gly Ser Gly Tyr Thr Phe Ser Ser Tyr
            20                  25                  30

tgg atc ggc tgg gtg cgc cag atg ccc ggg aaa ggc ccg gag tgg atg      144
Trp Ile Gly Trp Val Arg Gln Met Pro Gly Lys Gly Pro Glu Trp Met
        35                  40                  45

ggg atc atc tat cca ggt gac tct gat acc aga tac agc ccg tcc ttc      192
Gly Ile Ile Tyr Pro Gly Asp Ser Asp Thr Arg Tyr Ser Pro Ser Phe
    50                  55                  60

caa ggc cag gtc acc atc tca gcc gac agg tcc atc agc acc gcc tat      240
Gln Gly Gln Val Thr Ile Ser Ala Asp Arg Ser Ile Ser Thr Ala Tyr
65                  70                  75                  80

ttg cag tgg agc agc ctg aag gcc tcg gac acc gcc atg tat tac tgt      288
Leu Gln Trp Ser Ser Leu Lys Ala Ser Asp Thr Ala Met Tyr Tyr Cys
                85                  90                  95

gcg aga ctt aat aca gtt atg gtt ggt ttg gac tac tgg ggc cag gga      336
Ala Arg Leu Asn Thr Val Met Val Gly Leu Asp Tyr Trp Gly Gln Gly
            100                 105                 110

acc ctg gtc acc gtc tcg agt gct agc acc aag ggc ccc agc gtg ttc      384
Thr Leu Val Thr Val Ser Ser Ala Ser Thr Lys Gly Pro Ser Val Phe
        115                 120                 125

ccc ctg gcc ccc agc agc aag agc acc agc ggc ggc aca gcc gcc ctg      432
Pro Leu Ala Pro Ser Ser Lys Ser Thr Ser Gly Gly Thr Ala Ala Leu
    130                 135                 140

ggc tgc ctg gtg aag gac tac ttc ccc gag ccc gtg acc gtg agc tgg      480
Gly Cys Leu Val Lys Asp Tyr Phe Pro Glu Pro Val Thr Val Ser Trp
145                 150                 155                 160

aac agc ggc gcc ttg acc agc ggc gtg cac acc ttc ccc gcc gtg ctg      528
Asn Ser Gly Ala Leu Thr Ser Gly Val His Thr Phe Pro Ala Val Leu
                165                 170                 175

cag agc agc ggc ctg tac agc ctg agc agc gtg gtg acc gtg ccc agc      576
Gln Ser Ser Gly Leu Tyr Ser Leu Ser Ser Val Val Thr Val Pro Ser
            180                 185                 190

agc agc ctg ggc acc cag acc tac atc tgc aac gtg aac cac aag ccc      624
Ser Ser Leu Gly Thr Gln Thr Tyr Ile Cys Asn Val Asn His Lys Pro
        195                 200                 205

agc aac acc aag gtg gac aaa cgc gtg gag ccc aag agc tgc gac aag      672
Ser Asn Thr Lys Val Asp Lys Arg Val Glu Pro Lys Ser Cys Asp Lys
    210                 215                 220

acc cac acc tgc ccc ccc tgc cct gcc ccc gag ctg ctg ggc gga ccc      720
Thr His Thr Cys Pro Pro Cys Pro Ala Pro Glu Leu Leu Gly Gly Pro
225                 230                 235                 240

tcc gtg ttc ctg ttc ccc ccc aag ccc aag gac acc ctc atg atc agc      768
Ser Val Phe Leu Phe Pro Pro Lys Pro Lys Asp Thr Leu Met Ile Ser
                245                 250                 255
```

```
cgg acc ccc gag gtg acc tgc gtg gtg gtg gac gtg agc cac gag gac      816
Arg Thr Pro Glu Val Thr Cys Val Val Val Asp Val Ser His Glu Asp
            260                 265                 270

ccc gag gtg aag ttc aac tgg tac gtg gac ggc gtg gag gtg cac aac      864
Pro Glu Val Lys Phe Asn Trp Tyr Val Asp Gly Val Glu Val His Asn
        275                 280                 285

gcc aag acc aag ccc cgg gag gag cag tac aac agc acc tac cgg gtg      912
Ala Lys Thr Lys Pro Arg Glu Glu Gln Tyr Asn Ser Thr Tyr Arg Val
    290                 295                 300

gtg agc gtg ctc acc gtg ctg cac cag gac tgg ctg aac ggc aag gag      960
Val Ser Val Leu Thr Val Leu His Gln Asp Trp Leu Asn Gly Lys Glu
305                 310                 315                 320

tac aag tgc aag gtg agc aac aag gcc ctg cct gcc ccc atc gag aag     1008
Tyr Lys Cys Lys Val Ser Asn Lys Ala Leu Pro Ala Pro Ile Glu Lys
                325                 330                 335

acc atc agc aag gcc aag ggc cag ccc cgg gag ccc cag gtg tac acc     1056
Thr Ile Ser Lys Ala Lys Gly Gln Pro Arg Glu Pro Gln Val Tyr Thr
            340                 345                 350

ctg ccc ccc agc cgg gag gag atg acc aag aac cag gtg tcc ctc acc     1104
Leu Pro Pro Ser Arg Glu Glu Met Thr Lys Asn Gln Val Ser Leu Thr
        355                 360                 365

tgt ctg gtg aag ggc ttc tac ccc agc gac atc gcc gtg gag tgg gag     1152
Cys Leu Val Lys Gly Phe Tyr Pro Ser Asp Ile Ala Val Glu Trp Glu
    370                 375                 380

agc aac ggc cag ccc gag aac aac tac aag acc acc ccc cct gtg ctg     1200
Ser Asn Gly Gln Pro Glu Asn Asn Tyr Lys Thr Thr Pro Pro Val Leu
385                 390                 395                 400

gac agc gac ggc agc ttc ttc ctg tac agc aag ctc acc gtg gac aag     1248
Asp Ser Asp Gly Ser Phe Phe Leu Tyr Ser Lys Leu Thr Val Asp Lys
                405                 410                 415

agc cgg tgg cag cag ggc aac gtg ttc agc tgc agc gtg atg cac gag     1296
Ser Arg Trp Gln Gln Gly Asn Val Phe Ser Cys Ser Val Met His Glu
            420                 425                 430

gcc ctg cac aac cac tac acc cag aag agc ctg agc ctg agc ccc ggc     1344
Ala Leu His Asn His Tyr Thr Gln Lys Ser Leu Ser Leu Ser Pro Gly
        435                 440                 445

aag                                                                 1347
Lys


<210> SEQ ID NO 153
<211> LENGTH: 449
<212> TYPE: PRT
<213> ORGANISM: Homo sapiens

<400> SEQUENCE: 153

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Thr Phe Ser Ser Tyr
            20                  25                  30

Trp Ile Gly Trp Val Arg Gln Met Pro Gly Lys Gly Pro Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Arg Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu Asn Thr Val Met Val Gly Leu Asp Tyr Trp Gly Gln Gly
            100                 105                 110
```

```
Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 154
<211> LENGTH: 1341
<212> TYPE: DNA
<213> ORGANISM: Homo sapiens
<220> FEATURE:
<221> NAME/KEY: CDS
<222> LOCATION: (1)..(1341)

<400> SEQUENCE: 154

cag gtg cag ctg cag gag tcg ggg gga ggc gtg gtc cag cct ggg agg       48
Gln Val Gln Leu Gln Glu Ser Gly Gly Gly Val Val Gln Pro Gly Arg
1               5                   10                  15
```

-continued

```
tcc ctg aga ctc tcc tgt gca gcc tct gga ttc acc ttc agt agc tat        96
Ser Leu Arg Leu Ser Cys Ala Ala Ser Gly Phe Thr Phe Ser Ser Tyr
            20                  25                  30

ggc atg cac tgg gtc cgc cag gct cca ggc aag ggg ctg gag tgg gtg       144
Gly Met His Trp Val Arg Gln Ala Pro Gly Lys Gly Leu Glu Trp Val
        35                  40                  45

gca gtt ata tca tat gat gga agt aat aaa tac tat gca gac tcc gtg       192
Ala Val Ile Ser Tyr Asp Gly Ser Asn Lys Tyr Tyr Ala Asp Ser Val
    50                  55                  60

aag ggc cga ttc acc atc tcc aga gac aat tcc aag aac acg ctg tat       240
Lys Gly Arg Phe Thr Ile Ser Arg Asp Asn Ser Lys Asn Thr Leu Tyr
65                  70                  75                  80

ctg caa atg aac agc ctg aga gct gag gac acg gct gtg tat tac tgt       288
Leu Gln Met Asn Ser Leu Arg Ala Glu Asp Thr Ala Val Tyr Tyr Cys
                85                  90                  95

gcg aaa aat gga gcg aac gct ttt gat atc tgg ggc caa ggg aca atg       336
Ala Lys Asn Gly Ala Asn Ala Phe Asp Ile Trp Gly Gln Gly Thr Met
            100                 105                 110

gtc acc gtc tcg agt gct agc acc aag ggc ccc agc gtg ttc ccc ctg       384
Val Thr Val Ser Ser Ala Ser Thr Lys Gly Pro Ser Val Phe Pro Leu
        115                 120                 125

gcc ccc agc agc aag agc acc agc ggc ggc aca gcc gcc ctg ggc tgc       432
Ala Pro Ser Ser Lys Ser Thr Ser Gly Gly Thr Ala Ala Leu Gly Cys
    130                 135                 140

ctg gtg aag gac tac ttc ccc gag ccc gtg acc gtg agc tgg aac agc       480
Leu Val Lys Asp Tyr Phe Pro Glu Pro Val Thr Val Ser Trp Asn Ser
145                 150                 155                 160

ggc gcc ttg acc agc ggc gtg cac acc ttc ccc gcc gtg ctg cag agc       528
Gly Ala Leu Thr Ser Gly Val His Thr Phe Pro Ala Val Leu Gln Ser
                165                 170                 175

agc ggc ctg tac agc ctg agc agc gtg gtg acc gtg ccc agc agc agc       576
Ser Gly Leu Tyr Ser Leu Ser Ser Val Val Thr Val Pro Ser Ser Ser
            180                 185                 190

ctg ggc acc cag acc tac atc tgc aac gtg aac cac aag ccc agc aac       624
Leu Gly Thr Gln Thr Tyr Ile Cys Asn Val Asn His Lys Pro Ser Asn
        195                 200                 205

acc aag gtg gac aaa cgc gtg gag ccc aag agc tgc gac aag acc cac       672
Thr Lys Val Asp Lys Arg Val Glu Pro Lys Ser Cys Asp Lys Thr His
    210                 215                 220

acc tgc ccc ccc tgc cct gcc ccc gag ctg ctg ggc gga ccc tcc gtg       720
Thr Cys Pro Pro Cys Pro Ala Pro Glu Leu Leu Gly Gly Pro Ser Val
225                 230                 235                 240

ttc ctg ttc ccc ccc aag ccc aag gac acc ctc atg atc agc cgg acc       768
Phe Leu Phe Pro Pro Lys Pro Lys Asp Thr Leu Met Ile Ser Arg Thr
                245                 250                 255

ccc gag gtg acc tgc gtg gtg gtg gac gtg agc cac gag gac ccc gag       816
Pro Glu Val Thr Cys Val Val Val Asp Val Ser His Glu Asp Pro Glu
            260                 265                 270

gtg aag ttc aac tgg tac gtg gac ggc gtg gag gtg cac aac gcc aag       864
Val Lys Phe Asn Trp Tyr Val Asp Gly Val Glu Val His Asn Ala Lys
        275                 280                 285

acc aag ccc cgg gag gag cag tac aac agc acc tac cgg gtg gtg agc       912
Thr Lys Pro Arg Glu Glu Gln Tyr Asn Ser Thr Tyr Arg Val Val Ser
    290                 295                 300

gtg ctc acc gtg ctg cac cag gac tgg ctg aac ggc aag gag tac aag       960
Val Leu Thr Val Leu His Gln Asp Trp Leu Asn Gly Lys Glu Tyr Lys
305                 310                 315                 320

tgc aag gtg agc aac aag gcc ctg cct gcc ccc atc gag aag acc atc      1008
Cys Lys Val Ser Asn Lys Ala Leu Pro Ala Pro Ile Glu Lys Thr Ile
                325                 330                 335
```

```
agc aag gcc aag ggc cag ccc cgg gag ccc cag gtg tac acc ctg ccc      1056
Ser Lys Ala Lys Gly Gln Pro Arg Glu Pro Gln Val Tyr Thr Leu Pro
            340                 345                 350

ccc agc cgg gag gag atg acc aag aac cag gtg tcc ctc acc tgt ctg      1104
Pro Ser Arg Glu Glu Met Thr Lys Asn Gln Val Ser Leu Thr Cys Leu
        355                 360                 365

gtg aag ggc ttc tac ccc agc gac atc gcc gtg gag tgg gag agc aac      1152
Val Lys Gly Phe Tyr Pro Ser Asp Ile Ala Val Glu Trp Glu Ser Asn
    370                 375                 380

ggc cag ccc gag aac aac tac aag acc acc ccc cct gtg ctg gac agc      1200
Gly Gln Pro Glu Asn Asn Tyr Lys Thr Thr Pro Pro Val Leu Asp Ser
385                 390                 395                 400

gac ggc agc ttc ttc ctg tac agc aag ctc acc gtg gac aag agc cgg      1248
Asp Gly Ser Phe Phe Leu Tyr Ser Lys Leu Thr Val Asp Lys Ser Arg
                405                 410                 415

tgg cag cag ggc aac gtg ttc agc tgc agc gtg atg cac gag gcc ctg      1296
Trp Gln Gln Gly Asn Val Phe Ser Cys Ser Val Met His Glu Ala Leu
            420                 425                 430

cac aac cac tac acc cag aag agc ctg agc ctg agc ccc ggc aag          1341
His Asn His Tyr Thr Gln Lys Ser Leu Ser Leu Ser Pro Gly Lys
        435                 440                 445


<210> SEQ ID NO 155
<211> LENGTH: 447
<212> TYPE: PRT
<213> ORGANISM: Homo sapiens

<400> SEQUENCE: 155

Gln Val Gln Leu Gln Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asn Gly Ala Asn Ala Phe Asp Ile Trp Gly Gln Gly Thr Met
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240
```

```
Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445


<210> SEQ ID NO 156
<211> LENGTH: 1353
<212> TYPE: DNA
<213> ORGANISM: Homo sapiens
<220> FEATURE:
<221> NAME/KEY: CDS
<222> LOCATION: (1)..(1353)

<400> SEQUENCE: 156

gag gtg cag ctg gtg gag tcc gga gca gag gtg aaa aag ccc ggg gag       48
Glu Val Gln Leu Val Glu Ser Gly Ala Glu Val Lys Lys Pro Gly Glu
1               5                   10                  15

tct ctg aag atc tcc tgt aag ggt tct gga tac agc ttc acc agc tac       96
Ser Leu Lys Ile Ser Cys Lys Gly Ser Gly Tyr Ser Phe Thr Ser Tyr
            20                  25                  30

tgg atc ggc tgg gtg cgc cag ttg ccc ggg aaa ggc ctg gag tgg atg      144
Trp Ile Gly Trp Val Arg Gln Leu Pro Gly Lys Gly Leu Glu Trp Met
        35                  40                  45

ggg atc atc tat cct ggt gac tct gat acc aga tac agc ccg tcc ttc      192
Gly Ile Ile Tyr Pro Gly Asp Ser Asp Thr Arg Tyr Ser Pro Ser Phe
    50                  55                  60

caa ggc cag gtc acc atc tca gcc gac aag tcc acc agc acc gcc tac      240
Gln Gly Gln Val Thr Ile Ser Ala Asp Lys Ser Thr Ser Thr Ala Tyr
65                  70                  75                  80

ctg cag tgg agc agc ctg aag gcc tcg gac acc gcc atg tat tac tgt      288
Leu Gln Trp Ser Ser Leu Lys Ala Ser Asp Thr Ala Met Tyr Tyr Cys
                85                  90                  95

gcg aga cgc cgt ggt tct acc agc tcc acg gac ttt gac tac tgg ggc      336
Ala Arg Arg Arg Gly Ser Thr Ser Ser Thr Asp Phe Asp Tyr Trp Gly
            100                 105                 110

cag gga acc ctg gtc acc gtc tcg agt gct agc acc aag ggc ccc agc      384
```

```
Gln Gly Thr Leu Val Thr Val Ser Ser Ala Ser Thr Lys Gly Pro Ser
        115                 120                 125

gtg ttc ccc ctg gcc ccc agc agc aag agc acc agc ggc ggc aca gcc      432
Val Phe Pro Leu Ala Pro Ser Ser Lys Ser Thr Ser Gly Gly Thr Ala
    130                 135                 140

gcc ctg ggc tgc ctg gtg aag gac tac ttc ccc gag ccc gtg acc gtg      480
Ala Leu Gly Cys Leu Val Lys Asp Tyr Phe Pro Glu Pro Val Thr Val
145                 150                 155                 160

agc tgg aac agc ggc gcc ttg acc agc ggc gtg cac acc ttc ccc gcc      528
Ser Trp Asn Ser Gly Ala Leu Thr Ser Gly Val His Thr Phe Pro Ala
                165                 170                 175

gtg ctg cag agc agc ggc ctg tac agc ctg agc agc gtg gtg acc gtg      576
Val Leu Gln Ser Ser Gly Leu Tyr Ser Leu Ser Ser Val Val Thr Val
            180                 185                 190

ccc agc agc agc ctg ggc acc cag acc tac atc tgc aac gtg aac cac      624
Pro Ser Ser Ser Leu Gly Thr Gln Thr Tyr Ile Cys Asn Val Asn His
        195                 200                 205

aag ccc agc aac acc aag gtg gac aaa cgc gtg gag ccc aag agc tgc      672
Lys Pro Ser Asn Thr Lys Val Asp Lys Arg Val Glu Pro Lys Ser Cys
    210                 215                 220

gac aag acc cac acc tgc ccc ccc tgc cct gcc ccc gag ctg ctg ggc      720
Asp Lys Thr His Thr Cys Pro Pro Cys Pro Ala Pro Glu Leu Leu Gly
225                 230                 235                 240

gga ccc tcc gtg ttc ctg ttc ccc ccc aag ccc aag gac acc ctc atg      768
Gly Pro Ser Val Phe Leu Phe Pro Pro Lys Pro Lys Asp Thr Leu Met
                245                 250                 255

atc agc cgg acc ccc gag gtg acc tgc gtg gtg gtg gac gtg agc cac      816
Ile Ser Arg Thr Pro Glu Val Thr Cys Val Val Val Asp Val Ser His
            260                 265                 270

gag gac ccc gag gtg aag ttc aac tgg tac gtg gac ggc gtg gag gtg      864
Glu Asp Pro Glu Val Lys Phe Asn Trp Tyr Val Asp Gly Val Glu Val
        275                 280                 285

cac aac gcc aag acc aag ccc cgg gag gag cag tac aac agc acc tac      912
His Asn Ala Lys Thr Lys Pro Arg Glu Glu Gln Tyr Asn Ser Thr Tyr
    290                 295                 300

cgg gtg gtg agc gtg ctc acc gtg ctg cac cag gac tgg ctg aac ggc      960
Arg Val Val Ser Val Leu Thr Val Leu His Gln Asp Trp Leu Asn Gly
305                 310                 315                 320

aag gag tac aag tgc aag gtg agc aac aag gcc ctg cct gcc ccc atc     1008
Lys Glu Tyr Lys Cys Lys Val Ser Asn Lys Ala Leu Pro Ala Pro Ile
                325                 330                 335

gag aag acc atc agc aag gcc aag ggc cag ccc cgg gag ccc cag gtg     1056
Glu Lys Thr Ile Ser Lys Ala Lys Gly Gln Pro Arg Glu Pro Gln Val
            340                 345                 350

tac acc ctg ccc ccc agc cgg gag gag atg acc aag aac cag gtg tcc     1104
Tyr Thr Leu Pro Pro Ser Arg Glu Glu Met Thr Lys Asn Gln Val Ser
        355                 360                 365

ctc acc tgt ctg gtg aag ggc ttc tac ccc agc gac atc gcc gtg gag     1152
Leu Thr Cys Leu Val Lys Gly Phe Tyr Pro Ser Asp Ile Ala Val Glu
    370                 375                 380

tgg gag agc aac ggc cag ccc gag aac aac tac aag acc acc ccc cct     1200
Trp Glu Ser Asn Gly Gln Pro Glu Asn Asn Tyr Lys Thr Thr Pro Pro
385                 390                 395                 400

gtg ctg gac agc gac ggc agc ttc ttc ctg tac agc aag ctc acc gtg     1248
Val Leu Asp Ser Asp Gly Ser Phe Phe Leu Tyr Ser Lys Leu Thr Val
                405                 410                 415

gac aag agc cgg tgg cag cag ggc aac gtg ttc agc tgc agc gtg atg     1296
Asp Lys Ser Arg Trp Gln Gln Gly Asn Val Phe Ser Cys Ser Val Met
            420                 425                 430

cac gag gcc ctg cac aac cac tac acc cag aag agc ctg agc ctg agc     1344
```

-continued

```
His Glu Ala Leu His Asn His Tyr Thr Gln Lys Ser Leu Ser Leu Ser
        435                 440                 445

ccc ggc aag                                                       1353
Pro Gly Lys
    450


<210> SEQ ID NO 157
<211> LENGTH: 451
<212> TYPE: PRT
<213> ORGANISM: Homo sapiens

<400> SEQUENCE: 157

Glu Val Gln Leu Val Glu Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Leu Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Thr Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Arg Arg Gly Ser Thr Ser Ser Thr Asp Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350
```

```
Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450


<210> SEQ ID NO 158
<211> LENGTH: 1353
<212> TYPE: DNA
<213> ORGANISM: Homo sapiens
<220> FEATURE:
<221> NAME/KEY: CDS
<222> LOCATION: (1)..(1353)

<400> SEQUENCE: 158

cag gtg cag ctg gtg caa tct gga gca gag gtg aaa aag tcc ggg gag       48
Gln Val Gln Leu Val Gln Ser Gly Ala Glu Val Lys Lys Ser Gly Glu
1               5                   10                  15

tct ctg aag atc tcc tgt aag ggt ttt gga tac agc ttt acc agc cag       96
Ser Leu Lys Ile Ser Cys Lys Gly Phe Gly Tyr Ser Phe Thr Ser Gln
            20                  25                  30

tgg atc gtc tgg gtg cgc cag atg ccc ggg aaa ggc ctg gag tgg atg      144
Trp Ile Val Trp Val Arg Gln Met Pro Gly Lys Gly Leu Glu Trp Met
        35                  40                  45

ggg atc atc tat cct ggt gac tct gat acc aga tac agc ccg tcc ttc      192
Gly Ile Ile Tyr Pro Gly Asp Ser Asp Thr Arg Tyr Ser Pro Ser Phe
    50                  55                  60

caa ggc cag gtc acc atc tca gcc gac agg tcc atc agc acc gcc tac      240
Gln Gly Gln Val Thr Ile Ser Ala Asp Arg Ser Ile Ser Thr Ala Tyr
65                  70                  75                  80

ctg cag tgg agc agc ctg aag gcc tcc gac aac gcc atg tat tac tgt      288
Leu Gln Trp Ser Ser Leu Lys Ala Ser Asp Asn Ala Met Tyr Tyr Cys
                85                  90                  95

gcg agg gcc ctg cgg ggg tat agc agc tcg tcc ttt ggc tac tgg ggc      336
Ala Arg Ala Leu Arg Gly Tyr Ser Ser Ser Ser Phe Gly Tyr Trp Gly
            100                 105                 110

cag gga acc ctg gtc acc gtc tcg agt gct agc acc aag ggc ccc agc      384
Gln Gly Thr Leu Val Thr Val Ser Ser Ala Ser Thr Lys Gly Pro Ser
        115                 120                 125

gtg ttc ccc ctg gcc ccc agc agc aag agc acc agc ggc ggc aca gcc      432
Val Phe Pro Leu Ala Pro Ser Ser Lys Ser Thr Ser Gly Gly Thr Ala
    130                 135                 140

gcc ctg ggc tgc ctg gtg aag gac tac ttc ccc gag ccc gtg acc gtg      480
Ala Leu Gly Cys Leu Val Lys Asp Tyr Phe Pro Glu Pro Val Thr Val
145                 150                 155                 160

agc tgg aac agc ggc gcc ttg acc agc ggc gtg cac acc ttc ccc gcc      528
Ser Trp Asn Ser Gly Ala Leu Thr Ser Gly Val His Thr Phe Pro Ala
                165                 170                 175

gtg ctg cag agc agc ggc ctg tac agc ctg agc agc gtg gtg acc gtg      576
Val Leu Gln Ser Ser Gly Leu Tyr Ser Leu Ser Ser Val Val Thr Val
            180                 185                 190
```

```
ccc agc agc agc ctg ggc acc cag acc tac atc tgc aac gtg aac cac      624
Pro Ser Ser Ser Leu Gly Thr Gln Thr Tyr Ile Cys Asn Val Asn His
        195                 200                 205

aag ccc agc aac acc aag gtg gac aaa cgc gtg gag ccc aag agc tgc      672
Lys Pro Ser Asn Thr Lys Val Asp Lys Arg Val Glu Pro Lys Ser Cys
    210                 215                 220

gac aag acc cac acc tgc ccc ccc tgc cct gcc ccc gag ctg ctg ggc      720
Asp Lys Thr His Thr Cys Pro Pro Cys Pro Ala Pro Glu Leu Leu Gly
225                 230                 235                 240

gga ccc tcc gtg ttc ctg ttc ccc ccc aag ccc aag gac acc ctc atg      768
Gly Pro Ser Val Phe Leu Phe Pro Pro Lys Pro Lys Asp Thr Leu Met
                245                 250                 255

atc agc cgg acc ccc gag gtg acc tgc gtg gtg gtg gac gtg agc cac      816
Ile Ser Arg Thr Pro Glu Val Thr Cys Val Val Val Asp Val Ser His
            260                 265                 270

gag gac ccc gag gtg aag ttc aac tgg tac gtg gac ggc gtg gag gtg      864
Glu Asp Pro Glu Val Lys Phe Asn Trp Tyr Val Asp Gly Val Glu Val
        275                 280                 285

cac aac gcc aag acc aag ccc cgg gag gag cag tac aac agc acc tac      912
His Asn Ala Lys Thr Lys Pro Arg Glu Glu Gln Tyr Asn Ser Thr Tyr
    290                 295                 300

cgg gtg gtg agc gtg ctc acc gtg ctg cac cag gac tgg ctg aac ggc      960
Arg Val Val Ser Val Leu Thr Val Leu His Gln Asp Trp Leu Asn Gly
305                 310                 315                 320

aag gag tac aag tgc aag gtg agc aac aag gcc ctg cct gcc ccc atc     1008
Lys Glu Tyr Lys Cys Lys Val Ser Asn Lys Ala Leu Pro Ala Pro Ile
                325                 330                 335

gag aag acc atc agc aag gcc aag ggc cag ccc cgg gag ccc cag gtg     1056
Glu Lys Thr Ile Ser Lys Ala Lys Gly Gln Pro Arg Glu Pro Gln Val
            340                 345                 350

tac acc ctg ccc ccc agc cgg gag gag atg acc aag aac cag gtg tcc     1104
Tyr Thr Leu Pro Pro Ser Arg Glu Glu Met Thr Lys Asn Gln Val Ser
        355                 360                 365

ctc acc tgt ctg gtg aag ggc ttc tac ccc agc gac atc gcc gtg gag     1152
Leu Thr Cys Leu Val Lys Gly Phe Tyr Pro Ser Asp Ile Ala Val Glu
    370                 375                 380

tgg gag agc aac ggc cag ccc gag aac aac tac aag acc acc ccc cct     1200
Trp Glu Ser Asn Gly Gln Pro Glu Asn Asn Tyr Lys Thr Thr Pro Pro
385                 390                 395                 400

gtg ctg gac agc gac ggc agc ttc ttc ctg tac agc aag ctc acc gtg     1248
Val Leu Asp Ser Asp Gly Ser Phe Phe Leu Tyr Ser Lys Leu Thr Val
                405                 410                 415

gac aag agc cgg tgg cag cag ggc aac gtg ttc agc tgc agc gtg atg     1296
Asp Lys Ser Arg Trp Gln Gln Gly Asn Val Phe Ser Cys Ser Val Met
            420                 425                 430

cac gag gcc ctg cac aac cac tac acc cag aag agc ctg agc ctg agc     1344
His Glu Ala Leu His Asn His Tyr Thr Gln Lys Ser Leu Ser Leu Ser
        435                 440                 445

ccc ggc aag                                                         1353
Pro Gly Lys
    450
```

<210> SEQ ID NO 159
<211> LENGTH: 451
<212> TYPE: PRT
<213> ORGANISM: Homo sapiens

<400> SEQUENCE: 159

```
Gln Val Gln Leu Val Gln Ser Gly Ala Glu Val Lys Lys Ser Gly Glu
1               5                   10                  15
```

-continued

```
Ser Leu Lys Ile Ser Cys Lys Gly Phe Gly Tyr Ser Phe Thr Ser Gln
            20                  25                  30

Trp Ile Val Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Arg Ser Ile Ser Thr Ala Tyr
65                  70                  75                  80

Leu Gln Trp Ser Ser Leu Lys Ala Ser Asp Asn Ala Met Tyr Tyr Cys
                85                  90                  95

Ala Arg Ala Leu Arg Gly Tyr Ser Ser Ser Ser Phe Gly Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445
```

```
Pro Gly Lys
    450


<210> SEQ ID NO 160
<211> LENGTH: 1344
<212> TYPE: DNA
<213> ORGANISM: Homo sapiens
<220> FEATURE:
<221> NAME/KEY: CDS
<222> LOCATION: (1)..(1344)

<400> SEQUENCE: 160

gag gtc cag ctg gtg cag tct ggg gct gag gtg aag aag cct ggg gcc       48
Glu Val Gln Leu Val Gln Ser Gly Ala Glu Val Lys Lys Pro Gly Ala
1               5                   10                  15

tca gtg aag gtt tcc tgc aag gca tct gga tac acc ttc agc aac tac       96
Ser Val Lys Val Ser Cys Lys Ala Ser Gly Tyr Thr Phe Ser Asn Tyr
            20                  25                  30

tat atg cac tgg gtg cga cag gcc cct gga caa ggg ctt gag tgg atg      144
Tyr Met His Trp Val Arg Gln Ala Pro Gly Gln Gly Leu Glu Trp Met
        35                  40                  45

gga ata atc aac cct agt ggt ggt agc aca agt tac gca cag aag ttt      192
Gly Ile Ile Asn Pro Ser Gly Gly Ser Thr Ser Tyr Ala Gln Lys Phe
    50                  55                  60

cag ggc aga ttc acc gtg acc agg gac acg tcc acg agc aca gtc tac      240
Gln Gly Arg Phe Thr Val Thr Arg Asp Thr Ser Thr Ser Thr Val Tyr
65                  70                  75                  80

atg gag ctg agc agc ctg aga tct gag gac acg gcc gtg tat tac tgt      288
Met Glu Leu Ser Ser Leu Arg Ser Glu Asp Thr Ala Val Tyr Tyr Cys
                85                  90                  95

gcg act cga cgc ggg cag cgg tac ttc cag cac tgg ggc cag ggc acc      336
Ala Thr Arg Arg Gly Gln Arg Tyr Phe Gln His Trp Gly Gln Gly Thr
            100                 105                 110

ctg gtc act gtc tcg agt gct agc acc aag ggc ccc agc gtg ttc ccc      384
Leu Val Thr Val Ser Ser Ala Ser Thr Lys Gly Pro Ser Val Phe Pro
        115                 120                 125

ctg gcc ccc agc agc aag agc acc agc ggc ggc aca gcc gcc ctg ggc      432
Leu Ala Pro Ser Ser Lys Ser Thr Ser Gly Gly Thr Ala Ala Leu Gly
    130                 135                 140

tgc ctg gtg aag gac tac ttc ccc gag ccc gtg acc gtg agc tgg aac      480
Cys Leu Val Lys Asp Tyr Phe Pro Glu Pro Val Thr Val Ser Trp Asn
145                 150                 155                 160

agc ggc gcc ttg acc agc ggc gtg cac acc ttc ccc gcc gtg ctg cag      528
Ser Gly Ala Leu Thr Ser Gly Val His Thr Phe Pro Ala Val Leu Gln
                165                 170                 175

agc agc ggc ctg tac agc ctg agc agc gtg gtg acc gtg ccc agc agc      576
Ser Ser Gly Leu Tyr Ser Leu Ser Ser Val Val Thr Val Pro Ser Ser
            180                 185                 190

agc ctg ggc acc cag acc tac atc tgc aac gtg aac cac aag ccc agc      624
Ser Leu Gly Thr Gln Thr Tyr Ile Cys Asn Val Asn His Lys Pro Ser
        195                 200                 205

aac acc aag gtg gac aaa cgc gtg gag ccc aag agc tgc gac aag acc      672
Asn Thr Lys Val Asp Lys Arg Val Glu Pro Lys Ser Cys Asp Lys Thr
    210                 215                 220

cac acc tgc ccc ccc tgc cct gcc ccc gag ctg ctg ggc gga ccc tcc      720
His Thr Cys Pro Pro Cys Pro Ala Pro Glu Leu Leu Gly Gly Pro Ser
225                 230                 235                 240

gtg ttc ctg ttc ccc ccc aag ccc aag gac acc ctc atg atc agc cgg      768
Val Phe Leu Phe Pro Pro Lys Pro Lys Asp Thr Leu Met Ile Ser Arg
                245                 250                 255

acc ccc gag gtg acc tgc gtg gtg gtg gac gtg agc cac gag gac ccc      816
```

```
Thr Pro Glu Val Thr Cys Val Val Val Asp Val Ser His Glu Asp Pro
            260                 265                 270

gag gtg aag ttc aac tgg tac gtg gac ggc gtg gag gtg cac aac gcc      864
Glu Val Lys Phe Asn Trp Tyr Val Asp Gly Val Glu Val His Asn Ala
        275                 280                 285

aag acc aag ccc cgg gag gag cag tac aac agc acc tac cgg gtg gtg      912
Lys Thr Lys Pro Arg Glu Glu Gln Tyr Asn Ser Thr Tyr Arg Val Val
    290                 295                 300

agc gtg ctc acc gtg ctg cac cag gac tgg ctg aac ggc aag gag tac      960
Ser Val Leu Thr Val Leu His Gln Asp Trp Leu Asn Gly Lys Glu Tyr
305                 310                 315                 320

aag tgc aag gtg agc aac aag gcc ctg cct gcc ccc atc gag aag acc     1008
Lys Cys Lys Val Ser Asn Lys Ala Leu Pro Ala Pro Ile Glu Lys Thr
                325                 330                 335

atc agc aag gcc aag ggc cag ccc cgg gag ccc cag gtg tac acc ctg     1056
Ile Ser Lys Ala Lys Gly Gln Pro Arg Glu Pro Gln Val Tyr Thr Leu
            340                 345                 350

ccc ccc agc cgg gag gag atg acc aag aac cag gtg tcc ctc acc tgt     1104
Pro Pro Ser Arg Glu Glu Met Thr Lys Asn Gln Val Ser Leu Thr Cys
        355                 360                 365

ctg gtg aag ggc ttc tac ccc agc gac atc gcc gtg gag tgg gag agc     1152
Leu Val Lys Gly Phe Tyr Pro Ser Asp Ile Ala Val Glu Trp Glu Ser
    370                 375                 380

aac ggc cag ccc gag aac aac tac aag acc acc ccc cct gtg ctg gac     1200
Asn Gly Gln Pro Glu Asn Asn Tyr Lys Thr Thr Pro Pro Val Leu Asp
385                 390                 395                 400

agc gac ggc agc ttc ttc ctg tac agc aag ctc acc gtg gac aag agc     1248
Ser Asp Gly Ser Phe Phe Leu Tyr Ser Lys Leu Thr Val Asp Lys Ser
                405                 410                 415

cgg tgg cag cag ggc aac gtg ttc agc tgc agc gtg atg cac gag gcc     1296
Arg Trp Gln Gln Gly Asn Val Phe Ser Cys Ser Val Met His Glu Ala
            420                 425                 430

ctg cac aac cac tac acc cag aag agc ctg agc ctg agc ccc ggc aag     1344
Leu His Asn His Tyr Thr Gln Lys Ser Leu Ser Leu Ser Pro Gly Lys
        435                 440                 445


<210> SEQ ID NO 161
<211> LENGTH: 448
<212> TYPE: PRT
<213> ORGANISM: Homo sapiens

<400> SEQUENCE: 161

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asn Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Phe Thr Val Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Thr Arg Arg Gly Gln Arg Tyr Phe Gln His Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
```

```
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445


<210> SEQ ID NO 162
<211> LENGTH: 1353
<212> TYPE: DNA
<213> ORGANISM: Homo sapiens
<220> FEATURE:
<221> NAME/KEY: CDS
<222> LOCATION: (1)..(1353)

<400> SEQUENCE: 162

cag gta cag ctg cag cag tca ggt cca gga ctg gtg aag ccc tcg cag       48
Gln Val Gln Leu Gln Gln Ser Gly Pro Gly Leu Val Lys Pro Ser Gln
1               5                   10                  15

acc ctc tca ctc acc tgt gcc atc tcc gga gac agt gtc tct agc aac       96
Thr Leu Ser Leu Thr Cys Ala Ile Ser Gly Asp Ser Val Ser Ser Asn
            20                  25                  30

aga gct gct tgg aac tgg atc agg cag tcc cca tcg aga ggc ctt gag      144
Arg Ala Ala Trp Asn Trp Ile Arg Gln Ser Pro Ser Arg Gly Leu Glu
```

-continued

```
        35                  40                  45

tgg ctg gga agg aca tac tac agg tcc aag tgg tat aat gat tat gca      192
Trp Leu Gly Arg Thr Tyr Tyr Arg Ser Lys Trp Tyr Asn Asp Tyr Ala
    50                  55                  60

gta tct gtg aaa agt cga ata agc atc aac cca gac gca ttg aag aac      240
Val Ser Val Lys Ser Arg Ile Ser Ile Asn Pro Asp Ala Leu Lys Asn
65                  70                  75                  80

cag ttc tcc ctg cag ctg aac tct gtg act ccc gag gac acg gct gtg      288
Gln Phe Ser Leu Gln Leu Asn Ser Val Thr Pro Glu Asp Thr Ala Val
                85                  90                  95

tat tac tgt gca aga gat act ggc tgg tac cga ttt gac tcc tgg ggc      336
Tyr Tyr Cys Ala Arg Asp Thr Gly Trp Tyr Arg Phe Asp Ser Trp Gly
            100                 105                 110

cag gga acc ctg gtc acc gtc tcg agt gct agc acc aag ggc ccc agc      384
Gln Gly Thr Leu Val Thr Val Ser Ser Ala Ser Thr Lys Gly Pro Ser
        115                 120                 125

gtg ttc ccc ctg gcc ccc agc agc aag agc acc agc ggc ggc aca gcc      432
Val Phe Pro Leu Ala Pro Ser Ser Lys Ser Thr Ser Gly Gly Thr Ala
    130                 135                 140

gcc ctg ggc tgc ctg gtg aag gac tac ttc ccc gag ccc gtg acc gtg      480
Ala Leu Gly Cys Leu Val Lys Asp Tyr Phe Pro Glu Pro Val Thr Val
145                 150                 155                 160

agc tgg aac agc ggc gcc ttg acc agc ggc gtg cac acc ttc ccc gcc      528
Ser Trp Asn Ser Gly Ala Leu Thr Ser Gly Val His Thr Phe Pro Ala
                165                 170                 175

gtg ctg cag agc agc ggc ctg tac agc ctg agc agc gtg gtg acc gtg      576
Val Leu Gln Ser Ser Gly Leu Tyr Ser Leu Ser Ser Val Val Thr Val
            180                 185                 190

ccc agc agc agc ctg ggc acc cag acc tac atc tgc aac gtg aac cac      624
Pro Ser Ser Ser Leu Gly Thr Gln Thr Tyr Ile Cys Asn Val Asn His
        195                 200                 205

aag ccc agc aac acc aag gtg gac aaa cgc gtg gag ccc aag agc tgc      672
Lys Pro Ser Asn Thr Lys Val Asp Lys Arg Val Glu Pro Lys Ser Cys
    210                 215                 220

gac aag acc cac acc tgc ccc ccc tgc cct gcc ccc gag ctg ctg ggc      720
Asp Lys Thr His Thr Cys Pro Pro Cys Pro Ala Pro Glu Leu Leu Gly
225                 230                 235                 240

gga ccc tcc gtg ttc ctg ttc ccc ccc aag ccc aag gac acc ctc atg      768
Gly Pro Ser Val Phe Leu Phe Pro Pro Lys Pro Lys Asp Thr Leu Met
                245                 250                 255

atc agc cgg acc ccc gag gtg acc tgc gtg gtg gtg gac gtg agc cac      816
Ile Ser Arg Thr Pro Glu Val Thr Cys Val Val Val Asp Val Ser His
            260                 265                 270

gag gac ccc gag gtg aag ttc aac tgg tac gtg gac ggc gtg gag gtg      864
Glu Asp Pro Glu Val Lys Phe Asn Trp Tyr Val Asp Gly Val Glu Val
        275                 280                 285

cac aac gcc aag acc aag ccc cgg gag gag cag tac aac agc acc tac      912
His Asn Ala Lys Thr Lys Pro Arg Glu Glu Gln Tyr Asn Ser Thr Tyr
    290                 295                 300

cgg gtg gtg agc gtg ctc acc gtg ctg cac cag gac tgg ctg aac ggc      960
Arg Val Val Ser Val Leu Thr Val Leu His Gln Asp Trp Leu Asn Gly
305                 310                 315                 320

aag gag tac aag tgc aag gtg agc aac aag gcc ctg cct gcc ccc atc     1008
Lys Glu Tyr Lys Cys Lys Val Ser Asn Lys Ala Leu Pro Ala Pro Ile
                325                 330                 335

gag aag acc atc agc aag gcc aag ggc cag ccc cgg gag ccc cag gtg     1056
Glu Lys Thr Ile Ser Lys Ala Lys Gly Gln Pro Arg Glu Pro Gln Val
            340                 345                 350

tac acc ctg ccc ccc agc cgg gag gag atg acc aag aac cag gtg tcc     1104
Tyr Thr Leu Pro Pro Ser Arg Glu Glu Met Thr Lys Asn Gln Val Ser
```

```
        355                 360                 365

ctc acc tgt ctg gtg aag ggc ttc tac ccc agc gac atc gcc gtg gag      1152
Leu Thr Cys Leu Val Lys Gly Phe Tyr Pro Ser Asp Ile Ala Val Glu
    370                 375                 380

tgg gag agc aac ggc cag ccc gag aac aac tac aag acc acc ccc cct      1200
Trp Glu Ser Asn Gly Gln Pro Glu Asn Asn Tyr Lys Thr Thr Pro Pro
385                 390                 395                 400

gtg ctg gac agc gac ggc agc ttc ttc ctg tac agc aag ctc acc gtg      1248
Val Leu Asp Ser Asp Gly Ser Phe Phe Leu Tyr Ser Lys Leu Thr Val
                405                 410                 415

gac aag agc cgg tgg cag cag ggc aac gtg ttc agc tgc agc gtg atg      1296
Asp Lys Ser Arg Trp Gln Gln Gly Asn Val Phe Ser Cys Ser Val Met
            420                 425                 430

cac gag gcc ctg cac aac cac tac acc cag aag agc ctg agc ctg agc      1344
His Glu Ala Leu His Asn His Tyr Thr Gln Lys Ser Leu Ser Leu Ser
        435                 440                 445

ccc ggc aag                                                          1353
Pro Gly Lys
    450


<210> SEQ ID NO 163
<211> LENGTH: 451
<212> TYPE: PRT
<213> ORGANISM: Homo sapiens

<400> SEQUENCE: 163

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Arg Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Ser Ile Asn Pro Asp Ala Leu Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Asp Thr Gly Trp Tyr Arg Phe Asp Ser Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
```

```
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450


<210> SEQ ID NO 164
<211> LENGTH: 1353
<212> TYPE: DNA
<213> ORGANISM: Homo sapiens
<220> FEATURE:
<221> NAME/KEY: CDS
<222> LOCATION: (1)..(1353)

<400> SEQUENCE: 164

gag gtc cag ctg gtg cag tct gga gca gag gtg aaa aag ccc ggg gag       48
Glu Val Gln Leu Val Gln Ser Gly Ala Glu Val Lys Lys Pro Gly Glu
1               5                   10                  15

tct ctg aag atc tcc tgt aag ggt tct gga tac agc ttt acc acc tac       96
Ser Leu Lys Ile Ser Cys Lys Gly Ser Gly Tyr Ser Phe Thr Thr Tyr
            20                  25                  30

tgg atc ggc tgg gtg cgc cag atg ccc ggg aaa ggc ctg gag tgg atg      144
Trp Ile Gly Trp Val Arg Gln Met Pro Gly Lys Gly Leu Glu Trp Met
        35                  40                  45

ggg atg atc tat cct ggt gac tct gat acc aga tac agc ccg tcc ttc      192
Gly Met Ile Tyr Pro Gly Asp Ser Asp Thr Arg Tyr Ser Pro Ser Phe
    50                  55                  60

caa ggc cag gtc acc atc tca gcc gac aag tcc atc agc acc gcc tac      240
Gln Gly Gln Val Thr Ile Ser Ala Asp Lys Ser Ile Ser Thr Ala Tyr
65                  70                  75                  80

ctg cag tgg agc agc ctg aag gcc tcg gac acc gcc atg tat tac tgt      288
Leu Gln Trp Ser Ser Leu Lys Ala Ser Asp Thr Ala Met Tyr Tyr Cys
                85                  90                  95

gtg aga ccc ctc cgg agc ggg agc tcc tac ggt atg gac gtc tgg ggc      336
Val Arg Pro Leu Arg Ser Gly Ser Ser Tyr Gly Met Asp Val Trp Gly
            100                 105                 110
```

```
caa ggg acc acg gtc acc gtc tcg agt gct agc acc aag ggc ccc agc       384
Gln Gly Thr Thr Val Thr Val Ser Ser Ala Ser Thr Lys Gly Pro Ser
        115                 120                 125

gtg ttc ccc ctg gcc ccc agc agc aag agc acc agc ggc ggc aca gcc       432
Val Phe Pro Leu Ala Pro Ser Ser Lys Ser Thr Ser Gly Gly Thr Ala
    130                 135                 140

gcc ctg ggc tgc ctg gtg aag gac tac ttc ccc gag ccc gtg acc gtg       480
Ala Leu Gly Cys Leu Val Lys Asp Tyr Phe Pro Glu Pro Val Thr Val
145                 150                 155                 160

agc tgg aac agc ggc gcc ttg acc agc ggc gtg cac acc ttc ccc gcc       528
Ser Trp Asn Ser Gly Ala Leu Thr Ser Gly Val His Thr Phe Pro Ala
                165                 170                 175

gtg ctg cag agc agc ggc ctg tac agc ctg agc agc gtg gtg acc gtg       576
Val Leu Gln Ser Ser Gly Leu Tyr Ser Leu Ser Ser Val Val Thr Val
            180                 185                 190

ccc agc agc agc ctg ggc acc cag acc tac atc tgc aac gtg aac cac       624
Pro Ser Ser Ser Leu Gly Thr Gln Thr Tyr Ile Cys Asn Val Asn His
        195                 200                 205

aag ccc agc aac acc aag gtg gac aaa cgc gtg gag ccc aag agc tgc       672
Lys Pro Ser Asn Thr Lys Val Asp Lys Arg Val Glu Pro Lys Ser Cys
    210                 215                 220

gac aag acc cac acc tgc ccc ccc tgc cct gcc ccc gag ctg ctg ggc       720
Asp Lys Thr His Thr Cys Pro Pro Cys Pro Ala Pro Glu Leu Leu Gly
225                 230                 235                 240

gga ccc tcc gtg ttc ctg ttc ccc ccc aag ccc aag gac acc ctc atg       768
Gly Pro Ser Val Phe Leu Phe Pro Pro Lys Pro Lys Asp Thr Leu Met
                245                 250                 255

atc agc cgg acc ccc gag gtg acc tgc gtg gtg gtg gac gtg agc cac       816
Ile Ser Arg Thr Pro Glu Val Thr Cys Val Val Val Asp Val Ser His
            260                 265                 270

gag gac ccc gag gtg aag ttc aac tgg tac gtg gac ggc gtg gag gtg       864
Glu Asp Pro Glu Val Lys Phe Asn Trp Tyr Val Asp Gly Val Glu Val
        275                 280                 285

cac aac gcc aag acc aag ccc cgg gag gag cag tac aac agc acc tac       912
His Asn Ala Lys Thr Lys Pro Arg Glu Glu Gln Tyr Asn Ser Thr Tyr
    290                 295                 300

cgg gtg gtg agc gtg ctc acc gtg ctg cac cag gac tgg ctg aac ggc       960
Arg Val Val Ser Val Leu Thr Val Leu His Gln Asp Trp Leu Asn Gly
305                 310                 315                 320

aag gag tac aag tgc aag gtg agc aac aag gcc ctg cct gcc ccc atc      1008
Lys Glu Tyr Lys Cys Lys Val Ser Asn Lys Ala Leu Pro Ala Pro Ile
                325                 330                 335

gag aag acc atc agc aag gcc aag ggc cag ccc cgg gag ccc cag gtg      1056
Glu Lys Thr Ile Ser Lys Ala Lys Gly Gln Pro Arg Glu Pro Gln Val
            340                 345                 350

tac acc ctg ccc ccc agc cgg gag gag atg acc aag aac cag gtg tcc      1104
Tyr Thr Leu Pro Pro Ser Arg Glu Glu Met Thr Lys Asn Gln Val Ser
        355                 360                 365

ctc acc tgt ctg gtg aag ggc ttc tac ccc agc gac atc gcc gtg gag      1152
Leu Thr Cys Leu Val Lys Gly Phe Tyr Pro Ser Asp Ile Ala Val Glu
    370                 375                 380

tgg gag agc aac ggc cag ccc gag aac aac tac aag acc acc ccc cct      1200
Trp Glu Ser Asn Gly Gln Pro Glu Asn Asn Tyr Lys Thr Thr Pro Pro
385                 390                 395                 400

gtg ctg gac agc gac ggc agc ttc ttc ctg tac agc aag ctc acc gtg      1248
Val Leu Asp Ser Asp Gly Ser Phe Phe Leu Tyr Ser Lys Leu Thr Val
                405                 410                 415

gac aag agc cgg tgg cag cag ggc aac gtg ttc agc tgc agc gtg atg      1296
Asp Lys Ser Arg Trp Gln Gln Gly Asn Val Phe Ser Cys Ser Val Met
            420                 425                 430
```

```
cac gag gcc ctg cac aac cac tac acc cag aag agc ctg agc ctg agc      1344
His Glu Ala Leu His Asn His Tyr Thr Gln Lys Ser Leu Ser Leu Ser
        435                 440                 445

ccc ggc aag                                                          1353
Pro Gly Lys
    450


<210> SEQ ID NO 165
<211> LENGTH: 451
<212> TYPE: PRT
<213> ORGANISM: Homo sapiens

<400> SEQUENCE: 165

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Thr Tyr
            20                  25                  30

Trp Ile Gly Trp Val Arg Gln Met Pro Gly Lys Gly Leu Glu Trp Met
        35                  40                  45

Gly Met Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Val Arg Pro Leu Arg Ser Gly Ser Ser Tyr Gly Met Asp Val Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
```

```
        340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450


<210> SEQ ID NO 166
<211> LENGTH: 1359
<212> TYPE: DNA
<213> ORGANISM: Homo sapiens
<220> FEATURE:
<221> NAME/KEY: CDS
<222> LOCATION: (1)..(1359)

<400> SEQUENCE: 166

gag gtg cag ctg gtg gag acc gga gca gag gtg caa aag ccc ggg gag       48
Glu Val Gln Leu Val Glu Thr Gly Ala Glu Val Gln Lys Pro Gly Glu
1               5                   10                  15

tct ctg aag atc tcc tgt aag ggt tct gga tac acc ttt acc aac tac       96
Ser Leu Lys Ile Ser Cys Lys Gly Ser Gly Tyr Thr Phe Thr Asn Tyr
            20                  25                  30

tgg atc gcc tgg gtg cgc cag aag ccc ggg aaa ggc ctg gag tgg atg      144
Trp Ile Ala Trp Val Arg Gln Lys Pro Gly Lys Gly Leu Glu Trp Met
        35                  40                  45

ggg atc atc tat cct ggt gac tct gat acc aga tac agc ccg tcc ttc      192
Gly Ile Ile Tyr Pro Gly Asp Ser Asp Thr Arg Tyr Ser Pro Ser Phe
    50                  55                  60

caa ggc cag gtc acc atc tca gcc gac aag tcc atc agc acc gcc tac      240
Gln Gly Gln Val Thr Ile Ser Ala Asp Lys Ser Ile Ser Thr Ala Tyr
65                  70                  75                  80

ctg cag tgg agc agc ctg aag gcc tcg gac acc gcc atg tat tac tgt      288
Leu Gln Trp Ser Ser Leu Lys Ala Ser Asp Thr Ala Met Tyr Tyr Cys
                85                  90                  95

gcg aga cga tat tgt act act acc agc tgc agt gct ggg ttc gac ccc      336
Ala Arg Arg Tyr Cys Thr Thr Thr Ser Cys Ser Ala Gly Phe Asp Pro
            100                 105                 110

tgg ggc cag gga acc ctg gtc acc gtc tcg agt gct agc acc aag ggc      384
Trp Gly Gln Gly Thr Leu Val Thr Val Ser Ser Ala Ser Thr Lys Gly
        115                 120                 125

ccc agc gtg ttc ccc ctg gcc ccc agc agc aag agc acc agc ggc ggc      432
Pro Ser Val Phe Pro Leu Ala Pro Ser Ser Lys Ser Thr Ser Gly Gly
    130                 135                 140

aca gcc gcc ctg ggc tgc ctg gtg aag gac tac ttc ccc gag ccc gtg      480
Thr Ala Ala Leu Gly Cys Leu Val Lys Asp Tyr Phe Pro Glu Pro Val
145                 150                 155                 160

acc gtg agc tgg aac agc ggc gcc ttg acc agc ggc gtg cac acc ttc      528
Thr Val Ser Trp Asn Ser Gly Ala Leu Thr Ser Gly Val His Thr Phe
                165                 170                 175

ccc gcc gtg ctg cag agc agc ggc ctg tac agc ctg agc agc gtg gtg      576
Pro Ala Val Leu Gln Ser Ser Gly Leu Tyr Ser Leu Ser Ser Val Val
```

```
            180                 185                 190

acc gtg ccc agc agc agc ctg ggc acc cag acc tac atc tgc aac gtg      624
Thr Val Pro Ser Ser Ser Leu Gly Thr Gln Thr Tyr Ile Cys Asn Val
        195                 200                 205

aac cac aag ccc agc aac acc aag gtg gac aaa cgc gtg gag ccc aag      672
Asn His Lys Pro Ser Asn Thr Lys Val Asp Lys Arg Val Glu Pro Lys
    210                 215                 220

agc tgc gac aag acc cac acc tgc ccc ccc tgc cct gcc ccc gag ctg      720
Ser Cys Asp Lys Thr His Thr Cys Pro Pro Cys Pro Ala Pro Glu Leu
225                 230                 235                 240

ctg ggc gga ccc tcc gtg ttc ctg ttc ccc ccc aag ccc aag gac acc      768
Leu Gly Gly Pro Ser Val Phe Leu Phe Pro Pro Lys Pro Lys Asp Thr
                245                 250                 255

ctc atg atc agc cgg acc ccc gag gtg acc tgc gtg gtg gtg gac gtg      816
Leu Met Ile Ser Arg Thr Pro Glu Val Thr Cys Val Val Val Asp Val
            260                 265                 270

agc cac gag gac ccc gag gtg aag ttc aac tgg tac gtg gac ggc gtg      864
Ser His Glu Asp Pro Glu Val Lys Phe Asn Trp Tyr Val Asp Gly Val
        275                 280                 285

gag gtg cac aac gcc aag acc aag ccc cgg gag gag cag tac aac agc      912
Glu Val His Asn Ala Lys Thr Lys Pro Arg Glu Glu Gln Tyr Asn Ser
    290                 295                 300

acc tac cgg gtg gtg agc gtg ctc acc gtg ctg cac cag gac tgg ctg      960
Thr Tyr Arg Val Val Ser Val Leu Thr Val Leu His Gln Asp Trp Leu
305                 310                 315                 320

aac ggc aag gag tac aag tgc aag gtg agc aac aag gcc ctg cct gcc     1008
Asn Gly Lys Glu Tyr Lys Cys Lys Val Ser Asn Lys Ala Leu Pro Ala
                325                 330                 335

ccc atc gag aag acc atc agc aag gcc aag ggc cag ccc cgg gag ccc     1056
Pro Ile Glu Lys Thr Ile Ser Lys Ala Lys Gly Gln Pro Arg Glu Pro
            340                 345                 350

cag gtg tac acc ctg ccc ccc agc cgg gag gag atg acc aag aac cag     1104
Gln Val Tyr Thr Leu Pro Pro Ser Arg Glu Glu Met Thr Lys Asn Gln
        355                 360                 365

gtg tcc ctc acc tgt ctg gtg aag ggc ttc tac ccc agc gac atc gcc     1152
Val Ser Leu Thr Cys Leu Val Lys Gly Phe Tyr Pro Ser Asp Ile Ala
    370                 375                 380

gtg gag tgg gag agc aac ggc cag ccc gag aac aac tac aag acc acc     1200
Val Glu Trp Glu Ser Asn Gly Gln Pro Glu Asn Asn Tyr Lys Thr Thr
385                 390                 395                 400

ccc cct gtg ctg gac agc gac ggc agc ttc ttc ctg tac agc aag ctc     1248
Pro Pro Val Leu Asp Ser Asp Gly Ser Phe Phe Leu Tyr Ser Lys Leu
                405                 410                 415

acc gtg gac aag agc cgg tgg cag cag ggc aac gtg ttc agc tgc agc     1296
Thr Val Asp Lys Ser Arg Trp Gln Gln Gly Asn Val Phe Ser Cys Ser
            420                 425                 430

gtg atg cac gag gcc ctg cac aac cac tac acc cag aag agc ctg agc     1344
Val Met His Glu Ala Leu His Asn His Tyr Thr Gln Lys Ser Leu Ser
        435                 440                 445

ctg agc ccc ggc aag                                                  1359
Leu Ser Pro Gly Lys
    450


<210> SEQ ID NO 167
<211> LENGTH: 453
<212> TYPE: PRT
<213> ORGANISM: Homo sapiens

<400> SEQUENCE: 167

Glu Val Gln Leu Val Glu Thr Gly Ala Glu Val Gln Lys Pro Gly Glu
1               5                   10                  15
```

```
Ser Leu Lys Ile Ser Cys Lys Gly Ser Gly Tyr Thr Phe Thr Asn Tyr
            20                  25                  30

Trp Ile Ala Trp Val Arg Gln Lys Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Arg Tyr Cys Thr Thr Thr Ser Cys Ser Ala Gly Phe Asp Pro
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
```

```
        435                 440                 445

Leu Ser Pro Gly Lys
    450


<210> SEQ ID NO 168
<211> LENGTH: 1353
<212> TYPE: DNA
<213> ORGANISM: Homo sapiens
<220> FEATURE:
<221> NAME/KEY: CDS
<222> LOCATION: (1)..(1353)

<400> SEQUENCE: 168

cag gtc cag ctg gtg cag tct gga gca gag gtg aaa aag ccc ggg gag       48
Gln Val Gln Leu Val Gln Ser Gly Ala Glu Val Lys Lys Pro Gly Glu
1               5                   10                  15

tct ctg aag atc tcc tgt aag ggt tct ggc tac agc ttt acc aac tac       96
Ser Leu Lys Ile Ser Cys Lys Gly Ser Gly Tyr Ser Phe Thr Asn Tyr
            20                  25                  30

tgg atc gcc tgg gtg cgc cag atg ccc ggg aaa ggc ctg gag tgg atg      144
Trp Ile Ala Trp Val Arg Gln Met Pro Gly Lys Gly Leu Glu Trp Met
        35                  40                  45

gga atc atc tat cct ggt gac tct gat acc aga tac agc ccg tcc ttc      192
Gly Ile Ile Tyr Pro Gly Asp Ser Asp Thr Arg Tyr Ser Pro Ser Phe
    50                  55                  60

caa ggc cag gtc acc atc tca gcc gac agg tcc atc aac acc gcc tac      240
Gln Gly Gln Val Thr Ile Ser Ala Asp Arg Ser Ile Asn Thr Ala Tyr
65                  70                  75                  80

cta cag tgg agc agc ctg aag gcc tcg gac acc gct atg ttt tac tgt      288
Leu Gln Trp Ser Ser Leu Lys Ala Ser Asp Thr Ala Met Phe Tyr Cys
                85                  90                  95

gcg aga cgg ctc tat ggt tcg ggg aga cca tac ttt gac tac tgg ggc      336
Ala Arg Arg Leu Tyr Gly Ser Gly Arg Pro Tyr Phe Asp Tyr Trp Gly
            100                 105                 110

cag gga acc ctg gtc acc gtc tcg agt gct agc acc aag ggc ccc agc      384
Gln Gly Thr Leu Val Thr Val Ser Ser Ala Ser Thr Lys Gly Pro Ser
        115                 120                 125

gtg ttc ccc ctg gcc ccc agc agc aag agc acc agc ggc ggc aca gcc      432
Val Phe Pro Leu Ala Pro Ser Ser Lys Ser Thr Ser Gly Gly Thr Ala
    130                 135                 140

gcc ctg ggc tgc ctg gtg aag gac tac ttc ccc gag ccc gtg acc gtg      480
Ala Leu Gly Cys Leu Val Lys Asp Tyr Phe Pro Glu Pro Val Thr Val
145                 150                 155                 160

agc tgg aac agc ggc gcc ttg acc agc ggc gtg cac acc ttc ccc gcc      528
Ser Trp Asn Ser Gly Ala Leu Thr Ser Gly Val His Thr Phe Pro Ala
                165                 170                 175

gtg ctg cag agc agc ggc ctg tac agc ctg agc agc gtg gtg acc gtg      576
Val Leu Gln Ser Ser Gly Leu Tyr Ser Leu Ser Ser Val Val Thr Val
            180                 185                 190

ccc agc agc agc ctg ggc acc cag acc tac atc tgc aac gtg aac cac      624
Pro Ser Ser Ser Leu Gly Thr Gln Thr Tyr Ile Cys Asn Val Asn His
        195                 200                 205

aag ccc agc aac acc aag gtg gac aaa cgc gtg gag ccc aag agc tgc      672
Lys Pro Ser Asn Thr Lys Val Asp Lys Arg Val Glu Pro Lys Ser Cys
    210                 215                 220

gac aag acc cac acc tgc ccc ccc tgc cct gcc ccc gag ctg ctg ggc      720
Asp Lys Thr His Thr Cys Pro Pro Cys Pro Ala Pro Glu Leu Leu Gly
225                 230                 235                 240

gga ccc tcc gtg ttc ctg ttc ccc ccc aag ccc aag gac acc ctc atg      768
Gly Pro Ser Val Phe Leu Phe Pro Pro Lys Pro Lys Asp Thr Leu Met
                245                 250                 255
```

```
atc agc cgg acc ccc gag gtg acc tgc gtg gtg gtg gac gtg agc cac      816
Ile Ser Arg Thr Pro Glu Val Thr Cys Val Val Val Asp Val Ser His
            260                 265                 270

gag gac ccc gag gtg aag ttc aac tgg tac gtg gac ggc gtg gag gtg      864
Glu Asp Pro Glu Val Lys Phe Asn Trp Tyr Val Asp Gly Val Glu Val
        275                 280                 285

cac aac gcc aag acc aag ccc cgg gag gag cag tac aac agc acc tac      912
His Asn Ala Lys Thr Lys Pro Arg Glu Glu Gln Tyr Asn Ser Thr Tyr
    290                 295                 300

cgg gtg gtg agc gtg ctc acc gtg ctg cac cag gac tgg ctg aac ggc      960
Arg Val Val Ser Val Leu Thr Val Leu His Gln Asp Trp Leu Asn Gly
305                 310                 315                 320

aag gag tac aag tgc aag gtg agc aac aag gcc ctg cct gcc ccc atc     1008
Lys Glu Tyr Lys Cys Lys Val Ser Asn Lys Ala Leu Pro Ala Pro Ile
                325                 330                 335

gag aag acc atc agc aag gcc aag ggc cag ccc cgg gag ccc cag gtg     1056
Glu Lys Thr Ile Ser Lys Ala Lys Gly Gln Pro Arg Glu Pro Gln Val
            340                 345                 350

tac acc ctg ccc ccc agc cgg gag gag atg acc aag aac cag gtg tcc     1104
Tyr Thr Leu Pro Pro Ser Arg Glu Glu Met Thr Lys Asn Gln Val Ser
        355                 360                 365

ctc acc tgt ctg gtg aag ggc ttc tac ccc agc gac atc gcc gtg gag     1152
Leu Thr Cys Leu Val Lys Gly Phe Tyr Pro Ser Asp Ile Ala Val Glu
    370                 375                 380

tgg gag agc aac ggc cag ccc gag aac aac tac aag acc acc ccc cct     1200
Trp Glu Ser Asn Gly Gln Pro Glu Asn Asn Tyr Lys Thr Thr Pro Pro
385                 390                 395                 400

gtg ctg gac agc gac ggc agc ttc ttc ctg tac agc aag ctc acc gtg     1248
Val Leu Asp Ser Asp Gly Ser Phe Phe Leu Tyr Ser Lys Leu Thr Val
                405                 410                 415

gac aag agc cgg tgg cag cag ggc aac gtg ttc agc tgc agc gtg atg     1296
Asp Lys Ser Arg Trp Gln Gln Gly Asn Val Phe Ser Cys Ser Val Met
            420                 425                 430

cac gag gcc ctg cac aac cac tac acc cag aag agc ctg agc ctg agc     1344
His Glu Ala Leu His Asn His Tyr Thr Gln Lys Ser Leu Ser Leu Ser
        435                 440                 445

ccc ggc aag                                                         1353
Pro Gly Lys
    450


<210> SEQ ID NO 169
<211> LENGTH: 451
<212> TYPE: PRT
<213> ORGANISM: Homo sapiens

<400> SEQUENCE: 169

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Ile Ala Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Arg Ser Ile Asn Thr Ala Tyr
65                  70                  75                  80

Leu Gln Trp Ser Ser Leu Lys Ala Ser Asp Thr Ala Met Phe Tyr Cys
                85                  90                  95

Ala Arg Arg Leu Tyr Gly Ser Gly Arg Pro Tyr Phe Asp Tyr Trp Gly
            100                 105                 110
```

```
Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450
```

<210> SEQ ID NO 170
<211> LENGTH: 1356
<212> TYPE: DNA
<213> ORGANISM: Homo sapiens
<220> FEATURE:
<221> NAME/KEY: CDS
<222> LOCATION: (1)..(1356)

<400> SEQUENCE: 170

```
gag gtc cag ttg gtg cag tct gga gca gag gtg aaa aag ccc ggg gag        48
Glu Val Gln Leu Val Gln Ser Gly Ala Glu Val Lys Lys Pro Gly Glu
```

-continued

```
1               5                   10                  15

tct ctg aag atc tcc tgt aag ggt tct gga tac agc ttt acc aac tac       96
Ser Leu Lys Ile Ser Cys Lys Gly Ser Gly Tyr Ser Phe Thr Asn Tyr
            20                  25                  30

tgg atc ggc tgg gtg cgc cag atg ccc ggg aaa ggc ctg gag tgg atg      144
Trp Ile Gly Trp Val Arg Gln Met Pro Gly Lys Gly Leu Glu Trp Met
        35                  40                  45

ggg atc atc tat cct ggt gac tct gat acc aga tac agc ccg tcc ttc      192
Gly Ile Ile Tyr Pro Gly Asp Ser Asp Thr Arg Tyr Ser Pro Ser Phe
    50                  55                  60

caa ggc cag gtc acc atc tca gcc gac aag tcc atc agc acc gcc tac      240
Gln Gly Gln Val Thr Ile Ser Ala Asp Lys Ser Ile Ser Thr Ala Tyr
65                  70                  75                  80

ctg cag tgg agc agc ctg aag gcc tcg gac acc gcc atg tat tac tgt      288
Leu Gln Trp Ser Ser Leu Lys Ala Ser Asp Thr Ala Met Tyr Tyr Cys
                85                  90                  95

gcg aga cat acg cag aac aaa aat ggg atg aat act ttt gat atc tgg      336
Ala Arg His Thr Gln Asn Lys Asn Gly Met Asn Thr Phe Asp Ile Trp
            100                 105                 110

ggc caa ggg aca atg gtc acc gtc tcg agt gct agc acc aag ggc ccc      384
Gly Gln Gly Thr Met Val Thr Val Ser Ser Ala Ser Thr Lys Gly Pro
        115                 120                 125

agc gtg ttc ccc ctg gcc ccc agc agc aag agc acc agc ggc ggc aca      432
Ser Val Phe Pro Leu Ala Pro Ser Ser Lys Ser Thr Ser Gly Gly Thr
    130                 135                 140

gcc gcc ctg ggc tgc ctg gtg aag gac tac ttc ccc gag ccc gtg acc      480
Ala Ala Leu Gly Cys Leu Val Lys Asp Tyr Phe Pro Glu Pro Val Thr
145                 150                 155                 160

gtg agc tgg aac agc ggc gcc ttg acc agc ggc gtg cac acc ttc ccc      528
Val Ser Trp Asn Ser Gly Ala Leu Thr Ser Gly Val His Thr Phe Pro
                165                 170                 175

gcc gtg ctg cag agc agc ggc ctg tac agc ctg agc agc gtg gtg acc      576
Ala Val Leu Gln Ser Ser Gly Leu Tyr Ser Leu Ser Ser Val Val Thr
            180                 185                 190

gtg ccc agc agc agc ctg ggc acc cag acc tac atc tgc aac gtg aac      624
Val Pro Ser Ser Ser Leu Gly Thr Gln Thr Tyr Ile Cys Asn Val Asn
        195                 200                 205

cac aag ccc agc aac acc aag gtg gac aaa cgc gtg gag ccc aag agc      672
His Lys Pro Ser Asn Thr Lys Val Asp Lys Arg Val Glu Pro Lys Ser
    210                 215                 220

tgc gac aag acc cac acc tgc ccc ccc tgc cct gcc ccc gag ctg ctg      720
Cys Asp Lys Thr His Thr Cys Pro Pro Cys Pro Ala Pro Glu Leu Leu
225                 230                 235                 240

ggc gga ccc tcc gtg ttc ctg ttc ccc ccc aag ccc aag gac acc ctc      768
Gly Gly Pro Ser Val Phe Leu Phe Pro Pro Lys Pro Lys Asp Thr Leu
                245                 250                 255

atg atc agc cgg acc ccc gag gtg acc tgc gtg gtg gtg gac gtg agc      816
Met Ile Ser Arg Thr Pro Glu Val Thr Cys Val Val Val Asp Val Ser
            260                 265                 270

cac gag gac ccc gag gtg aag ttc aac tgg tac gtg gac ggc gtg gag      864
His Glu Asp Pro Glu Val Lys Phe Asn Trp Tyr Val Asp Gly Val Glu
        275                 280                 285

gtg cac aac gcc aag acc aag ccc cgg gag gag cag tac aac agc acc      912
Val His Asn Ala Lys Thr Lys Pro Arg Glu Glu Gln Tyr Asn Ser Thr
    290                 295                 300

tac cgg gtg gtg agc gtg ctc acc gtg ctg cac cag gac tgg ctg aac      960
Tyr Arg Val Val Ser Val Leu Thr Val Leu His Gln Asp Trp Leu Asn
305                 310                 315                 320

ggc aag gag tac aag tgc aag gtg agc aac aag gcc ctg cct gcc ccc     1008
Gly Lys Glu Tyr Lys Cys Lys Val Ser Asn Lys Ala Leu Pro Ala Pro
```

```
                325                 330                 335

atc gag aag acc atc agc aag gcc aag ggc cag ccc cgg gag ccc cag     1056
Ile Glu Lys Thr Ile Ser Lys Ala Lys Gly Gln Pro Arg Glu Pro Gln
            340                 345                 350

gtg tac acc ctg ccc ccc agc cgg gag gag atg acc aag aac cag gtg     1104
Val Tyr Thr Leu Pro Pro Ser Arg Glu Glu Met Thr Lys Asn Gln Val
        355                 360                 365

tcc ctc acc tgt ctg gtg aag ggc ttc tac ccc agc gac atc gcc gtg     1152
Ser Leu Thr Cys Leu Val Lys Gly Phe Tyr Pro Ser Asp Ile Ala Val
    370                 375                 380

gag tgg gag agc aac ggc cag ccc gag aac aac tac aag acc acc ccc     1200
Glu Trp Glu Ser Asn Gly Gln Pro Glu Asn Asn Tyr Lys Thr Thr Pro
385                 390                 395                 400

cct gtg ctg gac agc gac ggc agc ttc ttc ctg tac agc aag ctc acc     1248
Pro Val Leu Asp Ser Asp Gly Ser Phe Phe Leu Tyr Ser Lys Leu Thr
                405                 410                 415

gtg gac aag agc cgg tgg cag cag ggc aac gtg ttc agc tgc agc gtg     1296
Val Asp Lys Ser Arg Trp Gln Gln Gly Asn Val Phe Ser Cys Ser Val
            420                 425                 430

atg cac gag gcc ctg cac aac cac tac acc cag aag agc ctg agc ctg     1344
Met His Glu Ala Leu His Asn His Tyr Thr Gln Lys Ser Leu Ser Leu
        435                 440                 445

agc ccc ggc aag                                                     1356
Ser Pro Gly Lys
    450


<210> SEQ ID NO 171
<211> LENGTH: 452
<212> TYPE: PRT
<213> ORGANISM: Homo sapiens

<400> SEQUENCE: 171

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg His Thr Gln Asn Lys Asn Gly Met Asn Thr Phe Asp Ile Trp
            100                 105                 110

Gly Gln Gly Thr Met Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205
```

```
His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450


<210> SEQ ID NO 172
<211> LENGTH: 1338
<212> TYPE: DNA
<213> ORGANISM: Homo sapiens
<220> FEATURE:
<221> NAME/KEY: CDS
<222> LOCATION: (1)..(1338)

<400> SEQUENCE: 172

cag gtg cag cta cag cag tgg ggc gca gga ctg ttg aag cct tcg gag       48
Gln Val Gln Leu Gln Gln Trp Gly Ala Gly Leu Leu Lys Pro Ser Glu
1               5                   10                  15

acc ctg tcc ctc acc tgc gct gtc tat ggt gcg tcc ttc cgt ggt tac       96
Thr Leu Ser Leu Thr Cys Ala Val Tyr Gly Ala Ser Phe Arg Gly Tyr
            20                  25                  30

tac tgg agc tgg atc cgc cag ccc cca ggg aag ggg ctg gag tgg att      144
Tyr Trp Ser Trp Ile Arg Gln Pro Pro Gly Lys Gly Leu Glu Trp Ile
        35                  40                  45

ggg gaa atc aat cat agt gga agc acc aac tac aac ccg tcc ctc aag      192
Gly Glu Ile Asn His Ser Gly Ser Thr Asn Tyr Asn Pro Ser Leu Lys
    50                  55                  60

agt cga gtc acc ata tca gta gac acg tcc aaa aac cag ttc tcc ctg      240
Ser Arg Val Thr Ile Ser Val Asp Thr Ser Lys Asn Gln Phe Ser Leu
65                  70                  75                  80
```

```
aag ctg agt tct gtg acc gcc gca gac acg gct gtg tat tac tgt gcg       288
Lys Leu Ser Ser Val Thr Ala Ala Asp Thr Ala Val Tyr Tyr Cys Ala
                85                  90                  95

aga ggc cgc cct gat tct ttt gat atc tgg ggc caa ggg aca atg gtc       336
Arg Gly Arg Pro Asp Ser Phe Asp Ile Trp Gly Gln Gly Thr Met Val
            100                 105                 110

acc gtc tcg agt gct agc acc aag ggc ccc agc gtg ttc ccc ctg gcc       384
Thr Val Ser Ser Ala Ser Thr Lys Gly Pro Ser Val Phe Pro Leu Ala
        115                 120                 125

ccc agc agc aag agc acc agc ggc ggc aca gcc gcc ctg ggc tgc ctg       432
Pro Ser Ser Lys Ser Thr Ser Gly Gly Thr Ala Ala Leu Gly Cys Leu
    130                 135                 140

gtg aag gac tac ttc ccc gag ccc gtg acc gtg agc tgg aac agc ggc       480
Val Lys Asp Tyr Phe Pro Glu Pro Val Thr Val Ser Trp Asn Ser Gly
145                 150                 155                 160

gcc ttg acc agc ggc gtg cac acc ttc ccc gcc gtg ctg cag agc agc       528
Ala Leu Thr Ser Gly Val His Thr Phe Pro Ala Val Leu Gln Ser Ser
                165                 170                 175

ggc ctg tac agc ctg agc agc gtg gtg acc gtg ccc agc agc agc ctg       576
Gly Leu Tyr Ser Leu Ser Ser Val Val Thr Val Pro Ser Ser Ser Leu
            180                 185                 190

ggc acc cag acc tac atc tgc aac gtg aac cac aag ccc agc aac acc       624
Gly Thr Gln Thr Tyr Ile Cys Asn Val Asn His Lys Pro Ser Asn Thr
        195                 200                 205

aag gtg gac aaa cgc gtg gag ccc aag agc tgc gac aag acc cac acc       672
Lys Val Asp Lys Arg Val Glu Pro Lys Ser Cys Asp Lys Thr His Thr
    210                 215                 220

tgc ccc ccc tgc cct gcc ccc gag ctg ctg ggc gga ccc tcc gtg ttc       720
Cys Pro Pro Cys Pro Ala Pro Glu Leu Leu Gly Gly Pro Ser Val Phe
225                 230                 235                 240

ctg ttc ccc ccc aag ccc aag gac acc ctc atg atc agc cgg acc ccc       768
Leu Phe Pro Pro Lys Pro Lys Asp Thr Leu Met Ile Ser Arg Thr Pro
                245                 250                 255

gag gtg acc tgc gtg gtg gtg gac gtg agc cac gag gac ccc gag gtg       816
Glu Val Thr Cys Val Val Val Asp Val Ser His Glu Asp Pro Glu Val
            260                 265                 270

aag ttc aac tgg tac gtg gac ggc gtg gag gtg cac aac gcc aag acc       864
Lys Phe Asn Trp Tyr Val Asp Gly Val Glu Val His Asn Ala Lys Thr
        275                 280                 285

aag ccc cgg gag gag cag tac aac agc acc tac cgg gtg gtg agc gtg       912
Lys Pro Arg Glu Glu Gln Tyr Asn Ser Thr Tyr Arg Val Val Ser Val
    290                 295                 300

ctc acc gtg ctg cac cag gac tgg ctg aac ggc aag gag tac aag tgc       960
Leu Thr Val Leu His Gln Asp Trp Leu Asn Gly Lys Glu Tyr Lys Cys
305                 310                 315                 320

aag gtg agc aac aag gcc ctg cct gcc ccc atc gag aag acc atc agc      1008
Lys Val Ser Asn Lys Ala Leu Pro Ala Pro Ile Glu Lys Thr Ile Ser
                325                 330                 335

aag gcc aag ggc cag ccc cgg gag ccc cag gtg tac acc ctg ccc ccc      1056
Lys Ala Lys Gly Gln Pro Arg Glu Pro Gln Val Tyr Thr Leu Pro Pro
            340                 345                 350

agc cgg gag gag atg acc aag aac cag gtg tcc ctc acc tgt ctg gtg      1104
Ser Arg Glu Glu Met Thr Lys Asn Gln Val Ser Leu Thr Cys Leu Val
        355                 360                 365

aag ggc ttc tac ccc agc gac atc gcc gtg gag tgg gag agc aac ggc      1152
Lys Gly Phe Tyr Pro Ser Asp Ile Ala Val Glu Trp Glu Ser Asn Gly
    370                 375                 380

cag ccc gag aac aac tac aag acc acc ccc cct gtg ctg gac agc gac      1200
Gln Pro Glu Asn Asn Tyr Lys Thr Thr Pro Pro Val Leu Asp Ser Asp
385                 390                 395                 400
```

```
ggc agc ttc ttc ctg tac agc aag ctc acc gtg gac aag agc cgg tgg      1248
Gly Ser Phe Phe Leu Tyr Ser Lys Leu Thr Val Asp Lys Ser Arg Trp
                405                 410                 415

cag cag ggc aac gtg ttc agc tgc agc gtg atg cac gag gcc ctg cac      1296
Gln Gln Gly Asn Val Phe Ser Cys Ser Val Met His Glu Ala Leu His
            420                 425                 430

aac cac tac acc cag aag agc ctg agc ctg agc ccc ggc aag              1338
Asn His Tyr Thr Gln Lys Ser Leu Ser Leu Ser Pro Gly Lys
        435                 440                 445


<210> SEQ ID NO 173
<211> LENGTH: 446
<212> TYPE: PRT
<213> ORGANISM: Homo sapiens

<400> SEQUENCE: 173

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Ala Ser Phe Arg Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Arg Pro Asp Ser Phe Asp Ile Trp Gly Gln Gly Thr Met Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320
```

```
Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445


<210> SEQ ID NO 174
<211> LENGTH: 1359
<212> TYPE: DNA
<213> ORGANISM: Homo sapiens
<220> FEATURE:
<221> NAME/KEY: CDS
<222> LOCATION: (1)..(1359)

<400> SEQUENCE: 174

cag gtg cag ctg gtg caa tct gga gca gag gtg aaa aag ccg ggg gag       48
Gln Val Gln Leu Val Gln Ser Gly Ala Glu Val Lys Lys Pro Gly Glu
1               5                   10                  15

tct ctg aag atc tcc tgt aag ggt tct ggt tac agc ttt acc aac tac       96
Ser Leu Lys Ile Ser Cys Lys Gly Ser Gly Tyr Ser Phe Thr Asn Tyr
            20                  25                  30

tgg atc ggc tgg gtg cgc cag atg ccc ggg aaa ggc ctg gag tgg atg      144
Trp Ile Gly Trp Val Arg Gln Met Pro Gly Lys Gly Leu Glu Trp Met
        35                  40                  45

gga atc atc tat cct ggt gac tct gat acc aga tac agt ccg tcc ttc      192
Gly Ile Ile Tyr Pro Gly Asp Ser Asp Thr Arg Tyr Ser Pro Ser Phe
    50                  55                  60

cga ggc cag gtc acc atc tca gcc gac aag tcc atc agc acc gcc tac      240
Arg Gly Gln Val Thr Ile Ser Ala Asp Lys Ser Ile Ser Thr Ala Tyr
65                  70                  75                  80

ctg cag tgg agc agc ctg aag gcc tcg gac acc gcc atg tat tac tgt      288
Leu Gln Trp Ser Ser Leu Lys Ala Ser Asp Thr Ala Met Tyr Tyr Cys
                85                  90                  95

gcg aga ctt gga tac agc tat ggt tac agg ggg cct cac ttt gat tac      336
Ala Arg Leu Gly Tyr Ser Tyr Gly Tyr Arg Gly Pro His Phe Asp Tyr
            100                 105                 110

tgg ggc cag gga acc ctg gtc acc gtc tcg agt gct agc acc aag ggc      384
Trp Gly Gln Gly Thr Leu Val Thr Val Ser Ser Ala Ser Thr Lys Gly
        115                 120                 125

ccc agc gtg ttc ccc ctg gcc ccc agc agc aag agc acc agc ggc ggc      432
Pro Ser Val Phe Pro Leu Ala Pro Ser Ser Lys Ser Thr Ser Gly Gly
    130                 135                 140

aca gcc gcc ctg ggc tgc ctg gtg aag gac tac ttc ccc gag ccc gtg      480
Thr Ala Ala Leu Gly Cys Leu Val Lys Asp Tyr Phe Pro Glu Pro Val
145                 150                 155                 160

acc gtg agc tgg aac agc ggc gcc ttg acc agc ggc gtg cac acc ttc      528
Thr Val Ser Trp Asn Ser Gly Ala Leu Thr Ser Gly Val His Thr Phe
                165                 170                 175

ccc gcc gtg ctg cag agc agc ggc ctg tac agc ctg agc agc gtg gtg      576
```

```
Pro Ala Val Leu Gln Ser Ser Gly Leu Tyr Ser Leu Ser Ser Val Val
            180                 185                 190

acc gtg ccc agc agc agc ctg ggc acc cag acc tac atc tgc aac gtg      624
Thr Val Pro Ser Ser Ser Leu Gly Thr Gln Thr Tyr Ile Cys Asn Val
        195                 200                 205

aac cac aag ccc agc aac acc aag gtg gac aaa cgc gtg gag ccc aag      672
Asn His Lys Pro Ser Asn Thr Lys Val Asp Lys Arg Val Glu Pro Lys
    210                 215                 220

agc tgc gac aag acc cac acc tgc ccc ccc tgc cct gcc ccc gag ctg      720
Ser Cys Asp Lys Thr His Thr Cys Pro Pro Cys Pro Ala Pro Glu Leu
225                 230                 235                 240

ctg ggc gga ccc tcc gtg ttc ctg ttc ccc ccc aag ccc aag gac acc      768
Leu Gly Gly Pro Ser Val Phe Leu Phe Pro Pro Lys Pro Lys Asp Thr
                245                 250                 255

ctc atg atc agc cgg acc ccc gag gtg acc tgc gtg gtg gtg gac gtg      816
Leu Met Ile Ser Arg Thr Pro Glu Val Thr Cys Val Val Val Asp Val
            260                 265                 270

agc cac gag gac ccc gag gtg aag ttc aac tgg tac gtg gac ggc gtg      864
Ser His Glu Asp Pro Glu Val Lys Phe Asn Trp Tyr Val Asp Gly Val
        275                 280                 285

gag gtg cac aac gcc aag acc aag ccc cgg gag gag cag tac aac agc      912
Glu Val His Asn Ala Lys Thr Lys Pro Arg Glu Glu Gln Tyr Asn Ser
    290                 295                 300

acc tac cgg gtg gtg agc gtg ctc acc gtg ctg cac cag gac tgg ctg      960
Thr Tyr Arg Val Val Ser Val Leu Thr Val Leu His Gln Asp Trp Leu
305                 310                 315                 320

aac ggc aag gag tac aag tgc aag gtg agc aac aag gcc ctg cct gcc     1008
Asn Gly Lys Glu Tyr Lys Cys Lys Val Ser Asn Lys Ala Leu Pro Ala
                325                 330                 335

ccc atc gag aag acc atc agc aag gcc aag ggc cag ccc cgg gag ccc     1056
Pro Ile Glu Lys Thr Ile Ser Lys Ala Lys Gly Gln Pro Arg Glu Pro
            340                 345                 350

cag gtg tac acc ctg ccc ccc agc cgg gag gag atg acc aag aac cag     1104
Gln Val Tyr Thr Leu Pro Pro Ser Arg Glu Glu Met Thr Lys Asn Gln
        355                 360                 365

gtg tcc ctc acc tgt ctg gtg aag ggc ttc tac ccc agc gac atc gcc     1152
Val Ser Leu Thr Cys Leu Val Lys Gly Phe Tyr Pro Ser Asp Ile Ala
    370                 375                 380

gtg gag tgg gag agc aac ggc cag ccc gag aac aac tac aag acc acc     1200
Val Glu Trp Glu Ser Asn Gly Gln Pro Glu Asn Asn Tyr Lys Thr Thr
385                 390                 395                 400

ccc cct gtg ctg gac agc gac ggc agc ttc ttc ctg tac agc aag ctc     1248
Pro Pro Val Leu Asp Ser Asp Gly Ser Phe Phe Leu Tyr Ser Lys Leu
                405                 410                 415

acc gtg gac aag agc cgg tgg cag cag ggc aac gtg ttc agc tgc agc     1296
Thr Val Asp Lys Ser Arg Trp Gln Gln Gly Asn Val Phe Ser Cys Ser
            420                 425                 430

gtg atg cac gag gcc ctg cac aac cac tac acc cag aag agc ctg agc     1344
Val Met His Glu Ala Leu His Asn His Tyr Thr Gln Lys Ser Leu Ser
        435                 440                 445

ctg agc ccc ggc aag                                                 1359
Leu Ser Pro Gly Lys
    450


<210> SEQ ID NO 175
<211> LENGTH: 453
<212> TYPE: PRT
<213> ORGANISM: Homo sapiens

<400> SEQUENCE: 175

Gln Val Gln Leu Val Gln Ser Gly Ala Glu Val Lys Lys Pro Gly Glu
```

-continued

```
1               5                   10                  15

Ser Leu Lys Ile Ser Cys Lys Gly Ser Gly Tyr Ser Phe Thr Asn Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Arg Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu Gly Tyr Ser Tyr Gly Tyr Arg Gly Pro His Phe Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430
```

```
Val Met His Glu Ala Leu His Asn His Tyr Thr Gln Lys Ser Leu Ser
        435                 440                 445

Leu Ser Pro Gly Lys
    450


<210> SEQ ID NO 176
<211> LENGTH: 660
<212> TYPE: DNA
<213> ORGANISM: Homo sapiens
<220> FEATURE:
<221> NAME/KEY: CDS
<222> LOCATION: (1)..(660)

<400> SEQUENCE: 176

caa tct gcc ctg act cag cct ccc tcc gcg tcc ggg tct cct gga cag       48
Gln Ser Ala Leu Thr Gln Pro Pro Ser Ala Ser Gly Ser Pro Gly Gln
1               5                   10                  15

tca gtc acc atc tcc tgc act gga acc agc agt gac gtt ggt ggt tat       96
Ser Val Thr Ile Ser Cys Thr Gly Thr Ser Ser Asp Val Gly Gly Tyr
            20                  25                  30

aac tat gtc tcc tgg tac caa cag cac cca ggc aaa gcc ccc aaa ctc      144
Asn Tyr Val Ser Trp Tyr Gln Gln His Pro Gly Lys Ala Pro Lys Leu
        35                  40                  45

atg att tat gag gtc agt aag cgg ccc tca ggg gtc cct gat cgc ttc      192
Met Ile Tyr Glu Val Ser Lys Arg Pro Ser Gly Val Pro Asp Arg Phe
    50                  55                  60

tct ggc tcc aag tct ggc aac acg gcc tcc ctg acc gtc tct ggg ctc      240
Ser Gly Ser Lys Ser Gly Asn Thr Ala Ser Leu Thr Val Ser Gly Leu
65                  70                  75                  80

cag gct gag gat gag gct gat tat tac tgc agc tca tat gca ggc agc      288
Gln Ala Glu Asp Glu Ala Asp Tyr Tyr Cys Ser Ser Tyr Ala Gly Ser
                85                  90                  95

aac aat ttg gta ttc ggc gga ggg acc aag ctg acc gtc cta ggt gcg      336
Asn Asn Leu Val Phe Gly Gly Gly Thr Lys Leu Thr Val Leu Gly Ala
            100                 105                 110

gcc gca ggc cag ccc aag gcc gct ccc agc gtg acc ctg ttc ccc ccc      384
Ala Ala Gly Gln Pro Lys Ala Ala Pro Ser Val Thr Leu Phe Pro Pro
        115                 120                 125

tcc tcc gag gag ctg cag gcc aac aag gcc acc ctg gtg tgc ctc atc      432
Ser Ser Glu Glu Leu Gln Ala Asn Lys Ala Thr Leu Val Cys Leu Ile
    130                 135                 140

agc gac ttc tac cct ggc gcc gtg acc gtg gcc tgg aag gcc gac agc      480
Ser Asp Phe Tyr Pro Gly Ala Val Thr Val Ala Trp Lys Ala Asp Ser
145                 150                 155                 160

agc ccc gtg aag gcc ggc gtg gag acc acc acc ccc agc aag cag agc      528
Ser Pro Val Lys Ala Gly Val Glu Thr Thr Thr Pro Ser Lys Gln Ser
                165                 170                 175

aac aac aag tac gcc gcc agc agc tac ctg agc ctc acc ccc gag cag      576
Asn Asn Lys Tyr Ala Ala Ser Ser Tyr Leu Ser Leu Thr Pro Glu Gln
            180                 185                 190

tgg aag agc cac cgg agc tac agc tgc cag gtg acc cac gag ggc agc      624
Trp Lys Ser His Arg Ser Tyr Ser Cys Gln Val Thr His Glu Gly Ser
        195                 200                 205

acc gtg gag aag acc gtg gcc ccc acc gag tgc agc                      660
Thr Val Glu Lys Thr Val Ala Pro Thr Glu Cys Ser
    210                 215                 220


<210> SEQ ID NO 177
<211> LENGTH: 220
<212> TYPE: PRT
<213> ORGANISM: Homo sapiens

<400> SEQUENCE: 177
```

```
Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Ser
                85                  90                  95

Asn Asn Leu Val Phe Gly Gly Gly Thr Lys Leu Thr Val Leu Gly Ala
            100                 105                 110

Ala Ala Gly Gln Pro Lys Ala Ala Pro Ser Val Thr Leu Phe Pro Pro
        115                 120                 125

Ser Ser Glu Glu Leu Gln Ala Asn Lys Ala Thr Leu Val Cys Leu Ile
    130                 135                 140

Ser Asp Phe Tyr Pro Gly Ala Val Thr Val Ala Trp Lys Ala Asp Ser
145                 150                 155                 160

Ser Pro Val Lys Ala Gly Val Glu Thr Thr Thr Pro Ser Lys Gln Ser
                165                 170                 175

Asn Asn Lys Tyr Ala Ala Ser Ser Tyr Leu Ser Leu Thr Pro Glu Gln
            180                 185                 190

Trp Lys Ser His Arg Ser Tyr Ser Cys Gln Val Thr His Glu Gly Ser
        195                 200                 205

Thr Val Glu Lys Thr Val Ala Pro Thr Glu Cys Ser
    210                 215                 220


<210> SEQ ID NO 178
<211> LENGTH: 648
<212> TYPE: DNA
<213> ORGANISM: Homo sapiens
<220> FEATURE:
<221> NAME/KEY: CDS
<222> LOCATION: (1)..(648)

<400> SEQUENCE: 178

cag tct gtg ttg acg cag ccg ccc tca ctg tcc gtg tcc cca gga cag       48
Gln Ser Val Leu Thr Gln Pro Pro Ser Leu Ser Val Ser Pro Gly Gln
1               5                   10                  15

aca gcc agc atc tcc tgc tct gga gat aaa tta ggg gat aaa tat gtt       96
Thr Ala Ser Ile Ser Cys Ser Gly Asp Lys Leu Gly Asp Lys Tyr Val
            20                  25                  30

tcc tgg tat cag cag agg cct ggc cag tcc ccc gtc tta gtc atc tat      144
Ser Trp Tyr Gln Gln Arg Pro Gly Gln Ser Pro Val Leu Val Ile Tyr
        35                  40                  45

cac gat act aag cgg ccc tca ggg atc cct gag cga ttc tct ggt acc      192
His Asp Thr Lys Arg Pro Ser Gly Ile Pro Glu Arg Phe Ser Gly Thr
    50                  55                  60

aac tct ggg aac aca gcc act ctg acc atc agc ggg acc cag att ctg      240
Asn Ser Gly Asn Thr Ala Thr Leu Thr Ile Ser Gly Thr Gln Ile Leu
65                  70                  75                  80

gat gag gcc gac tat tac tgt cag gtg tgg gac agg agc act gtg gtt      288
Asp Glu Ala Asp Tyr Tyr Cys Gln Val Trp Asp Arg Ser Thr Val Val
                85                  90                  95

ttc ggc gga ggg acc cag ctc acc gtt tta agt gcg gcc gca ggc cag      336
Phe Gly Gly Gly Thr Gln Leu Thr Val Leu Ser Ala Ala Ala Gly Gln
```

```
            100                 105                 110

ccc aag gcc gct ccc agc gtg acc ctg ttc ccc ccc tcc tcc gag gag      384
Pro Lys Ala Ala Pro Ser Val Thr Leu Phe Pro Pro Ser Ser Glu Glu
        115                 120                 125

ctg cag gcc aac aag gcc acc ctg gtg tgc ctc atc agc gac ttc tac      432
Leu Gln Ala Asn Lys Ala Thr Leu Val Cys Leu Ile Ser Asp Phe Tyr
    130                 135                 140

cct ggc gcc gtg acc gtg gcc tgg aag gcc gac agc agc ccc gtg aag      480
Pro Gly Ala Val Thr Val Ala Trp Lys Ala Asp Ser Ser Pro Val Lys
145                 150                 155                 160

gcc ggc gtg gag acc acc acc ccc agc aag cag agc aac aac aag tac      528
Ala Gly Val Glu Thr Thr Thr Pro Ser Lys Gln Ser Asn Asn Lys Tyr
                165                 170                 175

gcc gcc agc agc tac ctg agc ctc acc ccc gag cag tgg aag agc cac      576
Ala Ala Ser Ser Tyr Leu Ser Leu Thr Pro Glu Gln Trp Lys Ser His
            180                 185                 190

cgg agc tac agc tgc cag gtg acc cac gag ggc agc acc gtg gag aag      624
Arg Ser Tyr Ser Cys Gln Val Thr His Glu Gly Ser Thr Val Glu Lys
        195                 200                 205

acc gtg gcc ccc acc gag tgc agc                                      648
Thr Val Ala Pro Thr Glu Cys Ser
    210                 215


<210> SEQ ID NO 179
<211> LENGTH: 216
<212> TYPE: PRT
<213> ORGANISM: Homo sapiens

<400> SEQUENCE: 179

Gln Ser Val Leu Thr Gln Pro Pro Ser Leu Ser Val Ser Pro Gly Gln
1               5                   10                  15

Thr Ala Ser Ile Ser Cys Ser Gly Asp Lys Leu Gly Asp Lys Tyr Val
            20                  25                  30

Ser Trp Tyr Gln Gln Arg Pro Gly Gln Ser Pro Val Leu Val Ile Tyr
        35                  40                  45

His Asp Thr Lys Arg Pro Ser Gly Ile Pro Glu Arg Phe Ser Gly Thr
    50                  55                  60

Asn Ser Gly Asn Thr Ala Thr Leu Thr Ile Ser Gly Thr Gln Ile Leu
65                  70                  75                  80

Asp Glu Ala Asp Tyr Tyr Cys Gln Val Trp Asp Arg Ser Thr Val Val
                85                  90                  95

Phe Gly Gly Gly Thr Gln Leu Thr Val Leu Ser Ala Ala Ala Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215
```

```
<210> SEQ ID NO 180
<211> LENGTH: 642
<212> TYPE: DNA
<213> ORGANISM: Homo sapiens
<220> FEATURE:
<221> NAME/KEY: CDS
<222> LOCATION: (1)..(642)

<400> SEQUENCE: 180

gaa att gtg ttg acg cag tct cca ggc acc ctg tct ttg tct cca ggg       48
Glu Ile Val Leu Thr Gln Ser Pro Gly Thr Leu Ser Leu Ser Pro Gly
1               5                   10                  15

gaa aga gcc acc ctc tcc tgc agg gcc agt cag agt gtt agc agc agc       96
Glu Arg Ala Thr Leu Ser Cys Arg Ala Ser Gln Ser Val Ser Ser Ser
            20                  25                  30

tac tta gcc tgg tac cag cag aaa cct ggc cag gct ccc agg ctc ctc      144
Tyr Leu Ala Trp Tyr Gln Gln Lys Pro Gly Gln Ala Pro Arg Leu Leu
        35                  40                  45

atc tat ggt gca tcc agc agg gcc act ggc atc cca gac agg ttc agt      192
Ile Tyr Gly Ala Ser Ser Arg Ala Thr Gly Ile Pro Asp Arg Phe Ser
    50                  55                  60

ggc agt ggg tct ggg aca gac ttc act ctc acc atc agc agc cta gag      240
Gly Ser Gly Ser Gly Thr Asp Phe Thr Leu Thr Ile Ser Ser Leu Glu
65                  70                  75                  80

cct gaa gat ttt gca gtg tat tac tgt cag cag tat ggt agc tca tcg      288
Pro Glu Asp Phe Ala Val Tyr Tyr Cys Gln Gln Tyr Gly Ser Ser Ser
                85                  90                  95

atc acc ttc ggc caa ggg aca cga ctg gag att aaa cgt gcg gcc gca      336
Ile Thr Phe Gly Gln Gly Thr Arg Leu Glu Ile Lys Arg Ala Ala Ala
            100                 105                 110

ccc agc gtg ttc atc ttc ccc ccc tcc gac gag cag ctg aag agc ggc      384
Pro Ser Val Phe Ile Phe Pro Pro Ser Asp Glu Gln Leu Lys Ser Gly
        115                 120                 125

acc gcc agc gtg gtg tgc ctg ctg aac aac ttc tac ccc cgg gag gcc      432
Thr Ala Ser Val Val Cys Leu Leu Asn Asn Phe Tyr Pro Arg Glu Ala
    130                 135                 140

aag gtg cag tgg aag gtg gac aac gcc ctg cag agc ggc aac agc cag      480
Lys Val Gln Trp Lys Val Asp Asn Ala Leu Gln Ser Gly Asn Ser Gln
145                 150                 155                 160

gag agc gtg acc gag cag gac agc aag gac tcc acc tac agc ctg agc      528
Glu Ser Val Thr Glu Gln Asp Ser Lys Asp Ser Thr Tyr Ser Leu Ser
                165                 170                 175

agc acc ctc acc ctg agc aag gcc gac tac gag aag cac aag gtg tac      576
Ser Thr Leu Thr Leu Ser Lys Ala Asp Tyr Glu Lys His Lys Val Tyr
            180                 185                 190

gcc tgc gag gtg acc cac cag ggc ctg agc agc ccc gtg acc aag agc      624
Ala Cys Glu Val Thr His Gln Gly Leu Ser Ser Pro Val Thr Lys Ser
        195                 200                 205

ttc aac cgg ggc gag tgt                                              642
Phe Asn Arg Gly Glu Cys
    210


<210> SEQ ID NO 181
<211> LENGTH: 214
<212> TYPE: PRT
<213> ORGANISM: Homo sapiens

<400> SEQUENCE: 181

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30
```

```
Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Tyr Gly Ser Ser Ser
                85                  90                  95

Ile Thr Phe Gly Gln Gly Thr Arg Leu Glu Ile Lys Arg Ala Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 182
<211> LENGTH: 657
<212> TYPE: DNA
<213> ORGANISM: Homo sapiens
<220> FEATURE:
<221> NAME/KEY: CDS
<222> LOCATION: (1)..(657)

<400> SEQUENCE: 182

gac atc cag ttg acc cag tct cca gac tcc ctg gct gtg tct ctg ggc       48
Asp Ile Gln Leu Thr Gln Ser Pro Asp Ser Leu Ala Val Ser Leu Gly
1               5                   10                  15

gag agg gcc acc atc aac tgc aag tcc agc cag agt ctt tta tac acc       96
Glu Arg Ala Thr Ile Asn Cys Lys Ser Ser Gln Ser Leu Leu Tyr Thr
            20                  25                  30

tcc aat aat aag aac ttc tta gct tgg tac caa caa aaa cca gga cag      144
Ser Asn Asn Lys Asn Phe Leu Ala Trp Tyr Gln Gln Lys Pro Gly Gln
        35                  40                  45

cct cct aaa ctg ctc att tac tgg gta tct acc cgg gat tcc ggg gtc      192
Pro Pro Lys Leu Leu Ile Tyr Trp Val Ser Thr Arg Asp Ser Gly Val
    50                  55                  60

cct gac cga ttc agt ggc agc ggg tct ggg aca gat ttc act ctc acc      240
Pro Asp Arg Phe Ser Gly Ser Gly Ser Gly Thr Asp Phe Thr Leu Thr
65                  70                  75                  80

atc agc agc ctg cag gct gag gat gtg gca gtt tat tac tgt cag caa      288
Ile Ser Ser Leu Gln Ala Glu Asp Val Ala Val Tyr Tyr Cys Gln Gln
                85                  90                  95

tat tat act act ccg tac act ttt ggc cag ggg acc aag gtg gag atc      336
Tyr Tyr Thr Thr Pro Tyr Thr Phe Gly Gln Gly Thr Lys Val Glu Ile
            100                 105                 110

aaa cgt gcg gcc gca ccc agc gtg ttc atc ttc ccc ccc tcc gac gag      384
Lys Arg Ala Ala Ala Pro Ser Val Phe Ile Phe Pro Pro Ser Asp Glu
        115                 120                 125
```

```
cag ctg aag agc ggc acc gcc agc gtg gtg tgc ctg ctg aac aac ttc      432
Gln Leu Lys Ser Gly Thr Ala Ser Val Val Cys Leu Leu Asn Asn Phe
    130                 135                 140

tac ccc cgg gag gcc aag gtg cag tgg aag gtg gac aac gcc ctg cag      480
Tyr Pro Arg Glu Ala Lys Val Gln Trp Lys Val Asp Asn Ala Leu Gln
145                 150                 155                 160

agc ggc aac agc cag gag agc gtg acc gag cag gac agc aag gac tcc      528
Ser Gly Asn Ser Gln Glu Ser Val Thr Glu Gln Asp Ser Lys Asp Ser
                165                 170                 175

acc tac agc ctg agc agc acc ctc acc ctg agc aag gcc gac tac gag      576
Thr Tyr Ser Leu Ser Ser Thr Leu Thr Leu Ser Lys Ala Asp Tyr Glu
            180                 185                 190

aag cac aag gtg tac gcc tgc gag gtg acc cac cag ggc ctg agc agc      624
Lys His Lys Val Tyr Ala Cys Glu Val Thr His Gln Gly Leu Ser Ser
        195                 200                 205

ccc gtg acc aag agc ttc aac cgg ggc gag tgt                          657
Pro Val Thr Lys Ser Phe Asn Arg Gly Glu Cys
    210                 215


<210> SEQ ID NO 183
<211> LENGTH: 219
<212> TYPE: PRT
<213> ORGANISM: Homo sapiens

<400> SEQUENCE: 183

Asp Ile Gln Leu Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Thr
            20                  25                  30

Ser Asn Asn Lys Asn Phe Leu Ala Trp Tyr Gln Gln Lys Pro Gly Gln
        35                  40                  45

Pro Pro Lys Leu Leu Ile Tyr Trp Val Ser Thr Arg Asp Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Thr Thr Pro Tyr Thr Phe Gly Gln Gly Thr Lys Val Glu Ile
            100                 105                 110

Lys Arg Ala Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 184
<211> LENGTH: 663
<212> TYPE: DNA
<213> ORGANISM: Homo sapiens
<220> FEATURE:
```

```
<221> NAME/KEY: CDS
<222> LOCATION: (1)..(663)

<400> SEQUENCE: 184

cag tct gtg ttg acg cag ccg ccc tca gtg tct ggg gcc ccg ggg cag       48
Gln Ser Val Leu Thr Gln Pro Pro Ser Val Ser Gly Ala Pro Gly Gln
1               5                   10                  15

agg gtc acc atc tcc tgc act ggg agc agc tcc aac atc ggg gca ggt       96
Arg Val Thr Ile Ser Cys Thr Gly Ser Ser Ser Asn Ile Gly Ala Gly
            20                  25                  30

tat gat gta cac tgg tac cag cag ctt cca gga aca gcc ccc aaa ctc      144
Tyr Asp Val His Trp Tyr Gln Gln Leu Pro Gly Thr Ala Pro Lys Leu
        35                  40                  45

ctc atc tat ggt aac agc aat cgg ccc tca ggg gtc cct gac cga ttt      192
Leu Ile Tyr Gly Asn Ser Asn Arg Pro Ser Gly Val Pro Asp Arg Phe
    50                  55                  60

tct ggc tcc aag tct ggc acc tca gcc tcc ctg gcc atc agt ggg ctc      240
Ser Gly Ser Lys Ser Gly Thr Ser Ala Ser Leu Ala Ile Ser Gly Leu
65                  70                  75                  80

cgg tcc ggg gat gag gct gat tat tac tgc cag tcc tat gac agc agc      288
Arg Ser Gly Asp Glu Ala Asp Tyr Tyr Cys Gln Ser Tyr Asp Ser Ser
                85                  90                  95

ctg agt gat gtg gta ttc ggc gga ggg acc aag ctg acc gtc cta ggt      336
Leu Ser Asp Val Val Phe Gly Gly Gly Thr Lys Leu Thr Val Leu Gly
            100                 105                 110

gcg gcc gca ggc cag ccc aag gcc gct ccc agc gtg acc ctg ttc ccc      384
Ala Ala Ala Gly Gln Pro Lys Ala Ala Pro Ser Val Thr Leu Phe Pro
        115                 120                 125

ccc tcc tcc gag gag ctg cag gcc aac aag gcc acc ctg gtg tgc ctc      432
Pro Ser Ser Glu Glu Leu Gln Ala Asn Lys Ala Thr Leu Val Cys Leu
    130                 135                 140

atc agc gac ttc tac cct ggc gcc gtg acc gtg gcc tgg aag gcc gac      480
Ile Ser Asp Phe Tyr Pro Gly Ala Val Thr Val Ala Trp Lys Ala Asp
145                 150                 155                 160

agc agc ccc gtg aag gcc ggc gtg gag acc acc acc ccc agc aag cag      528
Ser Ser Pro Val Lys Ala Gly Val Glu Thr Thr Thr Pro Ser Lys Gln
                165                 170                 175

agc aac aac aag tac gcc gcc agc agc tac ctg agc ctc acc ccc gag      576
Ser Asn Asn Lys Tyr Ala Ala Ser Ser Tyr Leu Ser Leu Thr Pro Glu
            180                 185                 190

cag tgg aag agc cac cgg agc tac agc tgc cag gtg acc cac gag ggc      624
Gln Trp Lys Ser His Arg Ser Tyr Ser Cys Gln Val Thr His Glu Gly
        195                 200                 205

agc acc gtg gag aag acc gtg gcc ccc acc gag tgc agc                  663
Ser Thr Val Glu Lys Thr Val Ala Pro Thr Glu Cys Ser
    210                 215                 220


<210> SEQ ID NO 185
<211> LENGTH: 221
<212> TYPE: PRT
<213> ORGANISM: Homo sapiens

<400> SEQUENCE: 185

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60
```

```
Ser Gly Ser Lys Ser Gly Thr Ser Ala Ser Leu Ala Ile Ser Gly Leu
65                  70                  75                  80

Arg Ser Gly Asp Glu Ala Asp Tyr Tyr Cys Gln Ser Tyr Asp Ser Ser
                85                  90                  95

Leu Ser Asp Val Val Phe Gly Gly Gly Thr Lys Leu Thr Val Leu Gly
            100                 105                 110

Ala Ala Ala Gly Gln Pro Lys Ala Ala Pro Ser Val Thr Leu Phe Pro
        115                 120                 125

Pro Ser Ser Glu Glu Leu Gln Ala Asn Lys Ala Thr Leu Val Cys Leu
    130                 135                 140

Ile Ser Asp Phe Tyr Pro Gly Ala Val Thr Val Ala Trp Lys Ala Asp
145                 150                 155                 160

Ser Ser Pro Val Lys Ala Gly Val Glu Thr Thr Thr Pro Ser Lys Gln
                165                 170                 175

Ser Asn Asn Lys Tyr Ala Ala Ser Ser Tyr Leu Ser Leu Thr Pro Glu
            180                 185                 190

Gln Trp Lys Ser His Arg Ser Tyr Ser Cys Gln Val Thr His Glu Gly
        195                 200                 205

Ser Thr Val Glu Lys Thr Val Ala Pro Thr Glu Cys Ser
    210                 215                 220


<210> SEQ ID NO 186
<211> LENGTH: 660
<212> TYPE: DNA
<213> ORGANISM: Homo sapiens
<220> FEATURE:
<221> NAME/KEY: CDS
<222> LOCATION: (1)..(660)

<400> SEQUENCE: 186

cag tct gcc ctg act cag cct gcc tcc gtg tct ggg tcg cct gga cag       48
Gln Ser Ala Leu Thr Gln Pro Ala Ser Val Ser Gly Ser Pro Gly Gln
1               5                   10                  15

acg atc acc atc tcc tgc tct gga acc agc agt gac gtt ggt ggt tat       96
Thr Ile Thr Ile Ser Cys Ser Gly Thr Ser Ser Asp Val Gly Gly Tyr
            20                  25                  30

aac tat gtc tcc tgg tac caa caa cac cca ggc aaa gcc ccc aaa ctc      144
Asn Tyr Val Ser Trp Tyr Gln Gln His Pro Gly Lys Ala Pro Lys Leu
        35                  40                  45

atg att tat gat gtc agt aaa cgg ccc tca ggg gtt tct aat cgc ttc      192
Met Ile Tyr Asp Val Ser Lys Arg Pro Ser Gly Val Ser Asn Arg Phe
    50                  55                  60

tct ggc tcc aag tct ggc aac acg gcc tcc ctg acc atc tct ggg ctc      240
Ser Gly Ser Lys Ser Gly Asn Thr Ala Ser Leu Thr Ile Ser Gly Leu
65                  70                  75                  80

cag gct gag gac gag gct gat tat tac tgc agt tca tct aca cgc agc      288
Gln Ala Glu Asp Glu Ala Asp Tyr Tyr Cys Ser Ser Ser Thr Arg Ser
                85                  90                  95

agc act ctg gta ttc ggc gga ggg acc aag ctg acc gtc cta ggt gcg      336
Ser Thr Leu Val Phe Gly Gly Gly Thr Lys Leu Thr Val Leu Gly Ala
            100                 105                 110

gcc gca ggc cag ccc aag gcc gct ccc agc gtg acc ctg ttc ccc ccc      384
Ala Ala Gly Gln Pro Lys Ala Ala Pro Ser Val Thr Leu Phe Pro Pro
        115                 120                 125

tcc tcc gag gag ctg cag gcc aac aag gcc acc ctg gtg tgc ctc atc      432
Ser Ser Glu Glu Leu Gln Ala Asn Lys Ala Thr Leu Val Cys Leu Ile
    130                 135                 140

agc gac ttc tac cct ggc gcc gtg acc gtg gcc tgg aag gcc gac agc      480
Ser Asp Phe Tyr Pro Gly Ala Val Thr Val Ala Trp Lys Ala Asp Ser
```

```
145                 150                 155                 160

agc ccc gtg aag gcc ggc gtg gag acc acc acc ccc agc aag cag agc       528
Ser Pro Val Lys Ala Gly Val Glu Thr Thr Thr Pro Ser Lys Gln Ser
                165                 170                 175

aac aac aag tac gcc gcc agc agc tac ctg agc ctc acc ccc gag cag       576
Asn Asn Lys Tyr Ala Ala Ser Ser Tyr Leu Ser Leu Thr Pro Glu Gln
            180                 185                 190

tgg aag agc cac cgg agc tac agc tgc cag gtg acc cac gag ggc agc       624
Trp Lys Ser His Arg Ser Tyr Ser Cys Gln Val Thr His Glu Gly Ser
        195                 200                 205

acc gtg gag aag acc gtg gcc ccc acc gag tgc agc                       660
Thr Val Glu Lys Thr Val Ala Pro Thr Glu Cys Ser
    210                 215                 220


<210> SEQ ID NO 187
<211> LENGTH: 220
<212> TYPE: PRT
<213> ORGANISM: Homo sapiens

<400> SEQUENCE: 187

Gln Ser Ala Leu Thr Gln Pro Ala Ser Val Ser Gly Ser Pro Gly Gln
1               5                   10                  15

Thr Ile Thr Ile Ser Cys Ser Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Ser Thr Arg Ser
                85                  90                  95

Ser Thr Leu Val Phe Gly Gly Gly Thr Lys Leu Thr Val Leu Gly Ala
            100                 105                 110

Ala Ala Gly Gln Pro Lys Ala Ala Pro Ser Val Thr Leu Phe Pro Pro
        115                 120                 125

Ser Ser Glu Glu Leu Gln Ala Asn Lys Ala Thr Leu Val Cys Leu Ile
    130                 135                 140

Ser Asp Phe Tyr Pro Gly Ala Val Thr Val Ala Trp Lys Ala Asp Ser
145                 150                 155                 160

Ser Pro Val Lys Ala Gly Val Glu Thr Thr Thr Pro Ser Lys Gln Ser
                165                 170                 175

Asn Asn Lys Tyr Ala Ala Ser Ser Tyr Leu Ser Leu Thr Pro Glu Gln
            180                 185                 190

Trp Lys Ser His Arg Ser Tyr Ser Cys Gln Val Thr His Glu Gly Ser
        195                 200                 205

Thr Val Glu Lys Thr Val Ala Pro Thr Glu Cys Ser
    210                 215                 220


<210> SEQ ID NO 188
<211> LENGTH: 660
<212> TYPE: DNA
<213> ORGANISM: Homo sapiens
<220> FEATURE:
<221> NAME/KEY: CDS
<222> LOCATION: (1)..(660)

<400> SEQUENCE: 188

cag tct gcc ctg act cag cct ccc tcc gcg tcc ggg tct cct gga cag        48
```

Gln Ser Ala Leu Thr Gln Pro Pro Ser Ala Ser Gly Ser Pro Gly Gln
1 5 10 15 tca gtc acc atc tcc tgc act gga acc agc agt gac gtt ggt ggt tat 96
Ser Val Thr Ile Ser Cys Thr Gly Thr Ser Ser Asp Val Gly Gly Tyr
20 25 30 gac tat gtc tcc tgg tac caa caa cac cca ggc aaa gcc ccc aaa ctc 144
Asp Tyr Val Ser Trp Tyr Gln Gln His Pro Gly Lys Ala Pro Lys Leu
35 40 45 atg att tat gat gtc agt aag cgg ccc tca ggg gtc cct gat cgc ttc 192
Met Ile Tyr Asp Val Ser Lys Arg Pro Ser Gly Val Pro Asp Arg Phe
50 55 60 tct ggc tcc aag tct ggc aac acg gcc tcc ctg acc atc tct ggg ctc 240
Ser Gly Ser Lys Ser Gly Asn Thr Ala Ser Leu Thr Ile Ser Gly Leu
65 70 75 80 cag gct gag gat gag gct gat tat tac tgc agc tca tat gca agc aat 288
Gln Ala Glu Asp Glu Ala Asp Tyr Tyr Cys Ser Ser Tyr Ala Ser Asn
85 90 95 agg gat gtg ctt ttc ggc gga ggg acc aag ctg acc gtc cta ggt gcg 336
Arg Asp Val Leu Phe Gly Gly Gly Thr Lys Leu Thr Val Leu Gly Ala
100 105 110 gcc gca ggc cag ccc aag gcc gct ccc agc gtg acc ctg ttc ccc ccc 384
Ala Ala Gly Gln Pro Lys Ala Ala Pro Ser Val Thr Leu Phe Pro Pro
115 120 125 tcc tcc gag gag ctg cag gcc aac aag gcc acc ctg gtg tgc ctc atc 432
Ser Ser Glu Glu Leu Gln Ala Asn Lys Ala Thr Leu Val Cys Leu Ile
130 135 140 agc gac ttc tac cct ggc gcc gtg acc gtg gcc tgg aag gcc gac agc 480
Ser Asp Phe Tyr Pro Gly Ala Val Thr Val Ala Trp Lys Ala Asp Ser
145 150 155 160 agc ccc gtg aag gcc ggc gtg gag acc acc acc ccc agc aag cag agc 528
Ser Pro Val Lys Ala Gly Val Glu Thr Thr Thr Pro Ser Lys Gln Ser
165 170 175 aac aac aag tac gcc gcc agc agc tac ctg agc ctc acc ccc gag cag 576
Asn Asn Lys Tyr Ala Ala Ser Ser Tyr Leu Ser Leu Thr Pro Glu Gln
180 185 190 tgg aag agc cac cgg agc tac agc tgc cag gtg acc cac gag ggc agc 624
Trp Lys Ser His Arg Ser Tyr Ser Cys Gln Val Thr His Glu Gly Ser
195 200 205 acc gtg gag aag acc gtg gcc ccc acc gag tgc agc 660
Thr Val Glu Lys Thr Val Ala Pro Thr Glu Cys Ser
210 215 220

<210> SEQ ID NO 189
<211> LENGTH: 220
<212> TYPE: PRT
<213> ORGANISM: Homo sapiens

<400> SEQUENCE: 189

Gln Ser Ala Leu Thr Gln Pro Pro Ser Ala Ser Gly Ser Pro Gly Gln
1 5 10 15

Ser Val Thr Ile Ser Cys Thr Gly Thr Ser Ser Asp Val Gly Gly Tyr
20 25 30

Asp Tyr Val Ser Trp Tyr Gln Gln His Pro Gly Lys Ala Pro Lys Leu
35 40 45

Met Ile Tyr Asp Val Ser Lys Arg Pro Ser Gly Val Pro Asp Arg Phe
50 55 60

Ser Gly Ser Lys Ser Gly Asn Thr Ala Ser Leu Thr Ile Ser Gly Leu
65 70 75 80

Gln Ala Glu Asp Glu Ala Asp Tyr Tyr Cys Ser Ser Tyr Ala Ser Asn
85 90 95

```
Arg Asp Val Leu Phe Gly Gly Gly Thr Lys Leu Thr Val Leu Gly Ala
            100                 105                 110

Ala Ala Gly Gln Pro Lys Ala Ala Pro Ser Val Thr Leu Phe Pro Pro
        115                 120                 125

Ser Ser Glu Glu Leu Gln Ala Asn Lys Ala Thr Leu Val Cys Leu Ile
    130                 135                 140

Ser Asp Phe Tyr Pro Gly Ala Val Thr Val Ala Trp Lys Ala Asp Ser
145                 150                 155                 160

Ser Pro Val Lys Ala Gly Val Glu Thr Thr Thr Pro Ser Lys Gln Ser
                165                 170                 175

Asn Asn Lys Tyr Ala Ala Ser Ser Tyr Leu Ser Leu Thr Pro Glu Gln
            180                 185                 190

Trp Lys Ser His Arg Ser Tyr Ser Cys Gln Val Thr His Glu Gly Ser
        195                 200                 205

Thr Val Glu Lys Thr Val Ala Pro Thr Glu Cys Ser
    210                 215                 220


<210> SEQ ID NO 190
<211> LENGTH: 654
<212> TYPE: DNA
<213> ORGANISM: Homo sapiens
<220> FEATURE:
<221> NAME/KEY: CDS
<222> LOCATION: (1)..(654)

<400> SEQUENCE: 190

tct tct gag ctg act cag gac cct gct gag tct gtg gcc ttg gga cag       48
Ser Ser Glu Leu Thr Gln Asp Pro Ala Glu Ser Val Ala Leu Gly Gln
1               5                   10                  15

aca gtc aag atc aca tgc caa gga gac agt ctc aga agg tat tat gca       96
Thr Val Lys Ile Thr Cys Gln Gly Asp Ser Leu Arg Arg Tyr Tyr Ala
            20                  25                  30

agt tgg tac cag cag aag cca gga cag gcc cct gtt ctt gtc atc tat      144
Ser Trp Tyr Gln Gln Lys Pro Gly Gln Ala Pro Val Leu Val Ile Tyr
        35                  40                  45

ggc aaa aac aac cgg ccc tca ggg atc cca gac cga ttc tct ggc tcc      192
Gly Lys Asn Asn Arg Pro Ser Gly Ile Pro Asp Arg Phe Ser Gly Ser
    50                  55                  60

agg tca gga aac aca gct tcc ttg acc ata act ggg gct cag gcg gaa      240
Arg Ser Gly Asn Thr Ala Ser Leu Thr Ile Thr Gly Ala Gln Ala Glu
65                  70                  75                  80

gat gag gct gtc tat tac tgt aac tcc cgg gac agc agt ggt aac tct      288
Asp Glu Ala Val Tyr Tyr Cys Asn Ser Arg Asp Ser Ser Gly Asn Ser
                85                  90                  95

gtg gtc ttc ggc gga ggg acc aag ctg acc gtc cta ggt gcg gcc gca      336
Val Val Phe Gly Gly Gly Thr Lys Leu Thr Val Leu Gly Ala Ala Ala
            100                 105                 110

ggc cag ccc aag gcc gct ccc agc gtg acc ctg ttc ccc ccc tcc tcc      384
Gly Gln Pro Lys Ala Ala Pro Ser Val Thr Leu Phe Pro Pro Ser Ser
        115                 120                 125

gag gag ctg cag gcc aac aag gcc acc ctg gtg tgc ctc atc agc gac      432
Glu Glu Leu Gln Ala Asn Lys Ala Thr Leu Val Cys Leu Ile Ser Asp
    130                 135                 140

ttc tac cct ggc gcc gtg acc gtg gcc tgg aag gcc gac agc agc ccc      480
Phe Tyr Pro Gly Ala Val Thr Val Ala Trp Lys Ala Asp Ser Ser Pro
145                 150                 155                 160

gtg aag gcc ggc gtg gag acc acc acc ccc agc aag cag agc aac aac      528
Val Lys Ala Gly Val Glu Thr Thr Thr Pro Ser Lys Gln Ser Asn Asn
                165                 170                 175
```

```
aag tac gcc gcc agc agc tac ctg agc ctc acc ccc gag cag tgg aag      576
Lys Tyr Ala Ala Ser Ser Tyr Leu Ser Leu Thr Pro Glu Gln Trp Lys
            180                 185                 190

agc cac cgg agc tac agc tgc cag gtg acc cac gag ggc agc acc gtg      624
Ser His Arg Ser Tyr Ser Cys Gln Val Thr His Glu Gly Ser Thr Val
        195                 200                 205

gag aag acc gtg gcc ccc acc gag tgc agc                              654
Glu Lys Thr Val Ala Pro Thr Glu Cys Ser
    210                 215


<210> SEQ ID NO 191
<211> LENGTH: 218
<212> TYPE: PRT
<213> ORGANISM: Homo sapiens

<400> SEQUENCE: 191

Ser Ser Glu Leu Thr Gln Asp Pro Ala Glu Ser Val Ala Leu Gly Gln
1               5                   10                  15

Thr Val Lys Ile Thr Cys Gln Gly Asp Ser Leu Arg Arg Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Arg Ser Gly Asn Thr Ala Ser Leu Thr Ile Thr Gly Ala Gln Ala Glu
65                  70                  75                  80

Asp Glu Ala Val Tyr Tyr Cys Asn Ser Arg Asp Ser Ser Gly Asn Ser
                85                  90                  95

Val Val Phe Gly Gly Gly Thr Lys Leu Thr Val Leu Gly Ala Ala Ala
            100                 105                 110

Gly Gln Pro Lys Ala Ala Pro Ser Val Thr Leu Phe Pro Pro Ser Ser
        115                 120                 125

Glu Glu Leu Gln Ala Asn Lys Ala Thr Leu Val Cys Leu Ile Ser Asp
    130                 135                 140

Phe Tyr Pro Gly Ala Val Thr Val Ala Trp Lys Ala Asp Ser Ser Pro
145                 150                 155                 160

Val Lys Ala Gly Val Glu Thr Thr Thr Pro Ser Lys Gln Ser Asn Asn
                165                 170                 175

Lys Tyr Ala Ala Ser Ser Tyr Leu Ser Leu Thr Pro Glu Gln Trp Lys
            180                 185                 190

Ser His Arg Ser Tyr Ser Cys Gln Val Thr His Glu Gly Ser Thr Val
        195                 200                 205

Glu Lys Thr Val Ala Pro Thr Glu Cys Ser
    210                 215


<210> SEQ ID NO 192
<211> LENGTH: 660
<212> TYPE: DNA
<213> ORGANISM: Homo sapiens
<220> FEATURE:
<221> NAME/KEY: CDS
<222> LOCATION: (1)..(660)

<400> SEQUENCE: 192

cag tct gcc ctg act cag cct gcc tcc gtg tct ggg tct cct gga cag       48
Gln Ser Ala Leu Thr Gln Pro Ala Ser Val Ser Gly Ser Pro Gly Gln
1               5                   10                  15

tcg atc acc atc tcc tgc act gga acc agc agt gac gtt ggt ggt tat       96
Ser Ile Thr Ile Ser Cys Thr Gly Thr Ser Ser Asp Val Gly Gly Tyr
            20                  25                  30
```

```
aac tat gtc tcc tgg tac caa cag cac cca ggc aaa gcc ccc aaa ctc      144
Asn Tyr Val Ser Trp Tyr Gln Gln His Pro Gly Lys Ala Pro Lys Leu
        35                  40                  45

atg att tat gat gtc att aag cgg ccc tca ggg gtc cct gat cgc ttc      192
Met Ile Tyr Asp Val Ile Lys Arg Pro Ser Gly Val Pro Asp Arg Phe
    50                  55                  60

tct ggc tcc aag tct ggc aac acg gcc tcc ctg acc atc tct ggg ctc      240
Ser Gly Ser Lys Ser Gly Asn Thr Ala Ser Leu Thr Ile Ser Gly Leu
65                  70                  75                  80

cag gct gag gat gag gct gat tat tac tgc agc tca tat gca ggc agc      288
Gln Ala Glu Asp Glu Ala Asp Tyr Tyr Cys Ser Ser Tyr Ala Gly Ser
                85                  90                  95

aac aat gtg gta ttc ggc gga ggg acc aag ctg acc gtc cta ggt gcg      336
Asn Asn Val Val Phe Gly Gly Gly Thr Lys Leu Thr Val Leu Gly Ala
            100                 105                 110

gcc gca ggc cag ccc aag gcc gct ccc agc gtg acc ctg ttc ccc ccc      384
Ala Ala Gly Gln Pro Lys Ala Ala Pro Ser Val Thr Leu Phe Pro Pro
        115                 120                 125

tcc tcc gag gag ctg cag gcc aac aag gcc acc ctg gtg tgc ctc atc      432
Ser Ser Glu Glu Leu Gln Ala Asn Lys Ala Thr Leu Val Cys Leu Ile
    130                 135                 140

agc gac ttc tac cct ggc gcc gtg acc gtg gcc tgg aag gcc gac agc      480
Ser Asp Phe Tyr Pro Gly Ala Val Thr Val Ala Trp Lys Ala Asp Ser
145                 150                 155                 160

agc ccc gtg aag gcc ggc gtg gag acc acc acc ccc agc aag cag agc      528
Ser Pro Val Lys Ala Gly Val Glu Thr Thr Thr Pro Ser Lys Gln Ser
                165                 170                 175

aac aac aag tac gcc gcc agc agc tac ctg agc ctc acc ccc gag cag      576
Asn Asn Lys Tyr Ala Ala Ser Ser Tyr Leu Ser Leu Thr Pro Glu Gln
            180                 185                 190

tgg aag agc cac cgg agc tac agc tgc cag gtg acc cac gag ggc agc      624
Trp Lys Ser His Arg Ser Tyr Ser Cys Gln Val Thr His Glu Gly Ser
        195                 200                 205

acc gtg gag aag acc gtg gcc ccc acc gag tgc agc                      660
Thr Val Glu Lys Thr Val Ala Pro Thr Glu Cys Ser
    210                 215                 220


<210> SEQ ID NO 193
<211> LENGTH: 220
<212> TYPE: PRT
<213> ORGANISM: Homo sapiens

<400> SEQUENCE: 193

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ile Lys Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Ala Gly Ser
                85                  90                  95

Asn Asn Val Val Phe Gly Gly Gly Thr Lys Leu Thr Val Leu Gly Ala
            100                 105                 110

Ala Ala Gly Gln Pro Lys Ala Ala Pro Ser Val Thr Leu Phe Pro Pro
        115                 120                 125
```

```
Ser Ser Glu Glu Leu Gln Ala Asn Lys Ala Thr Leu Val Cys Leu Ile
    130                 135                 140

Ser Asp Phe Tyr Pro Gly Ala Val Thr Val Ala Trp Lys Ala Asp Ser
145                 150                 155                 160

Ser Pro Val Lys Ala Gly Val Glu Thr Thr Thr Pro Ser Lys Gln Ser
                165                 170                 175

Asn Asn Lys Tyr Ala Ala Ser Ser Tyr Leu Ser Leu Thr Pro Glu Gln
            180                 185                 190

Trp Lys Ser His Arg Ser Tyr Ser Cys Gln Val Thr His Glu Gly Ser
        195                 200                 205

Thr Val Glu Lys Thr Val Ala Pro Thr Glu Cys Ser
    210                 215                 220


<210> SEQ ID NO 194
<211> LENGTH: 660
<212> TYPE: DNA
<213> ORGANISM: Homo sapiens
<220> FEATURE:
<221> NAME/KEY: CDS
<222> LOCATION: (1)..(660)

<400> SEQUENCE: 194

cag tct gcc ctg act cag cct ccc tcc gcg tcc ggg tct cct gga cag      48
Gln Ser Ala Leu Thr Gln Pro Pro Ser Ala Ser Gly Ser Pro Gly Gln
1               5                   10                  15

tca gtc acc atc tcc tgc act gga acc agc agt gac gtt ggt ggt tat      96
Ser Val Thr Ile Ser Cys Thr Gly Thr Ser Ser Asp Val Gly Gly Tyr
            20                  25                  30

aac tat gtc tcc tgg tac caa caa cac cca ggc aaa gcc ccc aaa ctc     144
Asn Tyr Val Ser Trp Tyr Gln Gln His Pro Gly Lys Ala Pro Lys Leu
        35                  40                  45

atg att tat gat gtc agt aag cgg ccc tca ggg gtc cct gat cgc ttc     192
Met Ile Tyr Asp Val Ser Lys Arg Pro Ser Gly Val Pro Asp Arg Phe
    50                  55                  60

tct ggc tcc aag tct ggc aac acg gcc tcc ctg acc gtc tct ggg ctc     240
Ser Gly Ser Lys Ser Gly Asn Thr Ala Ser Leu Thr Val Ser Gly Leu
65                  70                  75                  80

cag tct gag gat gag gct gat tat tac tgc agc tca tat gca ggc agc     288
Gln Ser Glu Asp Glu Ala Asp Tyr Tyr Cys Ser Ser Tyr Ala Gly Ser
                85                  90                  95

acc ggt tat gtc ttc gga act ggg acc aag gtc acc gtc cta ggt gcg     336
Thr Gly Tyr Val Phe Gly Thr Gly Thr Lys Val Thr Val Leu Gly Ala
            100                 105                 110

gcc gca ggc cag ccc aag gcc gct ccc agc gtg acc ctg ttc ccc ccc     384
Ala Ala Gly Gln Pro Lys Ala Ala Pro Ser Val Thr Leu Phe Pro Pro
        115                 120                 125

tcc tcc gag gag ctg cag gcc aac aag gcc acc ctg gtg tgc ctc atc     432
Ser Ser Glu Glu Leu Gln Ala Asn Lys Ala Thr Leu Val Cys Leu Ile
    130                 135                 140

agc gac ttc tac cct ggc gcc gtg acc gtg gcc tgg aag gcc gac agc     480
Ser Asp Phe Tyr Pro Gly Ala Val Thr Val Ala Trp Lys Ala Asp Ser
145                 150                 155                 160

agc ccc gtg aag gcc ggc gtg gag acc acc acc ccc agc aag cag agc     528
Ser Pro Val Lys Ala Gly Val Glu Thr Thr Thr Pro Ser Lys Gln Ser
                165                 170                 175

aac aac aag tac gcc gcc agc agc tac ctg agc ctc acc ccc gag cag     576
Asn Asn Lys Tyr Ala Ala Ser Ser Tyr Leu Ser Leu Thr Pro Glu Gln
            180                 185                 190

tgg aag agc cac cgg agc tac agc tgc cag gtg acc cac gag ggc agc     624
Trp Lys Ser His Arg Ser Tyr Ser Cys Gln Val Thr His Glu Gly Ser
```

```
        195                 200                 205

acc gtg gag aag acc gtg gcc ccc acc gag tgc agc                     660
Thr Val Glu Lys Thr Val Ala Pro Thr Glu Cys Ser
    210                 215                 220


<210> SEQ ID NO 195
<211> LENGTH: 220
<212> TYPE: PRT
<213> ORGANISM: Homo sapiens

<400> SEQUENCE: 195

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ser Glu Asp Glu Ala Asp Tyr Tyr Cys Ser Ser Tyr Ala Gly Ser
                85                  90                  95

Thr Gly Tyr Val Phe Gly Thr Gly Thr Lys Val Thr Val Leu Gly Ala
            100                 105                 110

Ala Ala Gly Gln Pro Lys Ala Ala Pro Ser Val Thr Leu Phe Pro Pro
        115                 120                 125

Ser Ser Glu Glu Leu Gln Ala Asn Lys Ala Thr Leu Val Cys Leu Ile
    130                 135                 140

Ser Asp Phe Tyr Pro Gly Ala Val Thr Val Ala Trp Lys Ala Asp Ser
145                 150                 155                 160

Ser Pro Val Lys Ala Gly Val Glu Thr Thr Thr Pro Ser Lys Gln Ser
                165                 170                 175

Asn Asn Lys Tyr Ala Ala Ser Ser Tyr Leu Ser Leu Thr Pro Glu Gln
            180                 185                 190

Trp Lys Ser His Arg Ser Tyr Ser Cys Gln Val Thr His Glu Gly Ser
        195                 200                 205

Thr Val Glu Lys Thr Val Ala Pro Thr Glu Cys Ser
    210                 215                 220


<210> SEQ ID NO 196
<211> LENGTH: 660
<212> TYPE: DNA
<213> ORGANISM: Homo sapiens
<220> FEATURE:
<221> NAME/KEY: CDS
<222> LOCATION: (1)..(660)

<400> SEQUENCE: 196

cag tct gtg ttg acg cag ccg ccc tcc gcg tcc ggg tct cct gga cag      48
Gln Ser Val Leu Thr Gln Pro Pro Ser Ala Ser Gly Ser Pro Gly Gln
1               5                   10                  15

tca gtc acc atc tcc tgc act gga acc agc agt gac gtt ggt ggt tat      96
Ser Val Thr Ile Ser Cys Thr Gly Thr Ser Ser Asp Val Gly Gly Tyr
            20                  25                  30

aac tat gtc tcc tgg tac caa caa cac cca ggc aaa gcc ccc aaa ctc     144
Asn Tyr Val Ser Trp Tyr Gln Gln His Pro Gly Lys Ala Pro Lys Leu
        35                  40                  45

atg att tat gag gtc act agg cgg ccc tca ggg gtc tct tat cgc ttc     192
```

-continued

```
Met Ile Tyr Glu Val Thr Arg Arg Pro Ser Gly Val Ser Tyr Arg Phe
    50                  55                  60

tct ggc tcc aag tct ggc aac acg gcc tcc ctg acc gtc tct ggg ctc      240
Ser Gly Ser Lys Ser Gly Asn Thr Ala Ser Leu Thr Val Ser Gly Leu
65                  70                  75                  80

cag gct gag gat gag gct gat tat tac tgc agc tca tat gca ggc agc      288
Gln Ala Glu Asp Glu Ala Asp Tyr Tyr Cys Ser Ser Tyr Ala Gly Ser
                85                  90                  95

aac aat ttg gtc ttc ggc gga ggg acc aag ctg acc gtc cta ggt gcg      336
Asn Asn Leu Val Phe Gly Gly Gly Thr Lys Leu Thr Val Leu Gly Ala
            100                 105                 110

gcc gca ggc cag ccc aag gcc gct ccc agc gtg acc ctg ttc ccc ccc      384
Ala Ala Gly Gln Pro Lys Ala Ala Pro Ser Val Thr Leu Phe Pro Pro
        115                 120                 125

tcc tcc gag gag ctg cag gcc aac aag gcc acc ctg gtg tgc ctc atc      432
Ser Ser Glu Glu Leu Gln Ala Asn Lys Ala Thr Leu Val Cys Leu Ile
    130                 135                 140

agc gac ttc tac cct ggc gcc gtg acc gtg gcc tgg aag gcc gac agc      480
Ser Asp Phe Tyr Pro Gly Ala Val Thr Val Ala Trp Lys Ala Asp Ser
145                 150                 155                 160

agc ccc gtg aag gcc ggc gtg gag acc acc acc ccc agc aag cag agc      528
Ser Pro Val Lys Ala Gly Val Glu Thr Thr Thr Pro Ser Lys Gln Ser
                165                 170                 175

aac aac aag tac gcc gcc agc agc tac ctg agc ctc acc ccc gag cag      576
Asn Asn Lys Tyr Ala Ala Ser Ser Tyr Leu Ser Leu Thr Pro Glu Gln
            180                 185                 190

tgg aag agc cac cgg agc tac agc tgc cag gtg acc cac gag ggc agc      624
Trp Lys Ser His Arg Ser Tyr Ser Cys Gln Val Thr His Glu Gly Ser
        195                 200                 205

acc gtg gag aag acc gtg gcc ccc acc gag tgc agc                      660
Thr Val Glu Lys Thr Val Ala Pro Thr Glu Cys Ser
    210                 215                 220


<210> SEQ ID NO 197
<211> LENGTH: 220
<212> TYPE: PRT
<213> ORGANISM: Homo sapiens

<400> SEQUENCE: 197

Gln Ser Val Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Thr Arg Arg Pro Ser Gly Val Ser Tyr Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Ser
                85                  90                  95

Asn Asn Leu Val Phe Gly Gly Gly Thr Lys Leu Thr Val Leu Gly Ala
            100                 105                 110

Ala Ala Gly Gln Pro Lys Ala Ala Pro Ser Val Thr Leu Phe Pro Pro
        115                 120                 125

Ser Ser Glu Glu Leu Gln Ala Asn Lys Ala Thr Leu Val Cys Leu Ile
    130                 135                 140

Ser Asp Phe Tyr Pro Gly Ala Val Thr Val Ala Trp Lys Ala Asp Ser
145                 150                 155                 160
```

```
Ser Pro Val Lys Ala Gly Val Glu Thr Thr Thr Pro Ser Lys Gln Ser
                165                 170                 175

Asn Asn Lys Tyr Ala Ala Ser Ser Tyr Leu Ser Leu Thr Pro Glu Gln
            180                 185                 190

Trp Lys Ser His Arg Ser Tyr Ser Cys Gln Val Thr His Glu Gly Ser
        195                 200                 205

Thr Val Glu Lys Thr Val Ala Pro Thr Glu Cys Ser
    210                 215                 220


<210> SEQ ID NO 198
<211> LENGTH: 660
<212> TYPE: DNA
<213> ORGANISM: Homo sapiens
<220> FEATURE:
<221> NAME/KEY: CDS
<222> LOCATION: (1)..(660)

<400> SEQUENCE: 198

cag tct gtc gtg acg cag ccg ccc tca gtg tct gcg gcc cca gga cag       48
Gln Ser Val Val Thr Gln Pro Pro Ser Val Ser Ala Ala Pro Gly Gln
1               5                   10                  15

aag gtc acc atc tcc tgc tct gga agc agc tcc aac att ggg aat aat       96
Lys Val Thr Ile Ser Cys Ser Gly Ser Ser Ser Asn Ile Gly Asn Asn
            20                  25                  30

tat gta tcc tgg tac cag cag ctc cca gga aca gcc ccc aaa ctc ctc      144
Tyr Val Ser Trp Tyr Gln Gln Leu Pro Gly Thr Ala Pro Lys Leu Leu
        35                  40                  45

att tat gac aat aat aag cga ccc tca ggg att cct gac cga ttc tct      192
Ile Tyr Asp Asn Asn Lys Arg Pro Ser Gly Ile Pro Asp Arg Phe Ser
    50                  55                  60

ggc tcc aag tct ggc acg tca gcc acc ctg ggc atc acc gga ctc cag      240
Gly Ser Lys Ser Gly Thr Ser Ala Thr Leu Gly Ile Thr Gly Leu Gln
65                  70                  75                  80

act ggg gac gag gcc gat tat tac tgc gga aca tgg gag agc agc ctg      288
Thr Gly Asp Glu Ala Asp Tyr Tyr Cys Gly Thr Trp Glu Ser Ser Leu
                85                  90                  95

agt gct gtg gta ttc ggc gga ggg acc aag ctg acc gtc cta ggt gcg      336
Ser Ala Val Val Phe Gly Gly Gly Thr Lys Leu Thr Val Leu Gly Ala
            100                 105                 110

gcc gca ggc cag ccc aag gcc gct ccc agc gtg acc ctg ttc ccc ccc      384
Ala Ala Gly Gln Pro Lys Ala Ala Pro Ser Val Thr Leu Phe Pro Pro
        115                 120                 125

tcc tcc gag gag ctg cag gcc aac aag gcc acc ctg gtg tgc ctc atc      432
Ser Ser Glu Glu Leu Gln Ala Asn Lys Ala Thr Leu Val Cys Leu Ile
    130                 135                 140

agc gac ttc tac cct ggc gcc gtg acc gtg gcc tgg aag gcc gac agc      480
Ser Asp Phe Tyr Pro Gly Ala Val Thr Val Ala Trp Lys Ala Asp Ser
145                 150                 155                 160

agc ccc gtg aag gcc ggc gtg gag acc acc acc ccc agc aag cag agc      528
Ser Pro Val Lys Ala Gly Val Glu Thr Thr Thr Pro Ser Lys Gln Ser
                165                 170                 175

aac aac aag tac gcc gcc agc agc tac ctg agc ctc acc ccc gag cag      576
Asn Asn Lys Tyr Ala Ala Ser Ser Tyr Leu Ser Leu Thr Pro Glu Gln
            180                 185                 190

tgg aag agc cac cgg agc tac agc tgc cag gtg acc cac gag ggc agc      624
Trp Lys Ser His Arg Ser Tyr Ser Cys Gln Val Thr His Glu Gly Ser
        195                 200                 205

acc gtg gag aag acc gtg gcc ccc acc gag tgc agc                      660
Thr Val Glu Lys Thr Val Ala Pro Thr Glu Cys Ser
    210                 215                 220
```

<210> SEQ ID NO 199
<211> LENGTH: 220
<212> TYPE: PRT
<213> ORGANISM: Homo sapiens

<400> SEQUENCE: 199

```
Gln Ser Val Val Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Glu Ser Ser Leu
                85                  90                  95

Ser Ala Val Val Phe Gly Gly Gly Thr Lys Leu Thr Val Leu Gly Ala
            100                 105                 110

Ala Ala Gly Gln Pro Lys Ala Ala Pro Ser Val Thr Leu Phe Pro Pro
        115                 120                 125

Ser Ser Glu Glu Leu Gln Ala Asn Lys Ala Thr Leu Val Cys Leu Ile
    130                 135                 140

Ser Asp Phe Tyr Pro Gly Ala Val Thr Val Ala Trp Lys Ala Asp Ser
145                 150                 155                 160

Ser Pro Val Lys Ala Gly Val Glu Thr Thr Thr Pro Ser Lys Gln Ser
                165                 170                 175

Asn Asn Lys Tyr Ala Ala Ser Ser Tyr Leu Ser Leu Thr Pro Glu Gln
            180                 185                 190

Trp Lys Ser His Arg Ser Tyr Ser Cys Gln Val Thr His Glu Gly Ser
        195                 200                 205

Thr Val Glu Lys Thr Val Ala Pro Thr Glu Cys Ser
    210                 215                 220
```

<210> SEQ ID NO 200
<211> LENGTH: 660
<212> TYPE: DNA
<213> ORGANISM: Homo sapiens
<220> FEATURE:
<221> NAME/KEY: CDS
<222> LOCATION: (1)..(660)

<400> SEQUENCE: 200

```
cag tct gcc ctg act cag cct gcc tcc gtg tct ggg tct cct gga cag       48
Gln Ser Ala Leu Thr Gln Pro Ala Ser Val Ser Gly Ser Pro Gly Gln
1               5                   10                  15

tcg atc acc atc tcc tgc act gga acc agc agt gac gtt ggt ggt tat       96
Ser Ile Thr Ile Ser Cys Thr Gly Thr Ser Ser Asp Val Gly Gly Tyr
            20                  25                  30

aac tat gtc tcc tgg tac caa cac cac cca ggc aaa gcc ccc aaa ctc      144
Asn Tyr Val Ser Trp Tyr Gln His His Pro Gly Lys Ala Pro Lys Leu
        35                  40                  45

atg att tat gat gtc agt gat cgg ccc tca ggg gtt tct aat cgc ttc      192
Met Ile Tyr Asp Val Ser Asp Arg Pro Ser Gly Val Ser Asn Arg Phe
    50                  55                  60

tct ggc tcc aag tct ggc aac gcg gcc tcc ctg acc atc tct ggg ctc      240
Ser Gly Ser Lys Ser Gly Asn Ala Ala Ser Leu Thr Ile Ser Gly Leu
65                  70                  75                  80
```

```
cag gct gag gac gag gct gat tat tac tgc agc tca tat gca ggc agc      288
Gln Ala Glu Asp Glu Ala Asp Tyr Tyr Cys Ser Ser Tyr Ala Gly Ser
                85                  90                  95

aac aat ttg gtc ttc gga act ggg acc aag gtc acc gtc cta ggt gcg      336
Asn Asn Leu Val Phe Gly Thr Gly Thr Lys Val Thr Val Leu Gly Ala
            100                 105                 110

gcc gca ggc cag ccc aag gcc gct ccc agc gtg acc ctg ttc ccc ccc      384
Ala Ala Gly Gln Pro Lys Ala Ala Pro Ser Val Thr Leu Phe Pro Pro
        115                 120                 125

tcc tcc gag gag ctg cag gcc aac aag gcc acc ctg gtg tgc ctc atc      432
Ser Ser Glu Glu Leu Gln Ala Asn Lys Ala Thr Leu Val Cys Leu Ile
    130                 135                 140

agc gac ttc tac cct ggc gcc gtg acc gtg gcc tgg aag gcc gac agc      480
Ser Asp Phe Tyr Pro Gly Ala Val Thr Val Ala Trp Lys Ala Asp Ser
145                 150                 155                 160

agc ccc gtg aag gcc ggc gtg gag acc acc acc ccc agc aag cag agc      528
Ser Pro Val Lys Ala Gly Val Glu Thr Thr Thr Pro Ser Lys Gln Ser
                165                 170                 175

aac aac aag tac gcc gcc agc agc tac ctg agc ctc acc ccc gag cag      576
Asn Asn Lys Tyr Ala Ala Ser Ser Tyr Leu Ser Leu Thr Pro Glu Gln
            180                 185                 190

tgg aag agc cac cgg agc tac agc tgc cag gtg acc cac gag ggc agc      624
Trp Lys Ser His Arg Ser Tyr Ser Cys Gln Val Thr His Glu Gly Ser
        195                 200                 205

acc gtg gag aag acc gtg gcc ccc acc gag tgc agc                      660
Thr Val Glu Lys Thr Val Ala Pro Thr Glu Cys Ser
    210                 215                 220


<210> SEQ ID NO 201
<211> LENGTH: 220
<212> TYPE: PRT
<213> ORGANISM: Homo sapiens

<400> SEQUENCE: 201

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln His His Pro Gly Lys Ala Pro Lys Leu
        35                  40                  45

Met Ile Tyr Asp Val Ser Asp Arg Pro Ser Gly Val Ser Asn Arg Phe
    50                  55                  60

Ser Gly Ser Lys Ser Gly Asn Ala Ala Ser Leu Thr Ile Ser Gly Leu
65                  70                  75                  80

Gln Ala Glu Asp Glu Ala Asp Tyr Tyr Cys Ser Ser Tyr Ala Gly Ser
                85                  90                  95

Asn Asn Leu Val Phe Gly Thr Gly Thr Lys Val Thr Val Leu Gly Ala
            100                 105                 110

Ala Ala Gly Gln Pro Lys Ala Ala Pro Ser Val Thr Leu Phe Pro Pro
        115                 120                 125

Ser Ser Glu Glu Leu Gln Ala Asn Lys Ala Thr Leu Val Cys Leu Ile
    130                 135                 140

Ser Asp Phe Tyr Pro Gly Ala Val Thr Val Ala Trp Lys Ala Asp Ser
145                 150                 155                 160

Ser Pro Val Lys Ala Gly Val Glu Thr Thr Thr Pro Ser Lys Gln Ser
                165                 170                 175

Asn Asn Lys Tyr Ala Ala Ser Ser Tyr Leu Ser Leu Thr Pro Glu Gln
            180                 185                 190
```

```
Trp Lys Ser His Arg Ser Tyr Ser Cys Gln Val Thr His Glu Gly Ser
        195                 200                 205

Thr Val Glu Lys Thr Val Ala Pro Thr Glu Cys Ser
    210                 215                 220


<210> SEQ ID NO 202
<211> LENGTH: 639
<212> TYPE: DNA
<213> ORGANISM: Homo sapiens
<220> FEATURE:
<221> NAME/KEY: CDS
<222> LOCATION: (1)..(639)

<400> SEQUENCE: 202

gac atc cag atg acc cag tct cca tct tcc gtg tct gca tct gta gga       48
Asp Ile Gln Met Thr Gln Ser Pro Ser Ser Val Ser Ala Ser Val Gly
1               5                   10                  15

gac aga gtc acc atc act tgt cgg gcg agt cag gga att agc agc agg       96
Asp Arg Val Thr Ile Thr Cys Arg Ala Ser Gln Gly Ile Ser Ser Arg
            20                  25                  30

tta gcc tgg tat cag cag aaa cca ggg aaa gcc cct aag ctc ctg atc      144
Leu Ala Trp Tyr Gln Gln Lys Pro Gly Lys Ala Pro Lys Leu Leu Ile
        35                  40                  45

tat gct gca tcc agt ttg caa agt ggg gtc cca tca agg ttc agc ggc      192
Tyr Ala Ala Ser Ser Leu Gln Ser Gly Val Pro Ser Arg Phe Ser Gly
    50                  55                  60

agt gga tct ggg aca gat ttc act ctc acc atc agc agc ctg cag cct      240
Ser Gly Ser Gly Thr Asp Phe Thr Leu Thr Ile Ser Ser Leu Gln Pro
65                  70                  75                  80

gaa gat ttt gga act tac tat tgt caa cag gct aag aat ttc cct cgg      288
Glu Asp Phe Gly Thr Tyr Tyr Cys Gln Gln Ala Lys Asn Phe Pro Arg
                85                  90                  95

acc ttc ggc caa ggg aca cga ctg gag att aaa cgt gcg gcc gca ccc      336
Thr Phe Gly Gln Gly Thr Arg Leu Glu Ile Lys Arg Ala Ala Ala Pro
            100                 105                 110

agc gtg ttc atc ttc ccc ccc tcc gac gag cag ctg aag agc ggc acc      384
Ser Val Phe Ile Phe Pro Pro Ser Asp Glu Gln Leu Lys Ser Gly Thr
        115                 120                 125

gcc agc gtg gtg tgc ctg ctg aac aac ttc tac ccc cgg gag gcc aag      432
Ala Ser Val Val Cys Leu Leu Asn Asn Phe Tyr Pro Arg Glu Ala Lys
    130                 135                 140

gtg cag tgg aag gtg gac aac gcc ctg cag agc ggc aac agc cag gag      480
Val Gln Trp Lys Val Asp Asn Ala Leu Gln Ser Gly Asn Ser Gln Glu
145                 150                 155                 160

agc gtg acc gag cag gac agc aag gac tcc acc tac agc ctg agc agc      528
Ser Val Thr Glu Gln Asp Ser Lys Asp Ser Thr Tyr Ser Leu Ser Ser
                165                 170                 175

acc ctc acc ctg agc aag gcc gac tac gag aag cac aag gtg tac gcc      576
Thr Leu Thr Leu Ser Lys Ala Asp Tyr Glu Lys His Lys Val Tyr Ala
            180                 185                 190

tgc gag gtg acc cac cag ggc ctg agc agc ccc gtg acc aag agc ttc      624
Cys Glu Val Thr His Gln Gly Leu Ser Ser Pro Val Thr Lys Ser Phe
        195                 200                 205

aac cgg ggc gag tgt                                                  639
Asn Arg Gly Glu Cys
    210


<210> SEQ ID NO 203
<211> LENGTH: 213
<212> TYPE: PRT
<213> ORGANISM: Homo sapiens
```

<400> SEQUENCE: 203

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Arg
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Gly Thr Tyr Tyr Cys Gln Gln Ala Lys Asn Phe Pro Arg
                85                  90                  95

Thr Phe Gly Gln Gly Thr Arg Leu Glu Ile Lys Arg Ala Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 204
<211> LENGTH: 642
<212> TYPE: DNA
<213> ORGANISM: Homo sapiens
<220> FEATURE:
<221> NAME/KEY: CDS
<222> LOCATION: (1)..(642)

<400> SEQUENCE: 204

```
gaa att gtg ttg acg cag tct cca ggc acc ctg tct ttg tct cca ggg       48
Glu Ile Val Leu Thr Gln Ser Pro Gly Thr Leu Ser Leu Ser Pro Gly
1               5                   10                  15

gaa aga gcc acc ctc tcc tgc agg gcc agt cag agt gtt agc agc aac       96
Glu Arg Ala Thr Leu Ser Cys Arg Ala Ser Gln Ser Val Ser Ser Asn
            20                  25                  30

tac tta gcc tgg tac cag cag aaa cct ggc cag gct ccc agg ctc ctc      144
Tyr Leu Ala Trp Tyr Gln Gln Lys Pro Gly Gln Ala Pro Arg Leu Leu
        35                  40                  45

gtc tat ggt gca tcc agc agg gcc act ggc atc cca gac agg ttc agt      192
Val Tyr Gly Ala Ser Ser Arg Ala Thr Gly Ile Pro Asp Arg Phe Ser
    50                  55                  60

ggc agt ggg tct ggg aca gac ttc act ctc acc atc agc aga ctg gag      240
Gly Ser Gly Ser Gly Thr Asp Phe Thr Leu Thr Ile Ser Arg Leu Glu
65                  70                  75                  80

cct gaa gat ttt gca gtg tat cac tgt cag cag tat gct ggc tca ccc      288
Pro Glu Asp Phe Ala Val Tyr His Cys Gln Gln Tyr Ala Gly Ser Pro
                85                  90                  95

tgg acg ttc ggc caa ggg acc aag gtg gag atc aaa cgt gcg gcc gca      336
```

```
Trp Thr Phe Gly Gln Gly Thr Lys Val Glu Ile Lys Arg Ala Ala Ala
            100                 105                 110

ccc agc gtg ttc atc ttc ccc ccc tcc gac gag cag ctg aag agc ggc      384
Pro Ser Val Phe Ile Phe Pro Pro Ser Asp Glu Gln Leu Lys Ser Gly
        115                 120                 125

acc gcc agc gtg gtg tgc ctg ctg aac aac ttc tac ccc cgg gag gcc      432
Thr Ala Ser Val Val Cys Leu Leu Asn Asn Phe Tyr Pro Arg Glu Ala
    130                 135                 140

aag gtg cag tgg aag gtg gac aac gcc ctg cag agc ggc aac agc cag      480
Lys Val Gln Trp Lys Val Asp Asn Ala Leu Gln Ser Gly Asn Ser Gln
145                 150                 155                 160

gag agc gtg acc gag cag gac agc aag gac tcc acc tac agc ctg agc      528
Glu Ser Val Thr Glu Gln Asp Ser Lys Asp Ser Thr Tyr Ser Leu Ser
                165                 170                 175

agc acc ctc acc ctg agc aag gcc gac tac gag aag cac aag gtg tac      576
Ser Thr Leu Thr Leu Ser Lys Ala Asp Tyr Glu Lys His Lys Val Tyr
            180                 185                 190

gcc tgc gag gtg acc cac cag ggc ctg agc agc ccc gtg acc aag agc      624
Ala Cys Glu Val Thr His Gln Gly Leu Ser Ser Pro Val Thr Lys Ser
        195                 200                 205

ttc aac cgg ggc gag tgt                                              642
Phe Asn Arg Gly Glu Cys
    210


<210> SEQ ID NO 205
<211> LENGTH: 214
<212> TYPE: PRT
<213> ORGANISM: Homo sapiens

<400> SEQUENCE: 205

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Tyr Leu Ala Trp Tyr Gln Gln Lys Pro Gly Gln Ala Pro Arg Leu Leu
        35                  40                  45

Val Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr His Cys Gln Gln Tyr Ala Gly Ser Pro
                85                  90                  95

Trp Thr Phe Gly Gln Gly Thr Lys Val Glu Ile Lys Arg Ala Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

```
<210> SEQ ID NO 206
<211> LENGTH: 660
<212> TYPE: DNA
<213> ORGANISM: Homo sapiens
<220> FEATURE:
<221> NAME/KEY: CDS
<222> LOCATION: (1)..(660)

<400> SEQUENCE: 206

caa tct gcc ctg act cag cct ccc tcc gcg tcc ggg tct cct gga cag       48
Gln Ser Ala Leu Thr Gln Pro Pro Ser Ala Ser Gly Ser Pro Gly Gln
1               5                   10                  15

tca gtc acc atc tcc tgc act gga acc agc agt gac gtt ggt ggt tat       96
Ser Val Thr Ile Ser Cys Thr Gly Thr Ser Ser Asp Val Gly Gly Tyr
            20                  25                  30

aac tat gtc tcc tgg tac caa cag cac cca ggc aaa gcc ccc aaa ctc      144
Asn Tyr Val Ser Trp Tyr Gln Gln His Pro Gly Lys Ala Pro Lys Leu
        35                  40                  45

atg att tat gag gtc agt aag cgg ccc tca ggg gtc cct gat cgc ttc      192
Met Ile Tyr Glu Val Ser Lys Arg Pro Ser Gly Val Pro Asp Arg Phe
    50                  55                  60

tct ggc tcc aag tct ggc aac acg gcc tcc ctg acc gtc tct ggg ctc      240
Ser Gly Ser Lys Ser Gly Asn Thr Ala Ser Leu Thr Val Ser Gly Leu
65                  70                  75                  80

cag gct gag gat gag gct gat tat tac tgc agc tca tat gca ggc agc      288
Gln Ala Glu Asp Glu Ala Asp Tyr Tyr Cys Ser Ser Tyr Ala Gly Ser
                85                  90                  95

aac aat ttg gta ttc ggc gga ggg acc aag ctg acc gtc cta ggt gcg      336
Asn Asn Leu Val Phe Gly Gly Gly Thr Lys Leu Thr Val Leu Gly Ala
            100                 105                 110

gcc gca ggc cag ccc aag gcc gct ccc agc gtg acc ctg ttc ccc ccc      384
Ala Ala Gly Gln Pro Lys Ala Ala Pro Ser Val Thr Leu Phe Pro Pro
        115                 120                 125

tcc tcc gag gag ctg cag gcc aac aag gcc acc ctg gtg tgc ctc atc      432
Ser Ser Glu Glu Leu Gln Ala Asn Lys Ala Thr Leu Val Cys Leu Ile
    130                 135                 140

agc gac ttc tac cct ggc gcc gtg acc gtg gcc tgg aag gcc gac agc      480
Ser Asp Phe Tyr Pro Gly Ala Val Thr Val Ala Trp Lys Ala Asp Ser
145                 150                 155                 160

agc ccc gtg aag gcc ggc gtg gag acc acc acc ccc agc aag cag agc      528
Ser Pro Val Lys Ala Gly Val Glu Thr Thr Thr Pro Ser Lys Gln Ser
                165                 170                 175

aac aac aag tac gcc gcc agc agc tac ctg agc ctc acc ccc gag cag      576
Asn Asn Lys Tyr Ala Ala Ser Ser Tyr Leu Ser Leu Thr Pro Glu Gln
            180                 185                 190

tgg aag agc cac cgg agc tac agc tgc cag gtg acc cac gag ggc agc      624
Trp Lys Ser His Arg Ser Tyr Ser Cys Gln Val Thr His Glu Gly Ser
        195                 200                 205

acc gtg gag aag acc gtg gcc ccc acc gag tgc agc                      660
Thr Val Glu Lys Thr Val Ala Pro Thr Glu Cys Ser
    210                 215                 220


<210> SEQ ID NO 207
<211> LENGTH: 220
<212> TYPE: PRT
<213> ORGANISM: Homo sapiens

<400> SEQUENCE: 207

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
```

```
            20                  25                  30

Asn Tyr Val Ser Trp Tyr Gln Gln His Pro Gly Lys Ala Pro Lys Leu
        35                  40                  45

Met Ile Tyr Glu Val Ser Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Ser
                85                  90                  95

Asn Asn Leu Val Phe Gly Gly Gly Thr Lys Leu Thr Val Leu Gly Ala
            100                 105                 110

Ala Ala Gly Gln Pro Lys Ala Ala Pro Ser Val Thr Leu Phe Pro Pro
        115                 120                 125

Ser Ser Glu Glu Leu Gln Ala Asn Lys Ala Thr Leu Val Cys Leu Ile
    130                 135                 140

Ser Asp Phe Tyr Pro Gly Ala Val Thr Val Ala Trp Lys Ala Asp Ser
145                 150                 155                 160

Ser Pro Val Lys Ala Gly Val Glu Thr Thr Thr Pro Ser Lys Gln Ser
                165                 170                 175

Asn Asn Lys Tyr Ala Ala Ser Ser Tyr Leu Ser Leu Thr Pro Glu Gln
            180                 185                 190

Trp Lys Ser His Arg Ser Tyr Ser Cys Gln Val Thr His Glu Gly Ser
        195                 200                 205

Thr Val Glu Lys Thr Val Ala Pro Thr Glu Cys Ser
    210                 215                 220


<210> SEQ ID NO 208
<211> LENGTH: 660
<212> TYPE: DNA
<213> ORGANISM: Homo sapiens
<220> FEATURE:
<221> NAME/KEY: CDS
<222> LOCATION: (1)..(660)

<400> SEQUENCE: 208

cag tct gcc ctg act cag cct cgc tca gtg tcc ggg tct cct gga cag       48
Gln Ser Ala Leu Thr Gln Pro Arg Ser Val Ser Gly Ser Pro Gly Gln
1               5                   10                  15

tca gtc acc atc tcc tgc act gga acc agc agt gat att ggt ggt tat       96
Ser Val Thr Ile Ser Cys Thr Gly Thr Ser Ser Asp Ile Gly Gly Tyr
            20                  25                  30

aac ttt gtc tcc tgg tac caa caa cac cca ggc aaa gcc ccc aaa ctc      144
Asn Phe Val Ser Trp Tyr Gln Gln His Pro Gly Lys Ala Pro Lys Leu
        35                  40                  45

atg att tat gat gtc agt aat cgg ccc tca ggg gtt tct aat cgc ttc      192
Met Ile Tyr Asp Val Ser Asn Arg Pro Ser Gly Val Ser Asn Arg Phe
    50                  55                  60

tct ggc tcc aag tct ggc aaa atg gcc tcc ctg acc atc tct ggg ctc      240
Ser Gly Ser Lys Ser Gly Lys Met Ala Ser Leu Thr Ile Ser Gly Leu
65                  70                  75                  80

cag gct gag gac gag gct gat tac tac tgc gcc tca tat aca agc aga      288
Gln Ala Glu Asp Glu Ala Asp Tyr Tyr Cys Ala Ser Tyr Thr Ser Arg
                85                  90                  95

agc act ctc gtc ttc gga act ggg acc aag gtc acc gtc cta ggt gcg      336
Ser Thr Leu Val Phe Gly Thr Gly Thr Lys Val Thr Val Leu Gly Ala
            100                 105                 110

gcc gca ggc cag ccc aag gcc gct ccc agc gtg acc ctg ttc ccc ccc      384
Ala Ala Gly Gln Pro Lys Ala Ala Pro Ser Val Thr Leu Phe Pro Pro
        115                 120                 125
```

-continued

```
tcc tcc gag gag ctg cag gcc aac aag gcc acc ctg gtg tgc ctc atc      432
Ser Ser Glu Glu Leu Gln Ala Asn Lys Ala Thr Leu Val Cys Leu Ile
    130                 135                 140

agc gac ttc tac cct ggc gcc gtg acc gtg gcc tgg aag gcc gac agc      480
Ser Asp Phe Tyr Pro Gly Ala Val Thr Val Ala Trp Lys Ala Asp Ser
145                 150                 155                 160

agc ccc gtg aag gcc ggc gtg gag acc acc acc ccc agc aag cag agc      528
Ser Pro Val Lys Ala Gly Val Glu Thr Thr Thr Pro Ser Lys Gln Ser
                165                 170                 175

aac aac aag tac gcc gcc agc agc tac ctg agc ctc acc ccc gag cag      576
Asn Asn Lys Tyr Ala Ala Ser Ser Tyr Leu Ser Leu Thr Pro Glu Gln
            180                 185                 190

tgg aag agc cac cgg agc tac agc tgc cag gtg acc cac gag ggc agc      624
Trp Lys Ser His Arg Ser Tyr Ser Cys Gln Val Thr His Glu Gly Ser
        195                 200                 205

acc gtg gag aag acc gtg gcc ccc acc gag tgc agc                      660
Thr Val Glu Lys Thr Val Ala Pro Thr Glu Cys Ser
    210                 215                 220


<210> SEQ ID NO 209
<211> LENGTH: 220
<212> TYPE: PRT
<213> ORGANISM: Homo sapiens

<400> SEQUENCE: 209

Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Ile Gly Gly Tyr
            20                  25                  30

Asn Phe Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Lys Met Ala Ser Leu Thr Ile Ser Gly Leu
65                  70                  75                  80

Gln Ala Glu Asp Glu Ala Asp Tyr Tyr Cys Ala Ser Tyr Thr Ser Arg
                85                  90                  95

Ser Thr Leu Val Phe Gly Thr Gly Thr Lys Val Thr Val Leu Gly Ala
            100                 105                 110

Ala Ala Gly Gln Pro Lys Ala Ala Pro Ser Val Thr Leu Phe Pro Pro
        115                 120                 125

Ser Ser Glu Glu Leu Gln Ala Asn Lys Ala Thr Leu Val Cys Leu Ile
    130                 135                 140

Ser Asp Phe Tyr Pro Gly Ala Val Thr Val Ala Trp Lys Ala Asp Ser
145                 150                 155                 160

Ser Pro Val Lys Ala Gly Val Glu Thr Thr Thr Pro Ser Lys Gln Ser
                165                 170                 175

Asn Asn Lys Tyr Ala Ala Ser Ser Tyr Leu Ser Leu Thr Pro Glu Gln
            180                 185                 190

Trp Lys Ser His Arg Ser Tyr Ser Cys Gln Val Thr His Glu Gly Ser
        195                 200                 205

Thr Val Glu Lys Thr Val Ala Pro Thr Glu Cys Ser
    210                 215                 220


<210> SEQ ID NO 210
<211> LENGTH: 639
<212> TYPE: DNA
<213> ORGANISM: Homo sapiens
```

<220> FEATURE:
<221> NAME/KEY: CDS
<222> LOCATION: (1)..(639)

<400> SEQUENCE: 210

```
gac atc cag atg acc cag tct cca tcc tcc ctg tct gca tct gta gga       48
Asp Ile Gln Met Thr Gln Ser Pro Ser Ser Leu Ser Ala Ser Val Gly
1               5                   10                  15

gac aga gtc acc atc act tgc cgg gca agt cag agc att agc agc tat       96
Asp Arg Val Thr Ile Thr Cys Arg Ala Ser Gln Ser Ile Ser Ser Tyr
            20                  25                  30

tta aat tgg tat cag cag aaa cca ggg aaa gcc cct aag ctc ctg atc      144
Leu Asn Trp Tyr Gln Gln Lys Pro Gly Lys Ala Pro Lys Leu Leu Ile
        35                  40                  45

tat gct gca tcc agt ttg caa agt ggg gtc cca tca agg ttt agc ggc      192
Tyr Ala Ala Ser Ser Leu Gln Ser Gly Val Pro Ser Arg Phe Ser Gly
    50                  55                  60

agt gga tct ggg aca gat ttc act ctc acc atc agc agc ctg cag cct      240
Ser Gly Ser Gly Thr Asp Phe Thr Leu Thr Ile Ser Ser Leu Gln Pro
65                  70                  75                  80

gaa gat ttt gca act tac tat tgt caa cag gct aac agt ttc ccg ctc      288
Glu Asp Phe Ala Thr Tyr Tyr Cys Gln Gln Ala Asn Ser Phe Pro Leu
                85                  90                  95

act ttc ggc gga ggg acc aag gtg gaa atc aaa cgt gcg gcc gca ccc      336
Thr Phe Gly Gly Gly Thr Lys Val Glu Ile Lys Arg Ala Ala Ala Pro
            100                 105                 110

agc gtg ttc atc ttc ccc ccc tcc gac gag cag ctg aag agc ggc acc      384
Ser Val Phe Ile Phe Pro Pro Ser Asp Glu Gln Leu Lys Ser Gly Thr
        115                 120                 125

gcc agc gtg gtg tgc ctg ctg aac aac ttc tac ccc cgg gag gcc aag      432
Ala Ser Val Val Cys Leu Leu Asn Asn Phe Tyr Pro Arg Glu Ala Lys
    130                 135                 140

gtg cag tgg aag gtg gac aac gcc ctg cag agc ggc aac agc cag gag      480
Val Gln Trp Lys Val Asp Asn Ala Leu Gln Ser Gly Asn Ser Gln Glu
145                 150                 155                 160

agc gtg acc gag cag gac agc aag gac tcc acc tac agc ctg agc agc      528
Ser Val Thr Glu Gln Asp Ser Lys Asp Ser Thr Tyr Ser Leu Ser Ser
                165                 170                 175

acc ctc acc ctg agc aag gcc gac tac gag aag cac aag gtg tac gcc      576
Thr Leu Thr Leu Ser Lys Ala Asp Tyr Glu Lys His Lys Val Tyr Ala
            180                 185                 190

tgc gag gtg acc cac cag ggc ctg agc agc ccc gtg acc aag agc ttc      624
Cys Glu Val Thr His Gln Gly Leu Ser Ser Pro Val Thr Lys Ser Phe
        195                 200                 205

aac cgg ggc gag tgt                                                  639
Asn Arg Gly Glu Cys
    210
```

<210> SEQ ID NO 211
<211> LENGTH: 213
<212> TYPE: PRT
<213> ORGANISM: Homo sapiens

<400> SEQUENCE: 211

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
```

```
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Leu
                85                  90                  95

Thr Phe Gly Gly Gly Thr Lys Val Glu Ile Lys Arg Ala Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210


<210> SEQ ID NO 212
<211> LENGTH: 660
<212> TYPE: DNA
<213> ORGANISM: Homo sapiens
<220> FEATURE:
<221> NAME/KEY: CDS
<222> LOCATION: (1)..(660)

<400> SEQUENCE: 212

cag tct gcc ctg act cag cct ccc tcc gcg tcc ggg tct cct gga cag       48
Gln Ser Ala Leu Thr Gln Pro Pro Ser Ala Ser Gly Ser Pro Gly Gln
1               5                   10                  15

tca gtc acc atc tcc tgc act gga acc agc agt gat gtt ggt ggt tat       96
Ser Val Thr Ile Ser Cys Thr Gly Thr Ser Ser Asp Val Gly Gly Tyr
            20                  25                  30

aac tat gtc tcc tgg tac caa cac cac cca ggc aaa gcc ccc aaa ctc      144
Asn Tyr Val Ser Trp Tyr Gln His His Pro Gly Lys Ala Pro Lys Leu
        35                  40                  45

atg att tat gat gtc agt aat cgg ccc tca ggg gtt tct aat cgc ttc      192
Met Ile Tyr Asp Val Ser Asn Arg Pro Ser Gly Val Ser Asn Arg Phe
    50                  55                  60

tct ggc tcc aag tct ggc aac acg gcc tcc ctg acc atc tct ggg ctc      240
Ser Gly Ser Lys Ser Gly Asn Thr Ala Ser Leu Thr Ile Ser Gly Leu
65                  70                  75                  80

cag gct gag gac gag gct gat tat tac tgc agc tca tat aca agc agc      288
Gln Ala Glu Asp Glu Ala Asp Tyr Tyr Cys Ser Ser Tyr Thr Ser Ser
                85                  90                  95

agc act ctt gtc ttc gga act ggg acc aag gtc acc gtc cta ggt gcg      336
Ser Thr Leu Val Phe Gly Thr Gly Thr Lys Val Thr Val Leu Gly Ala
            100                 105                 110

gcc gca ggc cag ccc aag gcc gct ccc agc gtg acc ctg ttc ccc ccc      384
Ala Ala Gly Gln Pro Lys Ala Ala Pro Ser Val Thr Leu Phe Pro Pro
        115                 120                 125

tcc tcc gag gag ctg cag gcc aac aag gcc acc ctg gtg tgc ctc atc      432
Ser Ser Glu Glu Leu Gln Ala Asn Lys Ala Thr Leu Val Cys Leu Ile
    130                 135                 140

agc gac ttc tac cct ggc gcc gtg acc gtg gcc tgg aag gcc gac agc      480
```

-continued

```
Ser Asp Phe Tyr Pro Gly Ala Val Thr Val Ala Trp Lys Ala Asp Ser
145                 150                 155                 160

agc ccc gtg aag gcc ggc gtg gag acc acc acc ccc agc aag cag agc      528
Ser Pro Val Lys Ala Gly Val Glu Thr Thr Thr Pro Ser Lys Gln Ser
                165                 170                 175

aac aac aag tac gcc gcc agc agc tac ctg agc ctc acc ccc gag cag      576
Asn Asn Lys Tyr Ala Ala Ser Ser Tyr Leu Ser Leu Thr Pro Glu Gln
            180                 185                 190

tgg aag agc cac cgg agc tac agc tgc cag gtg acc cac gag ggc agc      624
Trp Lys Ser His Arg Ser Tyr Ser Cys Gln Val Thr His Glu Gly Ser
        195                 200                 205

acc gtg gag aag acc gtg gcc ccc acc gag tgc agc                      660
Thr Val Glu Lys Thr Val Ala Pro Thr Glu Cys Ser
    210                 215                 220


<210> SEQ ID NO 213
<211> LENGTH: 220
<212> TYPE: PRT
<213> ORGANISM: Homo sapiens

<400> SEQUENCE: 213

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln His His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Leu Val Phe Gly Thr Gly Thr Lys Val Thr Val Leu Gly Ala
            100                 105                 110

Ala Ala Gly Gln Pro Lys Ala Ala Pro Ser Val Thr Leu Phe Pro Pro
        115                 120                 125

Ser Ser Glu Glu Leu Gln Ala Asn Lys Ala Thr Leu Val Cys Leu Ile
    130                 135                 140

Ser Asp Phe Tyr Pro Gly Ala Val Thr Val Ala Trp Lys Ala Asp Ser
145                 150                 155                 160

Ser Pro Val Lys Ala Gly Val Glu Thr Thr Thr Pro Ser Lys Gln Ser
                165                 170                 175

Asn Asn Lys Tyr Ala Ala Ser Ser Tyr Leu Ser Leu Thr Pro Glu Gln
            180                 185                 190

Trp Lys Ser His Arg Ser Tyr Ser Cys Gln Val Thr His Glu Gly Ser
        195                 200                 205

Thr Val Glu Lys Thr Val Ala Pro Thr Glu Cys Ser
    210                 215                 220


<210> SEQ ID NO 214
<211> LENGTH: 663
<212> TYPE: DNA
<213> ORGANISM: Homo sapiens
<220> FEATURE:
<221> NAME/KEY: CDS
<222> LOCATION: (1)..(663)

<400> SEQUENCE: 214
```

```
cag tct gcc ctg act cag cct ccc tcc gcg tcc ggg tct cct gga cag        48
Gln Ser Ala Leu Thr Gln Pro Pro Ser Ala Ser Gly Ser Pro Gly Gln
1               5                   10                  15

tca gtc acc atc tcc tgc act gga acc agc agt gac gtt ggt ggt tac        96
Ser Val Thr Ile Ser Cys Thr Gly Thr Ser Ser Asp Val Gly Gly Tyr
            20                  25                  30

aac tat gtc tcc tgg tac caa cag cgc cca ggc aaa gcc ccc aaa ctc       144
Asn Tyr Val Ser Trp Tyr Gln Gln Arg Pro Gly Lys Ala Pro Lys Leu
        35                  40                  45

atg att tat gat gtc agt aat cgg ccc tca ggg gtt tct gat cgc ttc       192
Met Ile Tyr Asp Val Ser Asn Arg Pro Ser Gly Val Ser Asp Arg Phe
    50                  55                  60

tct ggc tcc aag tct ggc aac acg gcc tcc ctg acc atc tct ggg ctc       240
Ser Gly Ser Lys Ser Gly Asn Thr Ala Ser Leu Thr Ile Ser Gly Leu
65                  70                  75                  80

cag gct gaa gac gag gct gat tat tac tgc agc tca tat aca act ggc       288
Gln Ala Glu Asp Glu Ala Asp Tyr Tyr Cys Ser Ser Tyr Thr Thr Gly
                85                  90                  95

agc act ctc gtg gtc ttc ggc gga ggg acc aag ctg acc gtc cta ggt       336
Ser Thr Leu Val Val Phe Gly Gly Gly Thr Lys Leu Thr Val Leu Gly
            100                 105                 110

gcg gcc gca ggc cag ccc aag gcc gct ccc agc gtg acc ctg ttc ccc       384
Ala Ala Ala Gly Gln Pro Lys Ala Ala Pro Ser Val Thr Leu Phe Pro
        115                 120                 125

ccc tcc tcc gag gag ctg cag gcc aac aag gcc acc ctg gtg tgc ctc       432
Pro Ser Ser Glu Glu Leu Gln Ala Asn Lys Ala Thr Leu Val Cys Leu
    130                 135                 140

atc agc gac ttc tac cct ggc gcc gtg acc gtg gcc tgg aag gcc gac       480
Ile Ser Asp Phe Tyr Pro Gly Ala Val Thr Val Ala Trp Lys Ala Asp
145                 150                 155                 160

agc agc ccc gtg aag gcc ggc gtg gag acc acc acc ccc agc aag cag       528
Ser Ser Pro Val Lys Ala Gly Val Glu Thr Thr Thr Pro Ser Lys Gln
                165                 170                 175

agc aac aac aag tac gcc gcc agc agc tac ctg agc ctc acc ccc gag       576
Ser Asn Asn Lys Tyr Ala Ala Ser Ser Tyr Leu Ser Leu Thr Pro Glu
            180                 185                 190

cag tgg aag agc cac cgg agc tac agc tgc cag gtg acc cac gag ggc       624
Gln Trp Lys Ser His Arg Ser Tyr Ser Cys Gln Val Thr His Glu Gly
        195                 200                 205

agc acc gtg gag aag acc gtg gcc ccc acc gag tgc agc                   663
Ser Thr Val Glu Lys Thr Val Ala Pro Thr Glu Cys Ser
    210                 215                 220


<210> SEQ ID NO 215
<211> LENGTH: 221
<212> TYPE: PRT
<213> ORGANISM: Homo sapiens

<400> SEQUENCE: 215

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln Arg Pro Gly Lys Ala Pro Lys Leu
        35                  40                  45

Met Ile Tyr Asp Val Ser Asn Arg Pro Ser Gly Val Ser Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Thr Gly
```

```
                85                  90                  95

Ser Thr Leu Val Val Phe Gly Gly Gly Thr Lys Leu Thr Val Leu Gly
            100                 105                 110

Ala Ala Ala Gly Gln Pro Lys Ala Ala Pro Ser Val Thr Leu Phe Pro
        115                 120                 125

Pro Ser Ser Glu Glu Leu Gln Ala Asn Lys Ala Thr Leu Val Cys Leu
    130                 135                 140

Ile Ser Asp Phe Tyr Pro Gly Ala Val Thr Val Ala Trp Lys Ala Asp
145                 150                 155                 160

Ser Ser Pro Val Lys Ala Gly Val Glu Thr Thr Thr Pro Ser Lys Gln
                165                 170                 175

Ser Asn Asn Lys Tyr Ala Ala Ser Ser Tyr Leu Ser Leu Thr Pro Glu
            180                 185                 190

Gln Trp Lys Ser His Arg Ser Tyr Ser Cys Gln Val Thr His Glu Gly
        195                 200                 205

Ser Thr Val Glu Lys Thr Val Ala Pro Thr Glu Cys Ser
    210                 215                 220


<210> SEQ ID NO 216
<211> LENGTH: 660
<212> TYPE: DNA
<213> ORGANISM: Homo sapiens
<220> FEATURE:
<221> NAME/KEY: CDS
<222> LOCATION: (1)..(660)

<400> SEQUENCE: 216

cag tct gcc ctg act cag cct ccc tcc gcg tcc ggg tct cct gga cag       48
Gln Ser Ala Leu Thr Gln Pro Pro Ser Ala Ser Gly Ser Pro Gly Gln
1               5                   10                  15

tca gtc acc atc tcc tgc act gga acc agc agt gac gtt ggt ggt tat       96
Ser Val Thr Ile Ser Cys Thr Gly Thr Ser Ser Asp Val Gly Gly Tyr
            20                  25                  30

aac tat gtc tcc tgg tac caa cag cac cca ggc aaa gcc ccc aaa ctc      144
Asn Tyr Val Ser Trp Tyr Gln Gln His Pro Gly Lys Ala Pro Lys Leu
        35                  40                  45

atg att tat gag gtc agt aag cgg ccc tca ggg gtc cct gat cgc ttc      192
Met Ile Tyr Glu Val Ser Lys Arg Pro Ser Gly Val Pro Asp Arg Phe
    50                  55                  60

tct ggc tcc aag tct ggc aac acg gcc tcc ctg acc gtc tct ggg ctc      240
Ser Gly Ser Lys Ser Gly Asn Thr Ala Ser Leu Thr Val Ser Gly Leu
65                  70                  75                  80

cag gct gag gat gag gct gat tat tac tgc agc tca tat gga ggc agc      288
Gln Ala Glu Asp Glu Ala Asp Tyr Tyr Cys Ser Ser Tyr Gly Gly Ser
                85                  90                  95

aac aat gtg gta ttc ggc gga ggg acc aag ctg acc gtc cta ggt gcg      336
Asn Asn Val Val Phe Gly Gly Gly Thr Lys Leu Thr Val Leu Gly Ala
            100                 105                 110

gcc gca ggc cag ccc aag gcc gct ccc agc gtg acc ctg ttc ccc ccc      384
Ala Ala Gly Gln Pro Lys Ala Ala Pro Ser Val Thr Leu Phe Pro Pro
        115                 120                 125

tcc tcc gag gag ctg cag gcc aac aag gcc acc ctg gtg tgc ctc atc      432
Ser Ser Glu Glu Leu Gln Ala Asn Lys Ala Thr Leu Val Cys Leu Ile
    130                 135                 140

agc gac ttc tac cct ggc gcc gtg acc gtg gcc tgg aag gcc gac agc      480
Ser Asp Phe Tyr Pro Gly Ala Val Thr Val Ala Trp Lys Ala Asp Ser
145                 150                 155                 160

agc ccc gtg aag gcc ggc gtg gag acc acc acc ccc agc aag cag agc      528
Ser Pro Val Lys Ala Gly Val Glu Thr Thr Thr Pro Ser Lys Gln Ser
                165                 170                 175
```

```
aac aac aag tac gcc gcc agc agc tac ctg agc ctc acc ccc gag cag      576
Asn Asn Lys Tyr Ala Ala Ser Ser Tyr Leu Ser Leu Thr Pro Glu Gln
            180                 185                 190

tgg aag agc cac cgg agc tac agc tgc cag gtg acc cac gag ggc agc      624
Trp Lys Ser His Arg Ser Tyr Ser Cys Gln Val Thr His Glu Gly Ser
        195                 200                 205

acc gtg gag aag acc gtg gcc ccc acc gag tgc agc                      660
Thr Val Glu Lys Thr Val Ala Pro Thr Glu Cys Ser
    210                 215                 220


<210> SEQ ID NO 217
<211> LENGTH: 220
<212> TYPE: PRT
<213> ORGANISM: Homo sapiens

<400> SEQUENCE: 217

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Gly Gly Ser
                85                  90                  95

Asn Asn Val Val Phe Gly Gly Gly Thr Lys Leu Thr Val Leu Gly Ala
            100                 105                 110

Ala Ala Gly Gln Pro Lys Ala Ala Pro Ser Val Thr Leu Phe Pro Pro
        115                 120                 125

Ser Ser Glu Glu Leu Gln Ala Asn Lys Ala Thr Leu Val Cys Leu Ile
    130                 135                 140

Ser Asp Phe Tyr Pro Gly Ala Val Thr Val Ala Trp Lys Ala Asp Ser
145                 150                 155                 160

Ser Pro Val Lys Ala Gly Val Glu Thr Thr Thr Pro Ser Lys Gln Ser
                165                 170                 175

Asn Asn Lys Tyr Ala Ala Ser Ser Tyr Leu Ser Leu Thr Pro Glu Gln
            180                 185                 190

Trp Lys Ser His Arg Ser Tyr Ser Cys Gln Val Thr His Glu Gly Ser
        195                 200                 205

Thr Val Glu Lys Thr Val Ala Pro Thr Glu Cys Ser
    210                 215                 220


<210> SEQ ID NO 218
<211> LENGTH: 660
<212> TYPE: DNA
<213> ORGANISM: Homo sapiens
<220> FEATURE:
<221> NAME/KEY: CDS
<222> LOCATION: (1)..(660)

<400> SEQUENCE: 218

cag tct gcc ctg act cag cct gcc tcc gtg tct ggg tct cct gga cag       48
Gln Ser Ala Leu Thr Gln Pro Ala Ser Val Ser Gly Ser Pro Gly Gln
1               5                   10                  15

tcg atc acc atc tcc tgc act gga acc agc agt gac gtt ggt gct tat       96
Ser Ile Thr Ile Ser Cys Thr Gly Thr Ser Ser Asp Val Gly Ala Tyr
```

```
            20                  25                  30

aac tat gtc tcc tgg tac caa caa cac cca ggc aaa gcc ccc aaa ctc      144
Asn Tyr Val Ser Trp Tyr Gln Gln His Pro Gly Lys Ala Pro Lys Leu
        35                  40                  45

atg att tat gat gtc agt aat cgg ccc tca ggg gtt tct aat cgc ttc      192
Met Ile Tyr Asp Val Ser Asn Arg Pro Ser Gly Val Ser Asn Arg Phe
    50                  55                  60

tct ggc tcc aag tct ggc aac acg gcc tcc ctg acc atc tct ggg ctc      240
Ser Gly Ser Lys Ser Gly Asn Thr Ala Ser Leu Thr Ile Ser Gly Leu
65                  70                  75                  80

cag gct gag gac gag gct gat tat tac tgc agc tca tat gca ggc agc      288
Gln Ala Glu Asp Glu Ala Asp Tyr Tyr Cys Ser Ser Tyr Ala Gly Ser
                85                  90                  95

aac agt gtg gta ttc ggc gga ggg acc aag ctc acc gtc cta ggt gcg      336
Asn Ser Val Val Phe Gly Gly Gly Thr Lys Leu Thr Val Leu Gly Ala
            100                 105                 110

gcc gca ggc cag ccc aag gcc gct ccc agc gtg acc ctg ttc ccc ccc      384
Ala Ala Gly Gln Pro Lys Ala Ala Pro Ser Val Thr Leu Phe Pro Pro
        115                 120                 125

tcc tcc gag gag ctg cag gcc aac aag gcc acc ctg gtg tgc ctc atc      432
Ser Ser Glu Glu Leu Gln Ala Asn Lys Ala Thr Leu Val Cys Leu Ile
    130                 135                 140

agc gac ttc tac cct ggc gcc gtg acc gtg gcc tgg aag gcc gac agc      480
Ser Asp Phe Tyr Pro Gly Ala Val Thr Val Ala Trp Lys Ala Asp Ser
145                 150                 155                 160

agc ccc gtg aag gcc ggc gtg gag acc acc acc ccc agc aag cag agc      528
Ser Pro Val Lys Ala Gly Val Glu Thr Thr Thr Pro Ser Lys Gln Ser
                165                 170                 175

aac aac aag tac gcc gcc agc agc tac ctg agc ctc acc ccc gag cag      576
Asn Asn Lys Tyr Ala Ala Ser Ser Tyr Leu Ser Leu Thr Pro Glu Gln
            180                 185                 190

tgg aag agc cac cgg agc tac agc tgc cag gtg acc cac gag ggc agc      624
Trp Lys Ser His Arg Ser Tyr Ser Cys Gln Val Thr His Glu Gly Ser
        195                 200                 205

acc gtg gag aag acc gtg gcc ccc acc gag tgc agc                      660
Thr Val Glu Lys Thr Val Ala Pro Thr Glu Cys Ser
    210                 215                 220


<210> SEQ ID NO 219
<211> LENGTH: 220
<212> TYPE: PRT
<213> ORGANISM: Homo sapiens

<400> SEQUENCE: 219

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ala Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Ala Gly Ser
                85                  90                  95

Asn Ser Val Val Phe Gly Gly Gly Thr Lys Leu Thr Val Leu Gly Ala
            100                 105                 110

Ala Ala Gly Gln Pro Lys Ala Ala Pro Ser Val Thr Leu Phe Pro Pro
```

```
        115                 120                 125

Ser Ser Glu Glu Leu Gln Ala Asn Lys Ala Thr Leu Val Cys Leu Ile
    130                 135                 140

Ser Asp Phe Tyr Pro Gly Ala Val Thr Val Ala Trp Lys Ala Asp Ser
145                 150                 155                 160

Ser Pro Val Lys Ala Gly Val Glu Thr Thr Thr Pro Ser Lys Gln Ser
                165                 170                 175

Asn Asn Lys Tyr Ala Ala Ser Ser Tyr Leu Ser Leu Thr Pro Glu Gln
            180                 185                 190

Trp Lys Ser His Arg Ser Tyr Ser Cys Gln Val Thr His Glu Gly Ser
        195                 200                 205

Thr Val Glu Lys Thr Val Ala Pro Thr Glu Cys Ser
    210                 215                 220


<210> SEQ ID NO 220
<211> LENGTH: 639
<212> TYPE: DNA
<213> ORGANISM: Homo sapiens
<220> FEATURE:
<221> NAME/KEY: CDS
<222> LOCATION: (1)..(639)

<400> SEQUENCE: 220

gac atc cag ttg acc cag tct cca tct tcc gtg tct gca tct gta gga       48
Asp Ile Gln Leu Thr Gln Ser Pro Ser Ser Val Ser Ala Ser Val Gly
1               5                   10                  15

ggc aga gtc acc atc act tgt cgg gcg agt cag ggt att agc agc tgg       96
Gly Arg Val Thr Ile Thr Cys Arg Ala Ser Gln Gly Ile Ser Ser Trp
            20                  25                  30

tta gcc tgg tat cag cag aga cca ggg aaa gcc cct aac ctc ctg atc      144
Leu Ala Trp Tyr Gln Gln Arg Pro Gly Lys Ala Pro Asn Leu Leu Ile
        35                  40                  45

tat ggt gca tcc aac ttg caa agt ggg gtc ccc tca agg ttc agc ggc      192
Tyr Gly Ala Ser Asn Leu Gln Ser Gly Val Pro Ser Arg Phe Ser Gly
    50                  55                  60

agt ggg tct ggg aca gat ttc agt ctc acc atc agc agc ctg caa cct      240
Ser Gly Ser Gly Thr Asp Phe Ser Leu Thr Ile Ser Ser Leu Gln Pro
65                  70                  75                  80

gaa gat ttt gca act tac tac tgt caa cag gct aag agt ttc ccg ctc      288
Glu Asp Phe Ala Thr Tyr Tyr Cys Gln Gln Ala Lys Ser Phe Pro Leu
                85                  90                  95

act ttc ggc ggc ggg acc aag gtg gaa atc aaa cgt gcg gcc gca ccc      336
Thr Phe Gly Gly Gly Thr Lys Val Glu Ile Lys Arg Ala Ala Ala Pro
            100                 105                 110

agc gtg ttc atc ttc ccc ccc tcc gac gag cag ctg aag agc ggc acc      384
Ser Val Phe Ile Phe Pro Pro Ser Asp Glu Gln Leu Lys Ser Gly Thr
        115                 120                 125

gcc agc gtg gtg tgc ctg ctg aac aac ttc tac ccc cgg gag gcc aag      432
Ala Ser Val Val Cys Leu Leu Asn Asn Phe Tyr Pro Arg Glu Ala Lys
    130                 135                 140

gtg cag tgg aag gtg gac aac gcc ctg cag agc ggc aac agc cag gag      480
Val Gln Trp Lys Val Asp Asn Ala Leu Gln Ser Gly Asn Ser Gln Glu
145                 150                 155                 160

agc gtg acc gag cag gac agc aag gac tcc acc tac agc ctg agc agc      528
Ser Val Thr Glu Gln Asp Ser Lys Asp Ser Thr Tyr Ser Leu Ser Ser
                165                 170                 175

acc ctc acc ctg agc aag gcc gac tac gag aag cac aag gtg tac gcc      576
Thr Leu Thr Leu Ser Lys Ala Asp Tyr Glu Lys His Lys Val Tyr Ala
            180                 185                 190

tgc gag gtg acc cac cag ggc ctg agc agc ccc gtg acc aag agc ttc      624
```

```
Cys Glu Val Thr His Gln Gly Leu Ser Ser Pro Val Thr Lys Ser Phe
        195                 200                 205

aac cgg ggc gag tgt                                                639
Asn Arg Gly Glu Cys
    210


<210> SEQ ID NO 221
<211> LENGTH: 213
<212> TYPE: PRT
<213> ORGANISM: Homo sapiens

<400> SEQUENCE: 221

Asp Ile Gln Leu Thr Gln Ser Pro Ser Ser Val Ser Ala Ser Val Gly
1               5                   10                  15

Gly Arg Val Thr Ile Thr Cys Arg Ala Ser Gln Gly Ile Ser Ser Trp
            20                  25                  30

Leu Ala Trp Tyr Gln Gln Arg Pro Gly Lys Ala Pro Asn Leu Leu Ile
        35                  40                  45

Tyr Gly Ala Ser Asn Leu Gln Ser Gly Val Pro Ser Arg Phe Ser Gly
    50                  55                  60

Ser Gly Ser Gly Thr Asp Phe Ser Leu Thr Ile Ser Ser Leu Gln Pro
65                  70                  75                  80

Glu Asp Phe Ala Thr Tyr Tyr Cys Gln Gln Ala Lys Ser Phe Pro Leu
                85                  90                  95

Thr Phe Gly Gly Gly Thr Lys Val Glu Ile Lys Arg Ala Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210


<210> SEQ ID NO 222
<211> LENGTH: 657
<212> TYPE: DNA
<213> ORGANISM: Homo sapiens
<220> FEATURE:
<221> NAME/KEY: CDS
<222> LOCATION: (1)..(657)

<400> SEQUENCE: 222

gat gtt gtg atg act cag tct cca gac tcc ctg gct gtg tct ctg ggc     48
Asp Val Val Met Thr Gln Ser Pro Asp Ser Leu Ala Val Ser Leu Gly
1               5                   10                  15

gag agg gcc acc atc aac tgc aag tcc agc cag agt gtt ttt tac agc     96
Glu Arg Ala Thr Ile Asn Cys Lys Ser Ser Gln Ser Val Phe Tyr Ser
            20                  25                  30

tcc aac aat aag aac tac tta gct tgg tac cag cac aaa cca gga cag    144
Ser Asn Asn Lys Asn Tyr Leu Ala Trp Tyr Gln His Lys Pro Gly Gln
        35                  40                  45
```

```
cct cct aag ttg ctc att tac tgg gca tct acc cgg caa tcc ggg gtc      192
Pro Pro Lys Leu Leu Ile Tyr Trp Ala Ser Thr Arg Gln Ser Gly Val
    50                  55                  60

cct gac cga ttc agt ggc agc ggg tct ggg aca gat ttc act ctc acc      240
Pro Asp Arg Phe Ser Gly Ser Gly Ser Gly Thr Asp Phe Thr Leu Thr
65                  70                  75                  80

atc aac agc ctg cag gct gaa gat gtg gca gtt tat tac tgt cag caa      288
Ile Asn Ser Leu Gln Ala Glu Asp Val Ala Val Tyr Tyr Cys Gln Gln
                85                  90                  95

tat tat agt act cct ccc act ttc ggc gga ggg acc aag gtg gaa atc      336
Tyr Tyr Ser Thr Pro Pro Thr Phe Gly Gly Gly Thr Lys Val Glu Ile
            100                 105                 110

aaa cgt gcg gcc gca ccc agc gtg ttc atc ttc ccc ccc tcc gac gag      384
Lys Arg Ala Ala Ala Pro Ser Val Phe Ile Phe Pro Pro Ser Asp Glu
        115                 120                 125

cag ctg aag agc ggc acc gcc agc gtg gtg tgc ctg ctg aac aac ttc      432
Gln Leu Lys Ser Gly Thr Ala Ser Val Val Cys Leu Leu Asn Asn Phe
    130                 135                 140

tac ccc cgg gag gcc aag gtg cag tgg aag gtg gac aac gcc ctg cag      480
Tyr Pro Arg Glu Ala Lys Val Gln Trp Lys Val Asp Asn Ala Leu Gln
145                 150                 155                 160

agc ggc aac agc cag gag agc gtg acc gag cag gac agc aag gac tcc      528
Ser Gly Asn Ser Gln Glu Ser Val Thr Glu Gln Asp Ser Lys Asp Ser
                165                 170                 175

acc tac agc ctg agc agc acc ctc acc ctg agc aag gcc gac tac gag      576
Thr Tyr Ser Leu Ser Ser Thr Leu Thr Leu Ser Lys Ala Asp Tyr Glu
            180                 185                 190

aag cac aag gtg tac gcc tgc gag gtg acc cac cag ggc ctg agc agc      624
Lys His Lys Val Tyr Ala Cys Glu Val Thr His Gln Gly Leu Ser Ser
        195                 200                 205

ccc gtg acc aag agc ttc aac cgg ggc gag tgt                          657
Pro Val Thr Lys Ser Phe Asn Arg Gly Glu Cys
    210                 215


<210> SEQ ID NO 223
<211> LENGTH: 219
<212> TYPE: PRT
<213> ORGANISM: Homo sapiens

<400> SEQUENCE: 223

Asp Val Val Met Thr Gln Ser Pro Asp Ser Leu Ala Val Ser Leu Gly
1               5                   10                  15

Glu Arg Ala Thr Ile Asn Cys Lys Ser Ser Gln Ser Val Phe Tyr Ser
            20                  25                  30

Ser Asn Asn Lys Asn Tyr Leu Ala Trp Tyr Gln His Lys Pro Gly Gln
        35                  40                  45

Pro Pro Lys Leu Leu Ile Tyr Trp Ala Ser Thr Arg Gln Ser Gly Val
    50                  55                  60

Pro Asp Arg Phe Ser Gly Ser Gly Ser Gly Thr Asp Phe Thr Leu Thr
65                  70                  75                  80

Ile Asn Ser Leu Gln Ala Glu Asp Val Ala Val Tyr Tyr Cys Gln Gln
                85                  90                  95

Tyr Tyr Ser Thr Pro Pro Thr Phe Gly Gly Gly Thr Lys Val Glu Ile
            100                 105                 110

Lys Arg Ala Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
```

-continued 145 150 155 160

Ser Gly Asn Ser Gln Glu Ser Val Thr Glu Gln Asp Ser Lys Asp Ser
165 170 175

Thr Tyr Ser Leu Ser Ser Thr Leu Thr Leu Ser Lys Ala Asp Tyr Glu
180 185 190

Lys His Lys Val Tyr Ala Cys Glu Val Thr His Gln Gly Leu Ser Ser
195 200 205

Pro Val Thr Lys Ser Phe Asn Arg Gly Glu Cys
210 215

<210> SEQ ID NO 224
<211> LENGTH: 660
<212> TYPE: DNA
<213> ORGANISM: Homo sapiens
<220> FEATURE:
<221> NAME/KEY: CDS
<222> LOCATION: (1)..(660)

<400> SEQUENCE: 224 cag tct gcc ctg act cag cct cgc tca gtg tcc ggg tct cct gga cag 48
Gln Ser Ala Leu Thr Gln Pro Arg Ser Val Ser Gly Ser Pro Gly Gln
1 5 10 15 gca gtc acc ctc tcc tgc aat gga acc agc agg gat gtt ggt ggt tat 96
Ala Val Thr Leu Ser Cys Asn Gly Thr Ser Arg Asp Val Gly Gly Tyr
20 25 30 aat tat gtc tcc tgg tac caa caa cac cca ggc aaa gcc ccc aaa ctc 144
Asn Tyr Val Ser Trp Tyr Gln Gln His Pro Gly Lys Ala Pro Lys Leu
35 40 45 atg att tat gat gtc act aag cgg ccc tca ggg gtc cct gat cgc ttc 192
Met Ile Tyr Asp Val Thr Lys Arg Pro Ser Gly Val Pro Asp Arg Phe
50 55 60 tct ggc tcc aag tct ggc aac acg gcc tcc ctg acc atc tct gga ctc 240
Ser Gly Ser Lys Ser Gly Asn Thr Ala Ser Leu Thr Ile Ser Gly Leu
65 70 75 80 cag gct gag gat gag gct gat tat tac tgc aac tca tac gca ggc agc 288
Gln Ala Glu Asp Glu Ala Asp Tyr Tyr Cys Asn Ser Tyr Ala Gly Ser
85 90 95 aac act tgg gtg ttc ggc gga ggg acc aag ctg acc gtc cta ggt gcg 336
Asn Thr Trp Val Phe Gly Gly Gly Thr Lys Leu Thr Val Leu Gly Ala
100 105 110 gcc gca ggc cag ccc aag gcc gct ccc agc gtg acc ctg ttc ccc ccc 384
Ala Ala Gly Gln Pro Lys Ala Ala Pro Ser Val Thr Leu Phe Pro Pro
115 120 125 tcc tcc gag gag ctg cag gcc aac aag gcc acc ctg gtg tgc ctc atc 432
Ser Ser Glu Glu Leu Gln Ala Asn Lys Ala Thr Leu Val Cys Leu Ile
130 135 140 agc gac ttc tac cct ggc gcc gtg acc gtg gcc tgg aag gcc gac agc 480
Ser Asp Phe Tyr Pro Gly Ala Val Thr Val Ala Trp Lys Ala Asp Ser
145 150 155 160 agc ccc gtg aag gcc ggc gtg gag acc acc acc ccc agc aag cag agc 528
Ser Pro Val Lys Ala Gly Val Glu Thr Thr Thr Pro Ser Lys Gln Ser
165 170 175 aac aac aag tac gcc gcc agc agc tac ctg agc ctc acc ccc gag cag 576
Asn Asn Lys Tyr Ala Ala Ser Ser Tyr Leu Ser Leu Thr Pro Glu Gln
180 185 190 tgg aag agc cac cgg agc tac agc tgc cag gtg acc cac gag ggc agc 624
Trp Lys Ser His Arg Ser Tyr Ser Cys Gln Val Thr His Glu Gly Ser
195 200 205 acc gtg gag aag acc gtg gcc ccc acc gag tgc agc 660
Thr Val Glu Lys Thr Val Ala Pro Thr Glu Cys Ser
210 215 220

<210> SEQ ID NO 225
<211> LENGTH: 220
<212> TYPE: PRT
<213> ORGANISM: Homo sapiens

<400> SEQUENCE: 225

```
Gln Ser Ala Leu Thr Gln Pro Arg Ser Val Ser Gly Ser Pro Gly Gln
1               5                   10                  15

Ala Val Thr Leu Ser Cys Asn Gly Thr Ser Arg Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Thr Lys Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Asn Ser Tyr Ala Gly Ser
                85                  90                  95

Asn Thr Trp Val Phe Gly Gly Gly Thr Lys Leu Thr Val Leu Gly Ala
            100                 105                 110

Ala Ala Gly Gln Pro Lys Ala Ala Pro Ser Val Thr Leu Phe Pro Pro
        115                 120                 125

Ser Ser Glu Glu Leu Gln Ala Asn Lys Ala Thr Leu Val Cys Leu Ile
    130                 135                 140

Ser Asp Phe Tyr Pro Gly Ala Val Thr Val Ala Trp Lys Ala Asp Ser
145                 150                 155                 160

Ser Pro Val Lys Ala Gly Val Glu Thr Thr Thr Pro Ser Lys Gln Ser
                165                 170                 175

Asn Asn Lys Tyr Ala Ala Ser Ser Tyr Leu Ser Leu Thr Pro Glu Gln
            180                 185                 190

Trp Lys Ser His Arg Ser Tyr Ser Cys Gln Val Thr His Glu Gly Ser
        195                 200                 205

Thr Val Glu Lys Thr Val Ala Pro Thr Glu Cys Ser
    210                 215                 220
```

<210> SEQ ID NO 226
<211> LENGTH: 660
<212> TYPE: DNA
<213> ORGANISM: Homo sapiens
<220> FEATURE:
<221> NAME/KEY: CDS
<222> LOCATION: (1)..(660)

<400> SEQUENCE: 226

```
cag tct gcc ctg act cag cct ccc tcc gcg tcc ggg tct cct gga cag       48
Gln Ser Ala Leu Thr Gln Pro Pro Ser Ala Ser Gly Ser Pro Gly Gln
1               5                   10                  15

tca gtc acc atc tcc tgc act gga acc agc agt gac gtt ggt ggt tat       96
Ser Val Thr Ile Ser Cys Thr Gly Thr Ser Ser Asp Val Gly Gly Tyr
            20                  25                  30

aac tat gtc tcc tgg tac caa caa cac cca ggc aaa gcc ccc aaa ctc      144
Asn Tyr Val Ser Trp Tyr Gln Gln His Pro Gly Lys Ala Pro Lys Leu
        35                  40                  45

atg att tat gat gtc agt aag cgg ccc tca ggg gtc cct gat cgc ttc      192
Met Ile Tyr Asp Val Ser Lys Arg Pro Ser Gly Val Pro Asp Arg Phe
    50                  55                  60

tct ggc tcc aag tct ggc aac acg gcc tcc ctg acc gtc tct ggg ctc      240
Ser Gly Ser Lys Ser Gly Asn Thr Ala Ser Leu Thr Val Ser Gly Leu
```

```
65                  70                  75                  80

cag tct gag gat gag gct gat tat tac tgc agc tca tat gca ggc agc       288
Gln Ser Glu Asp Glu Ala Asp Tyr Tyr Cys Ser Ser Tyr Ala Gly Ser
                85                  90                  95

acc ggt tat gtc ttc gga act ggg acc aag gtc acc gtc cta ggt gcg       336
Thr Gly Tyr Val Phe Gly Thr Gly Thr Lys Val Thr Val Leu Gly Ala
            100                 105                 110

gcc gca ggc cag ccc aag gcc gct ccc agc gtg acc ctg ttc ccc ccc       384
Ala Ala Gly Gln Pro Lys Ala Ala Pro Ser Val Thr Leu Phe Pro Pro
        115                 120                 125

tcc tcc gag gag ctg cag gcc aac aag gcc acc ctg gtg tgc ctc atc       432
Ser Ser Glu Glu Leu Gln Ala Asn Lys Ala Thr Leu Val Cys Leu Ile
    130                 135                 140

agc gac ttc tac cct ggc gcc gtg acc gtg gcc tgg aag gcc gac agc       480
Ser Asp Phe Tyr Pro Gly Ala Val Thr Val Ala Trp Lys Ala Asp Ser
145                 150                 155                 160

agc ccc gtg aag gcc ggc gtg gag acc acc acc ccc agc aag cag agc       528
Ser Pro Val Lys Ala Gly Val Glu Thr Thr Thr Pro Ser Lys Gln Ser
                165                 170                 175

aac aac aag tac gcc gcc agc agc tac ctg agc ctc acc ccc gag cag       576
Asn Asn Lys Tyr Ala Ala Ser Ser Tyr Leu Ser Leu Thr Pro Glu Gln
            180                 185                 190

tgg aag agc cac cgg agc tac agc tgc cag gtg acc cac gag ggc agc       624
Trp Lys Ser His Arg Ser Tyr Ser Cys Gln Val Thr His Glu Gly Ser
        195                 200                 205

acc gtg gag aag acc gtg gcc ccc acc gag tgc agc                       660
Thr Val Glu Lys Thr Val Ala Pro Thr Glu Cys Ser
    210                 215                 220


<210> SEQ ID NO 227
<211> LENGTH: 220
<212> TYPE: PRT
<213> ORGANISM: Homo sapiens

<400> SEQUENCE: 227

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ser Glu Asp Glu Ala Asp Tyr Tyr Cys Ser Ser Tyr Ala Gly Ser
                85                  90                  95

Thr Gly Tyr Val Phe Gly Thr Gly Thr Lys Val Thr Val Leu Gly Ala
            100                 105                 110

Ala Ala Gly Gln Pro Lys Ala Ala Pro Ser Val Thr Leu Phe Pro Pro
        115                 120                 125

Ser Ser Glu Glu Leu Gln Ala Asn Lys Ala Thr Leu Val Cys Leu Ile
    130                 135                 140

Ser Asp Phe Tyr Pro Gly Ala Val Thr Val Ala Trp Lys Ala Asp Ser
145                 150                 155                 160

Ser Pro Val Lys Ala Gly Val Glu Thr Thr Thr Pro Ser Lys Gln Ser
                165                 170                 175

Asn Asn Lys Tyr Ala Ala Ser Ser Tyr Leu Ser Leu Thr Pro Glu Gln
```

```
        180                 185                 190

Trp Lys Ser His Arg Ser Tyr Ser Cys Gln Val Thr His Glu Gly Ser
        195                 200                 205

Thr Val Glu Lys Thr Val Ala Pro Thr Glu Cys Ser
    210                 215                 220


<210> SEQ ID NO 228
<211> LENGTH: 660
<212> TYPE: DNA
<213> ORGANISM: Homo sapiens
<220> FEATURE:
<221> NAME/KEY: CDS
<222> LOCATION: (1)..(660)

<400> SEQUENCE: 228

cag tct gcc ctg act cag cct ccc tcc gcg tcc ggg tct cct gga cag       48
Gln Ser Ala Leu Thr Gln Pro Pro Ser Ala Ser Gly Ser Pro Gly Gln
1               5                   10                  15

tca gtc acc atc tcc tgc act gga acc agc agt gac gtt ggt ggt tat       96
Ser Val Thr Ile Ser Cys Thr Gly Thr Ser Ser Asp Val Gly Gly Tyr
            20                  25                  30

aac tat gtc tcc tgg tac caa caa tac cca ggc aaa gcc ccc aaa ctc      144
Asn Tyr Val Ser Trp Tyr Gln Gln Tyr Pro Gly Lys Ala Pro Lys Leu
        35                  40                  45

atg att tat gat gtc agt aat cgg ccc tca ggg gtt tct aat cgc ttc      192
Met Ile Tyr Asp Val Ser Asn Arg Pro Ser Gly Val Ser Asn Arg Phe
    50                  55                  60

tct ggc tcc aag tct ggc aac acg gcc tcc ctg acc atc tct ggg ctc      240
Ser Gly Ser Lys Ser Gly Asn Thr Ala Ser Leu Thr Ile Ser Gly Leu
65                  70                  75                  80

cag gct gag gac gag gct gat tat tac tgc agc tca tat aca agc agc      288
Gln Ala Glu Asp Glu Ala Asp Tyr Tyr Cys Ser Ser Tyr Thr Ser Ser
                85                  90                  95

agc act ctt gtc ttc gga act ggg acc aag gtc acc gtc cta ggt gcg      336
Ser Thr Leu Val Phe Gly Thr Gly Thr Lys Val Thr Val Leu Gly Ala
            100                 105                 110

gcc gca ggc cag ccc aag gcc gct ccc agc gtg acc ctg ttc ccc ccc      384
Ala Ala Gly Gln Pro Lys Ala Ala Pro Ser Val Thr Leu Phe Pro Pro
        115                 120                 125

tcc tcc gag gag ctg cag gcc aac aag gcc acc ctg gtg tgc ctc atc      432
Ser Ser Glu Glu Leu Gln Ala Asn Lys Ala Thr Leu Val Cys Leu Ile
    130                 135                 140

agc gac ttc tac cct ggc gcc gtg acc gtg gcc tgg aag gcc gac agc      480
Ser Asp Phe Tyr Pro Gly Ala Val Thr Val Ala Trp Lys Ala Asp Ser
145                 150                 155                 160

agc ccc gtg aag gcc ggc gtg gag acc acc acc ccc agc aag cag agc      528
Ser Pro Val Lys Ala Gly Val Glu Thr Thr Thr Pro Ser Lys Gln Ser
                165                 170                 175

aac aac aag tac gcc gcc agc agc tac ctg agc ctc acc ccc gag cag      576
Asn Asn Lys Tyr Ala Ala Ser Ser Tyr Leu Ser Leu Thr Pro Glu Gln
            180                 185                 190

tgg aag agc cac cgg agc tac agc tgc cag gtg acc cac gag ggc agc      624
Trp Lys Ser His Arg Ser Tyr Ser Cys Gln Val Thr His Glu Gly Ser
        195                 200                 205

acc gtg gag aag acc gtg gcc ccc acc gag tgc agc                      660
Thr Val Glu Lys Thr Val Ala Pro Thr Glu Cys Ser
    210                 215                 220


<210> SEQ ID NO 229
<211> LENGTH: 220
<212> TYPE: PRT
<213> ORGANISM: Homo sapiens
```

<400> SEQUENCE: 229

```
Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln Tyr Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Leu Val Phe Gly Thr Gly Thr Lys Val Thr Val Leu Gly Ala
            100                 105                 110

Ala Ala Gly Gln Pro Lys Ala Ala Pro Ser Val Thr Leu Phe Pro Pro
        115                 120                 125

Ser Ser Glu Glu Leu Gln Ala Asn Lys Ala Thr Leu Val Cys Leu Ile
    130                 135                 140

Ser Asp Phe Tyr Pro Gly Ala Val Thr Val Ala Trp Lys Ala Asp Ser
145                 150                 155                 160

Ser Pro Val Lys Ala Gly Val Glu Thr Thr Thr Pro Ser Lys Gln Ser
                165                 170                 175

Asn Asn Lys Tyr Ala Ala Ser Ser Tyr Leu Ser Leu Thr Pro Glu Gln
            180                 185                 190

Trp Lys Ser His Arg Ser Tyr Ser Cys Gln Val Thr His Glu Gly Ser
        195                 200                 205

Thr Val Glu Lys Thr Val Ala Pro Thr Glu Cys Ser
    210                 215                 220
```

<210> SEQ ID NO 230
<211> LENGTH: 663
<212> TYPE: DNA
<213> ORGANISM: Homo sapiens
<220> FEATURE:
<221> NAME/KEY: CDS
<222> LOCATION: (1)..(663)

<400> SEQUENCE: 230

```
cag tct gcc ctg act cag cct ccc tcc gcg tcc ggg tct cct gga cag       48
Gln Ser Ala Leu Thr Gln Pro Pro Ser Ala Ser Gly Ser Pro Gly Gln
1               5                   10                  15

tca gtc acc atc tcc tgc act gga acc agc agt gac att ggt ggt tat       96
Ser Val Thr Ile Ser Cys Thr Gly Thr Ser Ser Asp Ile Gly Gly Tyr
            20                  25                  30

aac tat gtc tcc tgg tac caa cag cac cca ggc aaa gcc ccc aaa ctc      144
Asn Tyr Val Ser Trp Tyr Gln Gln His Pro Gly Lys Ala Pro Lys Leu
        35                  40                  45

atg att tat gag gtc agt aat cgg ccc cca ggg gtt tct aat cgc ttc      192
Met Ile Tyr Glu Val Ser Asn Arg Pro Pro Gly Val Ser Asn Arg Phe
    50                  55                  60

tct ggc tcc aag tct ggc aac acg gcc tcc ctg acc atc tct ggg ctc      240
Ser Gly Ser Lys Ser Gly Asn Thr Ala Ser Leu Thr Ile Ser Gly Leu
65                  70                  75                  80

cag gct gag gac gag gct gat tat tac tgc agc tca tac tca acc acc      288
Gln Ala Glu Asp Glu Ala Asp Tyr Tyr Cys Ser Ser Tyr Ser Thr Thr
                85                  90                  95
```

```
acc acc cga gtg ata ttc ggc gga ggg acc aag ctg acc gtc cta ggt      336
Thr Thr Arg Val Ile Phe Gly Gly Gly Thr Lys Leu Thr Val Leu Gly
            100                 105                 110

gcg gcc gca ggc cag ccc aag gcc gct ccc agc gtg acc ctg ttc ccc      384
Ala Ala Ala Gly Gln Pro Lys Ala Ala Pro Ser Val Thr Leu Phe Pro
        115                 120                 125

ccc tcc tcc gag gag ctg cag gcc aac aag gcc acc ctg gtg tgc ctc      432
Pro Ser Ser Glu Glu Leu Gln Ala Asn Lys Ala Thr Leu Val Cys Leu
    130                 135                 140

atc agc gac ttc tac cct ggc gcc gtg acc gtg gcc tgg aag gcc gac      480
Ile Ser Asp Phe Tyr Pro Gly Ala Val Thr Val Ala Trp Lys Ala Asp
145                 150                 155                 160

agc agc ccc gtg aag gcc ggc gtg gag acc acc acc ccc agc aag cag      528
Ser Ser Pro Val Lys Ala Gly Val Glu Thr Thr Thr Pro Ser Lys Gln
                165                 170                 175

agc aac aac aag tac gcc gcc agc agc tac ctg agc ctc acc ccc gag      576
Ser Asn Asn Lys Tyr Ala Ala Ser Ser Tyr Leu Ser Leu Thr Pro Glu
            180                 185                 190

cag tgg aag agc cac cgg agc tac agc tgc cag gtg acc cac gag ggc      624
Gln Trp Lys Ser His Arg Ser Tyr Ser Cys Gln Val Thr His Glu Gly
        195                 200                 205

agc acc gtg gag aag acc gtg gcc ccc acc gag tgc agc                  663
Ser Thr Val Glu Lys Thr Val Ala Pro Thr Glu Cys Ser
    210                 215                 220


<210> SEQ ID NO 231
<211> LENGTH: 221
<212> TYPE: PRT
<213> ORGANISM: Homo sapiens

<400> SEQUENCE: 231

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Ile Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Asn Arg Pro Pro Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Ser Thr Thr
                85                  90                  95

Thr Thr Arg Val Ile Phe Gly Gly Gly Thr Lys Leu Thr Val Leu Gly
            100                 105                 110

Ala Ala Ala Gly Gln Pro Lys Ala Ala Pro Ser Val Thr Leu Phe Pro
        115                 120                 125

Pro Ser Ser Glu Glu Leu Gln Ala Asn Lys Ala Thr Leu Val Cys Leu
    130                 135                 140

Ile Ser Asp Phe Tyr Pro Gly Ala Val Thr Val Ala Trp Lys Ala Asp
145                 150                 155                 160

Ser Ser Pro Val Lys Ala Gly Val Glu Thr Thr Thr Pro Ser Lys Gln
                165                 170                 175

Ser Asn Asn Lys Tyr Ala Ala Ser Ser Tyr Leu Ser Leu Thr Pro Glu
            180                 185                 190

Gln Trp Lys Ser His Arg Ser Tyr Ser Cys Gln Val Thr His Glu Gly
        195                 200                 205

Ser Thr Val Glu Lys Thr Val Ala Pro Thr Glu Cys Ser
```

```
    210                 215                 220


<210> SEQ ID NO 232
<211> LENGTH: 660
<212> TYPE: DNA
<213> ORGANISM: Homo sapiens
<220> FEATURE:
<221> NAME/KEY: CDS
<222> LOCATION: (1)..(660)

<400> SEQUENCE: 232

cag tct gtc gtg acg cag ccg ccc tca gtg tct gcg gcc cca gga cag       48
Gln Ser Val Val Thr Gln Pro Pro Ser Val Ser Ala Ala Pro Gly Gln
1               5                   10                  15

aag gtc acc atc tcc tgc tct gga agc acc tcc aac att ggg aat tat       96
Lys Val Thr Ile Ser Cys Ser Gly Ser Thr Ser Asn Ile Gly Asn Tyr
            20                  25                  30

tat gta tcc tgg tac caa cag ctc cca gga aca gcc ccc aaa ctc ctc      144
Tyr Val Ser Trp Tyr Gln Gln Leu Pro Gly Thr Ala Pro Lys Leu Leu
        35                  40                  45

atc tat gaa aat aat aag cga ccc tca ggg att cct gac cga ttc tct      192
Ile Tyr Glu Asn Asn Lys Arg Pro Ser Gly Ile Pro Asp Arg Phe Ser
    50                  55                  60

ggc tcc aag tct ggc acg tca gcc acc ctg gac atc acc gga ctc cag      240
Gly Ser Lys Ser Gly Thr Ser Ala Thr Leu Asp Ile Thr Gly Leu Gln
65                  70                  75                  80

act ggg gac gag gcc gat tat tac tgc gga gca tgg gat ggc agc ctg      288
Thr Gly Asp Glu Ala Asp Tyr Tyr Cys Gly Ala Trp Asp Gly Ser Leu
                85                  90                  95

agt gct gtg gta ctc ggc gga ggc acc cag ctg acc gtc ctc ggt gcg      336
Ser Ala Val Val Leu Gly Gly Gly Thr Gln Leu Thr Val Leu Gly Ala
            100                 105                 110

gcc gca ggc cag ccc aag gcc gct ccc agc gtg acc ctg ttc ccc ccc      384
Ala Ala Gly Gln Pro Lys Ala Ala Pro Ser Val Thr Leu Phe Pro Pro
        115                 120                 125

tcc tcc gag gag ctg cag gcc aac aag gcc acc ctg gtg tgc ctc atc      432
Ser Ser Glu Glu Leu Gln Ala Asn Lys Ala Thr Leu Val Cys Leu Ile
    130                 135                 140

agc gac ttc tac cct ggc gcc gtg acc gtg gcc tgg aag gcc gac agc      480
Ser Asp Phe Tyr Pro Gly Ala Val Thr Val Ala Trp Lys Ala Asp Ser
145                 150                 155                 160

agc ccc gtg aag gcc ggc gtg gag acc acc acc ccc agc aag cag agc      528
Ser Pro Val Lys Ala Gly Val Glu Thr Thr Thr Pro Ser Lys Gln Ser
                165                 170                 175

aac aac aag tac gcc gcc agc agc tac ctg agc ctc acc ccc gag cag      576
Asn Asn Lys Tyr Ala Ala Ser Ser Tyr Leu Ser Leu Thr Pro Glu Gln
            180                 185                 190

tgg aag agc cac cgg agc tac agc tgc cag gtg acc cac gag ggc agc      624
Trp Lys Ser His Arg Ser Tyr Ser Cys Gln Val Thr His Glu Gly Ser
        195                 200                 205

acc gtg gag aag acc gtg gcc ccc acc gag tgc agc                      660
Thr Val Glu Lys Thr Val Ala Pro Thr Glu Cys Ser
    210                 215                 220


<210> SEQ ID NO 233
<211> LENGTH: 220
<212> TYPE: PRT
<213> ORGANISM: Homo sapiens

<400> SEQUENCE: 233

Gln Ser Val Val Thr Gln Pro Pro Ser Val Ser Ala Ala Pro Gly Gln
1               5                   10                  15
```

-continued

```
Lys Val Thr Ile Ser Cys Ser Gly Ser Thr Ser Asn Ile Gly Asn Tyr
            20                  25                  30

Tyr Val Ser Trp Tyr Gln Gln Leu Pro Gly Thr Ala Pro Lys Leu Leu
        35                  40                  45

Ile Tyr Glu Asn Asn Lys Arg Pro Ser Gly Ile Pro Asp Arg Phe Ser
    50                  55                  60

Gly Ser Lys Ser Gly Thr Ser Ala Thr Leu Asp Ile Thr Gly Leu Gln
65                  70                  75                  80

Thr Gly Asp Glu Ala Asp Tyr Tyr Cys Gly Ala Trp Asp Gly Ser Leu
                85                  90                  95

Ser Ala Val Val Leu Gly Gly Gly Thr Gln Leu Thr Val Leu Gly Ala
            100                 105                 110

Ala Ala Gly Gln Pro Lys Ala Ala Pro Ser Val Thr Leu Phe Pro Pro
        115                 120                 125

Ser Ser Glu Glu Leu Gln Ala Asn Lys Ala Thr Leu Val Cys Leu Ile
    130                 135                 140

Ser Asp Phe Tyr Pro Gly Ala Val Thr Val Ala Trp Lys Ala Asp Ser
145                 150                 155                 160

Ser Pro Val Lys Ala Gly Val Glu Thr Thr Thr Pro Ser Lys Gln Ser
                165                 170                 175

Asn Asn Lys Tyr Ala Ala Ser Ser Tyr Leu Ser Leu Thr Pro Glu Gln
            180                 185                 190

Trp Lys Ser His Arg Ser Tyr Ser Cys Gln Val Thr His Glu Gly Ser
        195                 200                 205

Thr Val Glu Lys Thr Val Ala Pro Thr Glu Cys Ser
    210                 215                 220


<210> SEQ ID NO 234
<211> LENGTH: 660
<212> TYPE: DNA
<213> ORGANISM: Homo sapiens
<220> FEATURE:
<221> NAME/KEY: CDS
<222> LOCATION: (1)..(660)

<400> SEQUENCE: 234

cag tct gcc ctg act cag cct cgc tca gtg tcc ggg tct cct gga cag       48
Gln Ser Ala Leu Thr Gln Pro Arg Ser Val Ser Gly Ser Pro Gly Gln
1               5                   10                  15

tca gtc acc atc tcc tgc act gga acc agc agt gat gtt ggt ggt tat       96
Ser Val Thr Ile Ser Cys Thr Gly Thr Ser Ser Asp Val Gly Gly Tyr
            20                  25                  30

aac tat gtc tcc tgg tac caa caa cac cca ggc aaa gcc ccc aaa ctc      144
Asn Tyr Val Ser Trp Tyr Gln Gln His Pro Gly Lys Ala Pro Lys Leu
        35                  40                  45

atg att tat gat gtc agt aat cgg ccc tca ggg gtt tct aat cgc ttc      192
Met Ile Tyr Asp Val Ser Asn Arg Pro Ser Gly Val Ser Asn Arg Phe
    50                  55                  60

tct ggc tcc aag tct ggc aac acg gcc tcc ctg acc atc tct ggg ctc      240
Ser Gly Ser Lys Ser Gly Asn Thr Ala Ser Leu Thr Ile Ser Gly Leu
65                  70                  75                  80

cag gct gag gac gag gct gat tat tac tgc agc tca tat aca agc agc      288
Gln Ala Glu Asp Glu Ala Asp Tyr Tyr Cys Ser Ser Tyr Thr Ser Ser
                85                  90                  95

agc act ctc gta ttc ggc gga ggg acc aag ctg acc gtc cta ggt gcg      336
Ser Thr Leu Val Phe Gly Gly Gly Thr Lys Leu Thr Val Leu Gly Ala
            100                 105                 110

gcc gca ggc cag ccc aag gcc gct ccc agc gtg acc ctg ttc ccc ccc      384
Ala Ala Gly Gln Pro Lys Ala Ala Pro Ser Val Thr Leu Phe Pro Pro
```

```
        115                 120                 125

tcc tcc gag gag ctg cag gcc aac aag gcc acc ctg gtg tgc ctc atc      432
Ser Ser Glu Glu Leu Gln Ala Asn Lys Ala Thr Leu Val Cys Leu Ile
    130                 135                 140

agc gac ttc tac cct ggc gcc gtg acc gtg gcc tgg aag gcc gac agc      480
Ser Asp Phe Tyr Pro Gly Ala Val Thr Val Ala Trp Lys Ala Asp Ser
145                 150                 155                 160

agc ccc gtg aag gcc ggc gtg gag acc acc acc ccc agc aag cag agc      528
Ser Pro Val Lys Ala Gly Val Glu Thr Thr Thr Pro Ser Lys Gln Ser
                165                 170                 175

aac aac aag tac gcc gcc agc agc tac ctg agc ctc acc ccc gag cag      576
Asn Asn Lys Tyr Ala Ala Ser Ser Tyr Leu Ser Leu Thr Pro Glu Gln
            180                 185                 190

tgg aag agc cac cgg agc tac agc tgc cag gtg acc cac gag ggc agc      624
Trp Lys Ser His Arg Ser Tyr Ser Cys Gln Val Thr His Glu Gly Ser
        195                 200                 205

acc gtg gag aag acc gtg gcc ccc acc gag tgc agc                      660
Thr Val Glu Lys Thr Val Ala Pro Thr Glu Cys Ser
    210                 215                 220


<210> SEQ ID NO 235
<211> LENGTH: 220
<212> TYPE: PRT
<213> ORGANISM: Homo sapiens

<400> SEQUENCE: 235

Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Leu Val Phe Gly Gly Gly Thr Lys Leu Thr Val Leu Gly Ala
            100                 105                 110

Ala Ala Gly Gln Pro Lys Ala Ala Pro Ser Val Thr Leu Phe Pro Pro
        115                 120                 125

Ser Ser Glu Glu Leu Gln Ala Asn Lys Ala Thr Leu Val Cys Leu Ile
    130                 135                 140

Ser Asp Phe Tyr Pro Gly Ala Val Thr Val Ala Trp Lys Ala Asp Ser
145                 150                 155                 160

Ser Pro Val Lys Ala Gly Val Glu Thr Thr Thr Pro Ser Lys Gln Ser
                165                 170                 175

Asn Asn Lys Tyr Ala Ala Ser Ser Tyr Leu Ser Leu Thr Pro Glu Gln
            180                 185                 190

Trp Lys Ser His Arg Ser Tyr Ser Cys Gln Val Thr His Glu Gly Ser
        195                 200                 205

Thr Val Glu Lys Thr Val Ala Pro Thr Glu Cys Ser
    210                 215                 220
```